(12) United States Patent
Bellenie et al.

(10) Patent No.: US 11,512,095 B2
(45) Date of Patent: Nov. 29, 2022

(54) BCL6 INHIBITORS

(71) Applicants: Cancer Research Technology Limited, London (GB); The Institute of Cancer Research: Royal Cancer Hospital, London (GB)

(72) Inventors: Benjamin Richard Bellenie, London (GB); Kwai Ming Jack Cheung, London (GB); Owen Alexander Davis, London (GB); Swen Hoelder, London (GB); Rosemary Huckvale, London (GB); Gavin Collie, London (GB); Mirco Meniconi, London (GB); Alfie Brennan, London (GB); Matthew Garth Lloyd, London (GB)

(73) Assignees: The Institute of Cancer Research: Royal Cancer Hospital, London (GB); Cancer Research Technology Limited, London (GB)

( * ) Notice: Subject to any disclaimer, the term of this patent is extended or adjusted under 35 U.S.C. 154(b) by 66 days.

(21) Appl. No.: 17/046,650

(22) PCT Filed: Apr. 12, 2019

(86) PCT No.: PCT/GB2019/051058
§ 371 (c)(1),
(2) Date: Oct. 9, 2020

(87) PCT Pub. No.: WO2019/197842
PCT Pub. Date: Oct. 17, 2019

(65) Prior Publication Data
US 2021/0163497 A1    Jun. 3, 2021

(30) Foreign Application Priority Data

Apr. 13, 2018 (GB) .................................... 1806132
Nov. 23, 2018 (GB) .................................... 1819136

(51) Int. Cl.
| | | |
|---|---|---|
| *C07D 498/04* | (2006.01) | |
| *A61P 35/00* | (2006.01) | |
| *C07D 471/04* | (2006.01) | |
| *C07D 498/14* | (2006.01) | |
| *C07D 498/20* | (2006.01) | |
| *C07D 513/04* | (2006.01) | |
| *C07D 519/00* | (2006.01) | |

(52) U.S. Cl.
CPC .......... *C07D 498/04* (2013.01); *A61P 35/00* (2018.01); *C07D 471/04* (2013.01); *C07D 498/14* (2013.01); *C07D 498/20* (2013.01); *C07D 513/04* (2013.01); *C07D 519/00* (2013.01)

(58) Field of Classification Search
CPC .. C07D 498/04; C07D 471/04; C07D 519/00; C07D 513/04; C07D 498/14; C07D 498/20; A61P 35/00
USPC ...................................................... 514/210.16
See application file for complete search history.

(56) References Cited

FOREIGN PATENT DOCUMENTS

| | | |
|---|---|---|
| EP | 2964642 B1 | 11/2017 |
| WO | WO-2001/094341 A1 | 12/2001 |
| WO | WO-2014/204859 A2 | 12/2014 |
| WO | WO-2018/108704 A1 | 6/2018 |
| WO | WO-2018/215798 A1 | 11/2018 |
| WO | WO-2018/215801 A1 | 11/2018 |

OTHER PUBLICATIONS

International Preliminary Report on Patentability for International Application No. PCT/GB2019/051058 dated Oct. 13, 2020.
International Search Report and Written Opinion for International Application No. PCT/GB2019/051058 dated Jul. 29, 2019.
Kerres et al., "Chemically Induced Degradation of the Oncogenic Transcription Factor BCL6," Cell Reports, 20(12): 2860-2875 (2017).
Search Report for GB Application No. 1819136.1 dated Feb. 20, 2019.

*Primary Examiner* — Kahsay Habte
(74) *Attorney, Agent, or Firm* — Foley Hoag LLP; David P. Halstead

(57) ABSTRACT

The present invention relates to compounds of formula I that function as inhibitors of BCL6 (B-cell lymphoma 6) activity:

Formula I wherein $X_1$, $X_2$, $R^1$, $R^2$, $R^{30}$, $R^{31}$ and Ring A are each as defined herein. The present invention also relates to processes for the preparation of these compounds, to pharmaceutical compositions comprising them, and to their use in the treatment of proliferative disorders, such as cancer, as well as other diseases or conditions in which BCL6 activity is implicated.

20 Claims, No Drawings

BCL6 INHIBITORS

RELATED APPLICATIONS

This application is the U.S. national phase of International Patent Application No. PCT/GB2019/051058, filed Apr. 12, 2019, which claims benefit of United Kingdom Patent Application Nos. GB 1806132.5 filed Apr. 13, 2018 and GB 1819136.1 filed Nov. 23, 2018, all of which are incorporated by reference.

INTRODUCTION

The present invention relates to certain compounds that function as inhibitors of BCL6 (B-cell lymphoma 6) activity. The present invention also relates to processes for the preparation of these compounds, to pharmaceutical compositions comprising them, and to their use in the treatment of proliferative disorders, such as cancer, as well as other diseases or conditions in which BCL6 activity is implicated.

BACKGROUND OF THE INVENTION

BCL6 is a zinc finger transcription repressor that plays a key role in the formation and development of germinal centres, in which B cells undergo somatic hypermutation and recombination of the immunoglobulin genes, in order to generate diversity in antibodies against a variety of foreign antigens (Dent et al., *Science.* 1997, 276, 589-592). BCL6 allows the proliferation of antibody producing B cells by repressing genes involved in DNA damage response, cell cycle arrest and apoptosis. BCL6 mediates this repression by recruiting the corepressor proteins SMRT, NCoR and BCoR to an extended groove motif that forms along the dimer interface of the BCL6 BTB (BR-C, Ttk and Bab) domain (Ahmad et al., *Mol Cell.* 2003, 12, 1551-1564; Ghetu et al., *Mol Cell.* 2008, 29, 384-391). Genetic upregulation of the BCL6 gene, as seen in many lymphomas, leads to malignant B cell proliferation (Hatzi & Melnick, *Trends Mol Med.* 2014, 20, 343-352). Therefore, there exists a need to develop agents that inhibit the tumourigenic effects of BCL6, either by selectively binding to the BTB domain and preventing corepressor recruitment, or by binding to the BTB domain and inducing protein degradation (Kerres et al. *Cell Rep.,* 2017, 20, 2860-2875).

SUMMARY OF THE INVENTION

According to a first aspect of the present invention, there is provided a compound, or a pharmaceutically acceptable salt, hydrate or solvate thereof, as defined herein.

According to a further aspect of the present invention, there is provided a pharmaceutical composition comprising a compound as defined herein, or a pharmaceutically acceptable salt, hydrate or solvate thereof, in admixture with a pharmaceutically acceptable diluent or carrier.

According to a further aspect of the present invention, there is provided a method of inhibiting BCL6 activity, in vitro or in vivo, said method comprising contacting a cell with an effective amount of a compound or a pharmaceutically acceptable salt, hydrate or solvate thereof as defined herein.

According to a further aspect of the present invention, there is provided a method of inhibiting cell proliferation, in vitro or in vivo, said method comprising contacting a cell with an effective amount of a compound or a pharmaceutically acceptable salt, hydrate or solvate thereof as defined herein, or a pharmaceutical composition as defined herein.

According to a further aspect of the present invention, there is provided a method of treating a disease or disorder in which BCL6 activity is implicated in a patient in need of such treatment, said method comprising administering to said patient a therapeutically effective amount of a compound or a pharmaceutically acceptable salt, hydrate or solvate thereof as defined herein, or a pharmaceutical composition as defined herein.

According to a further aspect of the present invention, there is provided a method of treating a proliferative disorder in a patient in need of such treatment, said method comprising administering to said patient a therapeutically effective amount of a compound or a pharmaceutically acceptable salt, hydrate or solvate thereof as defined herein, or a pharmaceutical composition as defined herein.

According to a further aspect of the present invention, there is provided a method of treating cancer in a patient in need of such treatment, said method comprising administering to said patient a therapeutically effective amount of a compound or a pharmaceutically acceptable salt, hydrate or solvate thereof as defined herein, or a pharmaceutical composition as defined herein.

According to a further aspect of the present invention, there is provided a compound, or a pharmaceutically acceptable salt, hydrate or solvate thereof, or a pharmaceutical composition as defined herein for use in therapy.

According to a further aspect of the present invention, there is provided a compound or a pharmaceutically acceptable salt, hydrate or solvate thereof as defined herein, or a pharmaceutical composition as defined herein, for use in the treatment of a proliferative condition.

According to a further aspect of the present invention, there is provided a compound, or a pharmaceutically acceptable salt, hydrate or solvate thereof, or a pharmaceutical composition as defined herein for use in the treatment of cancer. In a particular embodiment, the cancer is human cancer.

According to a further aspect of the present invention, there is provided a compound, or a pharmaceutically acceptable salt, hydrate or solvate thereof, as defined herein for use in the inhibition of BCL6 activity.

According to a further aspect of the present invention, there is provided a compound, or a pharmaceutically acceptable salt, hydrate or solvate thereof, as defined herein for use in the treatment of a disease or disorder in which BCL6 activity is implicated.

According to a further aspect of the present invention, there is provided the use of a compound, or a pharmaceutically acceptable salt, hydrate or solvate thereof, as defined herein in the manufacture of a medicament for the treatment of a proliferative condition.

Suitably, the proliferative disorder is cancer, suitably a human cancer (for example haematological cancers such as lymphomas (including diffuse large B-cell lymphoma (DLBCL), follicular lymphoma (FL), Burkitt lymphoma (BL) and angioimmunoblastic T-cell lymphoma (AITL)), leukaemias (including acute lymphoblastic leukaemia (ALL) and chronic myeloid leukaemia (CML)) and multiple myeloma, and solid tumours (including glioma, breast cancer, non-small cell lung cancer (NSCLC) and squamous cell carcinomas (SCC) (including SCC of the head and neck, oesophagus, lung and ovary)).

According to a further aspect of the present invention, there is provided the use of a compound, or a pharmaceutically acceptable salt, hydrate or solvate thereof, as defined herein in the manufacture of a medicament for the treatment of cancer.

According to a further aspect of the present invention, there is provided a use of a compound, or a pharmaceutically acceptable salt, hydrate or solvate thereof, as defined herein in the manufacture of a medicament for the inhibition of BCL6 activity.

According to a further aspect of the present invention, there is provided a use of a compound, or a pharmaceutically acceptable salt, hydrate or solvate thereof, as defined herein in the manufacture of a medicament for the treatment of a disease or disorder in which BCL6 activity is implicated.

According to a further aspect of the present invention, there is provided a process for preparing a compound, or a pharmaceutically acceptable salt, hydrate or solvate thereof, as defined herein.

According to a further aspect of the present invention, there is provided a compound, or a pharmaceutically acceptable salt, hydrate or solvate thereof, obtainable by, or obtained by, or directly obtained by a process of preparing a compound as defined herein.

According to a further aspect of the present invention, there are provided novel intermediates as defined herein which are suitable for use in any one of the synthetic methods set out herein.

Features, including optional, suitable, and preferred features in relation to one aspect of the invention may also be features, including optional, suitable and preferred features in relation to any other aspect of the invention.

DETAILED DESCRIPTION OF THE INVENTION

Definitions

Unless otherwise stated, the following terms used in the specification and claims have the following meanings set out below.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

In this specification the term "alkyl" includes both straight and branched chain alkyl groups. References to individual alkyl groups such as "propyl" are specific for the straight chain version only and references to individual branched chain alkyl groups such as "isopropyl" are specific for the branched chain version only. For example, "(1-6C)alkyl" includes (1-4C)alkyl, (1-3C)alkyl, propyl, isopropyl and t-butyl.

The term "(m-nC)" or "(m-nC) group" used alone or as a prefix, refers to any group having m to n carbon atoms.

An "alkylene" group is an alkyl group that is positioned between and serves to connect two other chemical groups. Thus, "(1-6C)alkylene" means a linear saturated divalent hydrocarbon radical of one to six carbon atoms or a branched saturated divalent hydrocarbon radical of three to six carbon atoms, for example, methylene (—CH$_2$—), ethylene (—CH$_2$CH$_2$—), propylene (—CH$_2$CH$_2$CH$_2$—), 2-methylpropylene (—CH$_2$CH(CH$_3$)CH$_2$—), pentylene (—CH$_2$CH$_2$CH$_2$CH$_2$CH$_2$—), and the like.

The term "alkenyl" refers to straight and branched chain alkyl groups comprising 2 or more carbon atoms, wherein at least one carbon-carbon double bond is present within the group. Examples of alkenyl groups include ethenyl, propenyl and but-2,3-enyl and includes all possible geometric (E/Z) isomers.

The term "alkynyl" refers to straight and branched chain alkyl groups comprising 2 or more carbon atoms, wherein at least one carbon-carbon triple bond is present within the group. Examples of alkynyl groups include acetylenyl and propynyl.

"(3-10C)cycloalkyl" means a hydrocarbon ring containing from 3 to 10 carbon atoms, for example, cyclopropyl, cyclobutyl, cyclopentyl, cyclohexyl, cycloheptyl and bicyclo[2.2.1]heptyl.

"(3-10C)cycloalkenyl" means a hydrocarbon ring containing from 3 to 10 carbon atoms and at least one double bond, for example, cyclobutenyl, cyclopentenyl, cyclohexenyl or cycloheptenyl, such as 3-cyclohexen-1-yl, or cyclooctenyl.

The term "alkoxy" refers to O-linked straight and branched chain alkyl groups. Examples of alkoxy groups include methoxy, ethoxy and t-butoxy.

The term "haloalkyl" or "haloalkoxy" is used herein to refer to an alkyl or alkoxy group respectively in which one or more hydrogen atoms have been replaced by halogen (e.g. fluorine) atoms. Examples of haloalkyl groups include —CH$_2$F, —CHF$_2$ and —CF$_3$. Examples of haloalkoxy groups include —OCH$_2$F, and —OCF$_3$.

The term "aminoalkyl" refers to an alkyl group in which one or more hydrogen atoms have been replaced by an amino group (NH$_2$). Examples of aminoalkyl groups include —CH$_2$NH$_2$ and —C$_2$H$_4$NH$_2$.

The term "halo" or "halogeno" refers to fluoro, chloro, bromo and iodo, suitably fluoro, chloro and bromo, more suitably, fluoro and chloro.

The term "carbocyclyl", "carbocyclic" or "carbocycle" means a non-aromatic saturated or partially saturated monocyclic, fused, bridged, or spiro bicyclic carbon-containing ring system(s). Monocyclic carbocyclic rings contain from about 3 to 12 (suitably from 3 to 7) ring atoms. Bicyclic carbocycles contain from 6 to 17 member atoms, suitably 7 to 12 member atoms, in the ring. Bicyclic carbocyclic(s) rings may be fused, spiro, or bridged ring systems. Examples of carbocyclic groups include cyclopropyl, cyclobutyl, cyclohexenyl and spiro[3.3]heptanyl, The term "heterocyclyl", "heterocyclic" or "heterocycle" means a non-aromatic saturated or partially saturated monocyclic, fused, bridged, or spiro bicyclic heterocyclic ring system(s). Monocyclic heterocyclic rings contain from about 3 to 12 (suitably from 3 to 7) ring atoms, with from 1 to 5 (suitably 1, 2 or 3) heteroatoms selected from nitrogen, oxygen or sulfur in the ring. Bicyclic heterocycles contain from 7 to 17 member atoms, suitably 7 to 12 member atoms, in the ring. Bicyclic heterocyclic(s) rings may be fused, spiro, or bridged ring systems. Examples of heterocyclic groups include cyclic ethers such as oxiranyl, oxetanyl, tetrahydrofuranyl, dioxanyl, and substituted cyclic ethers. Heterocycles containing nitrogen include, for example, azetidinyl, pyrrolidinyl, piperidinyl, piperazinyl, tetrahydrotriazinyl, tetrahydropyrazolyl, and the like. Typical sulfur containing heterocycles include tetrahydrothienyl, dihydro-1,3-dithiol, tetrahydro-2H-thiopyran, and hexahydrothiepine. Other heterocycles include dihydro-oxathiolyl, tetrahydro-oxazolyl, tetrahydro-oxadiazolyl, tetrahydrodioxazolyl, tetrahydro-oxathiazolyl, hexahydrotriazinyl, tetrahydro-oxazinyl, morpholinyl, thiomorpholinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or $SO_2$ groups are also included. Examples include the sulfoxide and sulfone forms of tetrahydrothienyl and thiomorpholinyl such as tetrahydrothiene 1,1-dioxide and thiomorpholinyl 1,1-dioxide. Heterocycles may comprise 1 or 2 oxo (=O) or thioxo (=S) substituents. A suitable value for a heterocyclyl group which bears 1 or 2 oxo (=O) or thioxo (=S) substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl. Particular heterocyclyl groups are saturated monocyclic 3 to 7 membered heterocyclyls containing 1, 2 or 3 heteroatoms selected from nitrogen, oxygen or sulfur, for example azetidinyl, tetrahydrofuranyl, tetrahydropyranyl, pyrrolidinyl, morpholinyl, tetrahydrothienyl, tetrahydrothienyl 1,1-dioxide, thiomorpholinyl, thiomorpholinyl 1,1-dioxide, piperidinyl, homopiperidinyl, piperazinyl or homopiperazinyl. As the skilled person would appreciate, any heterocycle may be linked to another group via any suitable atom, such as via a carbon or nitrogen atom. However, reference herein to piperidino or morpholino refers to a piperidin-1-yl or morpholin-4-yl ring that is linked via the ring nitrogen.

By "bridged ring systems" is meant ring systems in which two rings share more than two atoms, see for example *Advanced Organic Chemistry*, by Jerry March, 4$^{th}$ Edition, Wiley Interscience, pages 131-133, 1992. Examples of bridged heterocyclyl ring systems include, aza-bicyclo[2.2.1]heptane, 2-oxa-5-azabicyclo[2.2.1]heptane, aza-bicyclo[2.2.2]octane, aza-bicyclo[3.2.1]octane and quinuclidine.

By "spiro bi-cyclic ring systems" we mean that the two ring systems share one common spiro carbon atom, i.e. the heterocyclic ring is linked to a further carbocyclic or heterocyclic ring through a single common spiro carbon atom. Examples of spiro ring systems include 6-azaspiro[3.4]octane, 2-oxa-6-azaspiro[3.4]octane, 2-azaspiro[3.3]heptanes, 2-oxa-6-azaspiro[3.3]heptanes, 7-oxa-2-azaspiro[3.5]nonane, 6-oxa-2-azaspiro[3.4]octane, 2-oxa-7-azaspiro[3.5]nonane and 2-oxa-6-azaspiro[3.5]nonane.

The term "heteroaryl" or "heteroaromatic" means an aromatic mono-, bi-, or polycyclic ring incorporating one or more (for example 1-4, particularly 1, 2 or 3) heteroatoms selected from nitrogen, oxygen or sulfur. The term heteroaryl includes both monovalent species and divalent species. Examples of heteroaryl groups are monocyclic and bicyclic groups containing from five to twelve ring members, and more usually from five to ten ring members. The heteroaryl group can be, for example, a 5- or 6-membered monocyclic ring or a 9- or 10-membered bicyclic ring, for example a bicyclic structure formed from fused five and six membered rings or two fused six membered rings. Each ring may contain up to about four heteroatoms typically selected from nitrogen, sulfur and oxygen. Typically the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of heteroaryl include furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, isoindolyl, benzothienyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl, pteridinyl, naphthyridinyl, carbazolyl, phenazinyl, benzisoquinolinyl, pyridopyrazinyl, thieno[2,3-b]furanyl, 2H-furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl, imidazo[1,2-b][1,2,4]triazinyl. "Heteroaryl" also covers partially aromatic bi- or polycyclic ring systems wherein at least one ring is an aromatic ring and one or more of the other ring(s) is a non-aromatic, saturated or partially saturated ring, provided at least one ring contains one or more heteroatoms selected from nitrogen, oxygen or sulfur. Examples of partially aromatic heteroaryl groups include for example, tetrahydroisoquinolinyl, tetrahydroquinolinyl, 2-oxo-1,2,3,4-tetrahydroquinolinyl, dihydrobenzthienyl, dihydrobenzfuranyl, 2,3-dihydro-benzo[1,4]dioxinyl, benzo[1,3]dioxolyl, 2,2-dioxo-1,3-dihydro-2-benzothienyl, 4,5,6,7-tetrahydrobenzofuranyl, indolinyl, 1,2,3,4-tetrahydro-1,8-naphthyridinyl, 1,2,3,4-tetrahydropyrido[2,3-b]pyrazinyl and 3,4-dihydro-2H-pyrido[3,2-b][1,4]oxazinyl.

Examples of five membered heteroaryl groups include but are not limited to pyrrolyl, furanyl, thienyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six membered heteroaryl groups include but are not limited to pyridyl, pyrazinyl, pyridazinyl, pyrimidinyl and triazinyl.

A bicyclic heteroaryl group may be, for example, a group selected from:

a benzene ring fused to a 5- or 6-membered ring containing 1, 2 or 3 ring heteroatoms;

a pyridine ring fused to a 5- or 6-membered ring containing 1, 2 or 3 ring heteroatoms;

a pyrimidine ring fused to a 5- or 6-membered ring containing 1 or 2 ring heteroatoms;

a pyrrole ring fused to a 5- or 6-membered ring containing 1, 2 or 3 ring heteroatoms;

a pyrazole ring fused to a 5- or 6-membered ring containing 1 or 2 ring heteroatoms;

a pyrazine ring fused to a 5- or 6-membered ring containing 1 or 2 ring heteroatoms;

an imidazole ring fused to a 5- or 6-membered ring containing 1 or 2 ring heteroatoms;

an oxazole ring fused to a 5- or 6-membered ring containing 1 or 2 ring heteroatoms;

an isoxazole ring fused to a 5- or 6-membered ring containing 1 or 2 ring heteroatoms;

a thiazole ring fused to a 5- or 6-membered ring containing 1 or 2 ring heteroatoms;
an isothiazole ring fused to a 5- or 6-membered ring containing 1 or 2 ring heteroatoms;
a thiophene ring fused to a 5- or 6-membered ring containing 1, 2 or 3 ring heteroatoms;
a furan ring fused to a 5- or 6-membered ring containing 1, 2 or 3 ring heteroatoms;
a cyclohexyl ring fused to a 5- or 6-membered heteroaromatic ring containing 1, 2 or 3 ring heteroatoms; and
a cyclopentyl ring fused to a 5- or 6-membered heteroaromatic ring containing 1, 2 or 3 ring heteroatoms.

Particular examples of bicyclic heteroaryl groups containing a six membered ring fused to a five membered ring include but are not limited to benzfuranyl, benzthiophenyl, benzimidazolyl, benzoxazolyl, benzisoxazolyl, benzthiazolyl, benzisothiazolyl, isobenzofuranyl, indolyl, isoindolyl, indolizinyl, indolinyl, isoindolinyl, purinyl (e.g., adeninyl, guaninyl), indazolyl, benzodioxolyl and pyrazolopyridinyl groups.

Particular examples of bicyclic heteroaryl groups containing two fused six membered rings include but are not limited to quinolinyl, isoquinolinyl, chromanyl, thiochromanyl, chromenyl, isochromenyl, chromanyl, isochromanyl, benzodioxanyl, quinolizinyl, benzoxazinyl, benzodiazinyl, pyridopyridinyl, quinoxalinyl, quinazolinyl, cinnolinyl, phthalazinyl, naphthyridinyl and pteridinyl groups.

The term "aryl" means a cyclic or polycyclic aromatic ring having from 5 to 12 carbon atoms. The term aryl includes both monovalent species and divalent species. Examples of aryl groups include, but are not limited to, phenyl, biphenyl, naphthyl and the like. In a particular embodiment, an aryl is phenyl.

The term "optionally substituted" refers to either groups, structures, or molecules that are substituted and those that are not substituted. The term "wherein a/any CH, CH$_2$, CH$_3$ group or heteroatom (i.e. NH) within a R$^1$ group is optionally substituted" suitably means that (any) one of the hydrogen radicals of the R$^1$ group is substituted by a relevant stipulated group.

Where optional substituents are chosen from "one or more" groups it is to be understood that this definition includes all substituents being chosen from one of the specified groups or the substituents being chosen from two or more of the specified groups.

The phrase "compound of the invention" means those compounds which are disclosed herein, both generically and specifically.

Compounds of the Invention

In one aspect, the present invention relates to compounds, or pharmaceutically acceptable salts, hydrates or solvates thereof, having the structural formula (I), shown below:

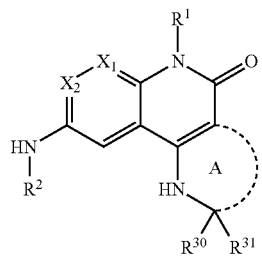

Formula (I)

wherein:
X$_1$ is selected from N or CR$^a$ wherein R$^a$ is selected from hydrogen, (1-2C)alkyl, halogen, (1-2C)alkoxy, (1-2C)haloalkyl, (1-2C)haloalkoxy, cyano or NR$^b$R$^c$, wherein R$^b$ and R$^c$ are each independently selected from hydrogen or (1-2C)alkyl;
X$_2$ is selected from N, CH, CF, CCl or C—CH$_3$;
R$^1$ is selected from hydrogen or a group of the formula:

-L-Y—Z wherein:
L is absent or (1-3C)alkylene;
Y is absent or O, C(O), C(O)O or C(O)N(R$^e$), wherein R$^e$ is selected from hydrogen or (1-4C)alkyl; and
Z is hydrogen, (1-6C)alkyl, aryl, (3-6C)cycloalkyl, (3-6C)cycloalkenyl, 5 or 6 membered heteroaryl or 4 to 7 membered heterocyclyl; wherein Z is optionally further substituted by one or more substituent groups independently selected from oxo, (1-2C)alkyl, halo, (1-2C)haloalkyl, (1-2C)haloalkoxy, (1-2C)aminoalkyl, cyano, NR$^g$R$^h$ or OR$^g$; wherein R$^g$ and R$^h$ are each independently selected from hydrogen or (1-4C)alkyl;

R$^2$ is selected from a group of Formula A shown below:

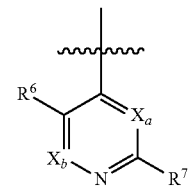

Formula A wherein:

denotes the point of attachment;
X$_a$ is selected from N, CH or CF;
X$_b$ is selected from N or CR$^{x1}$, wherein R$^{x1}$ is selected from hydrogen, fluoro, chloro, bromo, (1-2C)alkyl, (1-2C)alkoxy, cyano, acetylenyl, CH$_2$F, CF$_2$H or CF$_3$;
R$^6$ is selected from hydrogen, fluoro, chloro, bromo, (1-2C)alkyl, (1-2C)alkoxy, cyano, acetylenyl, CH$_2$F, CF$_2$H or CF$_3$;
R$^7$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—Y$_3$—Z$_3$ wherein:
Y$_3$ is absent or O, S, SO, SO$_2$, N(R$^j$)(CR$^j$R$^k$)$_q$, (where q$_1$ is 0, 1 or 2), C(O), C(O)O, OC(O), C(O)N(R$^j$), N(R$^j$)C(O), N(R$^j$)C(O)N(R$^k$), N(R$^j$)C(O)O, OC(O)N(R$^j$), S(O)$_2$N(R$^j$) or N(R$^j$)SO$_2$, wherein R$^j$ and R$^k$ are each independently selected from hydrogen or (1-4C)alkyl; and
Z$_3$ is hydrogen, (1-6C)alkyl, aryl, (3-6C)cycloalkyl, (2-4C)alkenyl, (2-4C)alkynyl, (3-6C)cycloalkenyl, heteroaryl or 4 to 12-membered heterocyclyl; wherein Z$_3$ is optionally further substituted by one or more substituent groups independently selected from (1-4C)alkyl, (3-6C)cycloalkyl, halo, oxo, (1-4C)haloalkyl, (1-4C)haloalkoxy, (1-4C)alkoxyalkyl, cyano, $CO_2H$, $SO_2NH_2$, $C(O)NR^lR^m$, $NR^lR^m$, $OR^l$ or $SR^l$ wherein $R^l$ and $R^m$ are each independently selected from hydrogen, (1-4C)alkyl or (3-6C)cycloalkyl; or $Z^3$ is optionally further substituted by a group of the formula:

-L$_Z$-W$_Z$ wherein:
L$_Z$ is a (1-5C)alkylene optionally substituted by one or more substituents selected from (1-2C)alkyl or oxo; and
W$_Z$ is halo, (1-4C)haloalkyl, (1-4C)haloalkoxy, cyano, hydroxy, (1-4C)alkoxy, $C(O)R^{xa}$, $COOR^{xa}$, $C(O)NR^{xa}R^{xb}$ or $NR^{xa}R^{xb}$, wherein $R^{xa}$ and $R^{xb}$ are each independently selected from hydrogen or (1-4C)alkyl;
$R^{30}$ is selected from (1-4C)alkyl, (3-6C)cycloalkyl, (1-4C)haloalkyl or cyano, wherein each (1-4C)alkyl and/or (3-6C)cycloalkyl substituent is optionally further substituted by one or more substituents selected from (1-4C)alkyl, (3-6C)cycloalkyl, hydroxy, (1-2C)alkoxy, $NR^uR^v$, (1-2C)aminoalkyl or halo, wherein $R^u$ and $R^v$ are independently selected from hydrogen or (1-2C)alkyl;
$R^{31}$ is selected from hydrogen, (1-4C)alkyl, cyano, (1-4C)haloalkyl or a group of the formula:

Y$_5$-L$_5$-Z$_5$ wherein:
Y$_5$ is absent or selected from C(O)O or C(O)N(R$^w$), wherein R$^w$ is selected from hydrogen or (1-2C)alkyl;
L$_5$ is absent or (1-2C)alkylene; and
Z$_5$ is hydrogen, (1-6C)alkyl, aryl, (3-6C)cycloalkyl, 5 or 6 membered heteroaryl or 4 to 6-membered heterocyclyl; wherein Z$_5$ is optionally substituted by one or more substituents selected from (1-2C)alkyl, halo, (1-2C)haloalkyl, (1-2C)haloalkoxy, (1-2C)alkoxy, $NH_2$, cyano, nitro or hydroxy; or
$R^{30}$ and $R^{31}$ are linked such that, together with the carbon atom to which they are attached, they form a 4-6 membered carbocyclic ring or a heterocyclic ring; and
Ring A is a 6- or 7-membered heterocyclic ring, which, in addition to the substituent groups $R^{30}$ and $R^{31}$, is optionally further substituted by one or more substituent groups selected from oxo, (1-2C)alkyl, cyclopropyl, spiro-cyclopropyl, halo, (1-2C)haloalkyl, (1-2C)haloalkoxy, (1-2C)alkoxy, $NH_2$, cyano or hydroxy.

In a particular group of compounds of the present invention, no more than one of $X_1$ and $X_2$ is nitrogen.

Particular compounds of the invention include, for example, compounds of the Formula I, or pharmaceutically acceptable salts, hydrates and/or solvates thereof, wherein, unless otherwise stated, each of $X_1$, $X_2$, $R^1$, $R^2$, $R^7$, $R^{30}$, $R^{31}$, Ring A and any associated substituent groups has any of the meanings defined hereinbefore or in any of paragraphs (1) to (64) hereinafter:—

(1) $X_1$ is selected from N or CR$^a$ wherein R$^a$ is selected from hydrogen, (1-2C)alkyl, fluoro, chloro, (1-2C)alkoxy, $CH_2F$, $CHF_2$, $CF_3$, $OCF_3$, cyano or NR$^b$R$^c$, wherein R$^b$ and R$^c$ are independently selected from hydrogen or (1-2C)alkyl;

(2) $X_1$ is selected from N or CR$^a$ wherein R$^a$ is selected from hydrogen, methyl, fluoro, chloro, hydroxy, $OCH_3$, $CH_2F$, $CHF_2$, $CF_3$, $OCF_3$, acetylenyl, cyano or $NH_2$;

(3) $X_1$ is selected from N or CR$^a$ wherein R$^a$ is selected from hydrogen, methyl, fluoro, chloro, hydroxy, $OCH_3$, $CH_2F$, $CHF_2$, acetylenyl or cyano;

(4) $X_1$ is selected from N or CR$^a$ wherein R$^a$ is selected from hydrogen, methyl, fluoro, chloro, $OCH_3$, acetylenyl or cyano;

(5) $X_1$ is selected from N or CR$^a$ wherein R$^a$ is selected from hydrogen, (1-2C)alkyl or (1-2C)alkoxy;

(6) $X_1$ is selected from N or CR$^a$ wherein R$^a$ is selected from hydrogen, methyl, $OCH_3$, fluoro or chloro;

(7) $X_1$ is selected from N or CH;

(8) $X_1$ is N;

(9) $X_1$ is CH;

(10) $X_2$ is selected from CH, CF or C—$CH_3$;

(11) $X_2$ is selected from CH or CF;

(12) $X_2$ is CH;

(13) $R^1$ is selected from hydrogen or a group of the formula:

-L-Y—Z wherein:
L is absent or (1-3C)alkylene;
Y is absent or C(O), C(O)O or C(O)N(R$^e$), wherein R$^e$ is selected from hydrogen or methyl; and
Z is hydrogen, (1-6C)alkyl, aryl, (3-6C)cycloalkyl, (3-6C)cycloalkenyl, 5 or 6 membered heteroaryl or 4 to 7 membered heterocyclyl; wherein Z is optionally further substituted by one or more substituent groups independently selected from oxo, (1-2C)alkyl, halo, (1-2C)haloalkyl, (1-2C)haloalkoxy, (1-2C)aminoalkyl, cyano, NR$^g$R$^h$ or OR$^g$; wherein R$^g$ and R$^h$ are each independently selected from hydrogen or (1-4C)alkyl;

(14) $R^1$ is selected from hydrogen or a group of the formula:

-L-Z wherein:
L is absent or (1-3C)alkylene; and
Z is (1-6C)alkyl, aryl, (3-6C)cycloalkyl, (3-6C)cycloalkenyl, 5 or 6 membered heteroaryl or 4 to 7 membered heterocyclyl; wherein Z is optionally further substituted by one or more substituent groups independently selected from oxo, (1-2C)alkyl, halo, (1-2C)haloalkyl, (1-2C)haloalkoxy, (1-2C)aminoalkyl, cyano, NR$^g$R$^h$ or OR$^g$; wherein R$^g$ and R$^h$ are each independently selected from hydrogen or (1-2C)alkyl;

(15) $R^1$ is selected from hydrogen or a group of the formula:

-L-Z wherein:
L is absent or (1-2C)alkylene; and
Z is (1-6C)alkyl, (3-6C)cycloalkyl or 4 to 7 membered heterocyclyl; wherein Z is optionally further substituted by one or more substituent groups independently selected from oxo, (1-2C)alkyl, halo, (1-2C)haloalkyl, (1-2C)haloalkoxy, (1-2C)aminoalkyl, cyano, NR$^g$R$^h$ or OR$^g$; wherein R$^g$ and R$^h$ are each independently selected from hydrogen or (1-2C)alkyl;

(16) $R^1$ is selected from hydrogen or a group of the formula:

-L-Z wherein:
L is absent or (1-2C)alkylene; and
Z is (1-6C)alkyl, (3-6C)cycloalkyl, 4 to 7 membered heterocyclyl; wherein Z is optionally further substituted by one or more substituent groups independently selected from oxo, methyl, fluoro, NR$^g$R$^h$ or OR$^g$ wherein R$^g$ and R$^h$ are each independently selected from hydrogen or (1-2C)alkyl;

(17) R$^1$ is selected from hydrogen, (1-6C)alkyl or a group of the formula:

-L-Z wherein:
L is (1-2C)alkylene; and
Z is (a 3-6C)cycloalkyl or a 4 to 7 membered heterocyclyl; wherein Z is optionally further substituted by one or more substituent groups independently selected from oxo, (1-2C)alkyl, halo, (1-2C)haloalkyl, (1-2C)haloalkoxy, (1-2C)aminoalkyl, cyano, NR$^g$R$^h$ or OR$^g$; wherein R$^g$ and R$^h$ are each independently selected from hydrogen or methyl;

(18) R$^1$ is selected from hydrogen or a group of the formula:

-L-Z wherein:
L is absent or (1-2C)alkylene; and
Z is a (3-6C)cycloalkyl or a 4 to 6 membered heterocyclyl; wherein Z is optionally further substituted by one or more substituent groups independently selected from oxo, methyl, fluoro, NR$^g$R$^h$ or OR$^g$, wherein R$^g$ and R$^h$ are each independently selected from hydrogen or (1-2C)alkyl;

(19) R$^1$ is selected from hydrogen, (1-6C)alkyl or (3-6C)cycloalkyl, wherein the (1-6C)alkyl or (3-6C)cycloalkyl groups are optionally further substituted by one or more substituent groups independently selected from methyl, fluoro, NR$^g$R$^h$ or OR$^g$, wherein R$^g$ and R$^h$ are each independently selected from hydrogen or (1-2C)alkyl;

(20) R$^1$ is (1-6C)alkyl optionally further substituted by one or more substituent groups independently selected from fluoro, NR$^g$R$^h$ or OR$^g$, wherein R$^g$ and R$^h$ are each independently selected from hydrogen or (1-2C)alkyl;

(21) R$^1$ is (1-3C)alkyl optionally further substituted by one or more substituent groups independently selected from NR$^g$R$^h$ or OH, wherein R$^g$ and R$^h$ are each independently selected from hydrogen or (1-2C)alkyl;

(22) R$^1$ is (1-6C)alkyl (e.g. methyl);

(23) R$^1$ is a group of the formula:

-L-Z wherein:
L is (1-2C)alkylene; and
Z is (3-6C)cycloalkyl; wherein Z is optionally further substituted by one or more substituent groups independently selected from oxo, methyl, fluoro, NR$^g$R$^h$ or OR$^g$, wherein R$^g$ and R$^h$ are each independently selected from hydrogen or (1-2C)alkyl;

(24) R$^1$ is a group of the formula:

-L-Z wherein:
L is CH$_2$; and
Z is (3-4C)cycloalkyl; wherein Z is optionally further substituted by one or more substituent groups independently selected from methyl, fluoro and OH;

(25) R$^2$ is a group of Formula A shown below:

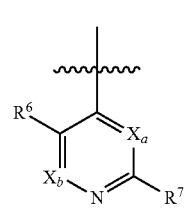

Formula A wherein:

denotes the point of attachment;

X$_a$ is selected from N, CH or OF;

X$_b$ is selected from N or CR$^{x1}$, wherein R$^{x1}$ is selected from hydrogen, fluoro, chloro, bromo, (1-2C)alkyl, (1-2C)alkoxy, cyano, acetylenyl, CH$_2$F, CF$_2$H or CF$_3$;

R$^6$ is selected from hydrogen, fluoro, chloro, bromo, (1-2C)alkyl, (1-2C)alkoxy, cyano, acetylenyl, CH$_2$F, CF$_2$H or CF$_3$;

R$^7$ is selected from hydrogen, halo, (1-4C)alkyl, (1-4C)alkoxy, (1-4C)haloalkyl, (1-4C)haloalkoxy, cyano, (2-4C)alkenyl, (2-4C)alkynyl or a group of the formula:

—Y$_3$—Z$_3$ wherein:
Y$_3$ is absent or O, S, N(R$^j$)(CR$^j$R$^k$)$_{q_1}$, (where q$_1$ is 0, 1 or 2), C(O), C(O)O, OC(O), C(O)N(R$^j$) or N(R$^j$)C(O), wherein R$^j$ and R$^k$ are each independently selected from hydrogen or (1-4C)alkyl; and Z$_3$ is hydrogen, (1-6C)alkyl, aryl, (3-6C)cycloalkyl, (3-6C)cycloalkenyl, 5- or 6-membered heteroaryl or 4 to 12-membered heterocyclyl; wherein Z$_3$ is optionally further substituted by one or more substituent groups independently selected from (1-4C)alkyl, cyclopropyl, halo, oxo, (1-4C)haloalkyl, (1-4C)haloalkoxy, cyano, C(O)NR$^l$R$^m$, NR$^l$R$^m$ or OR$^l$, wherein R$^l$ and R$^m$ are each independently selected from hydrogen, (1-4C)alkyl or (3-6C)cycloalkyl; or Z$^3$ is optionally further substituted by a group of the formula:

-L$_Z$-W$_Z$ wherein:
L$_Z$ is a (1-5C)alkylene optionally substituted by one or more substituents selected from (1-2C)alkyl or oxo; and W$_Z$ is halo, (1-4C)haloalkyl, (1-4C)haloalkoxy, cyano, hydroxy, (1-4C)alkoxy, C(O)R$^{xa}$, COOR$^{xa}$, C(O)NR$^{xa}$R$^{xb}$ or NR$^{xa}$R$^{xb}$, wherein R$^{xa}$ and R$^{xb}$ are each independently selected from hydrogen or (1-4C)alkyl;

(26) $R^2$ is a group of Formula A shown below:

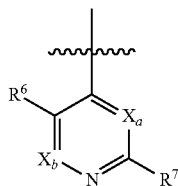

Formula A wherein:

denotes the point of attachment;
$X_a$ is selected from N, CH or CF;
$X_b$ is selected from N or $CR^{x1}$, wherein $R^{x1}$ is selected from hydrogen, fluoro, chloro, bromo, (1-2C)alkyl, cyano, acetylenyl, $CH_2F$, $CF_2H$ or $CF_3$;
$R^6$ is selected from hydrogen, fluoro, chloro, bromo, (1-2C)alkyl, (1-2C)alkoxy, cyano, acetylenyl, $CH_2F$, $CF_2H$ or $CF_3$;
$R^7$ is selected from hydrogen, halo, (1-2C)alkyl, (1-2C) alkoxy, (1-2C)haloalkyl, (1-2C)haloalkoxy, cyano or a group of the formula:

—$Y_3$—$Z_3$ wherein:
$Y_3$ is absent or O, S, C(O), C(O)O, OC(O), C(O)N($R^j$) or N($R^j$)C(O), wherein $R^j$ is selected from hydrogen or (1-4C)alkyl; and
$Z_3$ is hydrogen, (1-6C)alkyl, (3-6C)cycloalkyl, 5- or 6-membered heteroaryl or 4 to 12-membered heterocyclyl; wherein $Z_3$ is optionally further substituted by one or more substituent groups independently selected from (1-4C)alkyl, cyclopropyl, halo, oxo, (1-4C)haloalkyl, (1-4C)haloalkoxy, (1-4C)alkoxyalkyl, cyano, C(O)$NR^lR^m$, $NR^lR^m$ or $OR^l$, wherein $R^l$ and $R^m$ are each independently selected from hydrogen, (1-4C)alkyl or (3-6C)cycloalkyl;

(27) $R^2$ is a group of Formula A shown below:

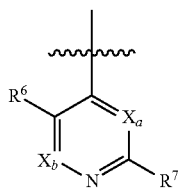

Formula A wherein:

denotes the point of attachment;
$X_a$ is selected from N, CH or CF;
$X_b$ is selected from N or $CR^{x1}$, wherein $R^{x1}$ is selected from hydrogen, fluoro, chloro, bromo or methyl;
$R^6$ is selected from fluoro, chloro, bromo, methyl, cyano or acetylenyl;
$R^7$ is selected from hydrogen, halo, (1-2C)alkyl, (1-2C) alkoxy, (1-2C)haloalkyl, (1-2C)haloalkoxy, cyano or a group of the formula:

—$Y_3$—$Z_3$ wherein:
$Y_3$ is absent or O, C(O), C(O)O or C(O)N($R^j$), wherein $R^j$ is selected from hydrogen or (1-4C)alkyl; and
$Z_3$ is hydrogen, (1-6C)alkyl, (3-6C)cycloalkyl, 5- or 6-membered heteroaryl or 4 to 11-membered heterocyclyl; wherein $Z_3$ is optionally further substituted by one or more substituent groups independently selected from (1-4C)alkyl, halo, oxo, (1-4C)haloalkyl, (1-4C)haloalkoxy, (1-4C)alkoxyalkyl, cyano, C(O)$NR^lR^m$, $NR^lR^m$ or $OR^l$, wherein $R^l$ and $R^m$ are each independently selected from hydrogen, (1-4C)alkyl or (3-6C)cycloalkyl;

(28) $R^2$ is a group of Formula A shown below:

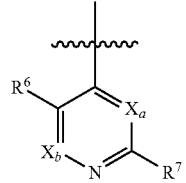

Formula A wherein:

denotes the point of attachment;
$X_a$ is selected from N or CH;
$X_b$ is selected from N or $CR^{x1}$, wherein $R^{x1}$ is selected from hydrogen, fluoro, chloro, bromo or methyl;
$R^6$ is selected from fluoro, chloro, bromo, methyl, cyano or acetylenyl;
$R^7$ is selected from hydrogen, halo, (1-2C)alkyl, (1-2C) alkoxy, (1-2C)haloalkyl, (1-2C)haloalkoxy, cyano, (2-4C)alkenyl, (2-4C)alkynyl or a group of the formula:

—$Y_3$—$Z_3$ wherein:
$Y_3$ is absent or O, C(O), C(O)O or C(O)N($R^j$), wherein $R^j$ is selected from hydrogen or (1-4C) alkyl; and
$Z_3$ is hydrogen, (1-6C)alkyl, (3-6C)cycloalkyl, 5- or 6-membered heteroaryl or a 4 to 8-membered heterocyclyl; wherein $Z_3$ is optionally further substituted by one or more substituent groups independently selected from (1-4C)alkyl, halo, oxo, (1-4C)haloalkyl, (1-4C)haloalkoxy, (1-4C)alkoxyalkyl, cyano, C(O)$NR^lR^m$, $NR^lR^m$ or $OR^l$, wherein $R^l$ and $R^m$ are each independently selected from hydrogen or (1-4C)alkyl;

(29) $R^2$ is a group of Formula A shown below:

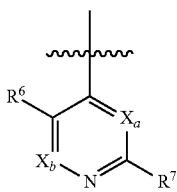

Formula A wherein:

denotes the point of attachment;
$X_a$ is selected from N or CH;
$X_b$ is selected from CH, CCl, CF, CBr or CCH$_3$;
$R^6$ is selected from chloro, fluoro or cyano;
$R^7$ is selected from (1-6C)alkyl, (3-6C)cycloalkyl, 5- or 6-membered heteroaryl or a 4 to 8-membered heterocyclyl; wherein each (1-6C)alkyl, (3-6C)cycloalkyl, 5- or 6-membered heteroaryl or 4 to 8-membered heterocyclyl is optionally further substituted by one or more substituent groups independently selected from (1-4C)alkyl, halo, oxo, (1-4C)haloalkyl, (1-4C)haloalkoxy, (1-4C)alkoxyalkyl, cyano, C(O)NR$^l$R$^m$, NR$^l$R$^m$ or OR$^l$, wherein R$^l$ and R$^m$ are each independently selected from hydrogen or (1-4C)alkyl;

(30) $R^2$ is a group of Formula A shown below:

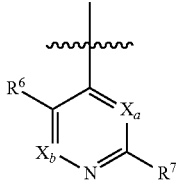

Formula A wherein:

denotes the point of attachment;
$X_a$ is selected from N or CH;
$X_b$ is selected from CH, CCl, CF, CBr or CCH$_3$;
$R^6$ is selected from chloro, fluoro or cyano;
$R^7$ is selected from a 5- or 6-membered heteroaryl or a 4 to 8-membered heterocyclyl; wherein said 5- or 6-membered heteroaryl or 4 to 8-membered heterocyclyl is optionally further substituted by one or more substituent groups independently selected from (1-4C)alkyl, halo, oxo, (1-4C)haloalkyl, (1-4C)haloalkoxy, (1-4C)alkoxyalkyl, cyano, C(O)NR$^l$R$^m$, NR$^l$R$^m$ or OR$^l$, wherein R$^l$ and R$^m$ are each independently selected from hydrogen or (1-4C)alkyl;

(31) $R^2$ is a group of Formula A shown below:

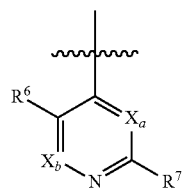

Formula A wherein:

denotes the point of attachment;
$X_a$ is selected from N or CH;
$X_b$ is selected from CH, CCl or CCH$_3$;
$R^6$ is selected from chloro, fluoro or cyano;
$R^7$ is selected from a 5- or 6-membered heteroaryl or a 4 to 8-membered heterocyclyl; wherein said 5- or 6-membered heteroaryl or 4 to 8-membered heterocyclyl is optionally further substituted by one or more substituent groups independently selected from (1-4C)alkyl, halo, oxo, (1-4C)haloalkyl, (1-4C)haloalkoxy, (1-4C)alkoxyalkyl, cyano or OH;

(32) $R^2$ is a group of Formula A shown below:

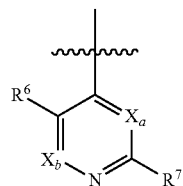

Formula A

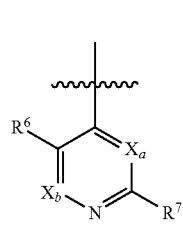

Formula A denotes the point of attachment;
$X_a$ is selected from N or CH;
$X_b$ is selected from CH, CCl or CCH$_3$;
$R^6$ is selected from chloro, fluoro or cyano;
$R^7$ is a 4 to 8-membered heterocyclyl (e.g. piperidinyl); wherein said 4 to 8-membered heterocyclyl is optionally further substituted by one or more substituent groups independently selected from (1-4C)alkyl, halo, oxo, (1-4C)haloalkyl, (1-4C)haloalkoxy, (1-4C)alkoxyalkyl, cyano or OH;

(33) R² is a group of Formula A shown below:

wherein:

denotes the point of attachment;
$X_a$ is selected from N or CH;
$X_b$ is selected from CH, CCl or CCH₃;
$R^6$ is selected from chloro, fluoro or cyano;
$R^7$ is piperidinyl or piperazinyl, each optionally substituted by one or more substituent groups independently selected from (1-4C)alkyl, halo, oxo, (1-4C)haloalkyl, (1-4C)haloalkoxy, (1-4C)alkoxyalkyl, cyano or OH;

(34) R² is a group of Formula A shown below:

Formula A

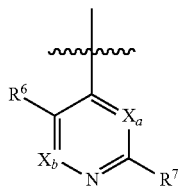

wherein:

denotes the point of attachment;
$X_a$ is CH;
$X_b$ is selected from CH or CCl;
$R^6$ is selected from chloro, fluoro or cyano;
$R^7$ is selected from hydrogen or a group of the formula:

—Y₃—Z₃ wherein:
$Y_3$ is O, C(O), C(O)O or C(O)N(R$^j$), wherein R$^j$ is hydrogen or (1-4C)alkyl; and
$Z_3$ is hydrogen, (1-6C)alkyl, (3-6C)cycloalkyl, or 4 to 11-membered heterocyclyl; wherein Z₃ is optionally further substituted by one or more substituent groups independently selected from (1-4C)alkyl, halo, oxo, (1-4C)haloalkyl, (1-4C)haloalkoxy, (1-4C)alkoxyalkyl, cyano or OH;

(35) R² is a group of Formula A shown below:

Formula A

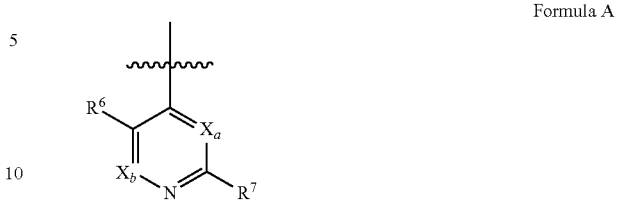

wherein:

denotes the point of attachment;
$X_a$ is CH;
$X_b$ is selected from CH or CCl;
$R^6$ is selected from chloro, fluoro or cyano;
$R^7$ is selected from hydrogen or a group of the formula:

—Y₃—Z₃ wherein:
$Y_3$ is C(O) or C(O)N(R$^j$), wherein R$^j$ is hydrogen or (1-4C)alkyl; and
$Z_3$ is hydrogen, (1-6C)alkyl, or 4 to 11-membered heterocyclyl; wherein Z₃ is optionally further substituted by one or more substituent groups independently selected from (1-4C)alkyl, halo, oxo, (1-4C)haloalkyl, (1-4C)haloalkoxy, (1-4C)alkoxyalkyl, cyano or OH;

(36) R² is a group of Formula A shown below:

Formula A

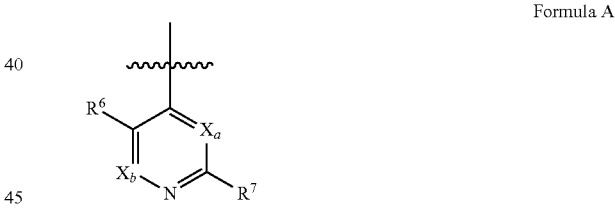

wherein:

denotes the point of attachment;
$X_a$ is CH;
$X_b$ is CCl;
$R^6$ is cyano;
$R^7$ is selected from hydrogen or a group of the formula:

—Y₃—Z₃ wherein:
$Y_3$ is C(O); and
$Z_3$ is azetidinyl, pyrrolidinyl, piperidinyl, piperazinyl or morpholinyl; wherein Z₃ is optionally further substituted by one or more substituent groups independently selected from (1-4C)alkyl, fluoro, oxo, (1-4C)haloalkyl, (1-4C)haloalkoxy, (1-4C)alkoxyalkyl, cyano or OH;

(37) R² is a group of Formula A shown below:

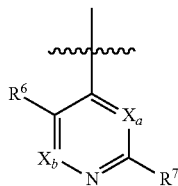

Formula A wherein:

denotes the point of attachment;
$X_a$ is N;
$X_b$ is selected from CH or CCl;
$R^6$ is selected from chloro, fluoro or cyano;
$R^7$ is selected from (3-6C)cycloalkyl, 5- or 6-membered heteroaryl or a 4 to 10-membered heterocyclyl; wherein $R^7$ is optionally further substituted by one or more substituent groups independently selected from (1-4C)alkyl, halo, oxo, (1-4C)haloalkyl, (1-4C)haloalkoxy, (1-4C)alkoxyalkyl, cyano, C(O)NR$^j$R$^m$, NR$^j$R$^m$ or OR$^j$, wherein R$^j$ and R$^m$ are each independently selected from hydrogen or (1-4C)alkyl; or R$^7$ is optionally further substituted by a group of the formula:

-L$_Z$-W$_Z$ wherein:
L$_Z$ is a (1-3C)alkylene; and
W$_Z$ is halo, (1-4C)haloalkyl, (1-4C)haloalkoxy, cyano, hydroxy, (1-4C)alkoxy, C(O)R$^{xa}$, COOR$^{xa}$, C(O)NR$^{xa}$R$^{xb}$ or NR$^{xa}$R$^{xb}$, wherein R$^{xa}$ and R$^{xb}$ are each independently selected from hydrogen or (1-4C)alkyl;

(38) R² is a group of Formula A shown below:

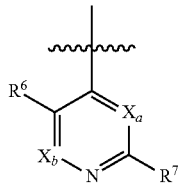

Formula A wherein:

denotes the point of attachment;
$X_a$ is N;
$X_b$ is selected from CH or CCl;
$R^6$ is chloro or fluoro;
$R^7$ is selected from 5- or 6-membered heteroaryl or 4 to 10-membered heterocyclyl; each $R^7$ is optionally further substituted by one or more substituent groups independently selected from (1-4C)alkyl, halo, oxo, (1-4C)haloalkyl, OH or C(O)NR$^j$R$^m$, wherein R$^j$ and R$^m$ are each independently selected from hydrogen or (1-4C)alkyl; or
$R^7$ is optionally further substituted by a group of the formula:

-L$_Z$-W$_Z$ wherein:
L$_Z$ is a (1-2C)alkylene; and
W$_Z$ is fluoro, (1-4C)haloalkyl, cyano, hydroxy or (1-2C)alkoxy;

(39) R² is a group of Formula A shown below:

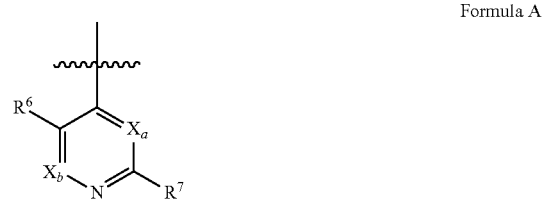

Formula A wherein:

denotes the point of attachment;
$X_a$ is N;
$X_b$ is CH;
$R^6$ is chloro or fluoro;
$R^7$ is 4 to 10-membered heterocyclyl optionally substituted by one or more substituent groups independently selected from (1-4C)alkyl, halo, oxo, (1-4C)haloalkyl, OH or C(O)NR$^j$R$^m$, wherein R$^j$ and R$^m$ are each independently selected from hydrogen or methyl; or
$R^7$ is optionally further substituted by a group of the formula:

-L$_Z$-W$_Z$ wherein:
L$_Z$ is CH$_2$; and
W$_Z$ is cyano, hydroxy or methoxy;

(40) R² is a group of Formula A shown below:

Formula A wherein:

denotes the point of attachment;
$X_a$ is N;
$X_b$ is CH;
$R^6$ is chloro or fluoro;

R⁷ is selected from piperidinyl, piperazinyl, morpholinyl, pyrrolidinyl, 7,8-dihydropyrido[4,3-d]pyrimidin-(5H)-yl, 3-oxa-8-azabicyclo[3.2.1]-octanyl, 8-oxa-3-azabicyclo[3.2.1]octanyl, 3-oxa-9-azabicyclo[3.3.1]nonanyl, 2-oxa-6-azaadamantanyl, 8-azabicyclo[3.2.1]octanyl, 3-azabicyclo[3.2.1]octanyl, 3,6-diazabicyclo[3.1.1]heptanyl, 3,8-diazabicyclo[3.2.1]octanyl, 2,6-diazaspiro[3.3]heptanyl and 3,3-dioxido-3-thia-8-azabicyclo[3.2.1]octanyl, each being optionally substituted by one or more substituent groups independently selected from (1-4C)alkyl, halo, oxo, (1-4C)haloalkyl, OH, or C(O)NR$^l$R$^m$, wherein R$^l$ and R$^m$ are each independently selected from hydrogen or methyl; or R⁷ is optionally further substituted by a group of the formula:

-L$_Z$-W$_Z$ wherein:
L$_Z$ is CH$_2$; and
W$_Z$ is cyano, hydroxy or methoxy;

(41) R² is a group of Formula A shown below:

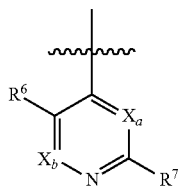

Formula A wherein:

denotes the point of attachment;
X$_a$ is N;
X$_b$ is CH;
R⁶ is chloro or fluoro;
R⁷ is selected from piperidinyl, piperazinyl, 3-oxa-8-azabicyclo[3.2.1]-octanyl, 3-oxa-9-azabicyclo[3.3.1]nonanyl, 2-oxa-6-azaadamantanyl, 8-azabicyclo[3.2.1]octanyl, 3-azabicyclo[3.2.1]octanyl and 3,3-dioxido-3-thia-8-azabicyclo[3.2.1]octanyl, each being optionally substituted by one or more substituent groups independently selected from methyl, fluoro, oxo, OH and CH$_2$OH;

(42) R⁷ is hydrogen;

(43) R⁷ is a 4 to 10-membered nitrogen-containing heterocyclyl ring linked via a ring nitrogen to the rest of the compound of formula (I) and optionally containing a second heteroatom selected from nitrogen, oxygen and sulfur, wherein the heterocyclyl ring is optionally substituted by one or more substituents independently selected from (1-4C)alkyl, halo, oxo, (1-4C)haloalkyl, (1-4C)haloalkoxy, (1-4C)alkoxyalkyl, cyano, C(O)NR$^l$R$^m$, NR$^l$R$^m$ or OR$^l$, wherein R$^l$ and R$^m$ are each independently selected from hydrogen, (1-4C)alkyl or (3-6C)cycloalkyl; or Z³ is optionally further substituted by a group of the formula:

-L$_Z$-W$_Z$ wherein:
L$_Z$ is a (1-5C)alkylene optionally substituted by one or more substituents selected from (1-2C)alkyl or oxo; and
W$_Z$ is halo, (1-4C)haloalkyl, (1-4C)haloalkoxy, cyano, hydroxy, (1-4C)alkoxy, C(O)R$^{xa}$, COOR$^{xa}$, C(O)NR$^{xa}$R$^{xb}$ or NR$^{xa}$R$^{xb}$, wherein R$^{xa}$ and R$^{xb}$ are each independently selected from hydrogen or (1-4C)alkyl;

(44) R⁷ is a 7 to 10-membered nitrogen-containing bicyclic heterocyclyl group linked via a ring nitrogen to the rest of the compound of formula (I) and optionally containing a second heteroatom selected from nitrogen, oxygen and sulfur, wherein the heterocyclyl group is optionally substituted by one or more substituents independently selected from (1-4C)alkyl, halo, oxo, (1-4C)haloalkyl, hydroxy, C(O)NR$^l$R$^m$, NR$^l$R$^m$ or OR$^l$, wherein R$^l$ and R$^m$ are each independently selected from hydrogen and (1-4C)alkyl;

(45) R⁷ is selected from one of the following heterocyclyl groups:

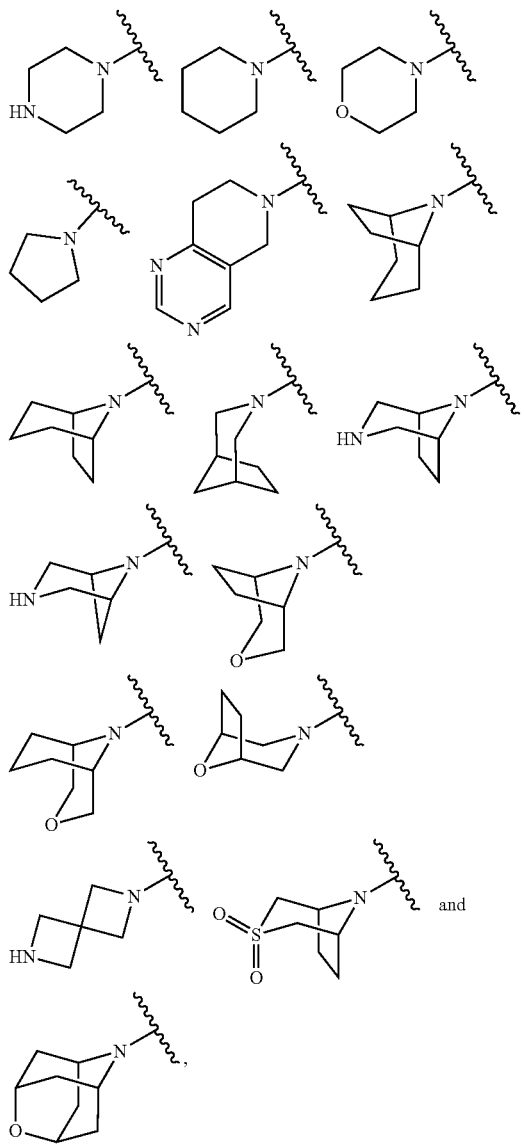

wherein the heterocyclyl ring is optionally substituted by one or more substituents independently selected from (1-4C)

alkyl, halo, oxo, (1-4C)haloalkyl, hydroxy, C(O)NR$^l$R$^m$, NR$^l$R$^m$ or OR$^l$, wherein R$^l$ and R$^m$ are each independently selected from hydrogen and (1-4C)alkyl; and wherein the heterocyclyl ring is optionally further substituted by CH$_2$CN, CH$_2$OH or CH$_2$OMe;

(46) R$^7$ is selected from one of the following heterocyclyl rings:

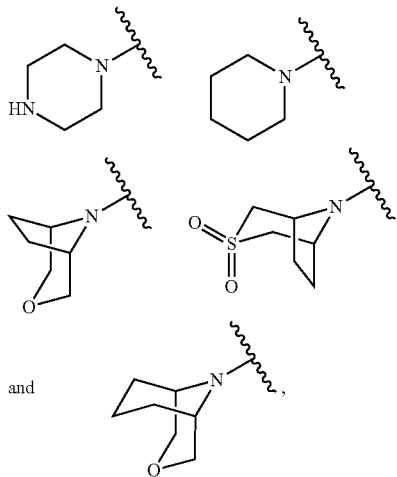

wherein the heterocyclyl ring is optionally substituted by one or more substituents independently selected from methyl, fluoro, oxo, OH and CH$_2$OH.

(47) R$^{30}$ is selected from (1-4C)alkyl, (3-6C)cycloalkyl, (1-4C)haloalkyl or cyano, wherein each (1-4C)alkyl and/or (3-6C)cycloalkyl substituent is optionally further substituted by one or more substituents selected from (1-4C) alkyl, cyclopropyl, hydroxy, (1-2C)alkoxy, NR$^u$R$^v$ or halo, wherein R$^u$ and R$^v$ are independently selected from hydrogen or (1-2C)alkyl;

(48) R$^{30}$ is selected from (1-4C)alkyl, (3-6C)cycloalkyl, (1-4C)haloalkyl, or cyano, wherein each (1-4C)alkyl and/or (3-6C)cycloalkyl substituent is optionally further substituted by one or more substituents selected from (1-4C) alkyl, cyclopropyl, hydroxy, (1-2C)alkoxy or halo;

(49) R$^{30}$ is selected from (1-4C)alkyl, (3-6C)cycloalkyl, (1-4C)haloalkyl or cyano, wherein each (1-4C)alkyl and/or (3-6C)cycloalkyl substituent is optionally further substituted by one or more substituents selected from (1-4C) alkyl, hydroxy, (1-2C)alkoxy or halo;

(50) R$^{30}$ is selected from (1-4C)alkyl, (3-6C)cycloalkyl or (1-4C)fluoroalkyl, wherein each (1-4C)alkyl and/or (3-6C)cycloalkyl substituent is optionally further substituted by one or more substituents selected from hydroxy, (1-2C)alkoxy or fluoro;

(51) R$^{30}$ is selected from (1-4C)alkyl or (3-4C)cycloalkyl, wherein each (1-4C)alkyl and/or (3-4C)cycloalkyl substituent is optionally further substituted by one or more fluoro groups;

(52) R$^{30}$ is (1-4C)alkyl (e.g. methyl or ethyl) or cyclopropyl;

(53) R$^{30}$ is cyclopropyl;

(54) R$^{31}$ is selected from hydrogen, (1-4C)alkyl, cyano, (1-4C)haloalkyl or a group of the formula:

Y$_5$-L$_5$-Z$_5$ wherein:
Y$_5$ is absent or selected from C(O)O or C(O)N(R$^w$), wherein R$^w$ is selected from hydrogen or (1-2C)alkyl;

L$_5$ is absent or (1-2C)alkylene; and
Z$_5$ is hydrogen, (1-6C)alkyl, (3-6C)cycloalkyl or a 5 or 6 membered heteroaryl; wherein Z$_5$ is optionally substituted by one or more substituents selected from (1-2C)alkyl, halo, (1-2C)haloalkyl, (1-2C)haloalkoxy, (1-2C)alkoxy, NH$_2$, cyano, nitro or hydroxy;

(55) R$^{31}$ is selected from hydrogen, (1-4C)alkyl, cyano, (1-4C)haloalkyl or a group of the formula:

Y$_5$-L$_5$-Z$_5$ wherein:
Y$_5$ is absent or C(O)N(R$^w$), wherein R$^w$ is selected from hydrogen or methyl;
L$_5$ is absent or (1-2C)alkylene; and
Z$_5$ is hydrogen, (1-6C)alkyl, (3-6C)cycloalkyl or a 5 or 6 membered heteroaryl; wherein Z$_5$ is optionally substituted by one or more substituents selected from (1-2C)alkyl, halo, (1-2C)haloalkyl, (1-2C)haloalkoxy, (1-2C)alkoxy, NH$_2$, cyano, nitro or hydroxy;

(56) R$^{31}$ is selected from hydrogen, (1-4C)alkyl, cyano, (1-4C)haloalkyl or a group of the formula:

Y$_5$-L$_5$-Z$_5$ wherein:
Y$_5$ is absent or C(O)N(R$^w$), wherein R$^w$ is selected from hydrogen or methyl;
L$_5$ is absent or (1-2C)alkylene; and
Z$_5$ is hydrogen, (1-6C)alkyl, cyclopropyl or a 5 or 6 membered heteroaryl; wherein is Z$_5$ optionally substituted by one or more substituents selected from (1-2C)alkyl, halo, (1-2C)haloalkyl, (1-2C)haloalkoxy, (1-2C)alkoxy, NH$_2$, cyano, nitro or hydroxy;

(57) R$^{31}$ is selected from hydrogen (1-4C)alkyl, (1-4C) haloalkyl or a group of the formula:

Y$_5$-L$_5$-Z$_5$ wherein:
Y$_5$ is absent or C(O)N(R$^w$), wherein R$^w$ is selected from hydrogen or methyl;
L$_5$ is absent or (1-2C)alkylene; and
Z$_5$ is (1-6C)alkyl or cyclopropyl; wherein Z$_5$ is optionally substituted by one or more substituents selected from halo, (1-2C)haloalkyl, (1-2C)alkoxy or cyano;

(58) R$^{31}$ is selected from hydrogen, methyl, CF$_3$, CH$_2$OCH$_3$ or C(O)NHCH$_3$;

(59) R$^{31}$ is hydrogen;

(60) R$^{30}$ and R$^{31}$ are linked such that, together with the carbon atom to which they are attached, they form a 4-6 membered carbocyclic ring;

(61) R$^{30}$ and R$^{31}$ are linked such that, together with the carbon atom to which they are attached, they form a 4-6 membered heterocyclic ring;

(62) Ring A is a 7-membered heterocyclic ring, which, in addition to the substituent groups R$^{30}$ and R$^{31}$, is optionally further substituted by one or more substituent groups selected from oxo, (1-2C)alkyl, cyclopropyl, spiro-cyclopropyl, halo, (1-2C)haloalkyl, (1-2C)haloalkoxy, (1-2C) alkoxy, amino, cyano or hydroxy;

(63) Ring A is a 7-membered heterocyclic ring, which, in addition to the substituent groups R$^{30}$ and R$^{31}$, is optionally further substituted by one or more substituent groups selected from oxo, (1-2C)alkyl, cyclopropyl, halo, (1-2C) haloalkyl, (1-2C)haloalkoxy, (1-2C)alkoxy, amino, cyano, nitro or hydroxy;

(64) Ring A is a 7-membered heterocyclic ring, which, in addition to the substituent groups $R^{30}$ and $R^{31}$, is optionally further substituted by one or more substituent groups selected from oxo, (1-2C)alkyl, cyclopropyl, fluoro, (1-2C)fluorooalkyl, (1-2C)alkoxy or cyano.

Suitably, a heteroaryl is a 5- or 6-membered heteroaryl ring comprising one, two or three heteroatoms selected from N, O or S.

Suitably an aryl group is phenyl.

Suitably, $X_1$ is as described in any one of paragraphs (1) to (9) above. Most suitably, $X_1$ is as described in paragraph (9) above.

Suitably, $X_2$ is as described in any one of paragraphs (10) to (12) above. Most suitably, $X_2$ is as described in paragraph (12) above.

Suitably, $R^1$ is as described in any one of paragraphs (13) to (24) above. Most suitably, $R^1$ is as described in any one of paragraphs (20) to (24) above.

Suitably, $R^2$ is as described in any one of paragraphs (25) to (41) above. More suitably, $R^2$ is as described in any one of paragraphs (29) to (41) above. Most suitably, $R^2$ is as described in any one of paragraphs (35) to (36) or paragraphs (40) to (41) above.

Suitably, $R^7$ is as described in any one of paragraphs (42) to (46) above. Most suitably, $R^{30}$ is as described in paragraph (46) above.

Suitably, $R^{30}$ is as described in any one of paragraphs (47) to (53), or (60) to (61) above. Most suitably, $R^{30}$ is as described in paragraph (53) above.

Suitably, $R^{31}$ is as described in any one of paragraphs (54) to (61) above. Most suitably, $R^{31}$ is as described in paragraph (59) above.

Suitably, Ring A is as described in any one of paragraphs (62) to (64) above. Most suitably, Ring A is as described in paragraph (64) above.

In a particular group of compounds of the invention, $X_2$ is CH, i.e. the compounds have the structural formula Ia (a sub-definition of Formula (I)) shown below, or a pharmaceutically acceptable salt, hydrate and/or solvate thereof:

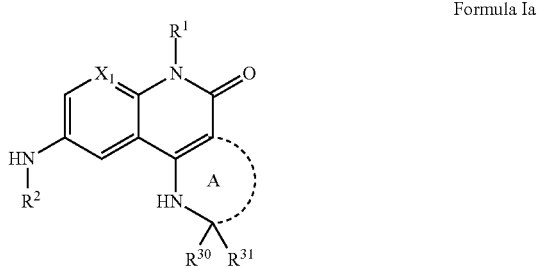

Formula Ia wherein each of $X_1$, $R^1$, $R^2$, $R^{30}$, $R^{31}$ and Ring A are as defined hereinabove.

In an embodiment of the compounds of Formula Ia:
$X_1$ is as defined in any one of paragraphs (1) to (9) above;
$R^1$ is as defined in any one of paragraphs (13) to (24) above;
$R^2$ is as defined in any one of paragraphs (25) to (41) above;
$R^{30}$ is as defined in any one of paragraphs (47) to (53) or (60) to (61) above;
$R^{31}$ is as defined in any one of paragraphs (54) to (61) above; and
Ring A is as defined in any one of paragraphs (62) to (64) above.

In another embodiment of the compounds of Formula Ia:
$X_1$ is as defined in paragraph (9) above;
$R^1$ is as defined in paragraphs (20) to (24) above;
$R^2$ is as defined in paragraphs (35) to (36) or paragraphs (40) to (41) above;
$R^{30}$ is as defined in paragraph (53) above;
$R^{31}$ is as defined in paragraph (59) above; and
Ring A is as defined in paragraph (64) above.

In a particular group of compounds of the invention, $X_1$ and $X_2$ are CH, i.e. the compounds have the structural formula Ib (a sub-definition of Formula (I)) shown below, or a pharmaceutically acceptable salt, hydrate and/or solvate thereof:

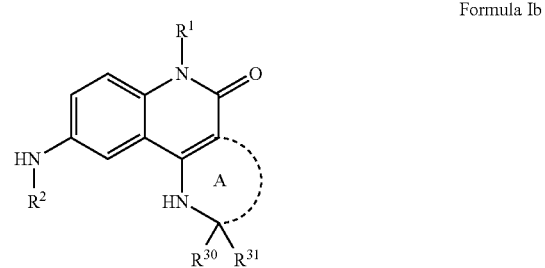

Formula Ib wherein each of $R^1$, $R^2$, $R^{30'}$ $R^{31}$ and Ring A are as defined hereinabove.

In an embodiment of the compounds of Formula Ib:
$R^1$ is as defined in any one of paragraphs (13) to (24) above;
$R^2$ is as defined in any one of paragraphs (25) to (41) above;
$R^{30}$ is as defined in any one of paragraphs (47) to (53) or (60) to (61) above;
$R^{31}$ is as defined in any one of paragraphs (54) to (61) above; and
Ring A is as defined in any one of paragraphs (62) to (64) above.

In another embodiment of the compounds of Formula Ib:
$R^1$ is as defined in paragraphs (20) to (24) above;
$R^2$ is as defined in paragraphs (35) to (36) or paragraphs (40) to (41) above;
$R^{30}$ is as defined in paragraph (53) above;
$R^{31}$ is as defined in paragraph (59) above; and
Ring A is as defined in paragraph (64) above.

In a particular group of compounds of the invention, $X_1$, $X_2$ and $X_a$ are CH and $R^2$ is as shown below, i.e. the compounds have the structural formula $Ic_1$ (a sub-definition of Formula (I)) shown below, or a pharmaceutically acceptable salt, hydrate and/or solvate thereof:

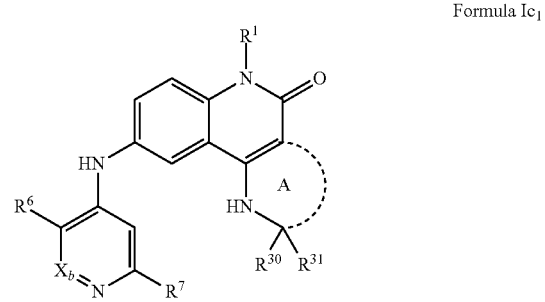

Formula $Ic_1$ wherein each of $R^1$, $R^6$, $R^7$, $X_b$, $R^{30}$, $R^{31}$ and Ring A are as defined hereinabove.

In an embodiment of the compounds of Formula Ice
$R^1$ is as defined in any one of paragraphs (13) to (24) above;
$R^6$ is as defined in any one of paragraphs (25) to (36) above;
$R^7$ is as defined in any one of paragraphs (25) to (36) above;
$X_b$ is as defined in any one of paragraphs (25) to (36) above;
$R^{30}$ is as defined in any one of paragraphs (47) to (53) or (60) to (61) above;
$R^{31}$ is as defined in any one of paragraphs (54) to (61) above; and
Ring A is as defined in any one of paragraphs (62) to (64) above.

In another embodiment of the compounds of Formula Ice
$R^1$ is as defined in paragraphs (20) to (24) above;
$R^6$ is as defined in paragraph (36) above;
$R^7$ is as defined in paragraph (36) above;
$X_b$ is as defined in paragraph (36) above;
$R^{30}$ is as defined in paragraph (53) above;
$R^{31}$ is as defined in paragraph (59) above; and
Ring A is as defined in paragraph (64) above.

In a particular group of compounds of the invention, $X_1$ and $X_2$, are CH, $X_a$ is N and $R^2$ is as shown below, i.e. the compounds have the structural formula Ic$_2$ (a sub-definition of Formula (I)) shown below, or a pharmaceutically acceptable salt, hydrate and/or solvate thereof:

Formula Ic$_2$ wherein each of $R^1$, $R^6$, $R^7$, $X_b$, $R^{30}$, $R^{31}$ and Ring A are as defined hereinabove.

In an embodiment of the compounds of Formula Ic$_2$:
$R^1$ is as defined in any one of paragraphs (13) to (24) above;
$R^6$ is as defined in any one of paragraphs (25) to (33) and (37) to (41) above;
$R^7$ is as defined in any one of paragraphs (25) to (33) and (37) to (46) above;
$X_b$ is as defined in any one of paragraphs (25) to (33) and (37) to (41) above;
$R^{30}$ is as defined in any one of paragraphs (47) to (53) or (60) to (61) above;
$R^{31}$ is as defined in any one of paragraphs (54) to (61) above; and
Ring A is as defined in any one of paragraphs (61) to (64) above.

In another embodiment of the compounds of Formula Ic$_2$:
$R^1$ is as defined in paragraph (20) to (24) above;
$R^6$ is as defined in paragraph (41) above;
$R^7$ is as defined in paragraph (46) above;
$X_b$ is as defined in paragraph (41) above;

$R^{30}$ is as defined in paragraph (53) above;
$R^{31}$ is as defined in paragraph (59) above; and
Ring A is as defined in paragraph (64) above.

In a particular group of compounds of the invention, the compounds have the structural formula Id, Ie, If or Ig (sub-definitions of Formula (I)) shown below, or a pharmaceutically acceptable salt, hydrate and/or solvate thereof:

Formula Id

Formula Ie

Formula If

Formula Ig wherein each of $X_1$, $X_2$, $R^1$, $R^2$, $R^{30}$ and $R^{31}$ are as defined hereinabove, $X_3$ is $CH_2$, O, S, $SO_2$ or NH and $R^{40}$, $R^{41}$, $R^{50}$ and $R^{51}$ are independently selected from hydrogen, (1-2C) alkyl, (3-6C)cycloalkyl, halo, (1-2C)haloalkyl, (1-2C)haloalkoxy, (1-2C)alkoxy, (1-4C)alkoxyalkyl, (1-2C)aminoalkyl, $NH_2$, cyano, nitro, OH, $C(O)OR^{z1}$, $C(O)N(R^{z2})R^{z1}$ $NR^{z2}C(O)R^{z1}$, wherein $R^{z1}$ and $R^{z2}$ are each independently selected from hydrogen or (1-2C)alkyl; or $R^{40}$ and $R^{41}$, and/or $R^{50}$ and $R^{51}$, are linked such that, together with the carbon atom to which they are attached, they form a 3-6 membered carbocyclic ring or heterocyclic ring.

In an embodiment of the compounds of Formula Id, Formula Ie, Formula If and/or Formula Ig:
- $X_1$ is as defined in any one of paragraphs (1) to (9) above;
- $X_2$ is as defined in any one of paragraphs (10) to (12) above;
- $X_3$ is O or S;
- $R^1$ is as defined in any one of paragraphs (13) to (24) above;
- $R^2$ is as defined in any one of paragraphs (25) to (41) above;
- $R^{30}$ is as defined in any one of paragraphs (47) to (53) or (60) to (61) above;
- $R^{31}$ is as defined in any one of paragraphs (54) to (61) above; and
- $R^{40}$, $R^{41}$, $R^{50}$ and $R^{51}$ are independently selected from hydrogen, (1-2C)alkyl, (3-6C)cycloalkyl, halo, (1-2C)haloalkyl, (1-2C)haloalkoxy, (1-2C)alkoxy, (1-4C)alkoxyalkyl, (1-2C)aminoalkyl, $NH_2$, cyano, nitro, OH, $C(O)OR^{z1}$, $C(O)N(R^{z2})R^{z1}$, $NR^{z2}C(O)R^{z1}$, wherein $R^{z1}$ and $R^{z2}$ are each independently selected from hydrogen or (1-2C)alkyl; or
- $R^{40}$ and $R^{41}$, and/or $R^{50}$ and $R^{51}$, are linked such that, together with the carbon atom to which they are attached, they form a 3-6 membered carbocyclic ring.

In another embodiment of the compounds of Formula Id, Formula Ie, Formula If and/or Formula Ig:
- $X_1$ is as defined in paragraph (9) above;
- $X_2$ is as defined in paragraph (12) above;
- $X_3$ is O or S;
- $R^1$ is as defined in paragraph (22) above;
- $R^2$ is as defined in paragraph (41) above;
- $R^{30}$ is as defined in paragraph (53) above;
- $R^{31}$ is as defined in paragraph (59) above;
- $R^{40}$, $R^{41}$ and $R^{50}$ are independently selected from hydrogen, (1-2C)alkyl, (1-2C)alkoxy, (1-2C)haloalkyl, (3-6C)cycloalkyl, halo or cyano; and
- $R^{51}$ is hydrogen; or
- $R^{40}$ and $R^{41}$, and/or $R^{50}$ and $R^{51}$, are linked such that, together with the carbon atom to which they are attached, they form a cyclopropyl ring.

In a particular group of compounds of the invention, the compounds have the structural formula Ih, Ij, Ik or Im (sub-definitions of Formula (I)) shown below, or a pharmaceutically acceptable salt, hydrate and/or solvate thereof:

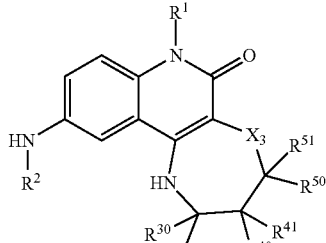

Formula Ih

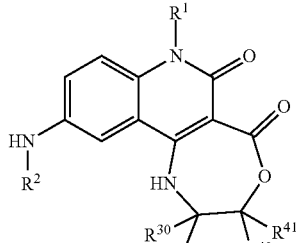

Fomrula Ij

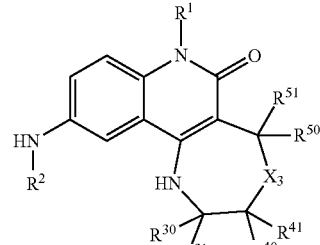

Formula Ik

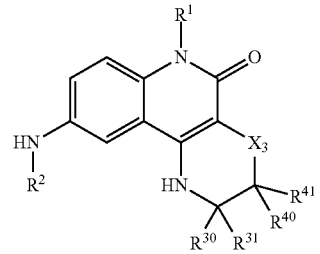

Formula Im wherein each of $R^1$, $R^2$, $R^{30}$ and $R^{31}$ are as defined hereinabove, $X_3$ is selected from $CH_2$, O, S, $SO_2$ or NH, and $R^{40}$, $R^{41}$, $R^{50}$ and $R^{51}$ are independently selected from hydrogen, (1-2C)alkyl, (3-6C)cycloalkyl, halo, (1-2C)haloalkyl, (1-2C)haloalkoxy, (1-2C)alkoxy, (1-4C)alkoxyalkyl, (1-2C)aminoalkyl, $NH_2$, cyano, nitro, OH, $C(O)OR^{z1}$, $C(O)N(R^{z2})R^{z1}$, $NR^{z2}C(O)R^{z1}$, wherein $R^{z1}$ and $R^{z2}$ are each independently selected from hydrogen or (1-2C)alkyl; or $R^{40}$ and $R^{41}$, and/or $R^{50}$ and $R^{51}$, are linked such that, together with the carbon atom to which they are attached, they form a 3-6 membered carbocyclic ring or heterocyclic ring.

In an embodiment of the compounds of Formula Ih, Ij, Ik and/or Im:
- $R^1$ is as defined in any one of paragraphs (13) to (24) above;
- $R^2$ is as defined in any one of paragraphs (25) to (41) above;
- $R^{30}$ is as defined in any one of paragraphs (47) to (53) or (60) to (61) above;
- $R^{31}$ is as defined in any one of paragraphs (54) to (61) above;
- $X_3$ is O or S; and
- $R^{40}$, $R^{41}$, $R^{50}$ and $R^{51}$ are independently selected from hydrogen, (1-2C)alkyl, (3-6C)cycloalkyl, halo, (1-2C)haloalkyl, (1-2C)haloalkoxy, (1-2C)alkoxy, (1-4C)alkoxyalkyl, (1-2C)aminoalkyl, $NH_2$, cyano, nitro, OH, $C(O)OR^{z1}$, $C(O)N(R^{z2})R^{z1}$, $NR^{z2}C(O)R^{z1}$, wherein $R^{z1}$ and $R^{z2}$ are each independently selected from hydrogen or (1-2C)alkyl; or
- $R^{40}$ and $R^{41}$, and/or $R^{50}$ and $R^{51}$, are linked such that, together with the carbon atom to which they are attached, they form a 3-6 membered carbocyclic ring.

In another embodiment of the compounds of Formula Ih, Ij, Ik and/or Im:
- $R^1$ is as defined in paragraph (22) above;
- $R^2$ is as defined in paragraph (41) above;
- $R^{30}$ is as defined in paragraph (53) above;
- $R^{31}$ is as defined in paragraph (59) above;
- $X_3$ is O or S;
- $R^{40}$, $R^{41}$ and $R^{50}$ are independently selected from hydrogen, (1-2C)alkyl, (1-2C)alkoxy, (1-2C)haloalkyl, (3-6C)cycloalkyl, halo or cyano; and $R^{51}$ is hydrogen; or $R^{40}$ and $R^{41}$, and/or $R^{50}$ and $R^{51}$, are linked such that, together with the carbon atom to which they are attached, they form a cyclopropyl ring.

In a particular group of compounds of the invention, the compounds have the structural formula In, Io, Ip or Iq (sub-definitions of Formula (I)) shown below, or a pharmaceutically acceptable salt, hydrate and/or solvate thereof:

Formula In

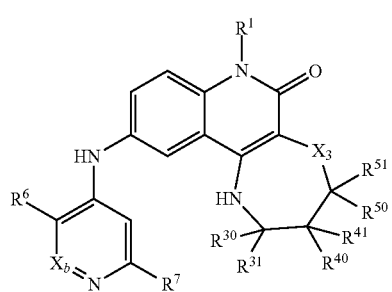

Formula Io

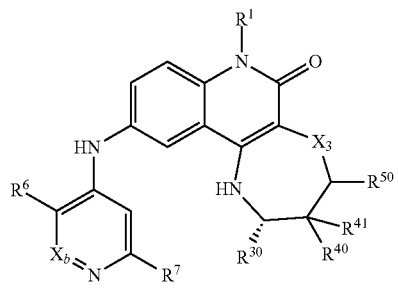

Formula Ip

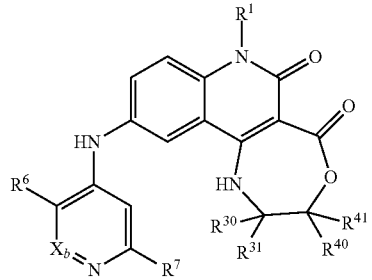

Formula Iq

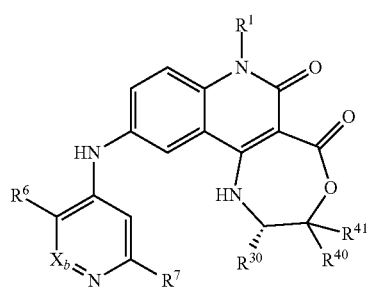

wherein each of $R^1$, $R^6$, $R^7$, $X_b$, $R^{30}$ and $R^{31}$ are as defined hereinabove, $X_3$ is selected from $CH_2$, O, S, $SO_2$ or NH and $R^{40}$, $R^{41}$, $R^{50}$ and $R^{51}$ are independently selected from hydrogen, (1-2C)alkyl, (3-6C)cycloalkyl, halo, (1-2C)haloalkyl, (1-2C)haloalkoxy, (1-2C)alkoxy, (1-4C)alkoxyalkyl, (1-2C)aminoalkyl, $NH_2$, cyano, nitro, OH, $C(O)OR^{z1}$, $C(O)N(R^{z2})R^{z1}$, $NR^{z2}C(O)R^{z1}$, wherein $R^{z1}$ and $R^{z2}$ are each independently selected from hydrogen or (1-2C)alkyl; or $R^{40}$ and $R^{41}$, and/or $R^{50}$ and $R^{51}$, are linked such that, together with the carbon atom to which they are attached, they form a 3-6 membered carbocyclic ring or heterocyclic ring.

In an embodiment of the compounds of Formula In, Io, Ip and/or Iq:

$R^1$ is as defined in any one of paragraphs (13) to (24) above;

$R^6$ is as defined in any one of paragraphs (25) to (36) above;

$R^7$ is as defined in any one of paragraphs (25) to (36) or (42) to (46) above;

$X_b$ is as defined in any one of paragraphs (25) to (36) above;

$R^{30}$ is as defined in any one of paragraphs (47) to (53) or (60) to (61) above;

$R^{31}$ is as defined in any one of paragraphs (54) to (61) above;

$X_3$ is selected from O or S; and $R^{40}$, $R^{41}$, $R^{50}$ and $R^{51}$ are independently selected from hydrogen, (1-2C)alkyl, (3-6C)cycloalkyl, halo, (1-2C)haloalkyl, (1-2C)haloalkoxy, (1-2C)alkoxy, (1-4C)alkoxyalkyl, (1-2C)aminoalkyl, $NH_2$, cyano, nitro, OH, $C(O)OR^{z1}$, $C(O)N(R^{z2})R^{z1}$, $NR^{z2}C(O)R^{z1}$, wherein $R^{z1}$ and $R^{z2}$ are each independently selected from hydrogen or (1-2C)alkyl; or $R^{40}$ and $R^{41}$, and/or $R^{50}$ and $R^{51}$, are linked such that, together with the carbon atom to which they are attached, they form a 3-6 membered carbocyclic ring.

In another embodiment of the compounds of Formula In, Io, Ip and/or Iq:

$R^1$ is as defined in paragraph (22) above;

$R^6$ is as defined in paragraph (36) above;

$R^7$ is as defined in paragraph (36) above;

$X_b$ is as defined in paragraph (36) above;

$R^{30}$ is as defined in paragraph (53) above;

$R^{31}$ is as defined in paragraph (59) above;

$X_3$ is O or S;

$R^{40}$, $R^{41}$ and $R^{50}$ are independently selected from hydrogen, (1-2C)alkyl, (1-2C)alkoxy, (1-2C)haloalkyl, (3-6C)cycloalkyl, halo or cyano; and $R^{51}$ is hydrogen; or $R^{40}$ and $R^{41}$, and/or $R^{50}$ and $R^{51}$, are linked such that, together with the carbon atom to which they are attached, they form a cyclopropyl ring.

In a particular group of compounds of the invention, the compounds have the structural formula Is or It (a sub-definition of Formula (I)) shown below, or a pharmaceutically acceptable salt, hydrate and/or solvate thereof:

Formula Is

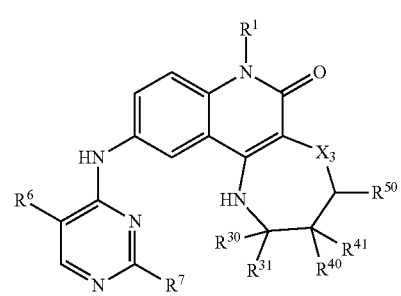

Formual It

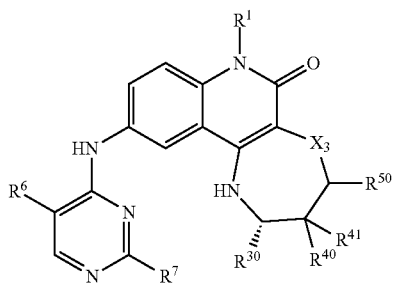

wherein each of $R^1$, $R^6$, $R^7$, $R^{30}$ and $R^{31}$ are as defined hereinabove, $X_3$ is selected from $CH_2$, O, S, $SO_2$ or NH and $R^{40}$, $R^{41}$ and $R^{50}$ are independently selected from hydrogen, (1-2C)alkyl, (3-6C)cycloalkyl, halo, (1-2C)haloalkyl, (1-2C)haloalkoxy, (1-2C)alkoxy, (1-4C)alkoxyalkyl, (1-2C)aminoalkyl, $NH_2$, cyano, nitro, OH, $C(O)OR^{z1}$, $C(O)N(R^{z2})R^{z1}$, $NR^{z2}C(O)R^{z1}$, wherein $R^{z1}$ and $R^{z2}$ are each independently selected from hydrogen or (1-2C)alkyl; or $R^{40}$ and $R^{41}$ are linked such that, together with the carbon atom to which they are attached, they form a 3-6 membered carbocyclic ring or heterocyclic ring.

In an embodiment of the compounds of Formula Is or It:
$R^1$ is as defined in any one of paragraphs (13) to (24) above;
$R^6$ is selected from chloro, fluoro or cyano;
$R^7$ is as defined in any one of paragraphs (25) to (33) and (37) to (46) above;
$R^{30}$ is as defined in any one of paragraphs (47) to (53) or (60) to (61) above;
$R^{31}$ is as defined in any one of paragraphs (54) to (61) above;
$X_3$ is selected from O or S; and
$R^{40}$, $R^{41}$ and $R^{50}$ are independently selected from hydrogen, (1-2C)alkyl, (3-6C)cycloalkyl, halo, (1-2C)haloalkyl, (1-2C)haloalkoxy, (1-2C)alkoxy, (1-4C)alkoxyalkyl, (1-2C)aminoalkyl, $NH_2$, cyano, nitro, OH, $C(O)OR^{z1}$, $C(O)N(R^{z2})R^{z1}$, $NR^{z2}C(O)R^{z1}$, wherein $R^{z1}$ and $R^{z2}$ are each independently selected from hydrogen or (1-2C)alkyl; or
$R^{40}$ and $R^{41}$ are linked such that, together with the carbon atom to which they are attached, they form a 3-6 membered carbocyclic ring.

In another embodiment of the compounds of Formula Is or It:
$R^1$ is as defined in paragraph (24) above;
$R^6$ is selected from chloro, fluoro or cyano;
$R^7$ is as defined in paragraph (46) above;
$R^{30}$ is as defined in paragraph (53) above;
$R^{31}$ is as defined in paragraph (59) above;
$X_3$ is selected from O or S; and
$R^{40}$, $R^{41}$ and $R^{50}$ are independently selected from hydrogen, (1-2C)alkyl, (3-6C)cycloalkyl, halo or hydroxy; or
$R^{40}$ and $R^{41}$ are linked such that, together with the carbon atom to which they are attached, they form a cyclopropyl ring.

In a particular group of compounds of the invention, the compounds have any of the structural formulae Id to It shown above, or a pharmaceutically acceptable salt, hydrate and/or solvate thereof, wherein $R^{40}$ and $R^{41}$ are independently selected from hydrogen and fluoro.

In a further embodiment, the compounds have any of the structural formulae Id to It shown above, or a pharmaceutically acceptable salt, hydrate and/or solvate thereof, wherein $R^{40}$ and $R^{41}$ are both fluoro.

In a further embodiment, the compounds have any of the structural formulae Id to It shown above, or a pharmaceutically acceptable salt, hydrate and/or solvate thereof, wherein $R^{40}$ and $R^{41}$ are independently selected from hydrogen and fluoro and $R^{30}$ is cyclopropyl.

In a further embodiment, the compounds have any of the structural formulae Id to It shown above, or a pharmaceutically acceptable salt, hydrate and/or solvate thereof, wherein $R^{40}$ and $R^{41}$ are independently selected from hydrogen and fluoro and $R^{30}$ is cyclopropyl and $R^{31}$ is hydrogen.

In a further embodiment, the compounds have any of the structural formulae Id to It shown above, or a pharmaceutically acceptable salt, hydrate and/or solvate thereof, wherein $R^{40}$ and $R^{41}$ both fluoro and $R^{30}$ is cyclopropyl.

In a further embodiment, the compounds have any of the structural formulae Id to It shown above, or a pharmaceutically acceptable salt, hydrate and/or solvate thereof, wherein $R^{40}$ and $R^{41}$ are both fluoro and $R^{30}$ is cyclopropyl and $R^{31}$ is hydrogen.

In a particular group of compounds of the invention, the compounds have the structural formula Iu or Iv (a sub-definition of Formula (I)) shown below, or a pharmaceutically acceptable salt, hydrate and/or solvate thereof:

Formula Iu

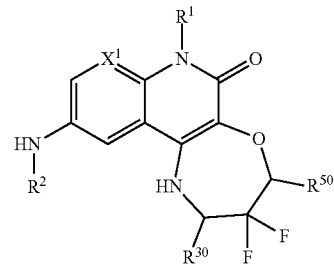

Formual Iv

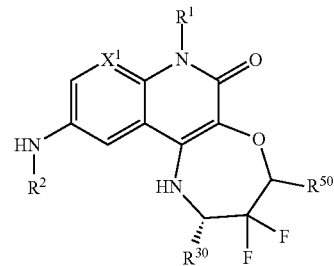

wherein each of $X^1$, $R^1$, $R^2$ and $R^{30}$ and $R^{50}$ are as defined hereinabove.

In an embodiment of the compounds of Formula Iu or Formula Iv:
$X^1$ is as defined in any one of paragraphs (1) to (9) above;
$R^1$ is as defined in any one of paragraphs (13) to (24) above;
$R^2$ is as defined in any one of paragraphs (25) to (41) above;
$R^{30}$ is as defined in any one of paragraphs (47) to (53) above; and
$R^{50}$ is hydrogen, (1-2C)alkyl, (3-6C)cycloalkyl or halo.

In another embodiment of the compounds of Formula Iu or Iv:
$X^1$ is as defined in paragraph (7) above;
$R^1$ is as defined paragraph (22) above;
$R^2$ is as defined in paragraph (41) above;
$R^{30}$ is as defined in paragraph (53) above; and
$R^{50}$ is hydrogen.

In a particular group of compounds of the invention, the compounds have the structural formula Iw or Ix (a sub-definition of Formula (I)) shown below, or a pharmaceutically acceptable salt, hydrate and/or solvate thereof:

Formula Iw

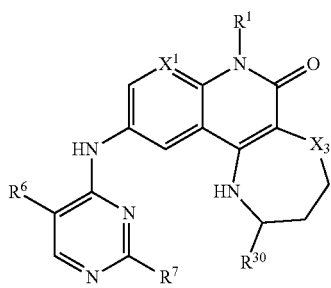

Formula Ix

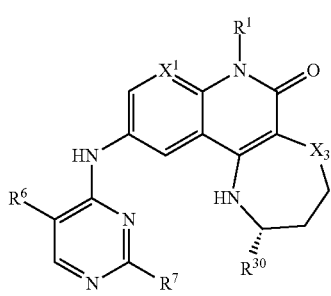

wherein each of $X^1$, $R^1$, $R^6$, $R^7$ and $R^{30}$ are as defined hereinabove and $X_3$ is selected from $CH_2$, O, S, $SO_2$ or NH.

In an embodiment of the compounds of Formula Iw or Ix:
$X^1$ is as defined in any one of paragraphs (1) to (9) above;
$R^1$ is as defined in any one of paragraphs (13) to (24) above;
$R^6$ is selected from chloro, fluoro or cyano;
$R^7$ is as defined in any one of paragraphs (25) to (33) and (37) to (46) above;
$R^{30}$ is as defined in any one of paragraphs (47) to (53) above; and
$X_3$ is selected from O or S.

In another embodiment of the compounds of Formula Iw or Ix:
$X^1$ is as defined in paragraph (7) above;
$R^1$ is as defined in paragraph (22) above;
$R^6$ is chloro;
$R^7$ is as defined in paragraph (46) above;
$R^{30}$ is as defined in paragraph (53) above; and
$X_3$ is O.

Particular compounds of the present invention include any of the compounds exemplified in the present application, or a pharmaceutically acceptable salt or solvate thereof, and, in particular, any of the following:

(S)-2-chloro-4-((2,7-dimethyl-6-oxo-1,2,3,4,6,7-hexahydro-[1,4]oxazepino[2,3-c]quinolin-10-yl)amino)nicotinonitrile;

(R)-2-chloro-4-((2,7-dimethyl-6-oxo-1,2,3,4,6,7-hexahydro-[1,4]oxazepino[2,3-c]quinolin-10-yl)amino)nicotinonitrile;

2-chloro-4-((2-ethyl-7-methyl-6-oxo-1,2,3,4,6,7-hexahydro-[1,4]oxazepino[2,3-c]quinolin-10-yl)amino)nicotinonitrile;

(R)-2-chloro-4-((2-cyclopropyl-7-methyl-6-oxo-1,2,3,4,6,7-hexahydro-[1,4]oxazepino[2,3-c]quinolin-10-yl)amino)nicotinonitrile;

(S)-2-chloro-4-((2-cyclopropyl-7-methyl-6-oxo-1,2,3,4,6,7-hexahydro-[1,4]oxazepino[2,3-c]quinolin-10-yl)amino)nicotinonitrile;

2-chloro-4-((2,2,7-trimethyl-6-oxo-1,2,3,4,6,7-hexahydro-[1,4]oxazepino[2,3-c]quinolin-10-yl)amino)nicotinonitrile;

2-chloro-4-((2-(methoxymethyl)-2,7-dimethyl-6-oxo-1,2,3,4,6,7-hexahydro-[1,4]oxazepino[2,3-c]quinolin-10-yl)amino)nicotinonitrile;

2-chloro-4-((2,3,3,7-tetramethyl-6-oxo-1,2,3,4,6,7-hexahydro-[1,4]oxazepino[2,3-c]quinolin-10-yl)amino)nicotinonitrile;

2-chloro-4-((2',7'-dimethyl-6'-oxo-1',2',6',7'-tetrahydro-4'H-spiro[cyclopropane-1,3'-[1,4]oxazepino[2,3-c]quinolin]-10'-yl)amino)nicotinonitrile;

2-chloro-4-(((2S,4S)-2,4,7-trimethyl-6-oxo-1,2,3,4,6,7-hexahydro-[1,4]oxazepino[2,3-c]quinolin-10-yl)amino)nicotinonitrile;

2-chloro-4-((2,6-dimethyl-5-oxo-2,3,5,6-tetrahydro-1H-[1,4]oxazino[2,3-c]quinolin-9-yl)amino)nicotinonitrile;

2-chloro-4-((2-ethyl-6-methyl-5-oxo-2,3,5,6-tetrahydro-1H-[1,4]oxazino[2,3-c]quinolin-9-yl)amino)nicotinonitrile;

2-chloro-4-((2-cyclopropyl-6-methyl-5-oxo-2,3,5,6-tetrahydro-1H-[1,4]oxazino[2,3-c]quinolin-9-yl)amino)nicotinonitrile;

2-chloro-4-((2-cyclobutyl-6-methyl-5-oxo-2,3,5,6-tetrahydro-1H-[1,4]oxazino[2,3-c]quinolin-9-yl)amino)nicotinonitrile;

2-chloro-4-((7'-methyl-6'-oxo-3',4,4',5,6',7'-hexahydro-1'H,2H-spiro[furan-3,2'-[1,4]oxazepino[2,3-c]quinolin]-10'-yl)amino)nicotinonitrile;

2-chloro-4-((2-(difluoromethyl)-7-methyl-6-oxo-1,2,3,4,6,7-hexahydro-[1,4]oxazepino[2,3-c]quinolin-10-yl)amino)nicotinonitrile;

2-chloro-4-((2-cyclopropyl-3,3-difluoro-7-methyl-6-oxo-1,2,3,4,6,7-hexahydro-[1,4]oxazepino[2,3-c]quinolin-10-yl)amino)nicotinonitrile;

(R)-2-cyclopropyl-10-((5,6-dichloro-2-((2S,6R)-2,6-dimethylmorpholino)pyrimidin-4-yl)amino)-7-methyl-1,2,3,4-tetrahydro-[1,4]oxazepino[2,3-c]quinolin-6(7H)-one;

(R)-2-chloro-4-((2-cyclopropyl-7-methyl-6-oxo-1,2,3,4,6,7-hexahydro-[1,4]thiazepino[2,3-c]quinolin-10-yl)amino)nicotinonitrile;

(S)-6-chloro-5-cyano-4-((2,7-dimethyl-6-oxo-1,2,3,4,6,7-hexahydro-[1,4]oxazepino[2,3-c]quinolin-10-yl)amino)picolinic acid;

(R)-6-chloro-5-cyano-4-((2-cyclopropyl-7-methyl-6-oxo-1,2,3,4,6,7-hexahydro-[1,4]oxazepino[2,3-c]quinolin-10-yl)amino)picolinic acid;

(S)-6-(azetidine-1-carbonyl)-2-chloro-4-((2,7-dimethyl-6-oxo-1,2,3,4,6,7-hexahydro-[1,4]oxazepino[2,3-c]quinolin-10-yl)amino)nicotinonitrile;

(R)-2-chloro-4-((2-cyclopropyl-7-methyl-6-oxo-1,2,3,4,6,7-hexahydro-[1,4]oxazepino[2,3-c]quinolin-10-yl)amino)-6-(3-(trifluoromethyl)azetidine-1-carbonyl)nicotinonitrile;

(S)-10-((2,3-dichloropyridin-4-yl)amino)-2,7-dimethyl-1,2,3,4-tetrahydro-[1,4]oxazepino[2,3-c]quinolin-6(7H)-one;

(S)-10-((5-chloro-2-((S)-2-(methoxymethyl)pyrrolidine-1-carbonyl)pyridin-4-yl)amino)-2,7-dimethyl-1,2,3,4-tetrahydro-[1,4]oxazepino[2,3-c]quinolin-6(7H)-one;

(R)-2-cyclopropyl-10-((2,3-dichloropyridin-4-yl)amino)-7-methyl-1,2,3,4-tetrahydro-[1,4]oxazepino[2,3-c]quinolin-6(7H)-one;

(R)-10-((5-chloro-2-(3-(trifluoromethyl)-1H-pyrazol-1-yl)pyrimidin-4-yl)amino)-2-cyclopropyl-7-methyl-1,2,3,4-tetrahydro-[1,4]oxazepino[2,3-c]quinolin-6(7H)-one;

10-((5-chloro-2-(3-(trifluoromethyl)-1H-pyrazol-1-yl)pyrimidin-4-yl)amino)-2-(methoxymethyl)-2,7-dimethyl-1,2,3,4-tetrahydro-[1,4]oxazepino[2,3-c]quinolin-6(7H)-one;

(S)-10-((5-chloro-2-(3-(trifluoromethyl)-1H-pyrazol-1-yl)pyrimidin-4-yl)amino)-2,7-dimethyl-1,2,3,4-tetrahydro-[1,4]oxazepino[2,3-c]quinolin-6(7H)-one;

(S)-1-(5-chloro-4-((2,7-dimethyl-6-oxo-1,2,3,4,6,7-hexahydro-[1,4]oxazepino[2,3-c]quinolin-10-yl)amino)pyrimidin-2-yl)-N,N-dimethylpiperidine-4-carboxamide;

(S)-10-((5-chloro-2-((3R,5S)-3,5-dimethylpiperidin-1-yl)pyrimidin-4-yl)amino)-2,7-dimethyl-1,2,3,4-tetrahydro-[1,4]oxazepino[2,3-c]quinolin-6(7H)-one;

('S)-10-((5-chloro-2-((3S,5R)-4,4-difluoro-3,5-dimethylpiperidin-1-yl)pyrimidin-4-yl)amino)-2,7-dimethyl-1,2,3,4-tetrahydro-[1,4]oxazepino[2,3-c]quinolin-6(7H)-one;

(S)-10-((5-chloro-2-((2S,6R)-2,6-dimethylmorpholino)pyrimidin-4-yl)amino)-2,7-dimethyl-1,2,3,4-tetrahydro-[1,4]oxazepino[2,3-c]quinolin-6(7H)-one;

(S)-10-((5-chloro-2-morpholinopyrimidin-4-yl)amino)-2,7-dimethyl-1,2,3,4-tetrahydro-[1,4]oxazepino[2,3-c]quinolin-6(7H)-one;

(R)-10-((5-chloro-2-((3S,5R)-4,4-difluoro-3,5-dimethylpiperidin-1-yl)pyrimidin-4-yl)amino)-2-cyclopropyl-7-methyl-1,2,3,4-tetrahydro-[1,4]oxazepino[2,3-c]quinolin-6(7H)-one;

10'-((5-chloro-2-(3-(trifluoromethyl)-1H-pyrazol-1-yl)pyrimidin-4-yl)amino)-7'-methyl-3',4,4',5-tetrahydro-1'H,2H-spiro[furan-3,2'-[1,4]oxazepino[2,3-c]quinolin]-6'(7'H)-one;

(R)-10-((5-chloro-2-(2,2,6,6-tetramethylmorpholino)pyrimidin-4-yl)amino)-2-cyclopropyl-7-methyl-1,2,3,4-tetrahydro-[1,4]oxazepino[2,3-c]quinolin-6(7H)-one;

(R)-10-((2-(3-oxa-8-azabicyclo[3.2.1]octan-8-yl)-5-chloropyrimidin-4-yl)amino)-2-cyclopropyl-7-methyl-1,2,3,4-tetrahydro-[1,4]oxazepino[2,3-c]quinolin-6(7H)-one;

(R)-10-((5-chloro-2-(4,4-difluoropiperidin-1-yl)pyrimidin-4-yl)amino)-2-cyclopropyl-7-methyl-1,2,3,4-tetrahydro-[1,4]oxazepino[2,3-c]quinolin-6(7H)-one;

(R)-10-((5-chloro-2-((1R,5S,7S)-7-hydroxy-3-oxa-9-azabicyclo[3.3.1]nonan-9-yl)pyrimidin-4-yl)amino)-2-cyclopropyl-7-methyl-1,2,3,4-tetrahydro-[1,4]oxazepino[2,3-c]quinolin-6(7H)-one;

(R)-10-((2-(2-oxa-6-azaadamantan-6-yl)-5-chloropyrimidin-4-yl)amino)-2-cyclopropyl-7-methyl-1,2,3,4-tetrahydro-[1,4]oxazepino[2,3-c]quinolin-6(7H)-one;

(R)-10-((5-chloro-2-((3S,5R)-4,4-difluoro-3,5-dimethylpiperidin-1-yl)pyrimidin-4-yl)amino)-2-cyclopropyl-1,2,3,4-tetrahydro-[1,4]oxazepino[2,3-c]quinolin-6(7H)-one;

(R)-10-((2-(3-oxa-8-azabicyclo[3.2.1]octan-8-yl)-5-chloropyrimidin-4-yl)amino)-2-cyclopropyl-7-((3,3-difluorocyclobutyl)methyl)-1,2,3,4-tetrahydro-[1,4]oxazepino[2,3-c]quinolin-6(7H)-one;

(R)-10-((2-(3-oxa-8-azabicyclo[3.2.1]octan-8-yl)-5-chloropyrimidin-4-yl)amino)-2-cyclopropyl-7-(cyclopropylmethyl)-1,2,3,4-tetrahydro-[1,4]oxazepino[2,3-c]quinolin-6(7H)-one;

(R)-10-((5-chloro-2-(4,4-difluoropiperidin-1-yl)pyrimidin-4-yl)amino)-2-cyclopropyl-7-methyl-1,2,3,4-tetrahydro-[1,4]oxazepino[2,3-c][1,8]naphthyridin-6(7H)-one;

(R)-10-((5-chloro-2-((3S,5R)-4,4-difluoro-3,5-dimethylpiperidin-1-yl)pyrimidin-4-yl)amino)-2-cyclopropyl-7-methyl-1,2,3,4-tetrahydro-[1,4]oxazepino[2,3-c][1,8]naphthyridin-6(7H)-one;

(R)-10-((5-chloro-2-((1R,5S,7S)-7-hydroxy-3-oxa-9-azabicyclo[3.3.1]nonan-9-yl)pyrimidin-4-yl)amino)-2-cyclopropyl-7-((3,3-difluorocyclobutyl)methyl)-1,2,3,4-tetrahydro-[1,4]oxazepino[2,3-c]quinolin-6(7H)-one;

(S)-2-chloro-4-((2,7-dimethyl-5,6-dioxo-1,2,3,5,6,7-hexahydro-[1,4]oxazepino[6,5-c]quinolin-10-yl)amino)nicotinonitrile;

(S)-2-chloro-4-((2-cyclopropyl-7-methyl-5,6-dioxo-1,2,3,5,6,7-hexahydro-[1,4]oxazepino[6,5-c]quinolin-10-yl)amino)nicotinonitrile;

2-chloro-4-((2-cyclopropyl-7-methyl-5,6-dioxo-1,2,3,5,6,7-hexahydro-[1,4]oxazepino[6,5-c]quinolin-10-yl)amino)nicotinonitrile;

2-chloro-4-((2,3,7-trimethyl-5,6-dioxo-1,2,3,5,6,7-hexahydro-[1,4]oxazepino[6,5-c]quinolin-10-yl)amino)nicotinonitrile;

(S)-10-((5-chloro-2-((tetrahydro-2H-pyran-4-yl)oxy)pyridin-4-yl)amino)-2,7-dimethyl-2,3-dihydro-[1,4]oxazepino[6,5-c]quinoline-5,6(1H, 7H)-dione;

(S)-10-((5-chloro-2-((2S,6R)-2,6-dimethylmorpholino)pyrimidin-4-yl)amino)-2,7-dimethyl-2,3-dihydro-[1,4]oxazepino[6,5-c]quinoline-5,6(1H, 7H)-dione;

(2S)-10-((2-(8-azabicyclo[3.2.1]octan-8-yl)-5-chloropyrimidin-4-yl)amino)-2,7-dimethyl-2,3-dihydro-[1,4]oxazepino[6,5-c]quinoline-5,6(1H, 7H)-dione;

(S)-10-((5-chloro-2-((3S,5R)-4,4-difluoro-3,5-dimethylpiperidin-1-yl)pyrimidin-4-yl)amino)-2,7-dimethyl-2,3-dihydro-[1,4]oxazepino[6,5-c]quinoline-5,6(1H,7H)-dione;

(S)-1-(5-chloro-4-((2,7-dimethyl-5,6-dioxo-1,2,3,5,6,7-hexahydro-[1,4]oxazepino[6,5-c]quinolin-10-yl)amino)pyrimidin-2-yl)-N,N-dimethylpiperidine-4-carboxamide;

(S)-10-((5-chloro-2-(2-methyl-1-oxo-2,9-diazaspiro[5.5]undecan-9-yl)pyrimidin-4-yl)amino)-2,7-dimethyl-2,3-dihydro-[1,4]oxazepino[6,5-c]quinoline-5,6(1H,7H)-dione;

(2S)-10-((5-chloro-2-(3,3-difluoro-8-azabicyclo[3.2.1]octan-8-yl)pyrimidin-4-yl)amino)-2,7-dimethyl-2,3-dihydro-[1,4]oxazepino[6,5-c]quinoline-5,6(1H,7H)-dione;

(S)-10-((5-chloro-2-((3R,5S)-3,5-dimethylpiperidin-1-yl)pyrimidin-4-yl)amino)-2,7-dimethyl-2,3-dihydro-[1,4]oxazepino[6,5-c]quinoline-5,6(1H, 7H)-dione;

(2S)-10-((2-(3-azabicyclo[3.2.1]octan-3-yl)-5-chloropyrimidin-4-yl)amino)-2,7-dimethyl-2,3-dihydro-[1,4]oxazepino[6,5-c]quinoline-5,6(1H, 7H)-dione;

(S)-10-((5-chloro-2-(2-oxopyrrolidin-1-yl)pyrimidin-4-yl)amino)-2,7-dimethyl-2,3-dihydro-[1,4]oxazepino[6,5-c]quinoline-5,6(1H, 7H)-dione;

(2S)-10-((2-(8-azabicyclo[3.2.1]octan-8-yl)-5-chloropyrimidin-4-yl)amino)-2-cyclopropyl-7-methyl-2,3-dihydro-[1,4]oxazepino[6,5-c]quinoline-5,6(1H,7H)-dione;

(S)-10-((5-chloro-2-((3S,5R)-4,4-difluoro-3,5-dimethylpiperidin-1-yl)pyrimidin-4-yl)amino)-2-cyclopropyl-7-methyl-2,3-dihydro-[1,4]oxazepino[6,5-c]quinoline-5,6(1H,7H)-dione;

(S)-10-((5-chloro-2-((3R,5S)-3,5-dimethylpiperidin-1-yl)pyrimidin-4-yl)amino)-2-cyclopropyl-7-methyl-2,3-dihydro-[1,4]oxazepino[6,5-c]quinoline-5,6(1H,7H)-dione;

(S)-1-(5-chloro-4-((2-cyclopropyl-7-methyl-5,6-dioxo-1,2,3,5,6,7-hexahydro-[1,4]oxazepino[6,5-c]quinolin-10-yl)amino)pyrimidin-2-yl)-N,N-dimethylpiperidine-4-carboxamide;

(S)-10-((5-chloro-2-((2S,6R)-2,6-dimethylmorpholino)pyrimidin-4-yl)amino)-2-cyclopropyl-7-methyl-2,3-dihydro-[1,4]oxazepino[6,5-c]quinoline-5,6(1H,7H)-dione;

10-((5-chloro-2-(4,4-difluoropiperidin-1-yl)pyrimidin-4-yl)amino)-2-cyclopropyl-7-methyl-2,3-dihydro-[1,4]oxazepino[6,5-c]quinoline-5,6(1H, 7H)-dione;

rac-(2S,3R)-10-((5-chloro-2-((3S,5R)-3,5-dimethylpiperidin-1-yl)pyrimidin-4-yl)amino)-2,3,7-trimethyl-2,3-dihydro-[1,4]oxazepino[6,5-c]quinoline-5,6(1H,7H)-dione;

rac-(2S,3S)-10-((5-chloro-2-((3S,5R)-3,5-dimethylpiperidin-1-yl)pyrimidin-4-yl)amino)-2,3,7-trimethyl-2,3-dihydro-[1,4]oxazepino[6,5-c]quinoline-5,6(1H,7H)-dione;

(S)-2-chloro-4-((2,7-dimethyl-6-oxo-1,2,3,5,6,7-hexahydro-[1,4]oxazepino[6,5-c]quinolin-10-yl)amino)nicotinonitrile;

(S)-2-chloro-4-((2-cyclopropyl-7-methyl-6-oxo-1,2,3,5,6,7-hexahydro-[1,4]oxazepino[6,5-c]quinolin-10-yl)amino)nicotinonitrile;

2-chloro-4-((2,6-dimethyl-5-oxo-1,2,3,4,5,6-hexahydrobenzo[h][1,6]naphthyridin-9-yl)amino)nicotinonitrile;

2-chloro-4-((2,6-dimethyl-5-oxo-2,3,5,6-tetrahydro-1H-[1,4]thiazino[2,3-c]quinolin-9-yl)amino)nicotinonitrile;

(S)-2-chloro-4-((2-cyclopropyl-3,3-difluoro-7-methyl-6-oxo-1,2,3,4,6,7-hexahydro-[1,4]oxazepino[2,3-c]quinolin-10-yl)amino)nicotinonitrile;

10-((5-chloro-2-((1R,5S,7s)-7-hydroxy-3-oxa-9-azabicyclo[3.3.1]nonan-9-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-((1R,5S,7R)-7-hydroxy-3-oxa-9-azabicyclo[3.3.1]nonan-9-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(R)-10-((5-chloro-2-((1R,5S,7S)-7-hydroxy-3-oxa-9-azabicyclo[3.3.1]nonan-9-yl)pyrimidin-4-yl)amino)-2-cyclopropyl-7-methyl-1,2,3,4-tetrahydro-[1,4]oxazepino[2,3-c][1,8]naphthyridin-6(7H)-one;

(R)-10-((5-chloro-2-((1R,5S,7S)-7-hydroxy-3-oxa-9-azabicyclo[3.3.1]nonan-9-yl)pyrimidin-4-yl)amino)-2-cyclopropyl-7-methyl-1,2,3,4-tetrahydro-[1,4]thiazepino[2,3-c]quinolin-6(7H)-one;

(R)-10-((5-chloro-2-((3S,5R)-4,4-difluoro-3,5-dimethylpiperidin-1-yl)pyrimidin-4-yl)amino)-2-cyclopropyl-7-methyl-1,2,3,4-tetrahydro-[1,4]thiazepino[2,3-c]quinolin-6(7H)-one;

(R)-10-((5-chloro-2-((3S,5R)-4,4-difluoro-3,5-dimethylpiperidin-1-yl)pyrimidin-4-yl)amino)-2-cyclopropyl-7-(2-hydroxyethyl)-1,2,3,4-tetrahydro-[1,4]oxazepino[2,3-c]quinolin-6(7H)-one;

(R)-10-((5-chloro-2-((3S,5R)-4,4-difluoro-3,5-dimethylpiperidin-1-yl)pyrimidin-4-yl)amino)-2-cyclopropyl-7-(2-(methylamino)ethyl)-1,2,3,4-tetrahydro-[1,4]oxazepino[2,3-c]quinolin-6(7H)-one;

(R)-10-((5-chloro-2-((1R,3R,5S)-3-hydroxy-8-azabicyclo[3.2.1]octan-8-yl)pyrimidin-4-yl)amino)-2-cyclopropyl-7-methyl-1,2,3,4-tetrahydro-[1,4]oxazepino[2,3-c]quinolin-6(7H)-one;

(R)-10-((5-chloro-2-(3,3-dioxido-3-thia-8-azabicyclo[3.2.1]octan-8-yl)pyrimidin-4-yl)amino)-2-cyclopropyl-7-methyl-1,2,3,4-tetrahydro-[1,4]oxazepino[2,3-c]quinolin-6(7H)-one;

(R)-10-((5-chloro-2-(3-methyl-3,8-diazabicyclo[3.2.1]octan-8-yl)pyrimidin-4-yl)amino)-2-cyclopropyl-7-methyl-1,2,3,4-tetrahydro-[1,4]oxazepino[2,3-c]quinolin-6(7H)-one;

(R)-10-((2-(8-oxa-3-azabicyclo[3.2.1]octan-3-yl)-5-chloropyrimidin-4-yl)amino)-2-cyclopropyl-7-methyl-1,2,3,4-tetrahydro-[1,4]oxazepino[2,3-c]quinolin-6(7H)-one;

(R)-10-((5-chloro-2-(4-methyl-3-oxopiperazin-1-yl)pyrimidin-4-yl)amino)-2-cyclopropyl-7-methyl-1,2,3,4-tetrahydro-[1,4]oxazepino[2,3-c]quinolin-6(7H)-one;

(R)-10-((5-chloro-2-((3S,5R)-3-hydroxy-5-methylpiperidin-1-yl)pyrimidin-4-yl)amino)-2-cyclopropyl-7-methyl-1,2,3,4-tetrahydro-[1,4]oxazepino[2,3-c]quinolin-6(7H)-one;

(R)-10-((5-chloro-2-((3R,5S)-3-hydroxy-5-methylpiperidin-1-yl)pyrimidin-4-yl)amino)-2-cyclopropyl-7-methyl-1,2,3,4-tetrahydro-[1,4]oxazepino[2,3-c]quinolin-6(7H)-one;

(R)-10-((5-chloro-2-((3S,4R,5R)-4-fluoro-3,5-dimethylpiperidin-1-yl)pyrimidin-4-yl)amino)-2-cyclopropyl-7-methyl-1,2,3,4-tetrahydro-[1,4]oxazepino[2,3-c]quinolin-6(7H)-one;

(R)-10-((5-chloro-2-((R)-4,4-difluoro-3-methylpiperidin-1-yl)pyrimidin-4-yl)amino)-2-cyclopropyl-7-methyl-1,2,3,4-tetrahydro-[1,4]oxazepino[2,3-c]quinolin-6(7H)-one;

(R)-10-((5-chloro-2-((S)-4,4-difluoro-3-methylpiperidin-1-yl)pyrimidin-4-yl)amino)-2-cyclopropyl-7-methyl-1,2,3,4-tetrahydro-[1,4]oxazepino[2,3-c]quinolin-6(7H)-one;

(R)-10-((5-chloro-2-((R)-4,4-difluoro-3-hydroxypiperidin-1-yl)pyrimidin-4-yl)amino)-2-cyclopropyl-7-methyl-1,2,3,4-tetrahydro-[1,4]oxazepino[2,3-c]quinolin-6(7H)-one;

(R)-10-((5-chloro-2-((S)-4,4-difluoro-3-hydroxypiperidin-1-yl)pyrimidin-4-yl)amino)-2-cyclopropyl-7-methyl-1,2,3,4-tetrahydro-[1,4]oxazepino[2,3-c]quinolin-6(7H)-one;

(R)-10-((5-chloro-2-((S)-4,4-difluoro-3-(hydroxymethyl)piperidin-1-yl)pyrimidin-4-yl)amino)-2-cyclopropyl-7-methyl-1,2,3,4-tetrahydro-[1,4]oxazepino[2,3-c]quinolin-6(7H)-one;

(R)-10-((5-chloro-2-((R)-4,4-difluoro-3-(hydroxymethyl)piperidin-1-yl)pyrimidin-4-yl)amino)-2-cyclopropyl-7-methyl-1,2,3,4-tetrahydro-[1,4]oxazepino[2,3-c]quinolin-6(7H)-one;

(R)-2-chloro-4-((2-cyclopropyl-7-methyl-5,5-dioxido-6-oxo-1,2,3,4,6,7-hexahydro-[1,4]thiazepino[2,3-c]quinolin-10-yl)amino)nicotinonitrile;

(R)-10-((5-chloro-2-((1R,5S,7S)-7-hydroxy-7-methyl-3-oxa-9-azabicyclo[3.3.1]nonan-9-yl)pyrimidin-4-yl)amino)-2-cyclopropyl-7-methyl-1,2,3,4-tetrahydro-[1,4]oxazepino[2,3-c]quinolin-6(7H)-one;

(S)-10-((5-chloro-2-((3R,5S)-3-hydroxy-5-methylpiperidin-1-yl)pyrimidin-4-yl)amino)-2,7-dimethyl-1,2,3,4-tetrahydro-[1,4]oxazepino[2,3-c]quinolin-6(7H)-one;

(S)-10-((5-chloro-2-((3S,5R)-3-hydroxy-5-methylpiperidin-1-yl)pyrimidin-4-yl)amino)-2,7-dimethyl-1,2,3,4-tetrahydro-[1,4]oxazepino[2,3-c]quinolin-6(7H)-one;

(S)-10-((5-chloro-2-(4,4-difluoropiperidin-1-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-((3S,5R)-4,4-difluoro-3,5-dimethylpiperidin-1-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-(4-methyl-3-oxopiperazin-1-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-((R)-4,4-difluoro-3-(hydroxymethyl)piperidin-1-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-((S)-4,4-difluoro-3-(hydroxymethyl)piperidin-1-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-morpholinopyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-((R)-2-methylmorpholino)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-((S)-2-methylmorpholino)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((2-(8-oxa-3-azabicyclo[3.2.1]octan-3-yl)-5-chloropyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((2-(3-oxa-8-azabicyclo[3.2.1]octan-8-yl)-5-chloropyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-(3,3-dioxido-3-thia-8-azabicyclo[3.2.1]octan-8-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-((R)-4,4-difluoro-2-(hydroxymethyl)pyrrolidin-1-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

2-chloro-4-((2,7-dimethyl-5,6-dioxo-2,3,4,5,6,7-hexahydro-1H-[1,4]diazepino[6,5-c]quinolin-10-yl)amino)nicotinonitrile;

(S)-10-((5-chloro-2-(4-hydroxy-7,8-dihydropyrido[4,3-d]pyrimidin-6(5H)-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-((3R,5S)-3-hydroxy-5-methylpiperidin-1-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-((3S,5R)-3-hydroxy-5-methylpiperidin-1-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-((1S,5R)-3-methyl-2-oxo-3,8-diazabicyclo[3.2.1]octan-8-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-((1R,5S)-3-methyl-2-oxo-3,8-diazabicyclo[3.2.1]octan-8-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(1R,5S,7S)-9-(5-chloro-4-(((S)-2-cyclopropyl-3,3-difluoro-7-methyl-6-oxo-1,2,3,4,6,7-hexahydro-[1,4]oxazepino[2,3-c]quinolin-10-yl)amino)pyrimidin-2-yl)-N,N-dimethyl-3-oxa-9-azabicyclo[3.3.1]nonane-7-carboxamide;

(1R,5S,7R)-9-(5-chloro-4-(((S)-2-cyclopropyl-3,3-difluoro-7-methyl-6-oxo-1,2,3,4,6,7-hexahydro-[1,4]oxazepino[2,3-c]quinolin-10-yl)amino)pyrimidin-2-yl)-N,N-dimethyl-3-oxa-9-azabicyclo[3.3.1]nonane-7-carboxamide;

(S)-10-((3-chloropyridin-4-yl)amino)-2-cyclopropyl-3,3-difluoro-7-methyl-1,2,3,4-tetrahydro-[1,4]oxazepino[2,3-c]quinolin-6(7H)-one;

(S)-3-(4-(5-chloro-4-((2-cyclopropyl-3,3-difluoro-7-methyl-6-oxo-1,2,3,4,6,7-hexahydro-[1,4]oxazepino[2,3-c]quinolin-10-yl)amino)pyrimidin-2-yl)piperazin-1-yl)propanenitrile;

(S)-2-cyclopropyl-3,3-difluoro-10-((5-fluoro-2-(4-methyl-3-oxopiperazin-1-yl)pyrimidin-4-yl)amino)-7-methyl-1,2,3,4-tetrahydro-[1,4]oxazepino[2,3-c]quinolin-6(7H)-one;

(S)-10-((2-(3-oxa-8-azabicyclo[3.2.1]octan-8-yl)-5-fluoropyrimidin-4-yl)amino)-2-cyclopropyl-3,3-difluoro-7-methyl-1,2,3,4-tetrahydro-[1,4]oxazepino[2,3-c]quinolin-6(7H)-one;

(2S)-10-((5-chloro-2-(3-methyl-3,6-diazabicyclo[3.1.1]heptan-6-yl)pyrimidin-4-yl)amino)-2-cyclopropyl-3,3-difluoro-7-methyl-1,2,3,4-tetrahydro-[1,4]oxazepino[2,3-c]quinolin-6(7H)-one; or (S)-10-((5-chloro-2-(6-methyl-2,6-diazaspiro[3.3]heptan-2-yl)pyrimidin-4-yl)amino)-2-cyclopropyl-3,3-difluoro-7-methyl-1,2,3,4-tetrahydro-[1,4]oxazepino[2,3-c]quinolin-6(7H)-one.

Further compounds of the present invention include any of the compounds exemplified in the present application, or a pharmaceutically acceptable salt or solvate thereof, and, in particular, any of the following:

(R)-2-chloro-4-((2-cyclopropyl-7-methyl-6-oxo-1,2,3,4,6,7-hexahydro-[1,4]oxazepino[2,3-c]quinolin-10-yl)amino)nicotinonitrile;

2-chloro-4-((2-cyclopropyl-3,3-difluoro-7-methyl-6-oxo-1,2,3,4,6,7-hexahydro-[1,4]oxazepino[2,3-c]quinolin-10-yl)amino)nicotinonitrile;

(R)-2-chloro-4-((2-cyclopropyl-7-methyl-6-oxo-1,2,3,4,6,7-hexahydro-[1,4]thiazepino[2,3-c]quinolin-10-yl)amino)nicotinonitrile;

(R)-2-chloro-4-((2-cyclopropyl-7-methyl-5,5-dioxido-6-oxo-1,2,3,4,6,7-hexahydro-[1,4]thiazepino[2,3-c]quinolin-10-yl)amino)nicotinonitrile;

(S)-2-chloro-4-((2-cyclopropyl-3,3-difluoro-7-methyl-6-oxo-1,2,3,4,6,7-hexahydro-[1,4]oxazepino[2,3-c]quinolin-10-yl)amino)nicotinonitrile;

(S)-6-chloro-5-cyano-4-((2,7-dimethyl-6-oxo-1,2,3,4,6,7-hexahydro-[1,4]oxazepino[2,3-c]quinolin-10-yl)amino)picolinic acid;

(R)-6-chloro-5-cyano-4-((2-cyclopropyl-7-methyl-6-oxo-1,2,3,4,6,7-hexahydro-[1,4]oxazepino[2,3-c]quinolin-10-yl)amino)picolinic acid;

(R)-2-chloro-4-((2-cyclopropyl-7-methyl-6-oxo-1,2,3,4,6,7-hexahydro-[1,4]oxazepino[2,3-c]quinolin-10-yl)amino)-6-(3-(trifluoromethyl)azetidine-1-carbonyl)nicotinonitrile;

(S)-10-((3-chloropyridin-4-yl)amino)-2-cyclopropyl-3,3-difluoro-7-methyl-1,2,3,4-tetrahydro-[1,4]oxazepino[2,3-c]quinolin-6(7H)-one;

(R)-10-((5-chloro-2-(3-(trifluoromethyl)-1H-pyrazol-1-yl)pyrimidin-4-yl)amino)-2-cyclopropyl-7-methyl-1,2,3,4-tetrahydro-[1,4]oxazepino[2,3-c]quinolin-6(7H)-one;

(S)-10-((5-chloro-2-morpholinopyrimidin-4-yl)amino)-2,7-dimethyl-1,2,3,4-tetrahydro-[1,4]oxazepino[2,3-c]quinolin-6(7H)-one;

(R)-10-((5-chloro-2-(2,2,6,6-tetramethylmorpholino)pyrimidin-4-yl)amino)-2-cyclopropyl-7-methyl-1,2,3,4-tetrahydro-[1,4]oxazepino[2,3-c]quinolin-6(7H)-one;

(R)-10-((2-(3-oxa-8-azabicyclo[3.2.1]octan-8-yl)-5-chloropyrimidin-4-yl)amino)-2-cyclopropyl-7-methyl-1,2,3,4-tetrahydro-[1,4]oxazepino[2,3-c]quinolin-6(7H)-one;

(R)-10-((5-chloro-2-((1R,5S,7S)-7-hydroxy-3-oxa-9-azabicyclo[3.3.1]nonan-9-yl)pyrimidin-4-yl)amino)-2-cyclopropyl-7-methyl-1,2,3,4-tetrahydro-[1,4]oxazepino[2,3-c]quinolin-6(7H)-one;

(R)-10-((2-(2-oxa-6-azaadamantan-6-yl)-5-chloropyrimidin-4-yl)amino)-2-cyclopropyl-7-methyl-1,2,3,4-tetrahydro-[1,4]oxazepino[2,3-c]quinolin-6(7H)-one;

(R)-10-((2-(3-oxa-8-azabicyclo[3.2.1]octan-8-yl)-5-chloropyrimidin-4-yl)amino)-2-cyclopropyl-7-((3,3-difluorocyclobutyl)methyl)-1,2,3,4-tetrahydro-[1,4]oxazepino[2,3-c]quinolin-6(7H)-one;

(R)-10-((2-(3-oxa-8-azabicyclo[3.2.1]octan-8-yl)-5-chloro-pyrimidin-4-yl)amino)-2-cyclopropyl-7-(cyclopropylmethyl)-1,2,3,4-tetrahydro-[1,4]oxazepino[2,3-c]quinolin-6(7H)-one;

(R)-10-((5-chloro-2-(4,4-difluoropiperidin-1-yl)pyrimidin-4-yl)amino)-2-cyclopropyl-7-methyl-1,2,3,4-tetrahydro-[1,4]oxazepino[2,3-c][1,8]naphthyridin-6(7H)-one;

(R)-10-((5-chloro-2-((1R,5S,7S)-7-hydroxy-3-oxa-9-azabicyclo[3.3.1]nonan-9-yl)pyrimidin-4-yl)amino)-2-cyclopropyl-7-((3,3-difluorocyclobutyl)methyl)-1,2,3,4-tetrahydro-[1,4]oxazepino[2,3-c]quinolin-6(7H)-one;

(S)-2-chloro-4-((2,7-dimethyl-5,6-dioxo-1,2,3,5,6,7-hexahydro-[1,4]oxazepino[6,5-c]quinolin-10-yl)amino)nicotinonitrile;

10-((5-chloro-2-((1R,5S,7s)-7-hydroxy-3-oxa-9-azabicyclo[3.3.1]nonan-9-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(R)-10-((5-chloro-2-((1R,5S,7S)-7-hydroxy-3-oxa-9-azabicyclo[3.3.1]nonan-9-yl)pyrimidin-4-yl)amino)-2-cyclopropyl-7-methyl-1,2,3,4-tetrahydro-[1,4]oxazepino[2,3-c][1,8]naphthyridin-6(7H)-one;

(S)-10-((5-chloro-2-((1R,5S,7R)-7-hydroxy-3-oxa-9-azabicyclo[3.3.1]nonan-9-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-(4-methyl-3-oxopiperazin-1-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(R)-10-((5-chloro-2-(4-methyl-3-oxopiperazin-1-yl)pyrimidin-4-yl)amino)-2-cyclopropyl-7-methyl-1,2,3,4-tetrahydro-[1,4]oxazepino[2,3-c]quinolin-6(7H)-one;

(R)-10-((5-chloro-2-((3R,5S)-3-hydroxy-5-methylpiperidin-1-yl)pyrimidin-4-yl)amino)-2-cyclopropyl-7-methyl-1,2,3,4-tetrahydro-[1,4]oxazepino[2,3-c]quinolin-6(7H)-one;

(R)-10-((5-chloro-2-((3S,5R)-3-hydroxy-5-methylpiperidin-1-yl)pyrimidin-4-yl)amino)-2-cyclopropyl-7-methyl-1,2,3,4-tetrahydro-[1,4]oxazepino[2,3-c]quinolin-6(7H)-one;

(R)-10-((5-chloro-2-((1R,3R,5S)-3-hydroxy-8-azabicyclo[3.2.1]octan-8-yl)pyrimidin-4-yl)amino)-2-cyclopropyl-7-methyl-1,2,3,4-tetrahydro-[1,4]oxazepino[2,3-c]quinolin-6(7H)-one;

(R)-10-((2-(8-oxa-3-azabicyclo[3.2.1]octan-3-yl)-5-chloro-pyrimidin-4-yl)amino)-2-cyclopropyl-7-methyl-1,2,3,4-tetrahydro-[1,4]oxazepino[2,3-c]quinolin-6(7H)-one;

(R)-10-((5-chloro-2-((1R,5S,7S)-7-hydroxy-7-methyl-3-oxa-9-azabicyclo[3.3.1]nonan-9-yl)pyrimidin-4-yl)amino)-2-cyclopropyl-7-methyl-1,2,3,4-tetrahydro-[1,4]oxazepino[2,3-c]quinolin-6(7H)-one;

(R)-10-((5-chloro-2-(3-methyl-3,8-diazabicyclo[3.2.1]octan-8-yl)pyrimidin-4-yl)amino)-2-cyclopropyl-7-methyl-1,2,3,4-tetrahydro-[1,4]oxazepino[2,3-c]quinolin-6(7H)-one;

(R)-10-((5-chloro-2-(3,3-dioxido-3-thia-8-azabicyclo[3.2.1]octan-8-yl)pyrimidin-4-yl)amino)-2-cyclopropyl-7-methyl-1,2,3,4-tetrahydro-[1,4]oxazepino[2,3-c]quinolin-6(7H)-one;

(S)-10-((5-chloro-2-((3R,5S)-3-hydroxy-5-methylpiperidin-1-yl)pyrimidin-4-yl)amino)-2,7-dimethyl-1,2,3,4-tetrahydro-[1,4]oxazepino[2,3-c]quinolin-6(7H)-one;

(S)-10-((5-chloro-2-((3S,5R)-3-hydroxy-5-methylpiperidin-1-yl)pyrimidin-4-yl)amino)-2,7-dimethyl-1,2,3,4-tetrahydro-[1,4]oxazepino[2,3-c]quinolin-6(7H)-one;

(S)-10-((5-chloro-2-(4,4-difluoropiperidin-1-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-((3S,5R)-4,4-difluoro-3,5-dimethylpiperidin-1-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-((R)-4,4-difluoro-3-(hydroxymethyl)piperidin-1-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-((S)-4,4-difluoro-3-(hydroxymethyl)piperidin-1-yl)pyrimidin-4-yl)amino)-2-cyclopropyl-3,3-difluoro-7-methyl-1,2,3,4-tetrahydro-[1,4]oxazepino[2,3-c]quinolin-6(7H)-one (S)-10-((5-chloro-2-morpholinopyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-((R)-2-methylmorpholino)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-((S)-2-methylmorpholino)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((2-(8-oxa-3-azabicyclo[3.2.1]octan-3-yl)-5-chloro-pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((2-(3-oxa-8-azabicyclo[3.2.1]octan-8-yl)-5-chloro-pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-(3,3-dioxido-3-thia-8-azabicyclo[3.2.1]octan-8-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-((R)-4,4-difluoro-2-(hydroxymethyl)pyrrolidin-1-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(R)-10-((5-chloro-2-((R)-4,4-difluoro-3-hydroxypiperidin-1-yl)pyrimidin-4-yl)amino)-2-cyclopropyl-7-methyl-1,2,3,4-tetrahydro-[1,4]oxazepino[2,3-c]quinolin-6(7H)-one;

(R)-10-((5-chloro-2-((S)-4,4-difluoro-3-hydroxypiperidin-1-yl)pyrimidin-4-yl)amino)-2-cyclopropyl-7-methyl-1,2,3,4-tetrahydro-[1,4]oxazepino[2,3-c]quinolin-6(7H)-one;

(S)-10-((5-chloro-2-(4-hydroxy-7,8-dihydropyrido[4,3-d]pyrimidin-6(5H)-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-((1S,5R)-3-methyl-2-oxo-3,8-diazabicyclo[3.2.1]octan-8-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-((1R,5S)-3-methyl-2-oxo-3,8-diazabicyclo[3.2.1]octan-8-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(1R,5S,7S)-9-(5-chloro-4-(((S)-2-cyclopropyl-3,3-difluoro-7-methyl-6-oxo-1,2,3,4,6,7-hexahydro-[1,4]oxazepino[2,3-c]quinolin-10-yl)amino)pyrimidin-2-yl)-N,N-dimethyl-3-oxa-9-azabicyclo[3.3.1]nonane-7-carboxamide;

(1R,5S,7R)-9-(5-chloro-4-(((S)-2-cyclopropyl-3,3-difluoro-7-methyl-6-oxo-1,2,3,4,6,7-hexahydro-[1,4]oxazepino[2,3-c]quinolin-10-yl)amino)pyrimidin-2-yl)-N,N-dimethyl-3-oxa-9-azabicyclo[3.3.1]nonane-7-carboxamide;

(S)-10-((5-chloro-2-((3R,5S)-3-hydroxy-5-methylpiperidin-1-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-((3S,5R)-3-hydroxy-5-methylpiperidin-1-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-3-(4-(5-chloro-4-((2-cyclopropyl-3,3-difluoro-7-methyl-6-oxo-1,2,3,4,6,7-hexahydro-[1,4]oxazepino[2,3-c]quinolin-10-yl)amino)pyrimidin-2-yl)piperazin-1-yl)propanenitrile;

(S)-10-((5-chloro-2-(6-methyl-2,6-diazaspiro[3.3]heptan-2-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(2S)-10-((5-chloro-2-(3-methyl-3,6-diazabicyclo[3.1.1]heptan-6-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-2-cyclopropyl-3,3-difluoro-10-((5-fluoro-2-(4-methyl-3-oxopiperazin-1-yl)pyrimidin-4-yl)amino)-7-methyl-1,2,3,4-tetrahydro-[1,4]oxazepino[2,3-c]quinolin-6(7H)-one;

(S)-10-((2-(3-oxa-8-azabicyclo[3.2.1]octan-8-yl)-5-fluoropyrimidin-4-yl)amino)-2-cyclopropyl-3,3-difluoro-7-methyl-1,2,3,4-tetrahydro-[1,4]oxazepino[2,3-c]quinolin-6(7H)-one;

(R)-10-((5-chloro-2-((1R,5S,7S)-7-hydroxy-3-oxa-9-azabicyclo[3.3.1]nonan-9-yl)pyrimidin-4-yl)amino)-2-cyclopropyl-7-methyl-1,2,3,4-tetrahydro-[1,4]thiazepino[2,3-c]quinolin-6(7H)-one;

(R)-10-((5-chloro-2-((R)-4,4-difluoro-3-(hydroxymethyl)piperidin-1-yl)pyrimidin-4-yl)amino)-2-cyclopropyl-7-methyl-1,2,3,4-tetrahydro-[1,4]oxazepino[2,3-c]quinolin-6(7H)-one;

(R)-10-((5-chloro-2-((S)-4,4-difluoro-3-(hydroxymethyl)piperidin-1-yl)pyrimidin-4-yl)amino)-2-cyclopropyl-7-methyl-1,2,3,4-tetrahydro-[1,4]oxazepino[2,3-c]quinolin-6(7H)-one;

(R)-10-((5-chloro-2-((3S,5R)-4,4-difluoro-3,5-dimethylpiperidin-1-yl)pyrimidin-4-yl)amino)-2-cyclopropyl-7-(2-hydroxyethyl)-1,2,3,4-tetrahydro-[1,4]oxazepino[2,3-c]quinolin-6(7H)-one; or (R)-10-((5-chloro-2-((3S,5R)-4,4-difluoro-3,5-dimethylpiperidin-1-yl)pyrimidin-4-yl)amino)-2-cyclopropyl-7-(2-(methylamino)ethyl)-1,2,3,4-tetrahydro-[1,4]oxazepino[2,3-c]quinolin-6(7H)-one.

Further compounds of the present invention include any of the compounds exemplified in the present application, or a pharmaceutically acceptable salt or solvate thereof, and, in particular, any of the following:

2-chloro-4-((2-cyclopropyl-3,3-difluoro-7-methyl-6-oxo-1,2,3,4,6,7-hexahydro-[1,4]oxazepino[2,3-c]quinolin-10-yl)amino)nicotinonitrile;

(R)-2-chloro-4-((2-cyclopropyl-7-methyl-5,5-dioxido-6-oxo-1,2,3,4,6,7-hexahydro-[1,4]thiazepino[2,3-c]quinolin-10-yl)amino)nicotinonitrile;

(S)-2-chloro-4-((2-cyclopropyl-3,3-difluoro-7-methyl-6-oxo-1,2,3,4,6,7-hexahydro-[1,4]oxazepino[2,3-c]quinolin-10-yl)amino)nicotinonitrile;

(R)-6-chloro-5-cyano-4-((2-cyclopropyl-7-methyl-6-oxo-1,2,3,4,6,7-hexahydro-[1,4]oxazepino[2,3-c]quinolin-10-yl)amino)picolinic acid;

(R)-10-((5-chloro-2-((1R,5S,7S)-7-hydroxy-3-oxa-9-azabicyclo[3.3.1]nonan-9-yl)pyrimidin-4-yl)amino)-2-cyclopropyl-7-((3,3-difluorocyclobutyl)methyl)-1,2,3,4-tetrahydro-[1,4]oxazepino[2,3-c]quinolin-6(7H)-one;

10-((5-chloro-2-((1R,5S,7s)-7-hydroxy-3-oxa-9-azabicyclo[3.3.1]nonan-9-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(R)-10-((5-chloro-2-((1R,5S,7S)-7-hydroxy-3-oxa-9-azabicyclo[3.3.1]nonan-9-yl)pyrimidin-4-yl)amino)-2-cyclopropyl-7-methyl-1,2,3,4-tetrahydro-[1,4]oxazepino[2,3-c][1,8]naphthyridin-6(7H)-one;

(S)-10-((5-chloro-2-((1R,5S,7R)-7-hydroxy-3-oxa-9-azabicyclo[3.3.1]nonan-9-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-(4-methyl-3-oxopiperazin-1-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(R)-10-((5-chloro-2-((3R,5S)-3-hydroxy-5-methylpiperidin-1-yl)pyrimidin-4-yl)amino)-2-cyclopropyl-7-methyl-1,2,3,4-tetrahydro-[1,4]oxazepino[2,3-c]quinolin-6(7H)-one;

(R)-10-((5-chloro-2-((3S,5R)-3-hydroxy-5-methylpiperidin-1-yl)pyrimidin-4-yl)amino)-2-cyclopropyl-7-methyl-1,2,3,4-tetrahydro-[1,4]oxazepino[2,3-c]quinolin-6(7H)-one;

(S)-10-((5-chloro-2-((R)-4,4-difluoro-3-(hydroxymethyl)piperidin-1-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-((S)-4,4-difluoro-3-(hydroxymethyl)piperidin-1-yl)pyrimidin-4-yl)amino)-2-cyclopropyl-3,3-difluoro-7-methyl-1,2,3,4-tetrahydro-[1,4]oxazepino[2,3-c]quinolin-6(7H)-one (S)-10-((5-chloro-2-morpholinopyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-((R)-2-methylmorpholino)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-((S)-2-methylmorpholino)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((2-(8-oxa-3-azabicyclo[3.2.1]octan-3-yl)-5-chloropyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((2-(3-oxa-8-azabicyclo[3.2.1]octan-8-yl)-5-chloropyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-(3,3-dioxido-3-thia-8-azabicyclo[3.2.1]octan-8-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-((R)-4,4-difluoro-2-(hydroxymethyl)pyrrolidin-1-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-(4-hydroxy-7,8-dihydropyrido[4,3-d]pyrimidin-6(5H)-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-((1S,5R)-3-methyl-2-oxo-3,8-diazabicyclo[3.2.1]octan-8-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-((1R,5S)-3-methyl-2-oxo-3,8-diazabicyclo[3.2.1]octan-8-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(1R,5S,7S)-9-(5-chloro-4-(((S)-2-cyclopropyl-3,3-difluoro-7-methyl-6-oxo-1,2,3,4,6,7-hexahydro-[1,4]oxazepino[2,3-c]quinolin-10-yl)amino)pyrimidin-2-yl)-N,N-dimethyl-3-oxa-9-azabicyclo[3.3.1]nonane-7-carboxamide;

(1R,5S,7R)-9-(5-chloro-4-(((S)-2-cyclopropyl-3,3-difluoro-7-methyl-6-oxo-1,2,3,4,6,7-hexahydro-[1,4]oxazepino[2,3-c]quinolin-10-yl)amino)pyrimidin-2-yl)-N,N-dimethyl-3-oxa-9-azabicyclo[3.3.1]nonane-7-carboxamide;

(S)-10-((5-chloro-2-((3R,5S)-3-hydroxy-5-methylpiperidin-1-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-((3S,5R)-3-hydroxy-5-methylpiperidin-1-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-3-(4-(5-chloro-4-((2-cyclopropyl-3,3-difluoro-7-methyl-6-oxo-1,2,3,4,6,7-hexahydro-[1,4]oxazepino[2,3-c]quinolin-10-yl)amino)pyrimidin-2-yl)piperazin-1-yl)propanenitrile;

(S)-10-((5-chloro-2-(6-methyl-2,6-diazaspiro[3.3]heptan-2-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(2S)-10-((5-chloro-2-(3-methyl-3,6-diazabicyclo[3.1.1]heptan-6-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-2-cyclopropyl-3,3-difluoro-10-((5-fluoro-2-(4-methyl-3-oxopiperazin-1-yl)pyrimidin-4-yl)amino)-7-methyl-1,2,3,4-tetrahydro-[1,4]oxazepino[2,3-c]quinolin-6(7H)-one;

(S)-10-((2-(3-oxa-8-azabicyclo[3.2.1]octan-8-yl)-5-fluoropyrimidin-4-yl)amino)-2-cyclopropyl-3,3-difluoro-7-methyl-1,2,3,4-tetrahydro-[1,4]oxazepino[2,3-c]quinolin-6(7H)-one; or (R)-10-((5-chloro-2-((1R,5S,7S)-7-hydroxy-3-oxa-9-azabicyclo[3.3.1]nonan-9-yl)pyrimidin-4-yl)amino)-2-cyclopropyl-7-methyl-1,2,3,4-tetrahydro-[1,4]thiazepino[2,3-c]quinolin-6(7H)-one.

Further compounds of the present invention include any of the compounds exemplified in the present application, or a pharmaceutically acceptable salt or solvate thereof, and, in particular, any of the following:

(S)-2-chloro-4-((2-cyclopropyl-3,3-difluoro-7-methyl-6-oxo-1,2,3,4,6,7-hexahydro-[1,4]oxazepino[2,3-c]quinolin-10-yl)amino)nicotinonitrile;

(R)-10-((5-chloro-2-(4,4-difluoropiperidin-1-yl)pyrimidin-4-yl)amino)-2-cyclopropyl-7-methyl-1,2,3,4-tetrahydro-[1,4]oxazepino[2,3-c][1,8]naphthyridin-6(7H)-one;

(S)-10-((5-chloro-2-((1R,5S,7R)-7-hydroxy-3-oxa-9-azabicyclo[3.3.1]nonan-9-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-(4-methyl-3-oxopiperazin-1-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-(4,4-difluoropiperidin-1-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-((3S,5R)-4,4-difluoro-3,5-dimethylpiperidin-1-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-((R)-4,4-difluoro-3-(hydroxymethyl)piperidin-1-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-((S)-4,4-difluoro-3-(hydroxymethyl)piperidin-1-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((2-(3-oxa-8-azabicyclo[3.2.1]octan-8-yl)-5-chloropyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-(3,3-dioxido-3-thia-8-azabicyclo[3.2.1]octan-8-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-((3R,5S)-3-hydroxy-5-methylpiperidin-1-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-((3S,5R)-3-hydroxy-5-methylpiperidin-1-yl)pyrimidin-4-yl)amino)-2-cyclopropyl-3,3-difluoro-7-methyl-1,2,3,4-tetrahydro-[1,4]oxazepino[2,3-c]quinolin-6(7H)-one; or (R)-10-((5-chloro-2-((3S,5R)-4,4-difluoro-3,5-dimethylpiperidin-1-yl)pyrimidin-4-yl)amino)-2-cyclopropyl-7-(2-hydroxyethyl)-1,2,3,4-tetrahydro-[1,4]oxazepino[2,3-c]quinolin-6(7H)-one.

The various functional groups and substituents making up the compounds of the Formula (I), or sub-formulae Ia to Ix, are typically chosen such that the molecular weight of the compound of the formula (I) does not exceed 1000. More usually, the molecular weight of the compound will be less than 900, for example less than 800, or less than 750, or less than 700, or less than 650. More preferably, the molecular weight is less than 600 and, for example, is 550 or less.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric methane sulfonate or maleic acid. In addition, a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a pharmaceutically acceptable cation, for example a salt with methylamine, dimethylamine, trimethylamine, piperidine, morpholine or tris-(2-hydroxyethyl)amine.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the invention may have geometric isomeric centres (E- and Z-isomers). It is to be understood that the present invention encompasses all optical, diastereoisomers and geometric isomers and mixtures thereof that possess antiproliferative activity.

The present invention also encompasses compounds of the invention as defined herein which comprise one or more isotopic substitutions. For example, H may be in any isotopic form, including 1H, 2H(D), and 3H (T); C may be in any isotopic form, including 12C, 13C, and 14C; and O may be in any isotopic form, including 16O and 18O; and the like.

It is also to be understood that certain compounds of the Formula (I), or sub-formulae Ia to Ix, may exist in solvated as well as unsolvated forms such as, for example, hydrated forms. It is to be understood that the invention encompasses all such solvated forms that possess antiproliferative activity.

It is also to be understood that certain compounds of the Formula I, or sub-formulae Ia to Ix, may exhibit polymorphism, and that the invention encompasses all such forms that possess antiproliferative activity.

Compounds of the Formula I, or sub-formulae Ia to Ix, may exist in a number of different tautomeric forms and references to compounds of the Formula I, or sub-formulae Ia to Ix, include all such forms. For the avoidance of doubt, where a compound can exist in one of several tautomeric forms, and only one is specifically described or shown, all others are nevertheless embraced by Formula I, or sub-formulae Ia to Ix. Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

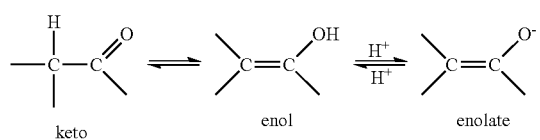

keto    enol    enolate

Compounds of the Formula I, or sub-formulae Ia to Ix, containing an amine function may also form N-oxides. A reference herein to a compound of the Formula I, or sub-formulae Ia to Ix, that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example Advanced Organic Chemistry, by Jerry March, 4th Edition, Wiley Interscience, pages. More particularly, N-oxides can be made by the procedure of L. W. Deady (Syn. Comm. 1977, 7, 509-514) in which the amine compound is reacted with m-chloroperoxybenzoic acid (mCPBA), for example, in an inert solvent such as dichloromethane.

The compounds of Formula (I), or sub-formulae Ia to Ix, may be administered in the form of a pro-drug which is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the Formula (I), or sub-formulae Ia to Ix, and in-vivo cleavable amide derivatives that may be formed at a carboxy group or an amino group in a compound of the Formula (I), or sub-formulae Ia to Ix.

Accordingly, the present invention includes those compounds of the Formula (I), or sub-formulae Ia to Ix, as defined hereinbefore, when made available by organic synthesis and when made available within the human or animal body by way of cleavage of a pro-drug thereof. Accordingly, the present invention includes those compounds of the Formula I, or sub-formulae Ia to Ix, that are produced by organic synthetic means and also such compounds that are produced in the human or animal body by way of metabolism of a precursor compound, that is a compound of the Formula (I), or sub-formulae Ia to Ix, may be a synthetically-produced compound or a metabolically-produced compound.

A suitable pharmaceutically acceptable pro-drug of a compound of the Formula (I), or sub-formulae Ia to Ix, is one that is based on reasonable medical judgement as being suitable for administration to the human or animal body without undesirable pharmacological activities and without undue toxicity.

Various forms of pro-drug have been described, for example in the following documents:—
a) Methods in Enzymology, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, Advanced Drug Delivery Reviews, 8, 1-38 (1992);
e) H. Bundgaard, et al., Journal of Pharmaceutical Sciences, 77, 285 (1988);
f) N. Kakeya, et al., Chem. Pharm. Bull., 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically acceptable pro-drug of a compound of the Formula I, or sub-formulae Ia to Ix, that possesses a carboxy group is, for example, an in vivo cleavable ester thereof. An in vivo cleavable ester of a compound of the Formula I, or sub-formulae Ia to Ix, containing a carboxy group is, for example, a pharmaceutically acceptable ester which is cleaved in the human or animal body to produce the parent acid. Suitable pharmaceutically acceptable esters for carboxy include (1-6C)alkyl esters such as methyl, ethyl and tert-butyl, (1-6C)alkoxymethyl esters such as methoxymethyl esters, (1-6C)alkanoyloxymethyl esters such as pivaloyloxymethyl esters, 3-phthalidyl esters, (3-8C)cycloalkylcarbonyloxy-(1-6C)alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and (1-6C)alkoxycarbonyloxy-(1-6C)alkyl esters such as methoxycarbonyloxymethyl and 1-methoxycarbonyloxyethyl esters.

A suitable pharmaceutically acceptable pro-drug of a compound of the Formula (I), or sub-formulae Ia to Ix, that possesses a hydroxy group is, for example, an in vivo cleavable ester or ether thereof. An in vivo cleavable ester or ether of a compound of the Formula I, or sub-formulae Ia to Ix, containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include (1-10C)alkanoyl groups such as acetyl, benzoyl, phenylacetyl and substituted benzoyl and phenylacetyl groups, (1-10C) alkoxycarbonyl groups such as ethoxycarbonyl, N,N-(1-6C)$_2$carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-(1-4C)alkylpiperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable pro-drug of a compound of the Formula (I), or sub-formulae Ia to Ix, that possesses a carboxy group is, for example, an in vivo cleavable amide thereof, for example an amide formed with an amine such as ammonia, a (1-4C)alkylamine such as methylamine, a [(1-4C)alkyl]$_2$amine such as dimethylamine, N-ethyl-N-methylamine or diethylamine, a (1-4C)alkoxy-(2-4C)alkylamine such as 2-methoxyethylamine, a phenyl-(1-4C)alkylamine such as benzylamine and amino acids such as glycine or an ester thereof.

A suitable pharmaceutically acceptable pro-drug of a compound of the Formula I, or sub-formulae Ia to Ix, that possesses an amino group is, for example, an in vivo cleavable amide derivative thereof. Suitable pharmaceutically acceptable amides from an amino group include, for example an amide formed with (1-10C)alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-(1-4C)alkyl)piperazin-1-ylmethyl.

The in vivo effects of a compound of the Formula (I), or sub-formulae Ia to Ix, may be exerted in part by one or more metabolites that are formed within the human or animal body after administration of a compound of the Formula (I), or sub-formulae Ia to Ix. As stated hereinbefore, the in vivo effects of a compound of the Formula (I), or sub-formulae Ia to Ix, may also be exerted by way of metabolism of a precursor compound (a pro-drug).

Though the present invention may relate to any compound or particular group of compounds defined herein by way of optional, preferred or suitable features or otherwise in terms of particular embodiments, the present invention may also relate to any compound or particular group of compounds that specifically excludes said optional, preferred or suitable features or particular embodiments.

Suitably, the present invention excludes any individual compounds not possessing the biological activity defined herein. The following compounds were tested in the HTRF assay described in the Examples section, but did not exhibit the desired activity, as they had IC$_{50}$ values greater than 2.50 µM:

(R)-2-cyclopropyl-10-((2-((3S,5R)-4,4-difluoro-3,5-dimethylpiperidin-1-yl)-5-methoxypyrimidin-4-yl)amino)-7-methyl-1,2,3,4-tetrahydro-[1,4]oxazepino[2,3-c]quinolin-6(7H)-one;

2-chloro-4-((2,4,4,7-tetramethyl-6-oxo-1,2,3,4,6,7-hexahydro-[1,4]oxazepino[2,3-c]quinolin-10-yl)amino)nicotinonitrile;

2-chloro-4-((2,2,7-trimethyl-5,6-dioxo-1,2,3,5,6,7-hexahydro-[1,4]oxazepino[6,5-c]quinolin-10-yl)amino)nicotinonitrile;

(2S)-10-((2-(7-acetyl-3,7-diazabicyclo[3.3.1]nonan-3-yl)-5-chloropyrimidin-4-yl)amino)-2,7-dimethyl-2,3-dihydro-[1,4]oxazepino[6,5-c]quinoline-5,6(1H,7H)-dione;

2-chloro-4-((2-isopropyl-7-methyl-6-oxo-1,2,3,4,6,7-hexahydro-[1,4]oxazepino[2,3-c]quinolin-10-yl)amino)nicotinonitrile;

2-chloro-4-((2-(cyclopropylmethyl)-6-methyl-5-oxo-2,3,5,6-tetrahydro-1H-[1,4]oxazino[2,3-c]quinolin-9-yl) amino)nicotinonitrile; and 2-chloro-4-((2-cyclobutyl-7-methyl-6-oxo-1,2,3,4,6,7-hexahydro-[1,4]oxazepino[2,3-c]quinolin-10-yl)amino) nicotinonitrile.

In an embodiment, the compounds of the invention are compounds of formula I as defined hereinbefore, with the proviso that the compound is not one of the compounds listed in the preceding paragraph.

Synthesis

The compounds of the present invention can be prepared by any suitable technique known in the art. Particular processes for the preparation of these compounds are described further in the accompanying examples.

In the description of the synthetic methods described herein and in any referenced synthetic methods that are used to prepare the starting materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

It will be appreciated that during the synthesis of the compounds of the invention in the processes defined herein, or during the synthesis of certain starting materials, it may be desirable to protect certain substituent groups to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule.

Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

Resins may also be used as a protecting group.

The methodology employed to synthesise a compound of Formula (I), or sub-formulae Ia to Ix, will vary depending on the nature of $X_1$, $X_2$, $R^1$, $R^2$, $R^{30}$, $R^{31}$, Ring A and any substituent groups associated therewith. Suitable processes for their preparation are described further in the accompanying Examples.

Once a compound of Formula (I), or sub-formulae Ia to Ix, has been synthesised by any one of the processes defined herein, the processes may then further comprise the additional steps of:

(i) removing any protecting groups present;
(ii) converting the compound Formula (I) into another compound of Formula (I);
(iii) forming a pharmaceutically acceptable salt, hydrate or solvate thereof; and/or
(iv) forming a prodrug thereof.

An example of (ii) above is when a compound of Formula (I) is synthesised and then one or more of the groups $X_1$, $X_2$, $R^1$, $R^2$, $R^{30}$, $R^{31}$, Ring A may be further reacted to change the nature of the group and provide an alternative compound of Formula (I).

The resultant compounds of Formula (I), or sub-formulae Ia to IxIx, can be isolated and purified using techniques well known in the art.

The compounds of Formula (I) may be synthesised by the general synthetic routes (Schemes 1 to 10b) below, specific examples of which are described in more detail in the Examples.

Scheme 1

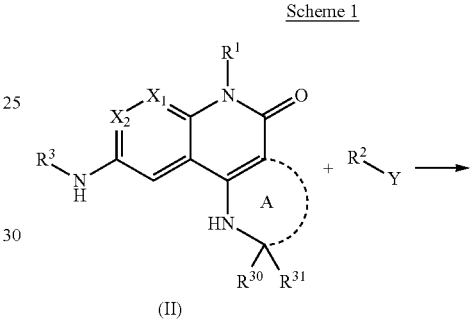

+ $R^2$—Y →

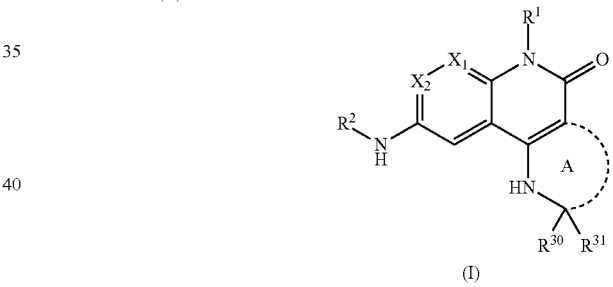

(I)

where Y is a halogen such as Cl, Br, I or a suitable alternative such as OTf, SOMe or $SO_2Me$, $R^3$ is H or formyl, and $R^1$, $R^2$, $R^{30}$, $R^{31}$, $X_1$, $X_2$ and Ring A are suitable groups chosen from those defined previously.

The reaction between aromatic amine (II) and aryl halide or equivalent $R^2$—Y to form compounds of formula (I) as shown in Scheme 1 may be carried out at elevated temperature (e.g. 60-180° C.), using conventional or microwave heating, in a suitable solvent or solvent mixture, such as NMP, DMA, DMF or acetonitrile. The reaction is carried out in the presence of a base (such as triethylamine or DIPEA) or with no base. Alternative reaction conditions include the use of a transition metal catalyst such as $Pd_2(dba)_3$ combined with a suitable ligand such as Xantphos, in the presence of a base such as cesium carbonate at elevated temperature, using a suitable solvent or solvent mixture, such as toluene or mixtures of toluene and DMF or NMP. When Y is SOMe or $SO_2Me$, alternative reaction conditions include the use of an acid such as TFA, at elevated temperature (e.g. 70° C.), using a suitable solvent, such as trifluoroethanol. When $R^3$ is formyl and Y is $SO_2Me$, alternative reaction conditions include the use of a base such NaH, at elevated temperature (e.g. 60° C.), using a suitable solvent, such as THF.

Compounds (II) may be prepared using methods such as those described in Schemes 2 and 3.

A compound of formula (I) may be converted to another compound of formula (I) by methods generally known to those skilled in the art.

Scheme 2a

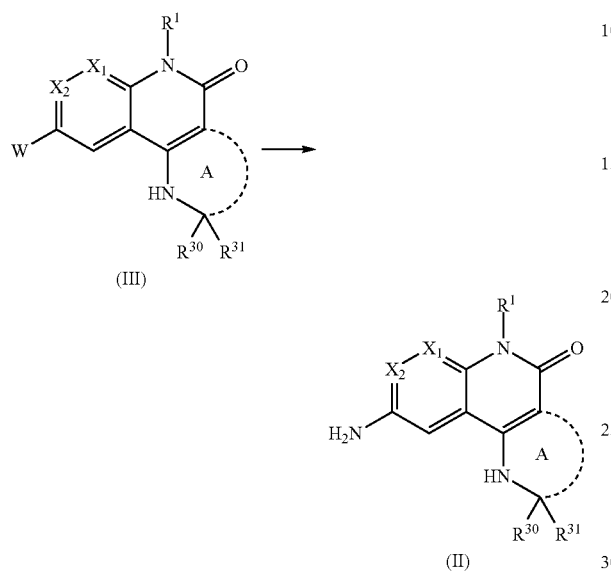

Where W is either NO$_2$, or a halogen such as Cl, Br, I or a suitable alternative such as OTf and R$^1$, R$^{30}$, R$^{31}$, X$^1$, X$^2$, Ring A are suitable groups chosen from those defined previously.

The reduction of nitro compounds (III, W=NO$_2$) to amino compounds (II) may be carried out by numerous methods which are well known in the art. Hydrogenation can be carried out in the presence of a metal catalyst such as palladium, often in the form of palladium on carbon, in an appropriate solvent or mixture of solvents such as ethanol, methanol, ethyl acetate or ethanol/NMP at ambient or elevated temperature (such as 40-80° C.) using conventional or microwave heating. These reactions are carried out under a hydrogen atmosphere, or alternatively by "transfer hydrogenation" using a reagent such as ammonium formate or triethylsilane. An alternative method uses tin(II) chloride in an appropriate solvent or solvent mixture, such as ethanol and trifluoroethanol, at elevated temperatures such as 120° C. using conventional or microwave heating. Other approaches are known in the art such as iron or zinc metal mediated reductions.

The amination of halo compounds (e.g. W=Cl) to aromatic amines (II) may be carried out by methods which are well known in the art. For example, metal catalysed amination may be employed, using a metal source and ligand. Conditions for this type of reaction are known in the literature and include the use of palladium acetate and benzophenone imine as described in Shen et al., *Angew. Chem. Int. Ed.* 2005, 44, 1371. Reactions are typically carried out using a base such as sodium tert-butoxide in an appropriate solvent or solvent mixture such as 1,2-dimethoxyethane at elevated temperatures. Hydrolysis of the imine intermediate can be carried out in a one-pot procedure at rt with the addition of an acid such as HCl. Aromatic amines (II) may also be formed from aryl halides (e.g. W=Br) by reaction with ammonia (for example, from ammonium hydroxide solution) in an appropriate solvent such as NMP, at elevated temperatures (such as 140° C.), using conventional or microwave heating. These reactions are typically catalysed using a metal catalyst such as copper (I) oxide.

Compounds (III) may be prepared by methods including those as shown in Schemes 4a-c, 7a-7b, 8 and 9.

Scheme 2b

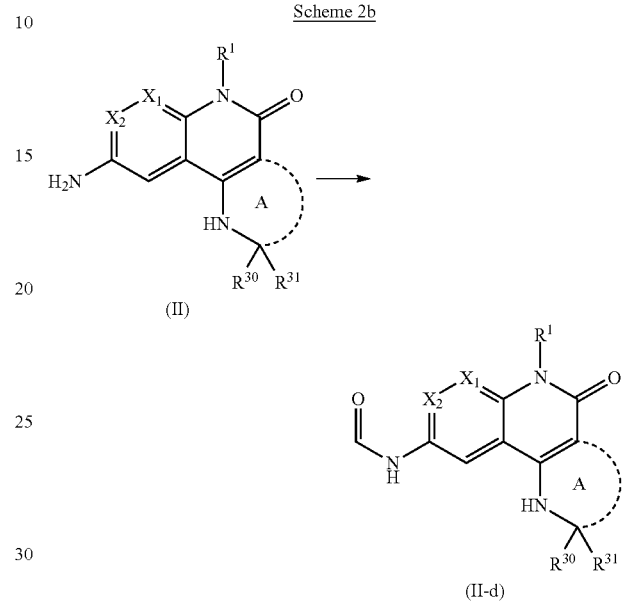

Where R$^1$, R$^{30}$, R$^{31}$, X$^1$, X$^2$, Ring A are suitable groups chosen from those defined previously.

Methods for the preparation of formamide compounds (II-d) are known in the art. For example, this may be carried out in the presence of phenyl formate in an appropriate solvent, such as dichloromethane at ambient temperature.

Compounds (II) may be prepared by methods including those as shown in Schemes 2a and 3.

Scheme 3

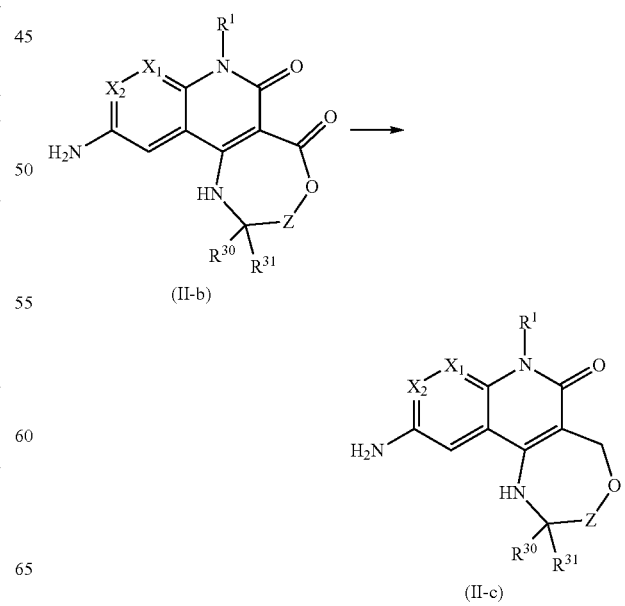

Where $R^1$, $R^{30}$, $R^{31}$, $X_1$, $X_2$ are suitable groups chosen from those defined previously. Z is an appropriately substituted methylene group (—$CR^{40}R^{41}$—), for example (—$CH_2$—) or (—CH(Me)-).

Aniline compounds (II-c) can be prepared by the reduction of compounds (II-b). This reaction can be carried out at low temperatures (such as 0° C.) in a suitable solvent such as THF with various reducing agents known in the art such as sodium borohydride. Various additives such as Lewis acids (e.g. boron trifluoride diethyl etherate) may be used.

Compounds (II-b) can be prepared as described in Scheme 2.

Scheme 4a

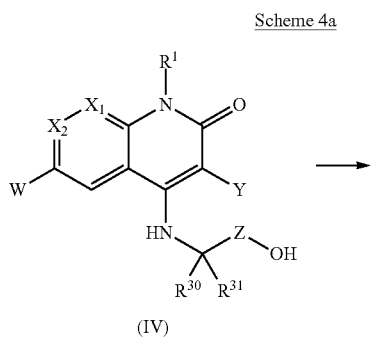

(IV)

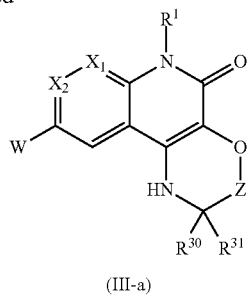

(III-a)

where W is as previously defined, Y is a halogen such as Br or I, and $R^1$, $R^{30}$, $R^{31}$, $X^1$, $X^2$ and Z is an appropriately substituted (1-2C)alkylene group, for example (—$CH_2$—), (—$CH_2CH_2$—), (—$CF_2CH_2$) or (—CH(Me)$CH_2$—).

Cyclised compounds (III-a) can be prepared by the intramolecular cyclisation of halogenated compounds (IV). This reaction can be carried out at elevated temperature (such as 60° C.) in a suitable solvent such as DMSO, DMF, 1,2-dichloroethane (DCE), 1,2-dimethoxyethane (DME) or THF (preferably in THF) in the presence of a base (e.g. potassium tert-butoxide or lithium tert-butoxide (preferably lithium tert-butoxide)). Alternative reaction conditions include the use of a transition metal catalyst (such as copper(I) iodide), combined with a suitable ligand (such as 1,10-phenanthroline), in the presence of a base (such as cesium carbonate) at elevated temperature, using a suitable solvent (such as NMP).

Halogenated compounds (IV) may be prepared as shown in Scheme 5.

Scheme 4b

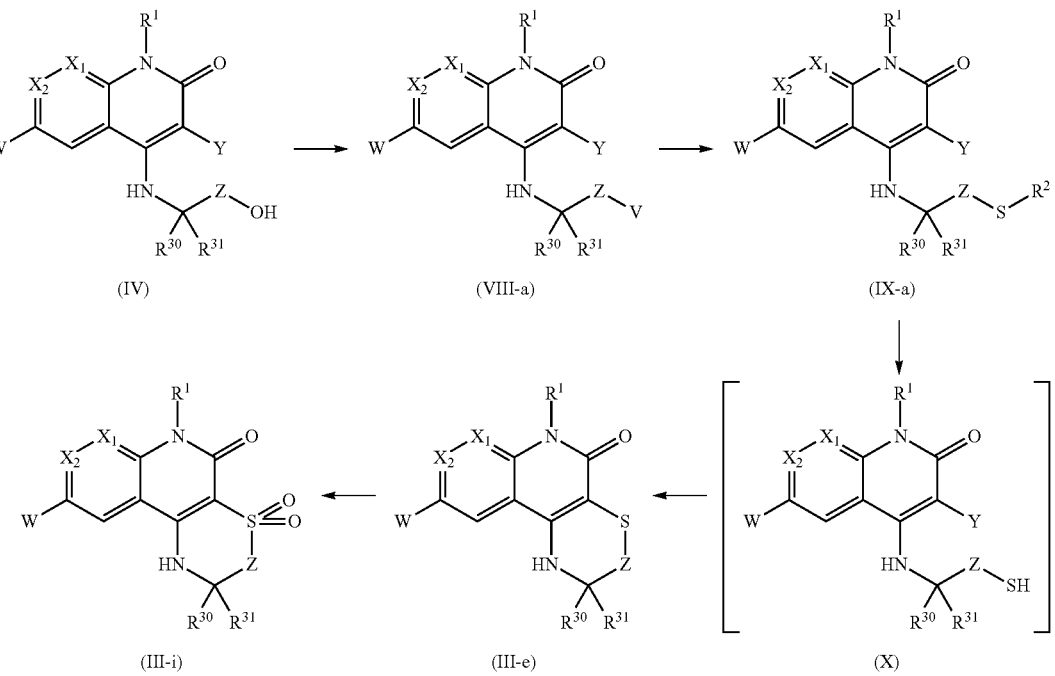

where V is a halogen such as Cl, Br, I or a suitable alternative such as OTs, $R^2$ is a suitable protecting group such as acetate, Y is a halogen such as Br or I and $R^1$, $R^{30}$, $R^{31}$, $X_1$, $X_2$ are suitable groups chosen from those defined previously, and Z is an appropriately substituted linker as defined previously.

The oxidation of sulfide compounds (III-e) to sulfone compounds (III-i) may be carried out by numerous methods which are well known in the art. For example, oxidation can be carried out using a suitable oxidising agent such as mCPBA, in an appropriate solvent or mixture of solvents such as dichloromethane/acetonitrile, at low (such as 0° C.), or ambient temperatures. Compound (III-e) can be formed by thiol deprotection of IX-a followed by in situ displacement of Y at the 3-position of the quinolinone (X). Suitable conditions for this transformation include the use of an additive (such as sodium hydroxide) in an appropriate solvent (such as methanol) at ambient temperature. Protected thiol (IX-a) can be formed from the displacement of leaving group V. Suitable conditions for this transformation include the use of elevated temperature (such as 50° C.) in an appropriate solvent (such as DMF). Various additives (such as sodium iodide) may also be used. Alkylating agent (VIII-a) can be formed from the corresponding alcohol (IV). Various conditions are known in the art for this activation of an alcohol; suitable methods include tosylation with tosyl chloride in pyridine at ambient temperature. Compound (IV) can be prepared as described in Scheme 5.

a hydrogen atmosphere, or alternatively by "transfer hydrogenation" using a reagent such as ammonium formate or triethylsilane. An alternative method uses tin(II) chloride in an appropriate solvent or solvent mixture, such as ethanol and trifluoroethanol, at elevated temperatures such as 120° C. using conventional or microwave heating. Other approaches are known in the art such as iron or zinc metal mediated reductions. In situ cyclisation to compounds (III-f) may occur spontaneously during the reduction step or with the addition of an additive (such as DIPEA) at ambient temperature. Nitro compound (VIII-b) can be formed from the corresponding alcohol (V-b). Various conditions are known in the art for this activation of an alcohol; suitable methods include tosylation with tosyl chloride in DCM at ambient temperature with the use of an appropriate base (such as triethylamine). Various additives (such as DMAP) may also be used. Further functionalisation of the C3-nitrogen may be carried out by numerous methods which are well known in the art to prepare compound (III-g).

Scheme 4c

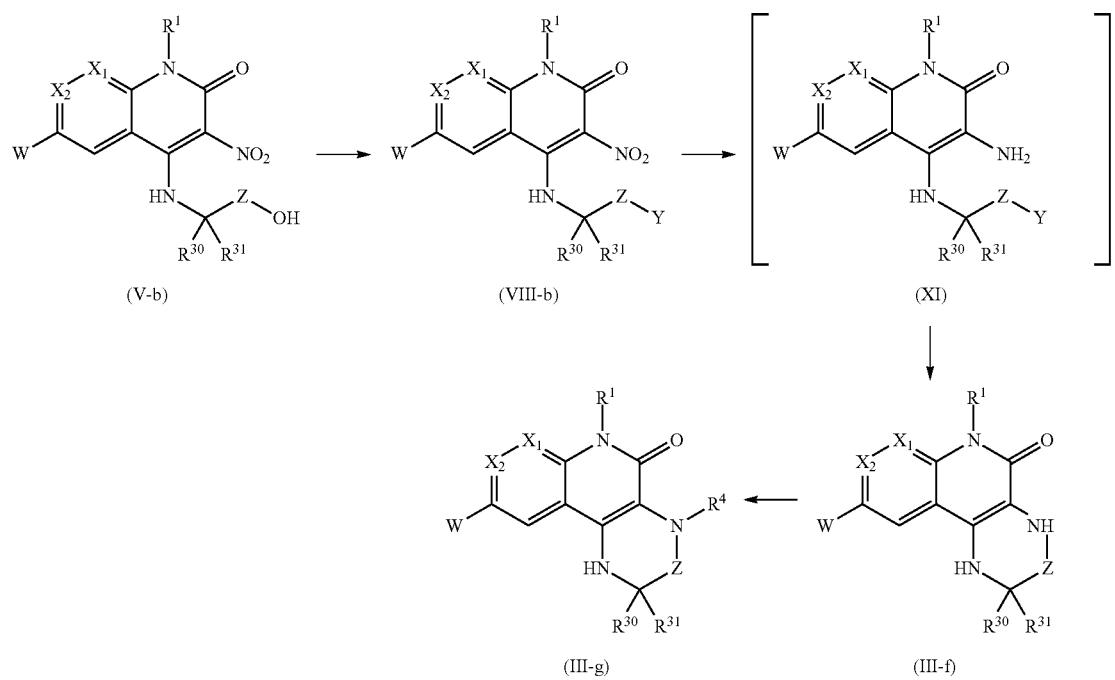

where W is as previously defined, Y is a halogen such as Cl, Br, I or a suitable alternative such as OTs and $R^1$, $R^{30}$, $R^{31}$, $X_1$, $X_2$ are suitable groups chosen from those defined previously, $R^4$ is (1-2C)alkyl, cyclopropyl, or (1-2C)haloalkyl, and Z is an appropriately substituted linker as defined previously.

The reduction of nitro compounds (VIII-b) to intermediate aromatic amines (XI) may be carried out by numerous methods which are well known in the art. Hydrogenation can be carried out in the presence of a metal catalyst such as palladium, often in the form of palladium on carbon, in an appropriate solvent or mixture of solvents such as ethanol, methanol, ethyl acetate or ethanol/NMP at ambient or elevated temperature (such as 60-75° C.) using conventional or microwave heating. These reactions are carried out under Compound (V-b) can be prepared as described in Scheme 6b.

Scheme 5

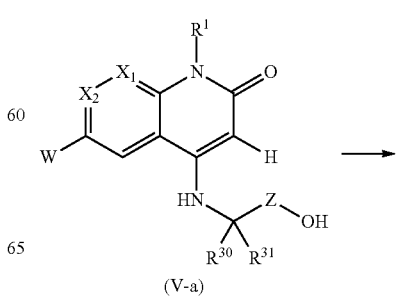

(V-a)

-continued

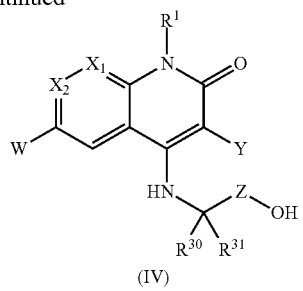

(IV)

where W is as previously defined, Y is a halogen such as Br or I, and $R^1$, $R^{30}$, $R^{31}$, $X^1$, $X^2$, suitable groups chosen from those defined previously and Z is an appropriately substituted linker as defined previously.

Preparation of compound (IV) may be carried out by the halogenation of compounds (V-a). This reaction can be carried out at a range of temperatures (such as 0° C., rt or 60° C.) in a suitable solvent or solvent mixture such as DCM, methanol/water with an appropriate halogenation reagent such as N-bromosuccinimide or iodine. Various additives such as acids (e.g. TFA) may be used.

Compounds (V-a) may be prepared as shown in Scheme 6a.

Scheme 6a

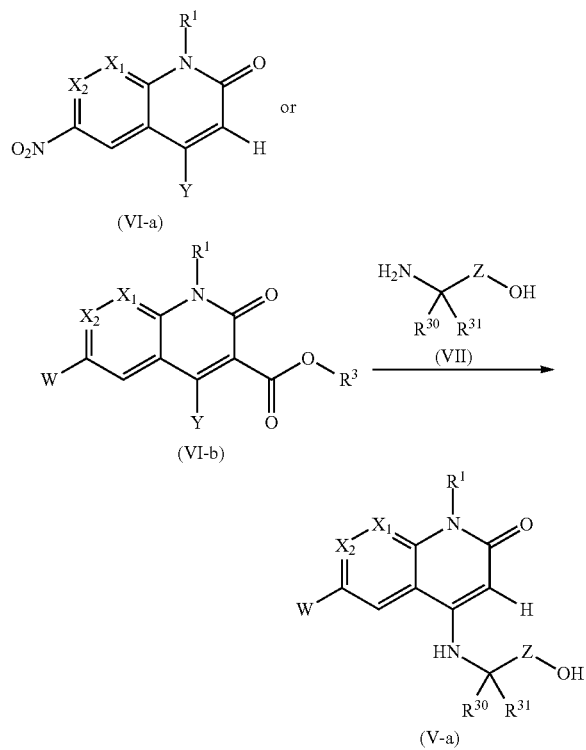

where Y is a halogen such as Cl, Br, I or a suitable alternative such as OTf, $R^3$ is a small alkyl such as methyl or ethyl, and $R^1$, $R^{30}$, $R^{31}$, $X_1$, $X_2$ are suitable groups chosen from those defined previously and Z is an appropriately substituted linker as defined previously.

Nitro compounds (V) can be prepared by the reaction of amino-alcohols (VII) with halo-aromatic or equivalent (VI-a). This reaction can be carried out at elevated temperatures (such as 80-200° C.) in a suitable solvent or solvent mixture such as NMP, NMP/THF or using the amine as solvent. Various additives such as bases (e.g DIPEA, triethylamine) and nucleophilic catalysts (e.g. DMAP) may be used. For less nucleophilic and more sterically hindered amines, alternative conditions may be required. For example, metal catalysed amination may be employed, using a metal source and ligand. Conditions for this type of reaction are known in the literature and include the use of palladium acetate and BINAP as described in Naik et al., *J. Med. Chem.* 2014, 57, 5419. Reactions are typically carried out using a base such as cesium carbonate in an appropriate solvent or solvent mixture such as toluene, again at elevated temperatures. Alternatively, use of an ester functionality (VI-b) can be used to aid the halogen displacement. Displacement of Y by (VII) is carried out at elevated temperature (such as 90-160° C.) in a suitable solvent such as NMP, MeCN or THF, typically using a base such as DIPEA. Removal of the ester group can be carried out by known methods, such as the addition of lithium chloride or sodium hydroxide to the reaction mixture and further heating (e.g. at 90-160° C.). Microwave or conventional heating may be employed for the above reactions.

Amino-alcohols (VII) were obtained from commercial suppliers or prepared by methods which are known in the art. Compounds (VI-a) and (VI-b) may be prepared as shown in Scheme 10a-b.

Scheme 6b

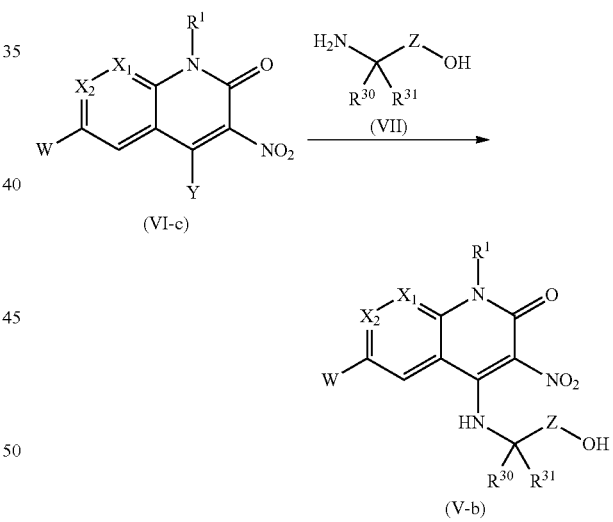

where W is as previously defined, Y is a halogen such as Cl, Br, I or a suitable alternative such as OTf and $R^1$, $R^{30}$, $R^{31}$, $X_1$, $X_2$ are suitable groups chosen from those defined previously and Z is an appropriately substituted linker as defined previously.

Compounds (V-b) can be prepared by the reaction of amino-alcohols (VII) with halo-aromatic or equivalent (VI-c). This reaction can be carried out at elevated temperatures (such as 140° C.) in a suitable solvent (such as NMP) with the use of an appropriate base (such as DIPEA). Amino-alcohols (VII) were obtained from commercial suppliers or prepared by methods which are known in the art. Compounds (VI-c) may be prepared as shown in Scheme 10b.

Scheme 7a

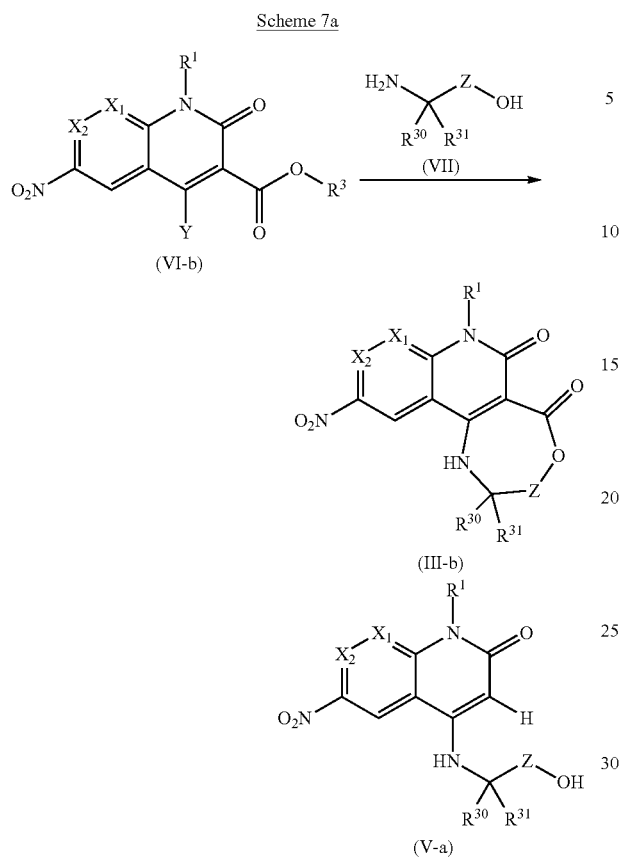

where Y is a halogen such as Cl, Br, I or a suitable alternative such as OTf, $R^3$ is a small alkyl such as methyl or ethyl, and $R^1$, $R^{30}$, $R^{31}$, $X_1$, $X_2$ are suitable groups chosen from those defined previously and Z is an appropriately substituted linker as defined previously.

Nitro compounds (III-b) can be prepared by the reaction of amino-alcohols (VII) with compound (VI-b). Displacement of Y by (VII) is carried out at elevated temperature (such as 160° C.) in a suitable solvent such as NMP, typically using a base such as DIPEA. Cyclisation to lactone (III-b) can be carried out with the addition of an additive, such as lithium chloride, to the reaction mixture and further heating (e.g. at 160° C.). Microwave or conventional heating may be employed for the above reactions. This procedure may form mixtures of compounds (III-b) and (V-a) which can be separated by standard methods.

Amino-alcohols (VII) were obtained from commercial suppliers or prepared by methods which are known in the art. Compounds (VI-b) may be prepared as shown in Scheme 10b.

Scheme 7b

where W is as previously defined, Y are a halogen such as Cl, Br, I or a suitable alternative such as OTf, $R^2$ is a suitable protecting group such as Boc, $R^3$ is a small alkyl such as methyl or ethyl, $R^4$ is H, (1-2C)alkyl, cyclopropyl, or (2C) haloalkyl, and $R^1$, $R^{30}$, $R^{31}$, $X_1$, $X_2$ are suitable groups chosen from those defined previously and Z is an appropriately substituted methylene linker as defined previously.

Cyclic lactam compounds (III-h) can be prepared in a one-pot procedure from compound (VI-b). Compounds (V-d) can be prepared by the reaction of a suitably protected diamine (XII) with a halo-aromatic (or equivalent) with an ester functionality (VI-b). Displacement of Y by diamine (XII) is carried out at elevated temperature (such as 100° C.) in a suitable solvent such as acetonitrile, typically using a base such as DIPEA. In situ amine deprotection can be achieved with the addition of an acid (such as HCl in dioxane) at elevated temperatures (such as 75° C.). Cyclisation can then be achieved with the addition of an excess of base (such as DIPEA) at elevated temperatures (such as 75° C.).

Suitably protected diamines (XII) were obtained from commercial suppliers or prepared by methods which are known in the art. Compounds (VI-b) may be prepared as shown in Scheme 10b.

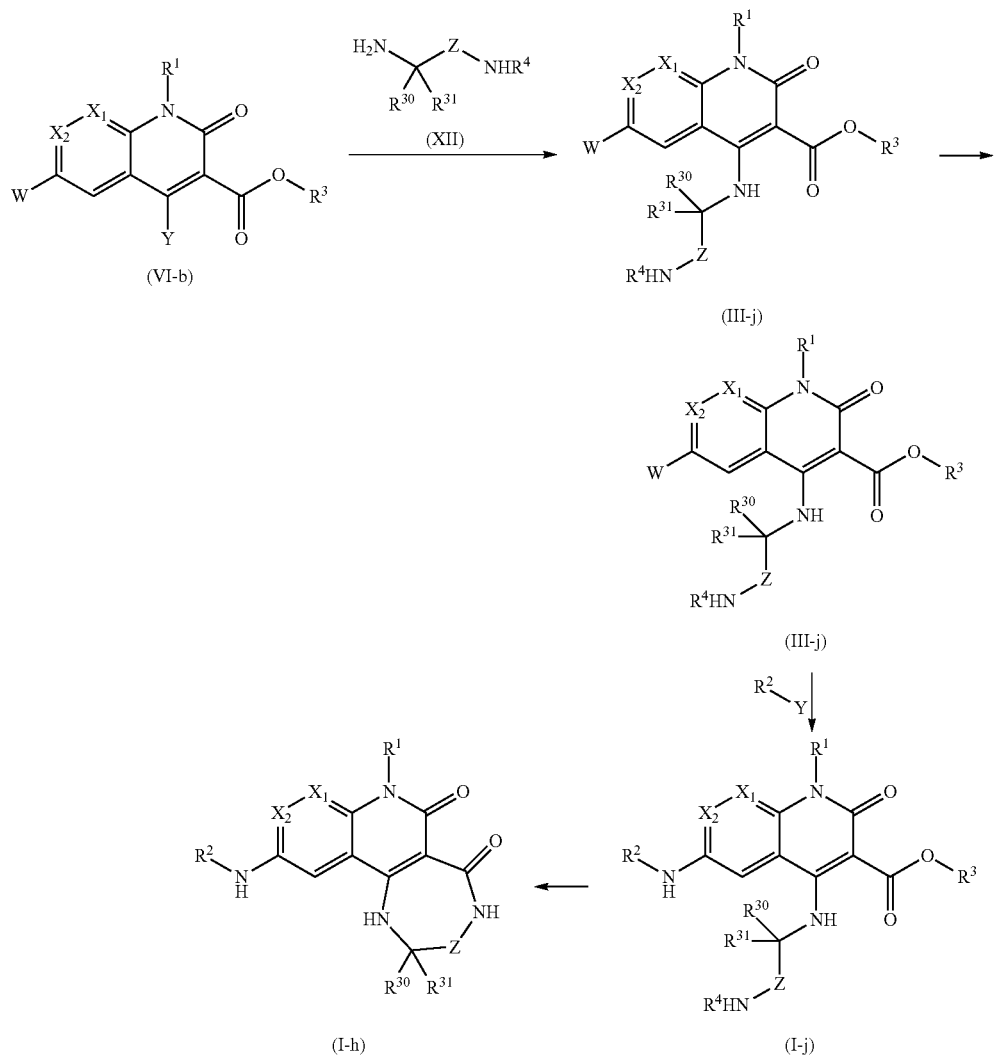

where W is as previously defined, Y is a halogen such as Cl, Br, I or a suitable alternative such as OTf, $R^4$ is a suitable protecting group such as Boc, $R^3$ is a small alkyl such as methyl or ethyl, and $R^1$, $R^2$, $R^{30}$, $R^{31}$, $X_1$, $X_2$ are suitable groups chosen from those defined previously and Z is an appropriately substituted methylene linker as defined previously.

An alternative route to cyclic lactam compounds (l-h) is shown in Scheme 7c. Compounds (III-j) can be prepared by the reaction of suitably protected diamines (XII) with use of halo-aromatic or equivalent (VI-b). Displacement of Y by diamine (XII) can be carried out at elevated temperature (such as 100° C.) in a suitable solvent, such as THF, typically using a base such as DIPEA. The conversion of (III-j) to (II-j) can be carried out using conditions described previously in Scheme 2a. The conversion of (II-j) to (l-j) can be carried out using conditions described previously in Scheme 1. Formation of cyclic lactam compounds (l-h) can be achieved in a one-pot procedure from compounds (l-j). Amine deprotection can be achieved in a suitable solvent, such as THF) with the addition of an acid (such as HCl in dioxane) at elevated temperatures (such as 70° C.). In situ cyclisation can then be achieved with the addition of an excess of base (such as triethylamine) at elevated temperatures (such as 70° C.).

Suitably protected diamines (XII) were obtained from commercial suppliers or prepared by methods which are known in the art. Compounds (VI-b) may be prepared as shown in Scheme 10b.

Scheme 8

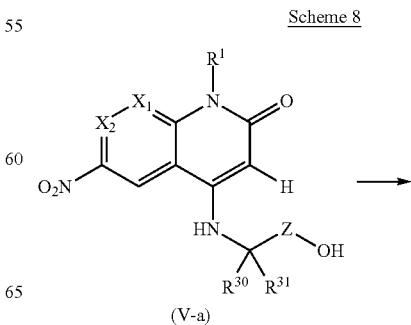

(V-a)

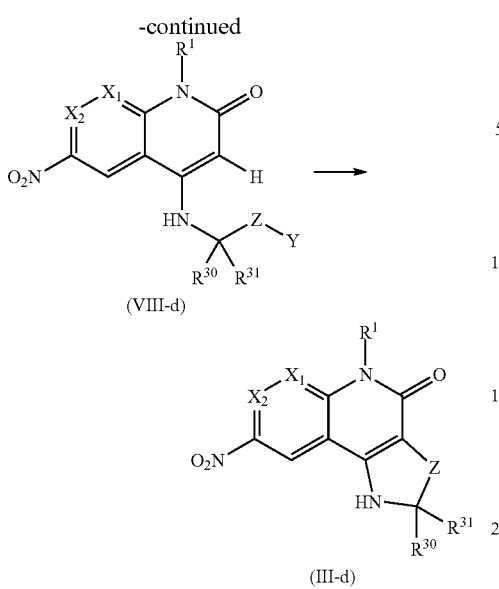

(VIII-d)

(III-d)

where Y is a halogen such as Cl, Br, I or a suitable alternative such as OTs, and $R^1$, $R^{30}$, $R^{31}$, $X_1$, $X_2$ are suitable groups chosen from those defined previously, and Z is an appropriately substituted ethylene linker as defined previously.

Compound (III-d) can be formed by cyclisation at the 3-position of quinolinone, displacing the leaving group Y. Suitable conditions for this transformation include the use of elevated temperatures (such as 160° C.) in an appropriate solvent (such as NMP) with the addition of a base (such as DIPEA). Alkylating agent (VIII-d) can be formed from the corresponding alcohol (V-a). Various conditions are known in the art for this activation of an alcohol; suitable methods include tosylation with tosyl chloride in pyridine/DCM at ambient temperature. Compound (V-a) can be prepared as described in Scheme 6a.

Scheme 9

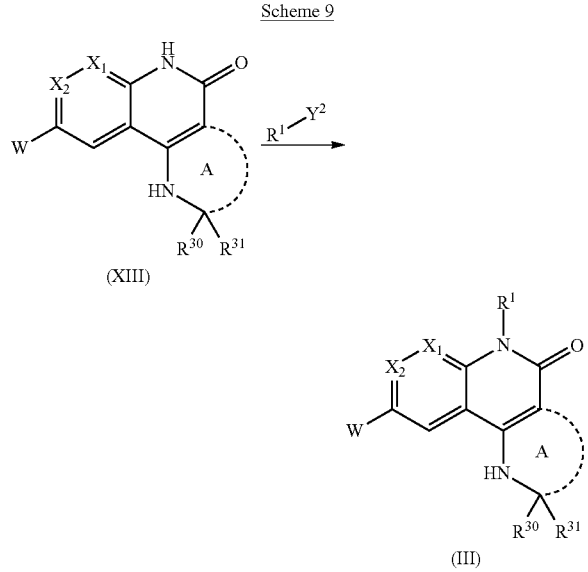

(XIII)

(III)

where $Y^2$ is a halogen such as Cl, Br, I or a suitable alternative such as OTf, W is as previously defined, and $R^1$, $R^{30}$, $R^{31}$, $X^1$, $X^2$, Ring A are suitable groups chosen from those defined previously.

Late-stage introduction of the $R^1$ group onto compounds (XIII) may be carried out by alkylation to form compounds (III). Alkylation conditions are well known in the art, and include the use of an alkyl halide or equivalent ($R^1$—$Y^2$, such as bromomethyl cyclopropane for $R^1$=$CH_2cPr$) in an appropriate solvent such as DMF, in the presence of a base such as sodium hydride, or cesium carbonate, at ambient or elevated temperature (e.g. 80° C.). Alkylation may occur on oxygen or on nitrogen; choice of reaction conditions may modulate selectivity, and these regioisomers can typically be separated using known methods. Compound (XIII) can be prepared as described in Schemes 4a-c and 7a-b where $R^1$=H. Further manipulation of compounds (III) by known methods can be used to modify $R^1$.

Scheme 10a

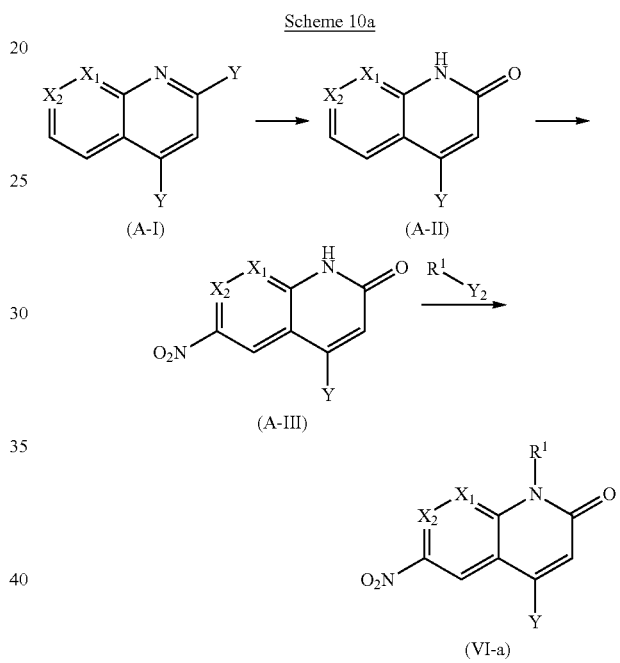

(A-I)   (A-II)

(A-III)

(VI-a)

where Y are halogens such as Cl and $R^1$, $X_1$, $X_2$ are suitable groups chosen from those defined previously.

Introduction of $R^1$ group onto compounds (A-III) may be carried out by alkylation to form compounds (VI-a). Alkylation conditions are well known in the art, and include the use of an alkyl halide or equivalent ($R^1$—$Y^2$, such as iodomethane for $R^1$=Me) in an appropriate solvent such as DMF, in the presence of a base such as sodium hydride, or cesium carbonate, at ambient or elevated temperature (e.g. 80° C.). Alkylation may occur on oxygen or on nitrogen; choice of reaction conditions may modulate selectivity, and these regioisomers can typically be separated using known methods. Compounds (A-III) are commercially available or can be prepared by known methods, such as the nitration of compounds (A-II) using conditions including those shown in van Oeveren et al., *Bioorg. Med. Chem. Lett.* 2007, 17, 1527. Compounds (A-II) are commercially available or can be prepared by known methods, such as hydrolysis of dihalo derivatives (A-I) using conditions including those shown in Naik et al., *J. Med. Chem.* 2014, 57, 5419.

Scheme 10B

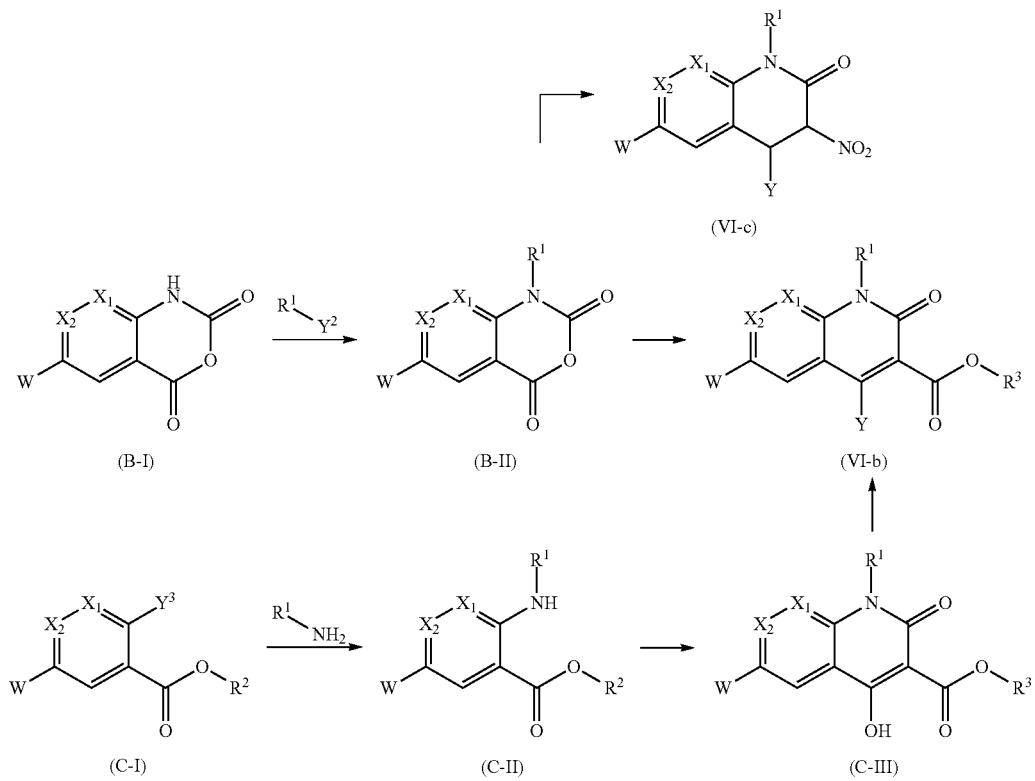

where W is as previously defined, Y and $Y^3$ are independently chosen from halogens such as F, Cl, Br, I or a suitable alternative such as OTf or OTs, $Y^2$ independently chosen from halogens such as Cl, Br, I or a suitable alternative such as OTf or OTs, $R^2$ and $R^3$ are small alkyl such as methyl or ethyl, and $R^1$, $X_1$, $X_2$ are suitable groups chosen from those defined previously.

Introduction of $R^1$ group onto compounds (B-I) may be carried out by alkylation to form compounds (B-II). Alkylation conditions are well known in the art, and include the use of an alkyl halide or equivalent ($R^1$—$Y^2$, such as iodomethane for $R^1$=Me) in an appropriate solvent such as DMF, in the presence of a base such as sodium hydride, or cesium carbonate, at ambient or elevated temperature (e.g. 80° C.). Alkylation may occur on oxygen or on nitrogen; choice of reaction conditions may modulate selectivity, and these regioisomers can typically be separated using known methods. Compounds (VI-b) and (VI-c) may be prepared by a multistep process starting from compound (B-II), by analogy to a process described in the literature (Coppola et al., *Synthesis* 1981, 391; Stadlbauer et al., *J. Het. Chem.* 1998, 35, 627; Tomassoli et al., *Eur. J. Med. Chem.* 2011, 46, 1; Ohashi et al., *Bioorg. Med. Chem.* 2012, 20, 5496; Tomassoli et al., *Monatsh. Chem.* 2016, 147, 1069; Gaeta et al., WO 02/094203).

Alternatively, introduction of an $R^1$ group onto compounds (C-I) may be carried out with the displacement of the $Y^3$ group by a substituted amine. $S_NAr$ conditions are well known in the art, and include the use of a substituted amine ($R^1$—$NH_2$, such as methylamine for $R^1$=Me) in an appropriate solvent such as THF, at ambient or elevated temperature (e.g. 40° C.). Compounds (C-III) can be formed by one-pot amide bond formation/cyclisation of compounds (C-II). Suitable conditions for this transformation include the use of elevated temperatures (such as 60° C.) in an appropriate solvent (such as DCM) with the addition of a base (such as triethylamine) and the suitable acylating reagent (e.g. ethyl 3-chloro-3-oxopropanoate). Compounds (C-III) can be converted to the corresponding halide (VI-b) using conditions that are well known in the art, and include the use of $POCl_3$ at elevated temperature (e.g. 80° C.).

Biological Activity

The biological assays described in the Examples section herein may be used to measure the pharmacological effects of the compounds of the present invention.

Although the pharmacological properties of the compounds of Formula I vary with structural change, as expected, the compounds of the invention were found to be active in the HTRF in vitro assay, the NanoBRET cell assay and in some cases also in the SUDHL4 degradation assay described in the Examples section.

In general, as illustrated by the Example compound data in Table 1, the compounds of the invention demonstrate an $IC_{50}$ of 2.5 µM or less, which corresponds to a $pIC_{50}$ of 5.6 or more, in the HTRF assay described in the Examples section. Preferred compounds of the invention demonstrate an $IC_{50}$ of 500 nM or less, which corresponds to a $pIC_{50}$ of 6.3 or more, or an $IC_{50}$ of 250 nM or less, which corresponds to a $pIC_{50}$ of 6.6 or more. The more preferred compounds of the invention demonstrate an $IC_{50}$ of 100 nM or less, which corresponds to a $pIC_{50}$ of 7.0 or more. The most preferred compounds of the invention demonstrate an $IC_{50}$ of 10 nM or less, which corresponds to a $pIC_{50}$ of 8.0 or more.

In the NanoBRET cell assay described herein in the Examples section, as illustrated by the Example compound data in Table 2, the compounds of Formula I typically demonstrate a $pIC_{50}$ of 5.0 or more (preferably 6.0 or more). The most preferred compounds of the invention demonstrate a $pIC_{50}$ of 7.0 or more.

In the SUDHL4 degradation assay described herein in the Examples section, as illustrated by the Example compound data in Table 3, the compounds of Formula I may also demonstrate a $pIC_{50}$ of 6.0 or more (preferably 6.5 or more).

The following data were generated for the Examples:
Table 1

TABLE 1

| Example | HTRF avg $pIC_{50}$ (1 nM) |
|---|---|
| 1a | 6.89 |
| 1b | 5.97 |
| 1c | 6.32 |
| 1d | 7.41 |
| 1e | 6.07 |
| 1f | 6.24 |
| 1g | 6.30 |
| 1h | 5.99 |
| 1i | 5.97 |
| 1j | 6.67 |
| 1k | 5.91 |
| 1l | 6.22 |
| 1m | 6.20 |
| 1n | 5.70 |
| 1o | 6.14 |
| 1p | 5.67 |
| 1q | 8.35 |
| 1r | 6.51 |
| 1s | 7.83 |
| 1t | 6.00 |
| 1u | 8.15 |
| 1v | 8.58 |
| 2a | 7.26 |
| 2b | 8.05 |
| 3a | 6.88 |
| 3b | 7.32 |
| 4a | 6.21 |
| 4b | 6.70 |
| 4c | 6.85 |
| 4d | 7.99 |
| 5a | 7.03 |
| 5b | 6.09 |
| 5c | 6.43 |
| 5d | 6.83 |
| 5e | 6.18 |
| 5f | 6.07 |
| 5g | 6.88 |
| 5h | 7.01 |
| 5i | 6.70 |
| 5j | 5.79 |
| 5k | 7.22 |
| 5l | 7.49 |
| 5m | 6.93 |
| 5n | 7.97 |
| 5o | 7.64 |
| 5p | 6.24 |
| 5q | 7.63 |
| 5r | 7.41 |
| 5s | 7.13 |
| 5t | 6.61 |
| 5u | 8.08 |
| 6a | 7.01 |
| 6b | 6.78 |
| 6c | 6.71 |
| 6d | 6.67 |
| 7a | 6.72 |
| 8a | 6.97 |
| 8b | 6.85 |
| 8c | 6.80 |
| 8d | 6.78 |
| 8e | 6.69 |
| 8f | 6.67 |
| 8g | 6.55 |
| 8h | 6.47 |
| 8i | 6.23 |
| 8j | 6.65 |
| 8k | 6.38 |
| 8l | 6.36 |
| 8m | 6.28 |
| 8n | 6.19 |
| 8o | 6.43 |
| 8p | 6.56 |
| 8q | 6.32 |
| 9a | 5.66 |
| 9b | 6.57 |
| 10a | 5.84 |
| 11a | 8.81 |
| 11b | 8.16 |
| 11c | 8.93 |
| 12a | 8.82 |
| 12b | 7.80 |
| 12c | 8.01 |
| 12d | 7.74 |
| 12e | 6.93 |
| 12f | 7.96 |
| 12g | 7.54 |
| 12h | 7.93 |
| 12i | 7.81 |
| 12j | 7.78 |
| 12k | 7.04 |
| 12l | 6.99 |
| 12m | 6.84 |
| 12n | 7.94 |
| 12o | 7.74 |
| 12p | 8.34 |
| 12q | 8.65 |
| 12r | 8.49 |
| 12s | 8.47 |
| 12t | 8.46 |
| 12u | 8.58 |
| 12v | 8.86 |
| 12w | 8.73 |
| 12x | 8.20 |
| 12y | 7.73 |
| 12z | 7.52 |
| 13a | 8.68 |
| 13b | 8.59 |
| 13c | 8.75 |
| 13d | 8.70 |
| 13e | 8.60 |
| 13f | 8.66 |
| 13g | 8.50 |
| 13h | 8.43 |
| 13i | 8.45 |
| 13j | 8.60 |
| 14a | 6.74 |
| 14b | 6.98 |
| 15a | 8.12 |
| 15b | 7.51 |
| 15c | 7.55 |
| 16a | 7.17 |
| 17a | 7.15 |
| 18a | 6.58 |

TABLE 2

| Example | NanoBRET cell avg $pIC_{50}$ |
|---|---|
| 1a | 5.62 |
| 1b | 5.26 |
| 1c | 5.06 |
| 1d | 6.69 |
| 1f | 5.29 |
| 1g | 5.60 |
| 1h | 5.32 |
| 1j | 5.57 |

TABLE 2-continued

| Example | NanoBRET cell avg pIC$_{50}$ |
|---|---|
| 1q | 7.52 |
| 1r | 5.99 |
| 1s | 7.20 |
| 1u | 5.51 |
| 1v | 7.83 |
| 3a | 5.32 |
| 3b | 6.19 |
| 4a | 5.31 |
| 4b | 5.48 |
| 4c | 6.15 |
| 5a | 6.21 |
| 5c | 5.33 |
| 5d | 5.85 |
| 5e | 5.28 |
| 5f | 5.21 |
| 5g | 5.69 |
| 5h | 5.76 |
| 5k | 6.95 |
| 5l | 6.92 |
| 5n | 7.44 |
| 5o | 7.05 |
| 5q | 7.01 |
| 5r | 7.36 |
| 5s | 6.63 |
| 5u | 7.54 |
| 7a | 4.72 |
| 8a | 5.02 |
| 8b | 5.66 |
| 8c | 4.75 |
| 8f | 5.16 |
| 8g | 4.87 |
| 8m | 4.50 |
| 8o | 5.03 |
| 8p | 4.59 |
| 9b | 5.70 |
| 11a | 8.30 |
| 11b | 7.49 |
| 11c | 8.19 |
| 12a | 7.73 |
| 12b | 7.22 |
| 12d | 7.06 |
| 12f | 6.53 |
| 12g | 6.11 |
| 12h | 6.84 |
| 12i | 6.83 |
| 12j | 6.63 |
| 12u | 7.83 |
| 12v | 8.08 |
| 12w | 7.96 |
| 12x | 6.84 |
| 15a | 7.54 |

TABLE 3

| Example | SUDHL4 avg pDC$_{50}$ |
|---|---|
| 5e | 6.22 |
| 5f | 6.63 |
| 5i | 6.79 |
| 5m | 6.84 |
| 5p | 6.87 |
| 5t | 6.54 |
| 8c | 6.78 |
| 8g | 6.50 |
| 12c | 7.83 |

Pharmaceutical Compositions

According to a further aspect of the invention there is provided a pharmaceutical composition which comprises a compound of the invention as defined hereinbefore, or a pharmaceutically acceptable salt, hydrate or solvate thereof, in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present invention for use in therapy is an amount sufficient to treat or prevent a proliferative condition referred to herein, slow its progression and/or reduce the symptoms associated with the condition.

The amount of active ingredient that is combined with one or more excipients to produce a single dosage form will necessarily vary depending upon the individual treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the formula I will naturally vary according to the nature and severity of the conditions, the age and sex of the animal or patient and the route of administration, according to well-known principles of medicine.

In using a compound of the invention for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration may also be suitable, particularly in tablet form. Typically, unit dosage forms will contain about 0.5 mg to 0.5 g of a compound of this invention.

Therapeutic Uses and Applications

The present invention provides compounds that function as inhibitors of BCL6 activity.

The present invention therefore provides a method of inhibiting BCL6 activity in vitro or in vivo, said method comprising contacting a cell with an effective amount of a compound, or a pharmaceutically acceptable salt, hydrate or solvate thereof, as defined herein.

The present invention also provides a method of treating a disease or disorder in which BCL6 activity is implicated in a patient in need of such treatment, said method comprising administering to said patient a therapeutically effective amount of a compound, or a pharmaceutically acceptable salt, hydrate or solvate thereof, or a pharmaceutical composition as defined herein.

The present invention provides a method of inhibiting cell proliferation, in vitro or in vivo, said method comprising contacting a cell with an effective amount of a compound, or a pharmaceutically acceptable salt, hydrate or solvate thereof, as defined herein.

The present invention provides a method of treating a proliferative disorder in a patient in need of such treatment, said method comprising administering to said patient a therapeutically effective amount of a compound, or a pharmaceutically acceptable salt, hydrate or solvate thereof, or a pharmaceutical composition as defined herein.

The present invention provides a method of treating cancer in a patient in need of such treatment, said method comprising administering to said patient a therapeutically effective amount of a compound, or a pharmaceutically acceptable salt, hydrate or solvate thereof, or a pharmaceutical composition as defined herein.

The present invention provides a compound, or a pharmaceutically acceptable salt, hydrate or solvate thereof, or a pharmaceutical composition as defined herein for use in therapy.

The present invention provides a compound, or a pharmaceutically acceptable salt, hydrate or solvate thereof, or a pharmaceutical composition as defined herein for use in the treatment of a proliferative condition.

The present invention provides a compound, or a pharmaceutically acceptable salt, hydrate or solvate thereof, or a pharmaceutical composition as defined herein for use in the treatment of cancer. In a particular embodiment, the cancer is human cancer.

The present invention provides a compound, or a pharmaceutically acceptable salt, hydrate or solvate thereof, as defined herein for use in the inhibition of BCL6 activity (i.e. in the inhibition of BCL6 transcriptional repression and/or co-repressor binding).

Certain compounds of the present invention have been found to bind to BCL6 and initiated the degradation of BCL6. Thus, the present invention also provides a compound, or a pharmaceutically acceptable salt, hydrate or solvate thereof, as defined herein for use in the degradation of BCL6.

The present invention provides a compound, or a pharmaceutically acceptable salt, hydrate or solvate thereof, as defined herein for use in the treatment of a disease or disorder in which BCL6 activity is implicated.

The present invention provides a use of a compound, or a pharmaceutically acceptable salt, hydrate or solvate thereof, as defined herein in the manufacture of a medicament for the treatment of a proliferative condition.

The present invention provides a use of a compound, or a pharmaceutically acceptable salt, hydrate or solvate thereof, as defined herein in the manufacture of a medicament for the treatment of cancer. Suitably, the medicament is for use in the treatment of human cancers.

The present invention provides a use of a compound, or a pharmaceutically acceptable salt, hydrate or solvate thereof, as defined herein in the manufacture of a medicament for the inhibition of BCL6 activity (i.e. in the inhibition of BCL6 transcriptional repression and/or co-repressor binding).

The present invention provides a use of a compound, or a pharmaceutically acceptable salt, hydrate or solvate thereof, as defined herein in the manufacture of a medicament for the degradation of BCL6.

The present invention provides a use of a compound, or a pharmaceutically acceptable salt, hydrate or solvate thereof, as defined herein in the manufacture of a medicament for the treatment of a disease or disorder in which BCL6 activity is implicated.

The term "proliferative disorder" and "proliferative condition" are used interchangeably herein and pertain to an unwanted or uncontrolled cellular proliferation of excessive or abnormal cells which is undesired, such as, neoplastic or hyperplastic growth, whether in vitro or in vivo. Examples of proliferative conditions include, but are not limited to, pre-malignant and malignant cellular proliferation, including but not limited to, malignant neoplasms and tumours, cancers (including breast cancer, non-small cell lung cancer (NSCLC) and squamous cell carcinomas (SCC) (including SCC of the head and neck, oesophagus, lung and ovary), leukemias (including acute lymphoblastic leukaemia (ALL) and chronic myeloid leukaemia (CML)), lymphomas (including acute lymphoblastic leukaemia (ALL) and chronic myeloid leukaemia (CML)), psoriasis, bone diseases, fibroproliferative disorders (e.g., of connective tissues), and atherosclerosis. Any type of cell may be treated, including but not limited to, lymphatic, blood, lung, colon, breast, ovarian, prostate, liver, pancreas, brain, and skin.

The anti-cancer effect may arise through one or more mechanisms, including but not limited to, the regulation of cell proliferation, the inhibition of angiogenesis (the formation of new blood vessels), the inhibition of metastasis (the spread of a tumour from its origin), the inhibition of invasion (the spread of tumour cells into neighbouring normal structures), or the promotion of apoptosis (programmed cell death).

The compound of Formula (I), or a pharmaceutically acceptable salt thereof, being an inhibitor of BCL6, has potential therapeutic uses in a variety of BCL6-mediated disease states. BCL6 expression has been linked to a variety of lymphomas (Wagner et al., *British J Haematology*, 2010, 152, 3-12). BCL6 is involved in chromosomal translocations in diffuse large B-cell lymphoma (DLBCL) and inhibitors of BCL6 have been reported to kill DLBCL cells (Cerchietti et al., *Cancer Cell*. 2010, 17, 400-411), primary low grade follicular lymphoma cells (Cardenas et al., *Clin Cancer Res*. 2017, 23(4), 885-893) and Burkitt lymphoma cells (Polo et al., *Nat Med*. 2004, 10, 1329-1335). BCL6 is required for the formation of follicular helper T cells (Hatzi et al., *J Exp Med*. 2015, 212(4), 539-553), which raises the possibility that BCL6 inhibitors may be used to treat angioimmunoblastic T-cell lymphoma (AITL), in which BCL6 is strongly expressed (Cortes & Palomero, *Curr Opin Hematol*, 2016, 23, 434-443).

BCL6 has also been implicated in leukaemia cells which have acquired resistance to tyrosine kinase inhibitors (TKIs). TKIs typically fail to eradicate leukaemia-initiating cells, which may often cause recurrence of leukaemia after initial treatment. BCL6 has been identified as an important component of the TKI drug-resistance pathway in both Ph+ acute lymphoblastic leukaemia (ALL) (Duy et al., *Nature*. 2011, 473, 384-388) and Ph+ chronic myeloid leukaemia (CML) (Hurtz et al., *J Exp Med*. 2011, 208(11), 2163-2174). Inhibitors of BCL6 may therefore be used to treat ALL and CML in combination with a TKI.

Further non-haematological, solid tumours may be treated with an inhibitor of BCL6. BCL6 is amplified in approximately 50% of breast tumours and is expressed in many breast cancer cell lines, including triple negative breast cancer cell lines (Walker et al., *Oncogene*, 2015, 34, 1073-1082). BCL6 is also important for the survival and proliferation of non-small cell lung cancer (NSCLC) cells, primarily due to repression of genes involved in DNA damage repair (Marullo et al., Proc 107$^{th}$ Annual Meeting AACR, 2016, Abstract nr 1271 and Deb et al., Cancer Res., 2017, Apr. 4, doi: 10.1158/0008-5472.CAN-15-3052). BCL6 amplification may also be prevalent in squamous cell carcinomas (SCC) (including SCC of the head & neck, oesophagus, lung and ovary). Furthermore, inhibition of BCL6 has recently been reported to be a suitable therapeutic target for glioma and glioblatoma (Xu et al., Proc. Natl. Acad. Sci. U.S.A, 2017, 114(15), 3981-3986).

According to a further aspect of the specification there is provided a compound of Formula (I), or a pharmaceutically acceptable salt thereof, as defined hereinbefore for use in the treatment of haematological cancers such as lymphomas (including diffuse large B-cell lymphoma (DLBCL), follicular lymphoma (FL), Burkitt lymphoma (BL) and angioimmunoblastic T-cell lymphoma (AITL)), leukaemias (including acute lymphoblastic leukaemia (ALL) and chronic myeloid leukaemia (CML)) and multiple myeloma, and of solid tumours (including glioma, breast cancer, non-small cell lung cancer (NSCLC) and squamous cell carcinomas (SCC) (including SCC of the head and neck, oesophagus, lung and ovary)).

According to a further feature of this aspect of the specification there is provided a compound of Formula (I), or a pharmaceutically acceptable salt thereof, as defined hereinbefore for use in the treatment of lymphomas, including DLBCL, FL, BL and AITL.

According to a further feature of this aspect of the specification there is provided a compound of Formula (I), or a pharmaceutically acceptable salt thereof, as defined hereinbefore for use in the treatment of DLBCL and FL.

According to a further feature of this aspect of the specification there is provided a compound of Formula (I), or a pharmaceutically acceptable salt thereof, as defined hereinbefore for use in the treatment of leukaemias, including ALL and CML.

According to a further feature of this aspect of the specification there is provided a compound of Formula (I), or a pharmaceutically acceptable salt thereof, as defined hereinbefore for use in the treatment of solid tumours, including glioma, breast cancer, NSCLC and SCC.

According to a further feature of this aspect of the specification there is provided a method for treating haematological cancers such as lymphomas (including DLBCL, FL, BL and AITL), leukaemias (including ALL and CML) and multiple myeloma, and of solid tumours (including glioma, breast cancer, NSCLC and SCC (including SCC of the head and neck, oesophagus, lung and ovary)) in a warm-blooded animal such as man that is in need of such treatment, which comprises administering an effective amount of a compound of Formula (I), or a pharmaceutically acceptable salt thereof, as defined hereinbefore.

According to a further feature of this aspect of the specification there is provided a method for treating lymphomas, including DLBCL, FL, BL and AITL, in a warm-blooded animal such as man that is in need of such treatment, which comprises administering an effective amount of a compound of Formula (I), or a pharmaceutically acceptable salt thereof, as defined hereinbefore.

According to a further feature of this aspect of the specification there is provided a method for treating DLBCL and FL, in a warm-blooded animal such as man that is in need of such treatment, which comprises administering an effective amount of a compound of Formula (I), or a pharmaceutically acceptable salt thereof, as defined hereinbefore.

According to a further feature of this aspect of the specification there is provided a method for treating leukaemias, including ALL and CML, in a warm-blooded animal such as man that is in need of such treatment, which comprises administering an effective amount of a compound of Formula (I), or a pharmaceutically acceptable salt thereof, as defined hereinbefore.

According to a further feature of this aspect of the specification there is provided a method for treating solid tumours (including glioma, breast cancer, NSCLC and SCC (including SCC of the head and neck, oesophagus, lung and ovary)), in a warm-blooded animal such as man that is in need of such treatment, which comprises administering an effective amount of a compound of Formula (I), or a pharmaceutically acceptable salt thereof, as defined hereinbefore.

According to a further feature of this aspect of the specification there is provided the use of a compound of Formula (I), or a pharmaceutically acceptable salt thereof, as defined hereinbefore in the manufacture of a medicament for use in the treatment of haematological cancers such as lymphomas (including DLBCL, FL, BL and AITL), leukaemias (including ALL and CML) and multiple myeloma, and of solid tumours (including glioma, breast cancer, NSCLC and SCC (including SCC of the head and neck, oesophagus, lung and ovary)).

According to a further feature of this aspect of the specification there is provided the use of a compound of Formula (I), or a pharmaceutically acceptable salt thereof, as defined hereinbefore in the manufacture of a medicament for use in the treatment of lymphomas, including DLBCL, FL, BL and AITL.

According to a further feature of this aspect of the specification there is provided the use of a compound of Formula (I), or a pharmaceutically acceptable salt thereof, as defined hereinbefore in the manufacture of a medicament for use in the treatment of DLBCL and FL.

According to a further feature of this aspect of the specification there is provided the use of a compound of Formula (I), or a pharmaceutically acceptable salt thereof, as defined hereinbefore in the manufacture of a medicament for use in the treatment of leukaemias, including ALL and CML.

According to a further feature of this aspect of the specification there is provided the use of a compound of Formula (I), or a pharmaceutically acceptable salt thereof, as defined hereinbefore in the manufacture of a medicament for use in the treatment of solid tumours (including glioma, breast cancer, NSCLC and SCC (including SCC of the head and neck, oesophagus, lung and ovary)).

Routes of Administration

The compounds of the invention or pharmaceutical compositions comprising these compounds may be administered to a subject by any convenient route of administration, whether systemically, peripherally or topically (i.e., at the site of desired action).

Routes of administration include, but are not limited to, oral (e.g, by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eye drops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intra-arterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

Combination Therapies

The antiproliferative treatment defined hereinbefore may be applied as a sole therapy or may involve, in addition to the compound of the invention, conventional surgery or radiotherapy or chemotherapy. Such chemotherapy may include one or more of the following categories of anti-tumour agents:—

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), steroid hormones, including progestogens (for example megestrol acetate) and corticosteroids (for example dexamethasone, prednisone and prednisolone), aromatase inhibitors (for example as anastrozole, letrozole, vorazole and exemestane) and inhibitors of 5a-reductase such as finasteride;

(iii) anti-invasion agents [for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; J. Med. Chem., 2004, 47, 6658-6661) and bosutinib (SKI-606), and metalloproteinase inhibitors like marimastat, inhibitors of urokinase plasminogen activator receptor function or antibodies to Heparanase];

(iv) inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB1 antibody cetuximab [Erbitux, C225] and any growth factor or growth factor receptor antibodies disclosed by Stern et al. (Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib (BAY 43-9006), tipifarnib (R115777) and lonafarnib (SCH66336)), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as vandetanib (ZD6474), vatalanib (PTK787), sunitinib (SU11248), axitinib (AG-013736), pazopanib (GW 786034) and 4-(4-fluoro-2-methylindol-5-yloxy)-6-methoxy-7-(3-pyrrolidin-1-ylpropoxy) quinazoline (AZD2171; Example 240 within WO 00/47212), compounds such as those disclosed in International Patent Applications WO97/22596, WO 97/30035, WO 97/32856 and WO 98/13354 and compounds that work by other mechanisms (for example linomide, inhibitors of integrin αvβ3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) an endothelin receptor antagonist, for example zibotentan (ZD4054) or atrasentan;

(viii) antisense therapies, for example those which are directed to the targets listed above, such as ISIS 2503, an anti-ras antisense;

(ix) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (x) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

In a particular embodiment, the antiproliferative treatment defined hereinbefore may involve, in addition to the compound of the invention, conventional surgery or radiotherapy or chemotherapy, wherein the chemotherapy may include one or more anti-tumour agents selected from procarbazine, carmustine, lomustine, irinotecan, temozolomide, cisplatin, carboplatin, methotrexate, etoposide, cyclophosphamide, ifosfamide, and vincristine.

In another particular embodiment, the antiproliferative treatment defined hereinbefore may involve, in addition to the compound of the invention, conventional surgery or radiotherapy or chemotherapy, wherein the chemotherapy may include one or more chemotherapeutic agents selected from a BCL-2 family inhibitor (e.g. Venetoclax and/or navitoclax), a BTK inhibitor (e.g. Ibrutinib, Acalabrutinib, Tirabrutinib (ONO/GS-4059), BGB-3111 or Spebrutinib (CC-292), a TNF inhibitor (e.g. Lenalidomide) or an EZH2 inhibitor (e.g. Tazmetostat, CPI-1205, PF-06821497, GSK126, GSK343 or EPZ011989).

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a combination for use in the treatment of a cancer (for example a cancer involving a solid tumour) comprising a compound of the invention as defined hereinbefore, or a pharmaceutically acceptable salt, hydrate or solvate thereof, and another anti-tumour agent.

According to this aspect of the invention there is provided a combination for use in the treatment of a proliferative condition, such as cancer (for example a cancer involving a solid tumour), comprising a compound of the invention as defined hereinbefore, or a pharmaceutically acceptable salt, hydrate or solvate thereof, and any one of the anti-tumour agents listed herein above.

According to this aspect of the invention there is provided a combination for use in the treatment of a cancer comprising a compound of the invention as defined hereinbefore, or a pharmaceutically acceptable salt, hydrate or solvate thereof, and a tyrosine kinase inhibitor.

According to this aspect of the invention there is provided a combination for use in the treatment of leukaemia (such as ALL or CML) comprising a compound of the invention as defined hereinbefore, or a pharmaceutically acceptable salt, hydrate or solvate thereof, and a tyrosine kinase inhibitor.

According to this aspect of the invention there is provided a combination for use in the treatment of lymphomas comprising a compound of the invention as defined hereinbefore, or a pharmaceutically acceptable salt, hydrate or solvate thereof, and an EZH2 inhibitor.

In a further aspect of the invention there is provided a compound of the invention or a pharmaceutically acceptable salt, hydrate or solvate thereof, for use in the treatment of cancer in combination with another anti-tumour agent, optionally selected from one listed herein above.

In a further aspect of the invention there is provided a compound of the invention or a pharmaceutically acceptable salt, hydrate or solvate thereof, for use in the treatment of cancer in combination with a tyrosine kinase inhibitor, optionally selected from one listed herein above.

In a further aspect of the invention there is provided a compound of the invention or a pharmaceutically acceptable salt, hydrate or solvate thereof, for use in the treatment of leukaemia (such as ALL or CML) in combination with a tyrosine kinase inhibitor, optionally selected from one listed herein above.

In a further aspect of the invention there is provided a compound of the invention or a pharmaceutically acceptable salt, hydrate or solvate thereof, for use in the treatment of cancer in combination with an EZH2 inhibitor, optionally selected from one listed herein above.

In a further aspect of the invention there is provided a compound of the invention or a pharmaceutically acceptable salt, hydrate or solvate thereof, for use in the treatment of lymphomas in combination with an EZH2 inhibitor, optionally selected from one listed herein above.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

According to a further aspect of the invention there is provided a pharmaceutical composition which comprises a compound of the invention, or a pharmaceutically acceptable salt, hydrate or solvate thereof, in combination with an anti-tumour agent (optionally selected from one listed herein above), in association with a pharmaceutically acceptable diluent or carrier.

EXAMPLES

Abbreviations

APCI Atmospheric pressure chemical ionization
aq. Aqueous
Ar Argon
br broad (in NMR spectrum)
conc. concentrated
d doublet (in NMR spectrum)
dba dibenzylideneacetone
DCM dichloromethane
DIPEA N,N-diisopropylethylamine
DMA dimethylacetamide
DMF N,N-dimethylformamide
DMSO dimethylsulfoxide
ESI electrospray ionisation
Et$_2$O diethyl ether
EtOAc ethyl acetate
EtOH ethanol
FID free induction decay
h hour(s)
HATU N-[(Dimethylamino)-1H-1,2,3-triazolo-[4,5-b]pyridin-1-ylmethylene]-N-methylmethanaminium hexafluorophosphate N-oxide
HPLC High Performance Liquid Chromatography
HRMS high resolution mass spectrometry
KP-Sil Biotage KP-Sil (50 uM irregular silica)
LCMS liquid chromatography and mass spectrometry
MeOH methanol
MeCN acetonitrile
MS mass spectrometry
Ms mesyl (methanesulfonyl)
m multiplet (in NMR spectrum)
MHz megahertz
min minute(s)
mins minute(s)
mL milliliter(s)
m/z mass to charge ratio
NMP N-methylpyrrolidinone
NMR nuclear magnetic resonance Pd/C palladium on activated charcoal
ppm parts per million
q quartet (in NMR spectrum)
QToF Quadrupole Time-of-flight
quin. quintet (in NMR spectrum)
Rt, RT retention time (in LCMS)
rt room temperature
s singlet (in NMR spectrum)
SCX-2 strong cation exchange (e.g. Isolute® SCX-2 columns)
sex. sextet (in NMR spectrum)
t triplet (in NMR spectrum)
Tf triflate (trifluoromethane sulfonate)
TFA trifluoroacetic acid
THF tetrahydrofuran
T3P propylphosphonic anhydride
uL microliters
UPLC Ultra-Performance Liquid Chromatography
Xantphos 4,5-Bis(diphenylphosphino)-9,9-dimethylxanthene Analytical Methods: LCMS
Method T2

LC/MS and HRMS analysis was performed on an Agilent 1200 series HPLC and diode array detector coupled to a 6210 time of flight mass spectrometer with dual multimode APCI/ESI source. Analytical separation was carried out at 40° C. on a Merck Chromolith Flash column (RP-18e, 25×2 mm) using a flow rate of 1.5 mL/min in a 2 minute gradient elution with detection at 254 nm. The mobile phase was a mixture of methanol (solvent A) and water (solvent B), both containing formic acid at 0.1%. Gradient elution was as follows: 5:95 (A/B) to 100:0 (A/B) over 1.25 min, 100:0 (A/B) for 0.5 min, and then reversion back to 5:95 (A/B) over 0.05 min, finally 5:95 (A/B) for 0.2 min.

Method T4

As for method T2 except at 30° C., using a flow rate of 0.75 mL/min in a 4 minute gradient elution as follows: 5:95 (A/B) to 100:0 (A/B) over 2.5 min, 100:0 (A/B) for 1 min, and then reversion back to 5:95 (A/B) over 0.1 min, finally 5:95 (A/B) for 0.4 min.

Method X2

LC/MS and HRMS analysis was performed on a Waters Acquity UPLC and diode array detector coupled to a Waters G2 QToF mass spectrometer fitted with a multimode ESI/APCI source. Analytical separation was carried out at 30° C. on a Phenomenex Kinetex C18 column (30×2.1 mm, 2.6 u, 100 A) using a flow rate of 0.5 mL/min in a 2 minute gradient elution with detection at 254 nm. The mobile phase was a mixture of methanol (solvent A) and water (solvent B), both containing formic acid at 0.1%. Gradient elution was as follows: 10:90 (A/B) to 90:10 (A/B) over 1.25 min, 90:10 (A/B) for 0.5 min, and then reversion back to 10:90 (A/B) over 0.15 min, finally 10:90 (A/B) for 0.1 min.

Method X4

As for method X2, except using a flow rate of 0.3 mL/min in a 4 minute gradient elution as follows: 10:90 (A/B) to 90:10 (A/B) over 3 min, 90:10 (A/B) for 0.5 min, and then reversion back to 10:90 (A/B) over 0.3 min, finally 10:90 (A/B) for 0.2 min.

Analytical Methods: NMR

NMR data was collected on a Bruker Avance 500 spectrometer equipped with a 5 mm BBO/QNP probe, or on a Bruker Avance Neo 600 spectrometer equipped with a 5 mm TCI Cryo-Probe. The $^1$H and $^{13}$C spectra were referenced to the internal deuterated solvent. All NMR data were acquired at the temperature of 298 K. All data were acquired and processed using Bruker Topspin 2.1 or Bruker Topspin 4.

The $^1$H NMR spectra were acquired using a Bruker standard 1D zg30 pulse sequence with 16 scans. The sweep width was 20.5 ppm, and the FID contained 64 k time-domain data points.

Purification Methods

Unless otherwise described in the text, preparative HPLC purification was carried out on an Agilent 6120 MS-Prep LC using an ACE 5 C18-PFP 250×21.2 mm (or 30 mm) column using a 15 min gradient of water:methanol (both modified with 0.1% formic acid)—for example 90:10 to 0:100 or 60:40 to 0:100—at a flow rate of 20 mLmin$^{-1}$ (or 40 mLmin$^{-1}$ for the 30 mm column).

Flash column chromatography was carried out using prepacked Biotage SNAP KP-Sil columns. Reverse phase chromatography was carried out using a Biotage SNAP Ultra C-18 12 g and 30 g columns as required.

Example Compounds

Example 1a: (S)-2-chloro-4-((2,7-dimethyl-6-oxo-1,2,3,4,6,7-hexahydro-[1,4]oxazepino-[2,3-c]quinolin-10-yl)amino)nicotinonitrile

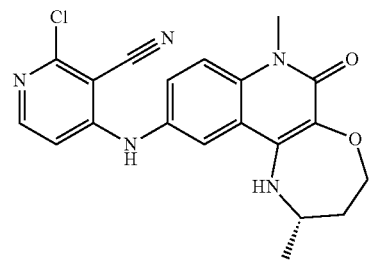 [SMILES: C[C@H]1CCOc2c(c3cc(Nc4ccnc(Cl)c4C#N)ccc3n(C)c2=O)N1]

A microwave vial (0.5-2.0 mL volume) was charged with (S)-10-amino-2,7-dimethyl-1,2,3,4-tetrahydro-[1,4]oxazepino[2,3-c]quinolin-6(7H)-one (Intermediate A1a, 9 mg, 0.034 mmol) and 2,4-dichloropyridine-3-carbonitrile (9 mg, 0.054 mmol). The reaction vial was flushed with Ar, sealed with a cap and then further flushed with Ar. Anhydrous NMP (0.6 mL) was added followed by triethylamine (14 uL, 0.10 mmol). The reaction mixture was heated at 160° C. under microwave irradiation for 90 min. The reaction mixture was allowed to cool to rt, diluted with DMSO (0.8 mL) and directly purified using reverse-phase chromatography (Biotage 12 g C-18; 10% to 100% MeOH in H$_2$O (both containing 0.1% formic acid) affording the title compound (7 mg, 53%) as an off-white solid. $^1$H NMR (600 MHz, Methanol-d$_4$) δ 7.98 (d, J=6.2 Hz, 1H), 7.94 (d, J=1.9 Hz, 1H), 7.61 (d, J=8.9 Hz, 1H), 7.50 (dd, J=8.9, 1.9 Hz, 1H), 6.69 (d, J=6.2 Hz, 1H), 4.37-4.30 (m, 1H), 4.28-4.22 (m, 1H), 4.07-4.00 (m, 1H), 3.73 (s, 3H), 2.26-2.19 (m, 1H), 1.92-1.84 (m, 1H), 1.38 (d, J=6.6 Hz, 3H); LCMS (Method T4) RT 2.58 min; m/z calcd for C$_{20}$H$_{19}$ClN$_5$O$_2^+$ [M+H]$^+$: 396.1222, Found: 396.1215.

The following tabulated examples were prepared by a method analogous to that used for the preparation of Example 1a, starting from the intermediate(s) shown in the table. For Example 1c, DIPEA was used instead of triethylamine and purification was conducted by HPLC. For Example 1t, an additional purification step by preparative HPLC was conducted. For Example 1u, DIPEA was used instead of trimethylamine and the reaction was heated at 140° C. under microwave irradiation for 4 h.

| Example | Data and comments | Intermediate |
| --- | --- | --- |
| Example 1b: (R)-2-chloro-4-((2,7-dimethyl-6-oxo-1,2,3,4,6,7-hexahydro-[1,4]oxazepino[2,3-c]quinolin-10-yl)amino)nicotinonitrile | $^1$H NMR (600 MHz, Methanol-$d_4$) δ 7.98 (d, J = 6.2 Hz, 1 H), 7.94 (d, J = 1.9 Hz, 1 H), 7.61 (d, J = 8.9 Hz, 1 H), 7.50 (dd, J = 8.9, 1.9 Hz, 1 H), 6.69 (d, J = 6.2 Hz, 1 H), 4.37-4.30 (m, 1 H), 4.28-4.22 (m, 1 H), 4.07-4.00 (m, 1 H), 3.73 (s, 3 H), 2.26-2.19 (m, 1 H), 1.92-1.84 (m, 1 H), 1.38 (d, J = 6.6 Hz, 3 H); LCMS (Method T4) RT 2.58 min; m/z calcd for $C_{20}H_{19}ClN_5O_2^+$ [M + H]$^+$: 396.1222, Found: 396.1213. | Intermediate A1b: (R)-10-amino-2,7-dimethyl-1,2,3,4-tetrahydro-[1,4]oxazepino[2,3-c]quinolin-6(7H)-one |
| Example 1c: 2-chloro-4-((2-ethyl-7-methyl-6-oxo-1,2,3,4,6,7-hexahydro-[1,4]oxazepino[2,3-c]quinolin-10-yl)amino)nicotinonitrile | $^1$H NMR (600 MHz, Methanol-$d_4$) δ 7.99 (d, J = 6.2 Hz, 1 H), 7.96 (d, J = 2.3 Hz, 1 H), 7.63 (d, J = 9.0 Hz, 1 H), 7.52 (dd, J = 9.0, 2.3 Hz, 1 H), 6.73 (d, J = 6.2 Hz, 1 H), 4.46-4.26 (m, 2 H), 3.84-3.77 (m, 1 H), 3.75 (s, 3 H), 2.34-2.25 (m, 1 H), 1.93-1.85 (m, 1 H), 1.85-1.80 (m, 1 H), 1.75-1.65 (m, 1 H), 1.04 (t, J = 7.4 Hz, 3 H); LCMS (Method T4) RT 2.69 min; m/z calcd for $C_{21}H_{21}ClN_5O_2^+$ [M + H]$^+$: 410.1378, Found: 410.1372. | Intermediate A1c: 10-amino-2-ethyl-7-methyl-1,2,3,4-tetrahydro-[1,4]oxazepino[2,3-c]quinolin-6(7H)-one |
| Example 1d: (R)-2-chloro-4((2-cyclopropyl-7-methyl-6-oxo-1,2,3,4,6,7-hexahydro-[1,4]oxazepino[2,3-c]quinolin-10-yl)amino)nicotinonitrile | $^1$H NMR (600 MHz, Methanol-$d_4$) δ 7.99 (d, J = 6.2 Hz, 1 H), 7.95 (d, J = 2.1 Hz, 1 H), 7.61 (d, J = 8.9 Hz, 1 H), 7.51 (dd, J = 8.9, 2.1 Hz, 1 H), 6.74 (d, J = 6.2 Hz, 1 H), 4.41-4.35 (m, 1 H), 4.24-4.19 (m, 1 H), 3.72 (s, 3 H), 2.92 (td, J = 9.4, 3.7 Hz, 1 H), 2.37-2.29 (m, 1 H), 2.12-2.06 (m, 1 1.24-1.16 (m, 1 H), 0.66-0.57 (m, 2 H), 0.39-0.34 (m, 1 H), 0.32-0.28 (m, 1 H). LCMS (Method T4) RT 2.73 min; m/z calcd for $C_{22}H_{21}ClN_5O_2^+$ [M + H]$^+$: 422.1378, Found: 422.1360. | Intermediate A1d: (R)-10-amino-2-cyclopropyl-7-methyl-1,2,3,4-tetrahydro-[1,4]oxazepino[2,3-c]quinolin-6(7H)-one |

-continued

| Example | Data and comments | Intermediate |
| --- | --- | --- |
| Example 1e: (S)-2-chloro-4((2-cyclopropyl-7-methyl-6-oxo-1,2,3,4,6,7-hexahydro-[1,4]oxazepino[2,3-c]quinolin-10-yl)amino)nicotinonitrile 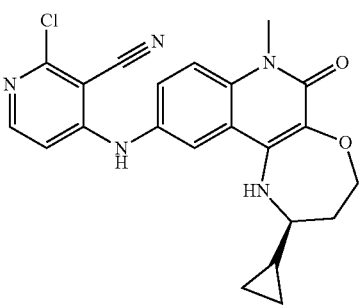 [SMILES: Cn1c(=O)c2c(c3cc(Nc4ccnc(Cl)c4C#N)ccc31)N[C@H](C1CC1)CCO2] | $^1$H NMR (600 MHz, Methanol-$d_4$) δ 7.99 (d, J = 6.2 Hz, 1 H), 7.95 (d, J = 2.1 Hz, 1 H), 7.61 (d, J = 8.9 Hz, 1 H), 7.51 (dd, J = 8.9, 2.1 Hz, 1 H), 6.74 (d, J = 6.2 Hz, 1 H), 4.41-4.35 (m, 1 H), 4.24-4.19 (m, 1 H), 3.72 (s, 3 H), 2.92 (td, J = 9.4, 3.7 Hz, 1 H), 2.37-2.29 (m, 1 H), 2.12-2.06 (m, 1 H), 1.24-1.16 (m, 1 H), 0.66-0.57 (m, 2 H), 0.39-0.34 (m, 1 H), 0.32-0.28 (m, 1 H). LCMS (Method T4) RT 2.73 min; m/z calcd for $C_{22}H_{21}ClN_5O_2^+$[M + H]$^+$: 422.1378, Found: 422.1369. | Intermediate A1e: (S)-10-amino-2-cyclopropyl-7-methyl-12,3,4-tetrahydro-[1,4]oxazepino[2,3-c]quinolin-6(7H)-one |
| Example 1f: 2-chloro-4-((2,2,7-trimethyl-6-oxo-1,2,3,4,6,7-hexahydro-[1,4]oxazepino[2,3-c]quinolin-10-yl)amino)nicotinonitrile 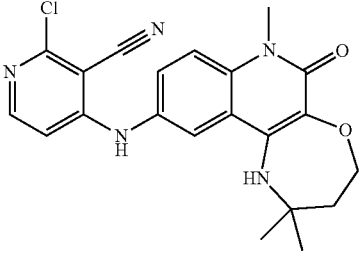 [SMILES: Cn1c(=O)c2c(c3cc(Nc4ccnc(Cl)c4C#N)ccc31)NC(C)(C)CCO2] | $^1$H NMR (600 MHz, Methanol-$d_4$) δ 7.98 (d, J = 6.3 Hz, 1 H), 7.95 (d, J = 2.3 Hz, 1 H), 7.62 (d, J = 8.9 Hz, 1 H), 7.52 (dd, J = 8.9, 2.3 Hz, 1 H), 6.70 (d, J = 6.3 Hz, 1 H), 4.25 (t, J = 6.0 Hz, 2 H), 3.75 (s, 3 H), 2.02 (t, J = 6.0 Hz, 2 H), 1.45 (s, 6 H); LCMS (Method T4) RT 2.64 min; m/z calcd for $C_{21}H_{21}ClN_5O_2^+$[M + H]$^+$: 410.1378, Found: 410.1370. | Intermediate A2a: 10-amino-2,2,7-trimethyl-1,2,3,4-tetrahydro-[1,4]oxazepino[2,3-c]quinolin-6(7H)-one |
| Example 1g: 2-chloro-4-((2-(methoxymethyl)-2,7-dimethyl-6-oxo-1,2,3,4,6,7-hexahydro-[1,4]oxazepino[2,3-c]quinolin-10-yl)amino)nicotinonitrile 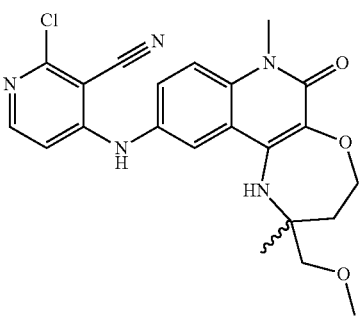 [SMILES: COCC1(C)CCOc2c(c3cc(Nc4ccnc(Cl)c4C#N)ccc3n(C)c2=O)N1] | $^1$H NMR (600 MHz, Methanol-$d_4$) δ 7.99 (d, J = 6.3 Hz, 1 H), 7.82 (d, J = 2.3 Hz, 1 H), 7.63 (d, J = 9.0 Hz, 1 H), 7.53 (dd, J = 9.0, 2.3 Hz, 1 H), 6.75 (d, J = 6.3 Hz, 1 H), 4.30-4.21 (m, 2 H), 3.75 (s, 3 H), 3.48 (d, J = 9.0 Hz, 1 H), 3.46 (d, J = 9.0 Hz, 1 H), 3.36 (s, 3 H), 2.10-2.04 (m, 1 H), 1.95-1.90 (m, 1 H), 1.42 (s, 3 H); LCMS (Method T4) RT 2.65 min; m/z calcd for $C_{22}H_{23}ClN_5O_3^+$ [M + H]$^+$: 440.1484, Found: 440.1437 | Intermediate A2b: 10-amino-2-(methoxymethyl)-2,7-dimethyl-1,2,3,4-tetrahydro-[1,4]oxazepino[2,3-c]quinolin-6(7H)-one |

| Example | Data and comments | Intermediate |
| --- | --- | --- |
| Example 1h: 2-chloro-4-((2,3,3,7-tetramethyl-6-oxo-1,2,3,4,6,7-hexahydro-[1,4]oxazepino[2,3-c]quinolin-10-yl)amino)nicotinonitrile | $^1$H NMR (600 MHz, CDCl$_3$) δ 8.09-8.07 (m, 1 H), 7.41 (d, J = 8.8 Hz, 1 H), 7.39-7.36 (m, 1 H), 7.32 (br s, 1 H), 6.94 (br s, 1 H), 6.63 (d, J = 6.0 Hz, 1 H), 4.07 (d, J = 11.9 Hz, 1 H), 4.05 (d, J = 11.9 Hz, 1 H), 3.87-3.81 (m, 1 H), 3.74 (s, 3 H), 3.62 (br s, 1 H), 1.25 (d, J = 6.8 Hz, 3 H), 1.15 (s, 3 H), 0.87 (s, 3 H); LCMS (Method T4) RT 2.80 min; m/z calcd for C$_{22}$H$_{23}$ClN$_5$O$_2$$^+$ [M + H]$^+$: 424.1535, Found: 424.1510. | Intermediate A1f: 10-amino-2,3,3,7-tetramethyl-1,2,3,4-tetrahydro-[1,4]oxazepino[2,3-c]quinolin-6(7H)-one |
| Example 1i: 2-chloro-4-((2',7'-dimethyl-6'-oxo-1',2',6',7'-tetrahydro-4'H-spiro[cyclopropane-1,3'-[1,4]oxazepino[2,3-c]quinolin]-10'-yl)amino)nicotinonitrile | $^1$H NMR (600 MHz, Methanol-d$_4$) δ 7.98 (d, J = 6.2 Hz, 1 H), 7.90 (d, J = 2.3 Hz, 1 H), 7.62 (d, J = 9.0 Hz, 1 H), 7.51 (dd, J = 9.0, 2.3 Hz, 1 H), 6.70 (d, J = 6.2 Hz, 1 H), 4.35 (d, J = 11.4 Hz, 1 H), 3.74 (s, 3 H), 3.67 (d, J = 11.4 Hz, 1 H), 3.32-3.30 (m, 1 H), 1.44 (d, J = 6.8 Hz, 3 H), 0.60-0.55 (m, 2 H), 0.49-0.45 (m, 1 H), 0.39-0.36 (m, 1 H); LCMS (Method T4) RT 2.63 min; m/z calcd for C$_{22}$H$_{21}$ClN$_5$O$_2$$^+$ [M + H]$^+$: 422.1378, Found: 422.1356. | Intermediate A1g: 10'-amino-2',7'-dimethyl-1',2'-dihydro-4'H-spiro[cyclopropane-1,3'-[1,4]oxazepino[2,3-c]quinolin]-6'(7'H)-one |
| Example 1j: 2-chloro-4-(((2S,4S)-2,4,7-trimethyl-6-oxo-1,2,3,4,6,7-hexahydro-[1,4]oxazepino[2,3-c]quinolin-10-yl)amino)nicotinonitrile | 1H NMR (600 MHz, Methanol-d$_4$) δ 7.99 (d, J = 6.2 Hz, 1 H), 7.94 (d, J = 2.2 Hz, 1 H), 7.62 (d, J = 8.9 Hz, 1 H), 7.50 (dd, J = 8.9, 2.2 Hz, 1 H), 6.70 (d, J = 6.2 Hz, 1 H), 4.53-4.47 (m, 1 H), 4.23-4.17 (m, 1 H), 3.74 (s, 3 H), 2.06-2.00 (m, 1 H), 1.98-1.93 (m, 1 H), 1.41 (d, J = 6.3 Hz, 3 H), 1.36 (d, J = 6.7 Hz, 3 H); LCMS (Method X4) RT 2.70 min; m/z calcd for C$_{21}$H$_{21}$ClN$_5$O$_2$$^+$ [M + H]$^+$: 410.1384, Found: 410.1389. | Intermediate A1h: (2S,4S)-10-amino-2,4,7-trimethyl-1,2,3,4-tetrahydro-[1,4]oxazepino[2,3-c]quinolin-6(7H)-one |
| Example 1k: 2-chloro-4-((2,6-dimethyl-5-oxo-2,3,5,6-tetrahydro-1H-[1,4]oxazino[2,3-c]quinolin-9-yl)amino)nicotinonitrile | $^1$H NMR (600 MHz, Methanol-d$_4$) δ 7.98 (d, J = 5.8 Hz, 1 H), 7.83 (s, 1 H), 7.62 (d, J = 8.8 Hz, 1 H), 7.47 (d, J = 8.4 Hz, 1 H), 6.72 (d, J = 5.8 Hz, 1 H), 4.25 (d, J = 10.3 Hz, 1 H), 3.80-3.72 (m, 4 H), 3.70-3.64 (m, 1 H), 1.30 (d, J = 6.0 Hz, 3 H); LCMS (Method T4) RT 2.51 min; m/z calcd for C$_{19}$H$_{17}$ClN$_5$O$_2$$^+$ [M + H]$^+$: 382.1065, Found: 382.1042. | Intermediate A3: 9-amino-2,6-dimethyl-2,3-dihydro-1H-[1,4]oxazino[2,3-c]quinolin-5(6H)-one |

-continued

| Example | Data and comments | Intermediate |
|---|---|---|
| Example 1l: 2-chloro-4-((2-ethyl-6-methyl-5-oxo-2,3,5,6-tetrahydro-1H-[1,4]oxazino[2,3-c]quinolin-9-yl)amino)nicotinonitrile 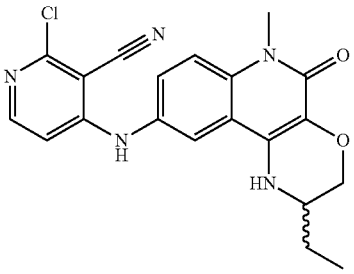 [SMILES: CCC1COc2c(c3cc(Nc4ccnc(Cl)c4C#N)ccc3n(C)c2=O)N1] | $^1$H NMR (500 MHz, Methanol-d$_4$) δ 7.96 (d, J = 6.2 Hz, 1 H), 7.84 (d, J = 2.3 Hz, 1 H), 7.60 (d, J = 8.9 Hz, 1 H), 7.47 (dd, J = 8.9, 2.3 Hz, 1 H), 6.72 (d, J = 6.2 Hz, 1 H), 4.19 (dd, J = 10.6, 2.8 Hz, 1 H), 3.97 (dd, J = 10.6, 5.2 Hz, 1 H), 3.72 (s, 3 H), 3.50-3.45 (m, 1 H), 1.77-1.69 (m, 1 H), 1.66-1.58 (m, 1 H), 1.05(t, J = 7.5 Hz, 3 H); LCMS (Method T4) RT 2.62 min; m/z calcd for C$_{20}$H$_{19}$ClN$_5$O$_2$$^+$ [M + H]$^+$: 396.1222, Found: 396.1211. | Intermediate A1i: 9-amino-2-ethyl-6-methyl-2,3-dihydro-1H-[1,4]oxazino[2,3-c]quinolin-5(6H)-one |
| Example 1m: 2-chloro-4((2-cyclopropyl-6-methyl-5-oxo-2,3,5,6-tetrahydro-1H-[1,4]oxazino[2,3-c]quinolin-9-yl)amino)nicotinonitrile 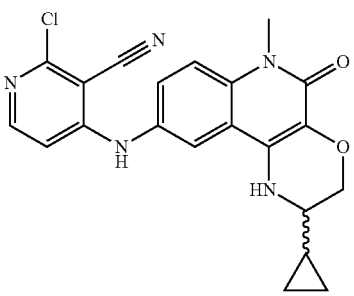 [SMILES: Cn1c(=O)c2c(c3cc(Nc4ccnc(Cl)c4C#N)ccc31)NC(C1CC1)CO2] | $^1$H NMR (600 MHz, Methanol-d$_4$) δ 8.00 (d, J = 6.2 Hz, 1 H), 7.94 (d, J = 2.3 Hz, 1 H), 7.65 (d, J = 8.9 Hz, 1 H), 7.50 (dd, J = 8.9, 2.3 Hz, 1 H), 6.74 (d, J = 6.2 Hz, 1 H), 4.30 (dd, J = 10.5, 3.0 Hz, 1 H), 4.08 (dd, J = 10.5, 5.8 Hz, 1 H), 3.77 (s, 3 H), 2.87-2.83 (m, 1 H), 1.02-0.95 (m, 1 H), 0.69-0.63 (m, 1 H), 0.62-0.56 (m, 1 H), 0.52-0.47 (m, 1 H), 0.43-0.37 (m, 1 H); LCMS (Method 14) RT 2.65 min; m/z calcd for C$_{21}$H$_{19}$ClN$_5$O$_2$$^+$ [M + H]$^+$: 408.1222, Found: 408.1211. | Intermediate A1j: 9-amino-2-cyclopropyl-6-methyl-2,3-dihydro-1H-[1,4]oxazino[2,3-c]quinolin-5(6H)-one |
| Example 1n: 2-chloro-4-((2-cyclobutyl-6-methyl-5-oxo-2,3,5,6-tetrahydro-1H-[1,4]oxazino[2,3-c]quinolin-9-yl)amino)nicotinonitrile 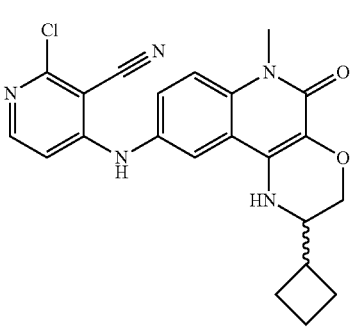 [SMILES: Cn1c(=O)c2c(c3cc(Nc4ccnc(Cl)c4C#N)ccc31)NC(C1CCC1)CO2] | $^1$H NMR (600 MHz, Methanol-d$_4$) δ 7.97 (d, J = 6.2 Hz, 1 H), 7.86 (d, J = 2.3 Hz, 1 H), 7.62 (d, J = 8.9 Hz, 1 H), 7.48 (dd, J = 8.9, 2.3 Hz, 1 H), 6.72 (d, J = 6.2 Hz, 1 H), 4.05-3.98 (m, 2 H), 3.74 (s, 3 H), 3.53-3.49 (m, 1 H), 2.60-2.50 (m, 1 H), 2.14-2.04 (m, 2 H), 2.03-1.84 (m, 4 H); LCMS (Method T4) RT 2.78 min; m/z calcd for C$_{22}$H$_{21}$ClN$_5$O$_2$$^+$ [M+H]$^+$: 422.1378, Found: 422.1264. | Intermediate A1k: 9-amino-2-cyclobutyl-6-methyl-2,3-dihydro-1H-[1,4]oxazino[2,3-c]quinolin-5(6H)-one |

-continued

| Example | Data and comments | Intermediate |
|---|---|---|
| Example 1o: 2-chloro-4-((7'-methyl-6'-oxo-3',4,4',5,6',7'-hexahydro-1'H,2H-spiro[furan-3,2'-[1,4]oxazepino[2,3-c]quinolin]-10'-yl)amino)nicotinonitrile 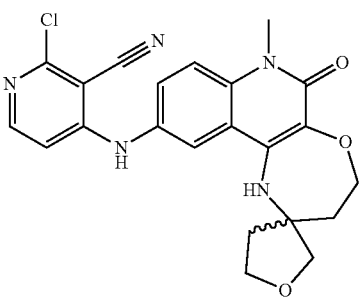 [SMILES: Cn1c(=O)c2c(c3cc(Nc4ccnc(Cl)c4C#N)ccc31)NC1(CCOC1)CCO2] | $^1$H NMR (600 MHz, DMSO-d$_6$) δ 9.60 (s, 1 H), 8.07-7.96 (m, 2 H), 7.49 (d, J = 8.9 Hz, 1 H), 7.42 (d, J = 8.9 Hz, 1 H), 6.62 (d, J = 5.9 Hz, 1 H), 5.67 (s, 1 H), 4.20-4.12 (m, 2 H), 3.97 (d, J = 9.0 Hz, 1 H), 3.86-3.80 (m, 1 H), 3.80-3.76 (m, 1 H), 3.58 (s, 3 H), 3.53 (d, J = 9.0 Hz, 1 H), 2.36-2.29 (m, 1 H), 2.19-2.09 (m, 2 H), 1.98-1.92 (m, 1 H); LCMS (Method T4) RT 2.46 min; m/z calcd for C$_{22}$H$_{21}$ClN$_5$O$_3$$^+$ [M + H]$^+$: 438.1327, Found: 438.1319. | Intermediate A2c: 10'-amino-7'-methyl-3',4,4',5-tetrahydro-1'H,2H-spiro[furan-3,2'-[1,4]oxazepino[2,3-c]quinolin]-6'(7'H)-one |
| Example 1p: 2-chloro-4-((2-(difluoromethyl)-7-methyl-6-oxo-1,2,3,4,6,7-hexahydro-[1,4]oxazepino[2,3-c]quinolin-10-yl)amino)nicotinonitrile 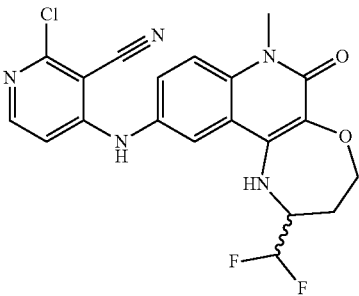 [SMILES: Cn1c(=O)c2c(c3cc(Nc4ccnc(Cl)c4C#N)ccc31)NC(C(F)F)CCO2] | 1H NMR (600 MHz, CDCl$_3$) δ 8.08 (d, J = 6.1 Hz, 1 H), 7.45-7.40 (m, 3 H), 6.94 (br s, 1 H), 6.63 (d, J = 6.1 Hz, 1 H), 6.04 (dt, J = 55.8 Hz (J$_{H-F}$), 4.8 Hz, 1 H), 4.53-4.44 (m, 2 H), 4.24 (br d, J = 3.4 Hz, 1 H), 4.14-4.05 (m, 1 H), 3.75 (s, 3 H), 2.40-2.33 (m, 1 H), 2.25-2.18 (m, 1 H); LCMS (Method T4) RT 2.56 min; m/z calcd for C$_{20}$H$_{17}$ClF$_2$N$_5$O$_2$$^+$ [M + H]$^+$: 432.1033, Found: 432.1027. | Intermediate A2d: 10-amino-2-(difluoromethyl)-7-methyl-1,2,3,4-tetrahydro-[1,4]oxazepino[2,3-c]quinolin-6(7H)-one |
| Example 1q: 2-chloro-4-((2-cyclopropyl-3,3-difluoro-7-methyl-6-oxo-1,2,3,4,6,7-hexahydro-[1,4]oxazepino[2,3-c]quinolin-10-yl)amino)nicotinonitrile 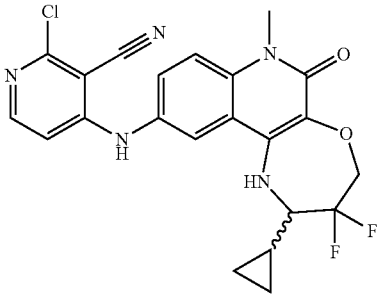 [SMILES: Cn1c(=O)c2c(c3cc(Nc4ccnc(Cl)c4C#N)ccc31)NC(C1CC1)C(F)(F)CO2] | $^1$H NMR (600 MHz, CDCl$_3$) δ 8.10 (d, J = 6.1 Hz, 1 H), 7.47-7.43 (m, 2 H), 7.39 (br s, 1 H), 7.00 (s, 1 H), 6.65 (d, J = 6.1 Hz, 1 H), 4.63 (dd, J = 16.3, 13.3 Hz, 1 H), 4.41 (ddd, J = 26.9, 13.3, 6.1 Hz, 1 H), 4.21-4.16 (m, 1 H), 3.74 (s, 3 H), 3.34 (ddt, J = 20.5, 10.0, 2.6 Hz, 1 H), 1.37-1.31 (m, 1 H), 0.91-0.86 (m, 1 H), 0.77-0.68 (m, 2 H), 0.33-0.28 (m, 1 H); LCMS (Method X4) RT 2.76 min; C$_{22}$H$_{19}$ClF$_2$N$_5$O$_2$$^+$ [M + H]$^+$: 458.1195, Found: 458.1189. | Intermediate A11: 10-amino-2-cyclopropyl-3,3-difluoro-7-methyl-1,2,3,4-tetrahydro-[1,4]oxazepino[2,3-c]quinolin-6(7H)-one |

| Example | Data and comments | Intermediate |
| --- | --- | --- |
| Example 1r: (R)-2-cyclopropyl-10-((5,6-dichloro-2-((2S,6R)-2,6-dimethylmorpholino)pyrimidin-4-yl)amino)-7-methyl-1,2,3,4-tetrahydro-[1,4]oxazepino[2,3-c]quinolin-6(7H)-one | $^1$H NMR (600 MHz, CDCl$_3$) δ 7.94-7.77 (m, 1 H), 7.60-7.54 (m, 1 H), 7.32 (d, J = 9.0 Hz, 1 H), 7.25 (s, 1 H), 4.49-4.40 (m, 3 H), 4.35-4.31 (m, 1H), 3.73 (s, 3 H), 3.64-3.56 (m, 2 H), 2.98 (td, J = 10.1, 3.7 Hz, 1 H), 2.64-2.55 (m, 2 H), 2.42-2.35 (m, 1 H), 2.05-1.98 (m, 1 H), 1.26 (d, J = 6.2 Hz, 6 H), 1.14-1.08 (m, 1 H), 0.74-0.63 (m, 2 H), 0.40-0.29 (m, 2 H); LCMS (Method T4) RT 3.65 min; m/z calcd for C$_{26}$H$_{31}$Cl$_2$N$_6$O$_3$$^+$ [M + H]$^+$: 545.1835, Found: 545.1837. | Intermediate A1d: (R)-10-amino-2-cyclopropyl-7-methyl-1,2,3,4-tetrahydro-[1,4]oxazepino[2,3-c]quinolin-6(7H)-one and Intermediate I1: (2S,6R)-2,6-dimethyl-4-(4,5,6-trichloropyrimidin-2-yl)morpholine |
| Example 1s: (R)-2-chloro-4-((2-cyclopropyl-7-methyl-6-oxo-1,2,3,4,6,7-hexahydro-[1,4]thiazepino[2,3-c]quinolin-10-yl)amino)nicotinonitrile | $^1$H NMR (600 MHz, CDCl$_3$) δ 8.07 (d, J = 6.1 Hz, 1 H), 7.39 (s, 2 H), 7.34 (s, 1 H), 6.97 (s, 1 H), 6.64 (d, J = 6.1 Hz, 1 H), 4.32-4.29 (m, 1 H), 3.99-3.91 (m, 1 H), 3.75 (ddd, J = 14.6, 11.8, 5.6 Hz, 1 H), 3.69 (s, 3 H), 2.94 (dd, J = 14.6, 6.2 Hz, 1 H), 2.25-2.16 (m, 1 H), 2.07-1.98 (m, 1 H), 1.06-0.99 (m, 1 H), 0.74-0.66 (m, 1 H), 0.63-0.56 (m, 1 H), 0.44-0.37 (m, 1 H), 0.30-0.23 (m, 1 H); LCMS (Method T4) RT 2.81 min; m/z calcd for C$_{22}$H$_{21}$ClN$_5$OS$^+$ [M + H]$^+$: 438.1150, Found: 438.1142. | Intermediate A8a: (R)-10-amino-2-cyclopropyl-7-methyl-1,2,3,4-tetrahydro-[1,4]thiazepino[2,3-c]quinolin-6(7H)-one |
| Example 1t: 2-chloro-4-((2,6-dimethyl-5-oxo-2,3,5,6-tetrahydro-1H-[1,4]thiazino[2,3-c]quinolin-9-yl)amino)nicotinonitrile | $^1$H NMR (600 MHz, CDCl$_3$) δ 8.05 (d, J = 6.1 Hz, 1 H), 7.43 (d, J = 8.7 Hz, 1 H), 7.41-7.36 (m, 2 H), 6.91 (s, 1 H), 6.61 (d, J = 6.1 Hz, 1 H), 4.66 (br s, 1 H), 3.90-3.82 (m, 1 H), 3.73 (s, 3 H), 3.02 (dd, J = 12.6, 2.6 Hz, 1 H), 2.77 (dd, J = 12.6, 7.5 Hz, 1 H), 1.46 (d, J = 6.4 Hz, 3 H); LCMS (Method T4) RT 2.57 min; m/z calcd for C$_{19}$H$_{17}$ClN$_5$OS$^+$ [M + H]$^+$: 398.0838, Found: 398.0837. | Intermediate A8b: 9-amino-2,6-dimethyl-2,3-dihydro-1H-[1,4]thiazino[2,3-c]quinolin-5(6H)-one |

-continued

| Example | Data and comments | Intermediate |
|---|---|---|
| Example 1u: (R)-2-chloro-4-((2-cyclopropyl-7-methyl-5,5-dioxido-6-oxo-1,2,3,4,6,7-hexahydro-[1,4]thiazepino[2,3-c]quinolin-10-yl)amino)nicotinonitrile | $^1$H NMR (500 MHz, DMSO-$d_6$) δ 9.64 (br s, 1 H), 8.36 (d, J = 2.2 Hz, 1 H), 8.06 (d, J = 6.2 Hz, 1 H), 7.89 (d, J = 5.7 Hz, 1 H), 7.60 (dd, J = 8.9, 2.2 Hz, 1 H), 7.54 (d, J = 8.9 Hz, 1 H), 6.70 (d, J = 6.2 Hz, 1 H), 3.60-3.51 (m, 1 H), 3.50 (s, 3 H), 3.20 (dd, J = 15.1, 6.2 Hz, 1 H), 3.05-3.00 (m, 1 H), 2.36-2.25 (m, 1 H), 2.10-2.04 (m, 1 H), 1.28-1.20 (m, 1 H), 0.67-0.58 (m, 1 H), 0.50-0.43 (m, 1 H), 0.23-0.21 (m, 2 H); LCMS (Method T4) RT 2.49 min; m/z calcd for $C_{22}H_{21}ClN_5O_3S^+$ [M + H]$^+$: 470.1048, Found: 470.1044. | Intermediate A9a: (R)-10-amino-2-cyclopropyl-7-methyl-1,2,3,4-tetrahydro-[1,4]thiazepino[2,3-c]quinolin-6(7H)-one 5,5-dioxide |
| Example 1v: (S)-2-chloro-4-((2-cyclopropyl-3,3-difluoro-7-methyl-6-oxo-1,2,3,4,6,7-hexahydro-[1,4]oxazepino[2,3-c]quinolin-10-yl)amino)nicotinonitrile | $^1$H NMR (600 MHz, CDCl$_3$) δ 8.10 (d, J = 6.1 Hz, 1 H), 7.47-7.43 (m, 2 H), 7.38 (br s, 1 H), 6.98 (s, 1 H), 6.65 (d, J = 6.1 Hz, 1 H), 4.64 (dd, J = 16.3, 13.3 Hz, 1 H), 4.41 (ddd, J = 26.9, 13.3, 6.1 Hz, 1 H), 4.18-4.14 (m, 1 H), 3.74 (s, 3 H), 3.38-3.30 (m, 1 H), 1.38-1.31 (m, 1 H), 0.91-0.86 (m, 1 H), 0.77-0.68 (m, 2 H), 0.33-0.28 (m, 1 H); LCMS (Method X4) RT 2.77 min m/z calcd for $C_{22}H_{19}ClF_2N_5O_2^+$ [M + H]$^+$: 458.1195, Found: 458.1194. | Intermediate A1m: (S)-10-amino-2-cyclopropyl-3,3-difluoro-7-methyl-1,2,3,4-tetrahydro-[1,4]oxazepino[2,3-c]quinolin-6(7H)-one |

Example 2a: (S)-6-chloro-5-cyano-4-((2,7-dimethyl-6-oxo-1,2,3,4,6,7-hexahydro-[1,4]ox-azepino[2,3-c]quinolin-10-yl)amino)picolinic acid

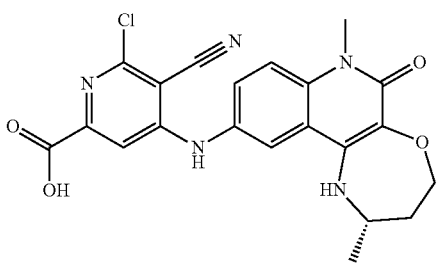 [SMILES: C[C@H]1CCOc2c(c3cc(Nc4cc(C(=O)O)nc(Cl)c4C#N)ccc3n(C)c2=O)N1]

A microwave vial (0.5-2.0 mL volume) was charged with (S)-10-amino-2,7-dimethyl-1,2,3,4-tetrahydro-[1,4]oxazepino[2,3-c]quinolin-6(7H)-one (Intermediate A1a, 13 mg, 0.049 mmol) and 4,6-dichloro-5-cyanopicolinic acid (15 mg, 0.071 mmol). The reaction vial was flushed with Ar, sealed with a cap and then further flushed with Ar. Anhydrous NMP (0.5 mL) was added and the reaction mixture was heated at 100° C. for 2 h. The reaction mixture was cooled to rt, diluted with DMSO (0.8 mL) and directly purified by reverse-phase chromatography (Biotage reverse-phase 12 g C-18 column; 10-100% MeOH in H$_2$O (containing 0.1% formic acid)), affording the title compound (13 mg, 61%) as a yellow solid. $^1$H NMR (500 MHz, DMSO-$d_6$) δ 13.67 (brs, 1H), 9.89 (s, 1H), 8.04 (d, J=2.1 Hz, 1H), 7.51 (d, J=9.0 Hz, 1H), 7.46 (dd, J=9.0, 2.1 Hz, 1H), 7.18 (s, 1H), 5.64 (d, J=2.8 Hz, 1H), 4.20-4.09 (m, 2H), 3.92-3.86 (m, 1H), 3.58 (s, 3H), 2.13-2.06 (m, 1H), 1.81-1.73 (m, 1H), 1.29 (d, J=6.6 Hz, 3H); LCMS (Method T4) RT 2.46 min; m/z calcd for $C_{21}H_{19}ClN_5O_4^+$ [M+H]$^+$: 440.1120, Found: 440.1114.

The following tabulated example was prepared by a method analogous to that used for the preparation of Example 2a, starting from the intermediate(s) shown in the table.

| Example | Data and comments | Intermediate |
|---|---|---|
| Example 2b: (R)-6-chloro-5-cyano-4-((2-cyclopropyl-7-methyl-6-oxo-1,2,3,4,6,7-hexahydro-[1,4]oxazepino[2,3-c]quinolin-10-yl)amino)picolinic acid | $^1$H NMR (600 MHz, Methanol-d$_4$) δ 7.97 (br s, 1 H), 7.65-7.61 (m, 1 H), 7.56-7.51 (m, 1 H), 7.37 (br s, 1 H), 4.43-4.36 (m, 1 H), 4.25-4.18 (m, 1 H), 3.74 (s, 3 H), 2.95-2.89 (m, 1 H), 2.37-2.28 (m, 1 H), 2.13-2.06 (m, 1 H), 1.23-1.17 (m, 1 H), 0.65-0.57 (m, 2 H), 0.41-0.34 (m, 1 H), 0.33-0.27 (m, 1 H); LCMS (Method X4) RT 2.49 min; m/z calcd for C$_{23}$H$_{21}$ClN$_5$O$_4^+$ [M + H]$^+$: 466.1282, Found: 466.1295. | Intermediate A1d: (R)-10-amino-2-cyclopropyl-7-methyl-1,2,3,4-tetrahydro-[1,4]oxazepino[2,3-c]quinolin-6(7H)-one |

Example 3a: (S)-6-(azetidine-1-carbonyl)-2-chloro-4-((2,7-dimethyl-6-oxo-1,2,3,4,6,7-hexahydro-[1,4]oxazepino[2,3-c]quinolin-10-yl)amino)nicotinonitrile DIPEA (14 uL, 0.079 mmol) followed by T3P (50 wt % in EtOAc, 25 mg, 0.040 mmol) and azetidine (2 uL, 0.0282 mmol) were added sequentially to a solution of (S)-6-chloro-5-cyano-4-((2,7-dimethyl-6-oxo-1,2,3,4,6,7-hexahydro-[1,4]oxazepino[2,3-c]quinolin-10-yl)amino)picolinic acid (Example 2a, 12 mg, 0.026 mmol) in DMF (0.5 mL) at rt. The reaction mixture was stirred at rt for 90 min. Water (8 drops) was added to quench the reaction. The aqueous suspension was dissolved in DMSO (0.8 mL) and directly purified by reverse-phase chromatography (Biotage reverse-phase 12 g C-18 column; 10-100% MeOH in H$_2$O (containing 0.1% formic acid)), affording the title compound (4 mg, 29%) as a yellow solid. $^1$H NMR (600 MHz, CDCl$_3$) δ 7.44-7.31 (m, 4H), 7.03 (s, 1H), 4.74-4.66 (m, 2H), 4.48-4.41 (m, 1H), 4.41-4.33 (m, 1H), 4.20-4.14 (m, 2H), 4.08-4.00 (m, 1H), 3.94-3.82 (m, 1H), 3.73 (s, 3H), 2.38-2.32 (m, 2H), 2.29-2.21 (m, 1H), 1.85-1.78 (m, 1H), 1.39 (d, J=6.1 Hz, 3H); LCMS (Method T4) RT 2.77 min; m/z calcd for C$_{24}$H$_{24}$ClN$_6$O$_3^+$ [M+H]$^+$: 479.1593, Found: 479.1578.

The following tabulated example was prepared by a method analogous to that used for the preparation of Example 3a, starting from the intermediate(s) shown in the table and appropriate amine.

| Example | Data and comments | Intermediate(s) |
|---|---|---|
| Example 3b: (R)-2-chloro-4-((2-cyclopropyl-7-methyl-6-oxo-1,2,3,4,6,7-hexahydro-[1,4]oxazepino[2,3-c]quinolin-10-yl)amino)-6-(3-(trifluoromethyl)azetidine-1-carbonyl)nicotinonitrile | $^1$H NMR (600 MHz, CDCl$_3$) δ 7.45 (d, J = 6.3 Hz, 1 H), 7.40 (d, J = 9.1 Hz, 1 H), 7.38-7.35 (m, 2 H), 7.09 (s, 1 H), 4.91 (dd, J = 11.5, 9.3 Hz, 1 H), 4.74 (dd, J = 11.5, 5.7 Hz, 1 H), 4.52-4.45 (m, 1 H), 4.34-4.27 (m, 2 H), 4.24-4.17 (m, 2 H), 3.73 (s, 3 H), 3.38-3.29 (m, 1 H), 3.03-2.95 (m, 1 H), 2.40-2.33 (m, 1 H), 2.08-2.00 (m, 1 H), 1.14-1.07 (m, 1 H), 0.72-0.61 (m, 2 H), 0.40-0.31 (m, 2 H); LCMS (Method X4) RT 3.18 min; m/z calcd for C$_{27}$H$_{25}$ClF$_3$N$_6$O$_3^+$ [M + H]$^+$: 573.1628, Found: 573.1646. | Example 2b: (R)-6-chloro-5-cyano-4-((2-cyclopropyl-7-methyl-6-oxo-1,2,3,4,6,7-hexahydro-[1,4]oxazepino[2,3-c]quinolin-10-yl)amino)picolinic acid |

Example 4a: (S)-10-((2,3-dichloropyridin-4-yl)amino)-2,7-dimethyl-1,2,3,4-tetrahydro-[1,4]oxazepino[2,3-c]quinolin-6(7H)-one

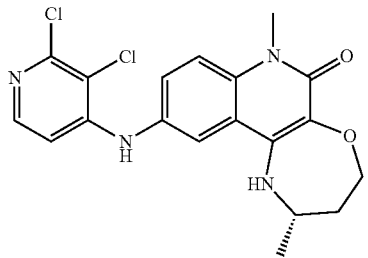 [SMILES: C[C@H]1CCOc2c(c3cc(Nc4ccnc(Cl)c4Cl)ccc3n(C)c2=O)N1]

A microwave vial (0.5-2.0 mL volume) was charged with (S)-10-amino-2,7-dimethyl-1,2,3,4-tetrahydro-[1,4]oxazepino[2,3-c]quinolin-6(7H)-one (Intermediate A1a, 7 mg, 0.027 mmol), 2,3-dichloro-4-iodopyridine (9 mg, 0.032 mmol), cesium carbonate (71 mg, 0.22 mmol), Pd$_2$(dba)$_3$ (2.5 mg, 0.003 mmol) and Xantphos (9 mg, 0.016 mmol). The reaction vial was flushed with Ar and sealed with a cap. Anhydrous DMF (0.2 mL) and toluene (0.6 mL) were added and Ar was bubbled through the reaction mixture for 5 mins. The reaction mixture was heated at 80° C. under microwave irradiation for 1 h. The reaction mixture was cooled to rt. Water (10 mL) was added and the aqueous mixture was extracted with EtOAc (3×10 mL). The organic extracts were combined, washed with brine (10 mL), dried (Na$_2$SO$_4$) and concentrated in vacuo. The crude product was dissolved in DMSO (1.2 mL) and directly purified by reverse-phase chromatography (Biotage reverse-phase 12 g Ultra C-18 column; 10-100% MeOH in H$_2$O (containing 0.1% formic acid)), affording the title compound (5 mg, 48%) as an off-white solid. $^1$H NMR (600 MHz, Methanol-d$_4$) δ 7.91 (d, J=1.8 Hz, 1H), 7.82 (d, J=5.8 Hz, 1H), 7.60 (d, J=8.9 Hz, 1H), 7.50 (dd, J=8.9, 1.8 Hz, 1H), 6.71 (d, J=5.8 Hz, 1H), 4.37-4.31 (m, 1H), 4.28-4.23 (m, 1H), 4.07-4.00 (m, 1H), 3.73 (s, 3H), 2.25-2.19 (m, 1H), 1.92-1.85 (m, 1H), 1.38 (d, J=6.6 Hz, 3H); LCMS (Method T4) RT 2.72 min; m/z calcd for C$_{19}$H$_{19}$Cl$_2$N$_4$O$_2^+$ [M+H]$^+$: 405.0880, Found: 405.0879.

The following tabulated example was prepared by a method analogous to that used for the preparation of Example 4a, starting from the intermediate(s) shown in the table. Example 4b was purified by preparative HPLC. For Example 4d, the reaction mixture was heated at 80° C. under microwave irradiation for 4 h.

| Example | Data and comments | Intermediate(s) |
|---|---|---|
| Example 4b: (S)-10-((5-chloro-2-((S)-2-(methoxymethyl)pyrrolidine-1-carbonyl)pyridin-4-yl)amino)-2,7-dimethyl-1,2,3,4-tetrahydro-[1,4]oxazepino[2,3-c]quinolin-6(7H)-one | Compound exists as a mixture of rotamers:<br>RotamerA: $^1$H NMR (600 MHz, Methanol-d$_4$) δ 8.32 (s, 1 H), 7.93 (s, 1 H), 7.67-7.59 (m, 1 H), 7.53 (dd, J = 8.9, 2.3 Hz, 1 H), 7.02 (s, 1 H), 4.40-4.33 (m, 1H), 4.33-4.25 (m, 1 H), 4.30-4.27 (m, 1 H), 4.10-4.03 (m, 1 H), 3.75 (s, 3 H), 3.65-3.58 (m, 2 H), 3.55-3.48 (m, 2 H), 3.34 (s, 3 H), 2.30-2.20 (m, 1 H), 2.08-1.85 (m, 4H), 1.85-1.75 (m, 1 H), 1.41 (d, J = 6.7 Hz, 3 H); Rotamer B: $^1$H NMR (600 MHz, Methanol-d$_4$) δ 8.32 (s, 1 H), 7.93 (s, 1 H), 7.67-7.59 (m, 1H), 7.53 (dd, J = 8.9, 2.3 Hz, 1H), 7.04 (s, 1 H), 4.62-4.55 (m, 1 H), 4.40-4.33 (m, 1 H), 4.33-4.25 (m, 1 H), 4.10-4.03 (m, 1 H), 3.75 (s, 3 H), 3.65-3.58 (m, 2 H), 3.55-3.48 (m, 2 H), 3.14 (s. 3 H), 2.30-2.20 (m, 1 H), 2.20-1.95 (m, 1 H), 2.08-1.85 (m, 4 H), 1.41 (d, J = 6.7 Hz, 3 H); LCMS (Method X4) RT 2.59 min; m/z calcd for C$_{26}$H$_{31}$ClN$_5$O$_4^+$ [M + H]$^+$: 512.2064, Found: 512.2062. | Intermediate A1a: (S)-10-amino-2,7-dimethyl-1,2,3,4-tetrahydro-[1,4]oxazepino[2,3-c]quinolin-6(7H) one and Intermediate G1: (S)-(4,5-dichloropyridin-2-yl)(2-(methoxymethyl)pyrrolidin-1-yl)methanone |
| Example 4c: (R)-2-cyclopropyl-10-(2,3-dichloropyridin-4-yl)amino)-7-methyl-1,2,3,4-tetrahydro-[1,4]oxazepino[2,3-c]quinolin-6(7H)-one | $^1$H NMR (600 MHz, CDCl$_3$) δ 7.94 (d, J = 5.7 Hz, 1 H), 7.40-7.38 (m, 2 H), 7.38-7.36 (m, 1 H), 6.71 (s, 1 H), 6.68 (d, J = 5.7 Hz, 1 H), 4.52-4.45 (m, 1 H), 4.33-4.28 (m, 1 H), 4.22 (s, 1 H), 3.73 (s, 3 H), 2.97 (dt, J = 10.0, 3.6 Hz, 1 H), 2.40-2.33 (m, 1 H), 2.08-2.00 (m, 1 H), 1.14-1.07 (m, 1 H), 0.73-0.62 (m, 2 H), 0.39-0.34 (m, 1 H), 0.34-0.29 (m, 1H); LCMS (Method T4) RT 2.85 min; m/z calcd for C$_{21}$H$_{21}$Cl$_2$N$_4$O$_2^+$ [M + H]$^+$: 431.1036, Found: 431.1017 | Intermediate A1d: (R)-10-amino-2-cyclopropyl-7-methyl-1,2,3,4-tetrahydro-[1,4]oxazepino[2,3-c]quinolin-6(7H)-one |

| Example | Data and comments | Intermediate(s) |
|---|---|---|
| Example 4d: (S)-10-((3-chloropyridin-4-yl)amino)-2-cyclopropyl-3,3-difluoro-7-methyl-1,2,3,4-tetrahydro-[1,4]oxazepino[2,3-c]quinolin-6(7H)-one | $^1$H NMR (600 MHz, methanol-$d_4$) δ 8.29 (s, 1 H), 8.02 (d, J = 5.7 Hz, 1 H), 8.00 (d, J = 1.9 Hz, 1 H), 7.63 (d, J = 9.0 Hz, 1 H), 7.55 (dd, J = 9.0, 1.9 Hz, 1 H), 6.84 (d, J = 5.7 Hz, 1 H), 4.53-4.36 (m, 2 H), 3.73 (s, 3 H), 3.32-3.24 (m, 1 H), 1.42-1.35 (m, 1 H), 0.81-0.73 (m, 1 H) 0.66-0.55 (m, 2 H), 0.35-0.28 (m, 1 H); LCMS (Method T4) RT 2.06 min; m/z calcd for $C_{21}H_{20}ClF_2N_4O_2^+$ [M + H]$^+$: 433.1233, Found: 433.1237. | Intermediate A1m: (S)-10-amino-2-cyclopropyl-3,3-difluoro-7-methyl-1,2,3,4-tetrahydro-[1,4]oxazepino[2,3-c]quinolin-6(7H)-one |

Example 5a: (R)-10-((5-chloro-2-(3-(trifluoromethyl)-1H-pyrazol-1-yl)pyrimidin-4-yl)amino)-2-cyclopropyl-7-methyl-1,2,3,4-tetrahydro-[1,4]oxazepino[2,3-c]quinolin-6(7H)-one

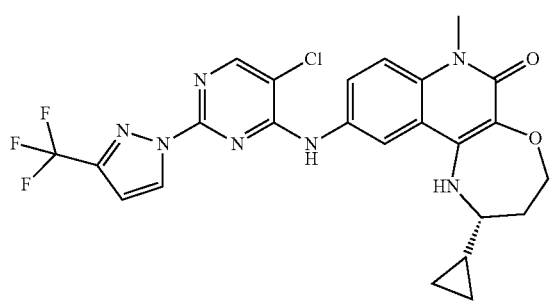 [SMILES: Cn1c(=O)c2c(c3cc(Nc4nc(-n5ccc(C(F)(F)F)n5)ncc4Cl)ccc31)N[C@@H](C1CC1)CCO2]

Step 1: (R)-2-cyclopropyl-10-((2,5-dichloropyrimidin-4-yl)amino)-7-methyl-1,2,3,4-tetrahydro-[1,4]oxazepino[2,3-c]quinolin-6(7H)-one An oven-dried microwave vial (0.5-2.0 mL volume) was charged with (R)-10-amino-2-cyclopropyl-7-methyl-1,2,3,4-tetrahydro-[1,4]oxazepino[2,3-c]quinolin-6(7H)-one (Intermediate A1d, 19 mg, 0.065 mmol) and 2,4,5-trichloropyrimidine (20 mg, 0.110 mmol). The reaction vial was flushed with Ar, sealed with a cap and then further flushed with Ar. Anhydrous NMP (0.65 mL) was added followed by DIPEA (45 uL, 0.26 mmol). The reaction mixture was heated at 140° C. under microwave irradiation for 1 h. The reaction mixture was cooled to rt, diluted with DMSO (0.8 mL) and directly purified by reverse-phase chromatography (Biotage reverse-phase 12 g C-18 column; 10-80% MeOH in H$_2$O (containing 0.1% formic acid)), affording (R)-2-cyclopropyl-10-((2,5-dichloropyrimidin-4-yl)amino)-7-methyl-1,2,3,4-tetrahydro-[1,4]oxazepino[2,3-c]quinolin-6(7H)-one (24 mg, 84%) as a red/brown solid. LCMS (Method X2) RT 1.42 min; m/z 432.1000 [M+H]$^+$.

Step 2: (R)-10-((5-chloro-2-(3-(trifluoromethyl)-1H-pyrazol-1-yl)pyrimidin-4-yl)amino)-2-cyclopropyl-7-methyl-1,2,3,4-tetrahydro-[1,4]oxazepino[2,3-c]quinolin-6(7H)-one A microwave vial (0.5-2.0 mL volume) was charged with (R)-2-cyclopropyl-10-((2,5-dichloropyrimidin-4-yl)amino)-7-methyl-1,2,3,4-tetrahydro-[1,4]oxazepino[2,3-c]quinolin-6(7H)-one (from step 1; 9 mg, 0.021 mmol), 3-(trifluoromethyl)-1H-pyrazole (28 mg, 0.207 mmol) and cesium carbonate (67 mg, 0.204 mmol). The reaction vial was flushed with Ar, sealed with a cap and then further flushed with Ar. Anhydrous NMP (0.8 mL) was added. The reaction mixture was heated at 180° C. under microwave irradiation for 1 h. The reaction mixture was cooled to rt, diluted with DMSO (0.8 mL) and directly purified by reverse-phase chromatography (Biotage reverse-phase 12 g C-18 column; 10-50-100% MeOH in H$_2$O (containing 0.1% formic acid)), affording the title compound (7 mg, 62%) as a beige solid. $^1$H NMR (600 MHz, CDCl$_3$) δ 8.48 (br d, J=2.4 Hz, 1H), 8.44 (s, 1H), 8.03 (d, J=1.9 Hz, 1H), 7.64 (dd, J=8.9, 1.9 Hz, 1H), 7.48 (s, 1H), 7.39 (d, J=8.9 Hz, 1H), 6.70 (d, J=2.4 Hz, 1H), 4.54-4.47 (m, 1H), 4.37 (br s, 1H), 4.35-4.29 (m, 1H), 3.75 (s, 3H), 2.96 (dt, J=9.7, 3.3 Hz, 1H), 2.41-2.32 (m, 1H), 2.11-2.03 (m, 1H), 1.13-1.05 (m, 1H), 0.66-0.59 (m, 1H), 0.50-0.43 (m, 1H), 0.35-0.28 (m, 1H), 0.27-0.21 (m, 1H); LCMS (Method X4) RT 3.25 min; m/z calcd for $C_{24}H_{22}ClF_3N_7O_2^+$ [M+H]$^+$: 532.1475, Found: 532.1500.

The following tabulated examples were prepared by a method analogous to that used for the preparation of Example 5a, starting from the intermediate(s) shown in the table and the appropriate amine. No purification was conducted during step 1 in Examples 5b-5h, 5k and 5p-5t. In Examples 5d-5i and 5k-5t DIPEA was used instead of cesium carbonate. Examples 5c-5f were purified by preparative HPLC.

| Example | Data and comments | Intermediate |
|---|---|---|
| Example 5b: 10-((5-chloro-2-(3-(trifluoromethyl)-1H-pyrazol-1-yl)pyrimidin-4-yl)amino)-2-(methoxymethyl)-2,7-dimethyl-1,2,3,4-tetrahydro-[1,4]oxazepino[2,3-c]quinolin-6(7H)-one | $^1$H NMR (600 MHz, Methanol-d$_4$) δ 8.48 (d, J = 2.6 Hz, 1 H), 8.41 (s, 1 H), 8.10 (d, J = 2.1 Hz, 1 H), 7.89 (dd, J = 9.0, 2.1 Hz, 1 H), 7.60 (d, J = 9.0 Hz, 1 H), 6.82 (d, J = 2.6 Hz, 1 H), 4.32-4.24 (m, 2 H), 3.76 (s, 3 H), 3.44 (d, J = 8.9 Hz, 1 H), 3.42 (d, J = 8.9 Hz, 1 H), 3.22 (s, 3 H), 2.07-2.02 (m, 1 H), 1.94-1.88 (m, 1 H), 1.39 (s, 3 H); LCMS (Method T4) RT 3.02 min; m/z calcd for C$_{24}$H$_{24}$ClF$_3$N$_7$O$_3^+$ [M + H]$^+$: 550.1576, Found: 550.1551. | Intermediate A2b: 10-amino-2-(methoxymethyl)-2,7-dimethyl-1,2,3,4-tetrahydro-[1,4]oxazepino[2,3-c]quinolin-6(7H)-one |
| Example 5c: (S)-10-((5-chloro-2-(3-(trifluoromethyl)-1H-pyrazol-1-yl)pyrimidin-4-yl)amino)-2,7-dimethyl-1,2,3,4-tetrahydro-[1,4]oxazepino[2,3-c]quinolin-6(7H)-one | $^1$H NMR (600 MHz, DMF-d$_7$) δ 9.83 (brs, 1 H), 8.75-8.63 (m, 1 H), 8.60 (s, 1 H), 8.53 (d, J = 2.3 Hz, 1 H), 7.94 (dd, J = 9.0, 2.3 Hz, 1 H), 7.54 (d, J = 9.0 Hz, 1 H), 7.08 (d, J = 2.7 Hz, 1 H), 5.60 (d, J = 2.7 Hz, 1 H), 4.34 (ddd, J = 11.8, 7.8, 5.5 Hz, 1 H), 4.17 (ddd, J = 11.8, 6.3, 5.5 Hz, 1 H), 4.03-3.97 (m, 1 H), 3.00 (s, 3 H), 2.19 (dddd, J= 13.9, 7.8, 6.3, 3.4 Hz, 1 H), 1.87 (ddt, J = 13.9, 9.8, 5.4 Hz, 1 H), 1.36 (d, J = 6.6 Hz, 3 H); LCMS (Method T4) RT 3.01 min; m/z calcd for C$_{22}$H$_{20}$ClF$_3$N$_7$O$_2^+$ [M + H]$^+$: 506.1314, Found: 506.1282. | Intermediate A1a: (S)-10-amino-2,7-dimethyl-1,2,3,4-tetrahydro-[1,4]oxazepino[2,3-c]quinolin-6(7H)-one |
| Example 5d: (S)-1-(5-chloro-4-((2,7-dimethyl-6-oxo-1,2,3,4,6,7-hexahydro-[1,4]oxazepino[2,3-c]quinolin-10-yl)amino)pyrimidin-2-yl)-N,N-dimethylpiperidine-4-carboxamide | $^1$H NMR (600 MHz, Methanol-d$_4$) δ 8.06 (s, 1 H), 7.95 (d, J = 2.0 Hz, 1 H), 7.87 (d, J = 9.0 Hz, 1 H), 7.50 (dd, J = 9.1, 2.0 Hz, 1 H), 4.60 (d, J = 13.2 Hz, 2 H), 4.41-4.30 (m, 1 H), 4.27-4.18 (m, 1 H), 4.07-3.98 (m, 1 H), 3.72 (s, 3 H), 3.15 (s, 3 H), 3.02-2.88 (m, 3H), 2.94 (s, 3 H), 2.25-2.18 (m, 1 H), 1.94-1.82 (m, 1 H), 1.77-1.58 (m, 4 H), 1.42 (d, J = 6.7 Hz, 3 H); LCMS (Method T4) RT 2.37 min; m/z calcd for C$_{26}$H$_{33}$ClN$_7$O$_3^+$ [M + H]$^+$: 526.2328, Found: 526.2297. | Intermediate A1a: (S)-10-amino-2,7-dimethyl-1,2,3,4-tetrahydro-[1,4]oxazepino[2,3-c]quinolin-6(7H)-one |
| Example 5e: (S)-10-((5-chloro-2-((3R,5S)-3,5-dimethylpiperidin-1-yl)pyrimidin-4-yl)amino)-2,7-dimethyl-1,2,3,4-tetrahydro-[1,4]oxazepino[2,3-c]quinolin-6(7H)-one | $^1$H NMR (600 MHz, Methanol-d$_4$) δ 8.08 (d, J = 2.3 Hz, 1 H), 7.92 (s, 1 H), 7.86 (dd, J = 9.1, 2.3 Hz, 1 H), 7.49 (d, J = 9.1 Hz, 1 H), 4.56-4.50 (m, 2 H), 4.35 (ddd, J = 11.9, 8.1, 5.6 Hz, 1 H), 4.24 (ddd, J = 11.8, 6.6, 5.0 Hz, 1 H), 4.10-4.00 (m, 1 H), 3.72 (s, 3 H), 2.28 (ddd, J = 13.2, 11.5, 3.3 Hz, 2 H), 2.24-2.19 (m, 1 H), 1.89 (ddt, J = 13.8, 10.3,5.3 Hz, 1 H), 1.85-1.78 (m, 1 H), 1.60-1.50 (m, 2 H), 1.43 (d, J = 6.6 Hz, 3 H), 0.90 (d, J = 6.6 Hz, 6 H), 0.80 (q, J = 12.1 Hz, 1 H); LCMS (Method T4) RT 2.94 min; m/z calcd for C$_{25}$H$_{32}$ClN$_6$O$_2^+$ [M + H]$^+$: 483.2270, Found: 483.2358. | Intermediate A1a: (S)-10-amino-2,7-dimethyl-1,2,3,4-tetrahydro-[1,4]oxazepino[2,3-c]quinolin-6(7H)-one |

| Example | Data and comments | Intermediate |
| --- | --- | --- |
| Example 5f: (S)-10-((5-chloro-2-((3S,5R)-4,4-difluoro-3,5-dimethylpiperidin-1-yl)pyrimidin-4-yl)amino)-2,7-dimethyl-1,2,3,4-tetrahydro-[1,4]oxazepino[2,3-c]quinolin-6(7H)-one | $^1$H NMR (600 MHz, Methanol-$d_4$) δ 8.07 (s, 1 H), 7.97 (d, J = 4.0 Hz, 1 H), 7.80 (dd, J = 9.5, 3.7 Hz, 1 H), 7.51 (dd, J = 9.2, 3.9 Hz, 1 H), 4.56-4.48 (m, 2 H), 4.40-4.30 (m, 1 H), 4.30-4.22 (m, 1 H), 4.10-4.00 (m, 1 H), 3.73 (s, 3 H), 2.75-2.62 (m, 2 H), 2.37-2.15 (m, 1 H), 2.05-1.82 (m, 3 H), 1.42 (t, J = 5.1 Hz, 3 H), 1.00 (t, J = 5.4 Hz, 6 H);<br>LCMS (Method T4) RT 3.19 min; m/z calcd for $C_{25}H_{30}ClF_2N_6O_2^+$ [M + H]$^+$: 519.2081, Found: 519.2082. | Intermediate A1a: (S)-10-amino-2,7-dimethyl-1,2,3,4-tetrahydro-[1,4]oxazepino[2,3-c]quinolin-6(7H)-one |
| Example 5g: (S)-10-((5-chloro-2-((2S,6R)-2,6-dimethylmorpholino)pyrimidin-4-yl)amino)-2,7-dimethyl-1,2,3,4-tetrahydro-[1,4]oxazepino[2,3-c]quinolin-6(7H)-one | $^1$H NMR (600 MHz, Methanol-$d_4$) δ 8.11-8.07 (m, 1 H), 7.95 (s, 1 H), 7.79 (dd, J = 8.9, 1.7 Hz, 1 H), 7.49 (d, J = 8.9 Hz, 1 H), 4.38-4.31 (m, 3 H), 4.25-4.20 (m, 1 H), 4.06-3.99 (m, 1 H), 3.71 (s, 3 H), 3.60-3.54 (m, 2 H), 2.53-2.45 (m, 2 H), 2.25-2.19 (m, 1 H), 1.91-1.84 (m, 1 H), 1.41 (d, J = 6.6 Hz, 3 H), 1.16 (d, J = 6.2 Hz, 6 H);<br>LCMS (Method T4) RT 2.82 min; m/z calcd for $C_{24}H_{30}ClN_6O_3^+$ [M + H]$^+$: 485.2062, Found: 485.2047. | Intermediate A1a: (S)-10-amino-2,7-dimethyl-1,2,3,4-tetrahydro-[1,4]oxazepino[2,3-c]quinolin-6(7H)-one |
| Example 5h: (S)-10-((5-chloro-2-morpholinopyrimidin-4-yl)amino)-2,7-dimethyl-1,2,3,4-tetrahydro-[1,4]oxazepino[2,3-c]quinolin-6(7H)-one | $^1$H NMR (600 MHz, Methanol-$d_4$) δ 8.07-8.03 (m, 1 H), 7.99-7.96 (m, 1 H), 7.86 (dd, J = 9.0, 2.1 Hz, 1 H), 7.53-7.48 (m, 1 H), 4.37-4.30 (m, 1 H), 4.24-1.19 (m, 1 H), 4.05-3.98 (m, 1 H), 3.71 (s, 3 H), 3.70-3.67 (m, 4 H), 3.67-3.62 (m, 4 H), 2.26-2.18 (m, 1 H), 1.92-1.85 (m, 1 H), 1.41 (d, J = 6.6 Hz, 3H);<br>LCMS (Method X4) RT 2.62 min; m/z calcd for $C_{22}H_{26}ClN_6O_3^+$ [M + H]$^+$: 457.1755, Found: 457.1758. | Intermediate A1a: (S)-10-amino-2,7-dimethyl-1,2,3,4-tetrahydro-[1,4]oxazepino[2,3-c]quinolin-6(7H)-one |

| Example | Data and comments | Intermediate |
| --- | --- | --- |
| Example 5i: (R)-10-((5-chloro-2-((3S,5R)-4,4-difluoro-3,5-dimethylpiperidin-1-yl)pyrimidin-4-yl)amino)-2-cyclopropyl-7-methyl-1,2,3,4-tetrahydro-[1,4]oxazepino[2,3-c]quinolin-6(7H)-one | $^1$H NMR (600 MHz, CDCl$_3$) δ 8.04 (s, 1 H), 7.78 (brs, 1 H), 7.64 (dd, J = 9.0, 1.5 Hz, 1 H), 7.32 (d, J = 9.0 Hz, 1 H), 7.08 (s, 1 H), 4.66-4.58 (m, 2 H), 4.45 (ddd, J = 12.1, 8.8, 5.3 Hz, 1 H), 4.37-4.20 (m, 2 H), 3.73 (s, 3 H), 3.00 (dt, J = 10.2, 3.7 Hz, 1 H), 2.79-2.70 (m, 2 H), 2.41-2.35 (m, 1 H), 2.06-1.91 (m, 3 H), 1.13-1.09 (m, 1 H), 1.08 (d, J = 6.7 Hz, 6 H), 0.73-0.68 (m, 1 H), 0.68-0.63 (m, 1 H), 0.40-0.35 (m, 1 H), 0.35-0.30 (m, 1 H); LCMS (Method T4) RT 3.28 min; m/z calcd for $C_{27}H_{32}ClF_2N_6O_2^+$ [M + H]$^+$: 545.2238, Found: 545.2222. | Intermediate A1d: (R)-10-amino-2-cyclopropyl-7-methyl-1,2,3,4-tetrahydro-[1,4]oxazepino[2,3-c]quinolin-6(7H)-one |
| Example 5j: 10'-((5-chloro-2-(3-(trifluoromethyl)-1H-pyrazol-1-yl)pyrimidin-4-yl)amino)-7'-methyl-3',4,4',5-tetrahydro-1'H,2H-spiro[furan-3,2'-[1,4]oxazepino[2,3-c]quinolin]-6'(7'H)-one | $^1$H NMR (600 MHz, CDCl$_3$) δ 8.51 (br s, 1 H), 8.42 (s, 1 H), 8.11-8.06 (m, 1 H), 7.63 (dd, J = 9.0, 1.6 Hz, 1 H), 7.48 (s, 1 H), 7.39 (d, J = 9.0 Hz, 1 H), 6.72 (d, J = 2.1 Hz, 1 H), 4.49 (t, J = 5.9 Hz, 2 H), 4.35 (s, 1 H), 3.99 (d, J = 9.4 Hz, 1 H), 3.89 (dd, J = 8.4, 6.3 Hz, 2 H), 3.77 (s, 3 H), 3.63 (d, J = 9.4 Hz, 1 H), 2.44-2.38 (m, 1 H), 2.25 (t, J = 5.9 Hz, 2 H), 2.07-2.00 (m, 1 H); LCMS (Method T4) RT 2.91 min; m/z calcd for $C_{24}H_{22}ClF_3N_7O_3^+$ [M + H]$^+$: 548.1419, Found: 548.1404. | Intermediate A2c: 10'-amino-7'-methyl-3',4,4',5-tetrahydro-1'H,2H-spiro[furan-3,2'-[1,4]oxazepino[2,3-c]quinolin]-6'(7'H)-one |
| Example 5k: (R)-10-((5-chloro-2-(2,2,6,6-tetramethylmorpholino)pyrimidin-4-yl)amino)-2-cyclopropyl-7-methyl-1,2,3,4-tetrahydro-[1,4]oxazepino[2,3-c]quinolin-6(7H)-one | $^1$H NMR (600 MHz, CDCl$_3$) δ 8.03 (s, 1 H), 7.76 (d, J = 2.2 Hz, 1 H), 7.66 (dd, J = 9.0, 2.2 Hz, 1 H), 7.30 (d, J = 9.0 Hz, 1 H), 7.05 (S, 1 H), 4.49-4.43 (m, 1 H), 4.38-4.33 (m, 1 H), 4.26 (s, 1 H), 3.73 (s, 3 H), 3.63-3.57 (m, 4 H), 2.99 (dt, J = 10.1, 3.7 Hz, 1 H), 2.42-2.35 (m, 1 H), 2.05-1.97 (m, 1 H), 1.26 (s, 6 H), 1.23 (s, 6 H), 1.14-1.07 (m, 1 H), 0.73-0.67 (m, 1 H), 0.67-0.62 (m, 1 H), 0.39-0.34 (m, 1 H), 0.34-0.29 (m, 1 H); LCMS (Method T4) RT 3.10 min; m/z calcd for $C_{28}H_{36}ClN_6O_3^+$ [M + H]$^+$: 539.2532, Found: 539.2506. | Intermediate A1d: (R)-10-amino-2-cyclopropyl-7-methyl-1,2,3,4-tetrahydro-[1,4]oxazepino[2,3-c]quinolin-6(7H)-one |

| Example | Data and comments | Intermediate |
| --- | --- | --- |
| Example 5l: (R)-10-((2-(3-oxa-8-azabicyclo[3.2.1]octan-8-yl)-5-chloropyrimidin-4-yl)amino)-2-cyclopropyl-7-methyl-1,2,3,4-tetrahydro-[1,4]oxazepino[2,3-c]quinolin-6(7H)-one 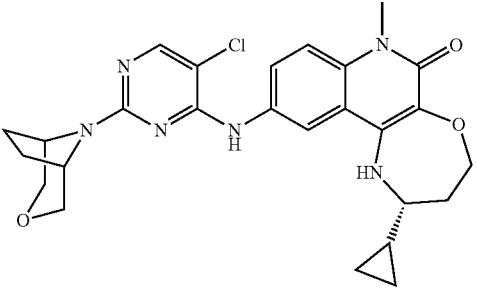 [SMILES: Cn1c(=O)c2c(c3cc(Nc4nc(N5C6CCC5COC6)ncc4Cl)ccc31)N[C@@H](C1CC1)CCO2] | $^1$H NMR (600 MHz, CDCl$_3$) δ 8.04 (s, 1 H), 7.73-7.66 (m, 2 H), 7.31 (d, J = 9.4 Hz, 1 H), 7.07 (s, 1 H), 4.55 (br s, 2 H), 4.50-4.44 (m, 1 H), 4.34-4.29 (m, 1 H), 4.24 (s, 1 H), 3.80 (dd, J = 10.5, 7.4 Hz, 2 H), 3.72 (s, 3 H), 3.63 (app t, J = 10.6 Hz, 2 H), 2.96 (dt, J = 10.1, 3.4 Hz, 1 H), 2.41-2.34 (m, 1 H), 2.10-1.95 (m, 5 H), 1.13-1.06 (m, 1 H), 0.73-0.63 (m, 2 H), 0.39-0.30 (m, 2 H); LCMS (Method X4) RT 2.77 min; m/z calcd for C$_{26}$H$_{30}$ClN$_6$O$_3$$^+$ [M + H]$^+$: 509.2068, Found: 509.2059. | Intermediate A1d: (R)-10-amino-2-cyclopropyl-7-methyl-1,2,3,4-tetrahydro-[1,4]oxazepino[2,3-c]quinolin-6(7H)-one |
| Example 5m: (R)-10-((5-chloro-2-(4,4-difluoropiperidin-1-yl)pyrimidin-4-yl)amino)-2-cyclopropyl-7-methyl-1,2,3,4-tetrahydro-[1,4]oxazepino[2,3-c]quinolin-6(7H)-one 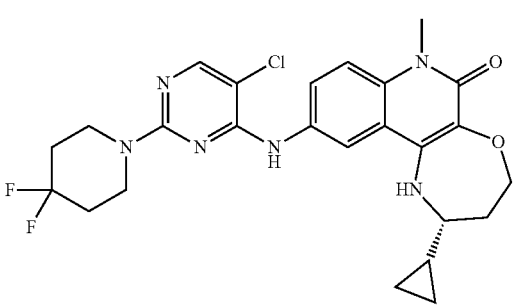 | $^1$H NMR (600 MHz, DMSO-d$_6$) δ 8.92 (s, 1 H), 8.12 (d, J = 2.3 Hz, 1 H), 8.09 (s, 1 H), 7.68 (dd, J = 9.0, 2.3 Hz, 1 H), 7.40 (d, J = 9.0 Hz, 1 H), 5.75 (d, J = 3.7 Hz, 1 H), 4.26-4.21 (m, 1 H), 4.15-4.11 (m, 1 H), 3.76-3.70 (m, 4 H), 3.55 (s, 3 H), 2.89-2.84 (m, 1 H), 2.22-2.15 (m, 1 H), 2.02-1.90 (m, 4 H), 1.28-1.17 (m, 2 H), 0.58-0.48 (m, 2 H), 0.40-0.35 (m, 1 H), 0.29-0.24 (m, 1 H); LCMS (Method T4) RT 3.07 min; m/z calcd for C$_{25}$H$_{28}$F$_2$ClN$_6$O$_2$$^+$ [M + H]$^+$: 517.1925, Found: 517.1924. | Intermediate A1d: (R)-10-amino-2-cyclopropyl-7-methyl-1,2,3,4-tetrahydro-[1,4]oxazepino[2,3-c]quinolin-6(7H)-one |
| Example 5n: (R)-10-((5-chloro-2-((1R,5S,7S)-7-hydroxy-3-oxa-9-azabicyclo[3.3.1]nonan-9-yl)pyrimidin-4-yl)amino)-2-cyclopropyl-7-methyl-1,2,3,4-tetrahydro-[1,4]oxazepino[2,3-c]quinolin-6(7H)-one 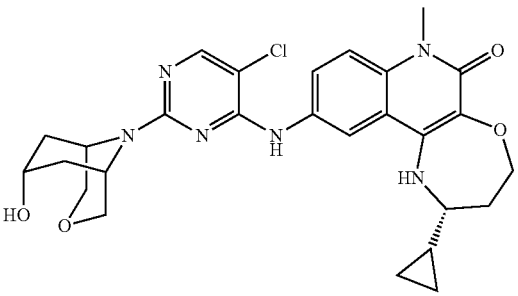 [SMILES: Cn1c(=O)c2c(c3cc(Nc4nc(N5C6COCC5CC(O)C6)ncc4Cl)ccc31)N[C@@H](C1CC1)CCO2] | $^1$H NMR (600 MHz, DMSO-d$_6$) δ 8.90 (s, 1 H), 8.09 (s, 1 H), 8.06 (s, 1 H), 7.68 (d, J = 8.9 Hz, 1 H), 7.39 (d, J = 8.9 Hz, 1 H), 5.74 (d, J = 3.8 Hz, 1 H), 5.15 (s, 1 H), 4.58 (s, 1 H), 4.33-4.17 (m, 2 H), 4.15-4.10 (m, 1 H), 3.89-3.73 (m, 2 H), 3.69 (s, 1 H), 3.64 (dt, J = 11.7, 3.5 Hz, 2 H), 3.55 (s, 3 H), 2.86 (tt, J = 7.9, 3.5 Hz, 1 H), 2.25-1.90 (m, 4 H), 1.73-.49 (m, 2 H), 1.26-1.20 (m, 1 H), 0.58-0.49 (m, 2 H), 0.40-0.35 (m, 1 H), 0.29-0.24 (m, 1 H); LCMS (Method T4) RT 2.80 min; m/z calcd for C$_{27}$H$_{32}$ClN$_6$O$_4$$^+$ [M + H]$^+$: 539.2168, Found: 539.2187. | Intermediate A1d: (R)-10-amino-2-cyclopropyl-7-methyl-1,2,3,4-tetrahydro-[1,4]oxazepino[2,3-c]quinolin-6(7H)-one |

-continued

| Example | Data and comments | Intermediate |
| --- | --- | --- |
| Example 5o: (R)-10-((2-(2-oxa-6-azaadamantan-6-yl)-5-chloropyrimidin-4-yl)amino)-2-cyclopropyl-7-methyl-1,2,3,4-tetrahydro-[1,4]oxazepino[2,3-c]quinolin-6(7H)-one | $^1$H NMR (600 MHz, DMSO-$d_6$) δ 8.81 (s, 1 H), 8.08 (d, J = 2.3 Hz, 1 H), 8.07 (s, 1 H), 7.70 (dd, J= 9.1, 2.3 Hz, 1 H), 7.39 (d, J = 9.1 Hz, 1 H), 5.70 (d, J = 3.5 Hz, 1 H), 4.97 (br s, 1 H), 4.71 (br s, 1 H), 4.28-4.21 (m, 1 H), 4.16-4.10 (m, 1 H), 4.10-4.05 (m, 2 H), 3.55 (s, 3 H), 2.88-2.82 (m, 1 H), 2.23-2.15 (m, 1 H), 2.03-1.93 (m, 2 H), 1.74-1.65 (m, 4 H), 1.30-1.18 (m, 4 H), 0.57-0.47 (m, 2 H), 0.40-0.34 (m, 1 H), 0.29-0.23 (m, 1 H); LCMS (Method T4) RT 2.71 min; m/z calcd for $C_{28}H_{32}ClN_6O_3^+$ [M + H]$^+$: 535.2219, Found: 535.2209. | Intermediate A1d: (R)-10-amino-2-cyclopropyl-7-methyl-1,2,3,4-tetrahydro-[1,4]oxazepino[2,3-c]quinolin-6(7H)-one |
| Example 5p: (R)-10-((5-chloro-2-((3S,5R)-4,4-difluoro-3,5-dimethylpiperidin-1-yl)pyrimidin-4-yl)amino)-2-cyclopropyl-1,2,3,4-tetrahydro-[1,4]oxazepino[2,3-c]quinolin-6(7H)-one | $^1$H NMR (600 MHz, DMSO-$d_6$) δ 11.10 (s, 1 H), 8.89 (s, 1 H), 8.06 (s, 1 H), 7.99 (d, J = 2.1 Hz, 1 H), 7.52 (dd, J = 8.7, 2.1 Hz, 1 H), 7.18 (d, J = 8.7 Hz, 1 H), 5.74 (d, J = 3.6 Hz, 1 H), 4.43 (br s, 2 H), 4.24-4.20 (m, 1 H), 4.12-4.08 (m, 1 H), 2.88-2.84 (m, 1 H), 2.62-2.57 (m, 2 H), 2.26-2.21 (m, 1 H), 2.02-1.95 (m, 3 H), 1.26-1.20 (m, 1 H), 0.93 (d, J = 6.7 Hz, 6 H), 0.57-0.48 (m, 2 H), 0.39-0.35 (m, 1 H), 0.28-0.24 (m, 1 H); LCMS (Method X4) RT 3.47 min; m/z calcd for $C_{26}H_{30}ClF_2N_6O_2^+$ [M + H]$^+$: 531.2087, Found: 531.2095. | Intermediate A6a: (R)-10-amino-2-cyclopropyl-1,2,3,4-tetrahydro-[1,4]oxazepino[2,3-c]quinolin-6(7H)-one |
| Example 5q: (R)-10-((2-(3-oxa-8-azabicyclo[3.2.1]octan-8-yl)-5-chloropyrimidin-4-yl)amino)-2-cyclopropyl-7-((3,3-difluorocyclobutyl)methyl)-1,2,3,4-tetrahydro-[1,4]oxazepino[2,3-c]quinolin-6(7H)-one | $^1$H NMR (600 MHz, CDCl$_3$) δ 8.05 (s, 1 H), 7.73 (brs, 1 H), 7.67 (dd, J = 9.1, 2.2 Hz, 1 H), 7.27 (d, J = 9.1 Hz, 1 H), 7.08 (s, 1 H), 4.64-4.50 (m, 3 H), 4.49-4.42 (m, 2 H), 4.36-4.31 (m, 1 H), 4.25 (s, 1 H), 3.80 (dd, J = 10.6, 7.4 Hz, 2 H), 3.63 (app t, J = 11.0 Hz, 2 H), 2.98 (dt, J = 10.0, 3.5 Hz, 1 H), 2.71-2.56 (m, 5 H), 2.43-2.36 (m, 1 H), 2.11-2.06 (m, 2 H), 2.05-1.95 (m, 3 H), 1.13-1.05 (m, 1 H), 0.73-0.68 (m, 1 H), 0.68-0.63 (m, 1 H), 0.39-0.30 (m, 2 H); LCMS (Method T4) RT 2.99 min; m/z calcd for $C_{30}H_{34}ClF_2N_6O_3^+$ [M + H]$^+$: 599.2343, Found: 599.2379. | Intermediate A5b: (R)-10-amino-2-cyclopropyl-7-((3,3-difluorocyclobutyl)methyl)-1,2,3,4-tetrahydro-[1,4]oxazepino[2,3-c]quinolin-6(7H)-one |

| Example | Data and comments | Intermediate |
| --- | --- | --- |
| Example 5r: (R)-10-((2-(3-oxa-8-azabicyclo[3.2.1]octan-8-yl)-5-chloropyrimidin-4-yl)amino)-2-cyclopropyl-7-(cyclopropylmethyl)-1,2,3,4-tetrahydro-[1,4]oxazepino[2,3-c]quinolin-6(7H)-one | $^1$H NMR (600 MHz, methanol-$d_4$) δ 8.01-7.97 (m, 2 H), 7.94 (dd, J = 9.1 2.2 Hz, 1 H), 7.65 (dd, J = 9.2, 2.5 Hz, 1 H), 4.52-4.46 (m, 2 H), 4.44-4.38 (m, 1 H), 4.28 (dt, J = 7.0, 2.2 Hz, 2 H), 4.23-4.17 (m, 1 H), 3.76 (dd, J = 10.9, 5.6 Hz, 2 H), 3.59 (dd, J = 10.9, 5.5 Hz, 2 H), 2.99-2.92 (m, 1 H), 2.38-2.31 (m, 1 H), 2.15-2.06 (m, 1 H), 2.04 (d, J= 7.2 Hz, 2 H), 1.99-1.94 (m, 2 H), 1.35-1.19 (m, 2 H), 0.67 (d, J = 8.2 Hz, 2 H), 0.56-0.49 (m, 4 H), 0.45-0.40 (m, 1 H), 0.37-0.32 (m, 1 H); LCMS (Method T4) RT 2.98 min; m/z calcd for $C_{29}H_{34}ClN_6O_3^+$ [M + H]$^+$: 549.2375, Found: 549.2381. | Intermediate A5a: (R)-10-amino-2-cyclopropyl-7-(cyclopropylmethyl)-1,2,3,4-tetrahydro-[1,4]oxazepino[2,3-c]quinolin-6(7H)-one |
| Example 5s: (R)-10-((5-chloro-2-(4,4-difluoropiperidin-1-yl)pyrimidin-4-yl)amino)-2-cyclopropyl-7-methyl-1,2,3,4-tetrahydro-[1,4]oxazepino[2,3-c][1,8]naphthyridin-6(7H)-one | $^1$H NMR (600 MHz, methanol-$d_4$) δ 8.80 (d, J = 2.3 Hz, 1 H), 8.47 (d, J = 2.3 Hz, 1 H), 8.02 (s, 1 H), 4.44-4.38 (m, 1 H), 4.25-4.19 (m, 1 H), 3.85-3.80 (m, 4 H), 3.79 (s, 3 H), 2.96 (dt, J = 9.4, 3.6 Hz, 1 H), 2.38-2.31 (m, 1 H), 2.15-2.08 (m, 1 H), 1.98-1.90 (m, 4 H), 1.25-1.18 (m, 1 H), 0.68-0.61 (m, 2 H), 0.43-0.38 (m, 1 H), 0.35-0.30 (m, 1 H); LCMS (Method T4) RT 3.09 min; m/z calcd for $C_{24}H_{27}ClF_2N_7O_2^+$ [M + H]$^+$: 518.1877, Found: 518.1898. | Intermediate A7a: (R)-10-amino-2-cyclopropyl-7-methyl-1,2,3,4-tetrahydro-[1,4]oxazepino[2,3-c][1,8]naphthyridin-6(7H)-one |
| Example 5t: (R)-10-((5-chloro-2-((3S,5R)-4,4-difluoro-3,5-dimethylpiperidin-1-yl)pyrimidin-4-yl)amino)-2-cyclopropyl-7-methyl-1,2,3,4-tetrahydro-[1,4]oxazepino[2,3-c][1,8]naphthyridin-6(7H)-one | $^1$H NMR (600 MHz, methanol-$d_4$) δ 8.77 (d, J = 2.3 Hz, 1 H), 8.47 (d, J = 2.3 Hz, 1 H), 8.01 (s, 1 H), 4.54-4.46 (m, 2 H), 4.44-4.37 (m, 1 H), 4.25-4.19 (m, 1 H), 3.79 (s, 3 H), 2.95 (dt, J = 9.4, 3.7 Hz, 1 H), 2.69 (dt, J = 12.7, 6.8 Hz, 2 H), 2.38-2.30 (m, 1 H), 2.15-2.07 (m, 1 H), 2.01-1.88 (m, 2 H), 1.25-1.18 (m, 1 H), 1.00 (d, J = 6.6 Hz, 6 H), 0.67-0.60 (m, 2 H), 0.42-0.38 (m, 1 H), 0.35-0.30 (m, 1 H); LCMS (Method X4) RT 3.67 min; m/z calcd for $C_{26}H_{31}ClF_2N_7O_2^+$ [M + H]$^+$: 546.2195, Found: 546.2197. | Intermediate A7a: (R)-10-amino-2-cyclopropyl-7-methyl-12,3,4-tetrahydro-[1,4]oxazepino[2,3-c][1,8]naphthyridin-6(7H)-one |

Example 5u: (R)-10-((5-chloro-2-((1R,5S,7S)-7-hydroxy-3-oxa-9-azabicyclo[3.3.1]nonan-9-yl)pyrimidin-4-yl)amino)-2-cyclopropyl-7-((3,3-difluorocyclobutyl)methyl)-1,2,3,4-tetrahydro-[1,4]oxazepino[2,3-c]quinolin-6(7H)-one

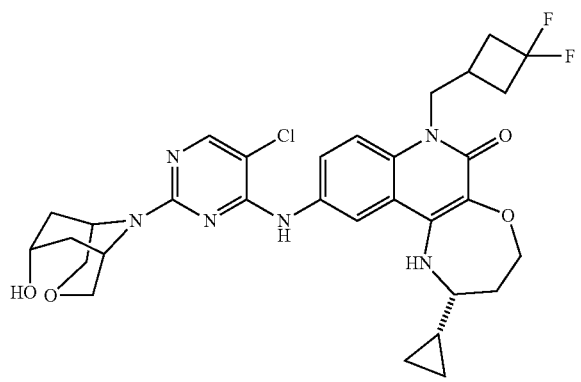 [SMILES: O=c1c2c(c3cc(Nc4nc(N5C6COCC5CC(O)C6)ncc4Cl)ccc3n1CC1CC(F)(F)C1)N[C@@H](C1CC1)CCO2]

A microwave vial (0.5-2.0 mL volume) was charged with (R)-10-amino-2-cyclopropyl-7-((3,3-difluorocyclobutyl)methyl)-1,2,3,4-tetrahydro-[1,4]oxazepino[2,3-c]quinolin-6(7H)-one (Intermediate A5b; 6.5 mg, 0.017 mmol) and DIPEA (12 uL, 0.069 mmol). A solution of (1R,5S,7s)-9-(5-chloro-4-(methylsulfinyl)pyrimidin-2-yl)-3-oxa-9-azabicyclo[3.3.1]nonan-7-ol (Intermediate J1; 7.0 mg, 0.022 mmol) in isopropanol (0.7 mL) was then added and the vial was flushed with Ar and sealed with a cap. The reaction mixture was heated at 140° C. in a heating block for 18 h. After this time, the reaction mixture was cooled to rt and additional DIPEA (20 uL, 0.11 mmol) was added. The vial was re-sealed with a cap and heated at 140 C in a heating block for a further 6 h. The reaction mixture was cooled to rt and concentrated in vacuo. The reaction mixture was dissolved in DMSO (1 mL) and directly purified by reverse-phase chromatography (Biotage reverse-phase 12 g C-18 column; 60-90% MeOH in $H_2O$ (containing 0.1% formic acid)), affording the desired product which co-ran with an impurity. The crude product was further purified by flash chromatography (10 g KP-sil; 50% to 100% EtOAc in cyclohexane followed by 0% to 20% MeOH in EtOAc) affording an off-white solid. The solid was dissolved in MeOH and passed through an SCX-2 (1 g) column, eluting with MeOH (15 mL) followed by 2 N methanolic ammonia (20 mL). The basic fraction was concentrated in vacuo affording the title compound (1.8 mg, 17%) as an off-white solid. $^1$H NMR (600 MHz, methanol-$d_4$) δ 8.01 (s, 1H), 7.94 (d, J=2.3 Hz, 1H), 7.86 (dd, J=9.1, 2.3 Hz, 1H), 7.54 (d, J=9.1 Hz, 1H), 4.56 (dd, J=14.4, 7.2 Hz, 2H), 4.54 (dd, J=14.4, 6.9 Hz, 2H), 4.41-4.36 (m, 1H), 4.24-4.19 (m, 1H), 3.94-3.86 (m, 3H), 3.80-3.74 (m, 2H), 2.96 (dt, J=9.5, 3.6 Hz, 1H), 2.70-2.50 (m, 5H), 2.38-2.30 (m, 1H), 2.25-2.16 (m, 2H), 2.13-2.06 (m, 1H), 1.82-1.74 (m, 2H), 1.25-1.19 (m, 1H), 0.68-0.61 (m, 2H), 0.44-0.37 (m, 1H), 0.37-0.30 (m, 1H); LCMS (Method T4) RT 3.02 min; m/z calcd for $C_{31}H_{36}ClF_2N_6O_4^+[M+H]^+$: 629.2449, Found: 629.2436.

Example 6a: (S)-2-chloro-4-((2,7-dimethyl-5,6-dioxo-1,2,3,5,6,7-hexahydro-[1,4]oxazepino[6,5-c]quinolin-10-yl)amino)nicotinonitrile

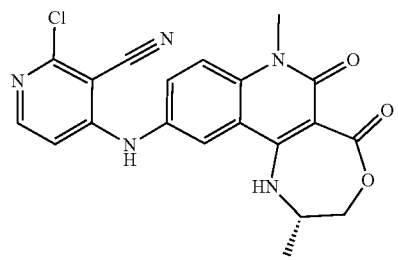 [SMILES: C[C@H]1COC(=O)c2c(c3cc(Nc4ccnc(Cl)c4C#N)ccc3n(C)c2=O)N1]

A suspension of DIPEA (10 uL, 0.077 mmol), 2,4-dichloropyridine-3-carbonitrile (6 mg, 0.036 mmol) and (S)-10-amino-2,7-dimethyl-2,3-dihydro-[1,4]oxazepino[6,5-c]quinoline-5,6(1H,7H)-dione (Intermediate B1a, 7 mg, 0.026 mmol) in NMP (1.5 mL) was stirred under microwave irradiation at 160° C. for 1 h. The crude reaction mixture was directly purified by preparative HPLC (15 min gradient of 60:40 to 0:100 $H_2O$:MeOH (both modified with 0.1% formic acid); flow rate 20 mLmin$^{-1}$) affording the title compound (1 mg, 10%) as a light brown solid which was subsequently washed with $Et_2O$ and dried. $^1$H NMR (500 MHz, DMF-$d_7$) δ 8.43 (d, J=2.2 Hz, 1H), 8.27 (d, J=6.2 Hz, 1H), 7.87 (dd, J=9.0, 2.2 Hz, 1H), 7.80 (s, 1H), 7.78 (d, J=9.0 Hz, 1H), 7.03 (d, J=6.2 Hz, 1H), 4.81 (dd, J=13.0, 1.5 Hz, 1H), 4.63 (dd, J=13.0, 5.5 Hz, 1H), 4.24-4.30 (m, 1H), 3.80 (s, 3H), 1.52 (d, J=6.6 Hz, 3H); LCMS (Method T4) RT 2.35 min; m/z calcd for $C_{20}H_{17}ClN_5O_3^+$ [M+H]+: 410.1014, Found: 410.1007.

The following tabulated examples were prepared by a method analogous to that used for the preparation of Example 6a, starting from the intermediate(s) shown in the table.

| Example | Data and comments | Intermediate |
|---|---|---|
| Example 6b: (S)-2-chloro-4-((2-cyclopropyl-7-methyl-5,6-dioxo-1,2,3,5,6,7-hexahydro-[1,4]oxazepino[6,5-c]quinolin-10-yl)amino)nicotinonitrile | $^1$H NMR (600 MHz, Methanol-$d_4$) δ 8.10 (d, J = 2.0 Hz, 1 H), 8.02 (d, J = 6.2 Hz, 1 H), 7.70-7.65 (m, 2 H), 6.73 (d, J = 6.2 Hz, 1 H), 4.72 (dd, J = 12.9, 1.5 Hz, 1 H), 4.60 (dd, J = 12.9, 5.7 Hz, 1 H), 3.69 (s, 3 H), 3.26 (ddd, J = 8.7, 5.6, 1.5 Hz, 1 H), 1.11 (qt, J = 8.2, 4.9 Hz, 1 H), 0.70 (tdd, J = 8.2, 5.6, 4.4 Hz, 1 H), 0.64 (tdd, J = 8.7, 5.6, 4.4 Hz, 1 H), 0.57 (dq, J = 9.8, 4.9 Hz, 1 H), 0.43 (ddd, J = 10.4, 9.4, 5.0 Hz, 1 H); LCMS (Method T4) RT 2.46 min; m/z calcd for $C_{22}H_{19}ClN_5O_3^+$ [M + H]$^+$: 436.1171, Found: 436.1158. | Intermediate B1b: (S)-10-amino-2-cyclopropyl-7-methyl-2,3-dihydro-[1,4]oxazepino[6,5-c]quinoline-5,6(1H,7H)-dione |
| Example 6c: 2-chloro-4-((2-cyclopropyl-7-methyl-5,6-dioxo-1,2,3,5,6,7-hexahydro-[1,4]oxazepino[6,5-c]quinolin-10-yl)amino)nicotinonitrile | $^1$H NMR (500 MHz, Methanol-$d_4$) δ 8.11 (d, J = 2.0 Hz, 1 H), 8.02 (d, J = 6.2 Hz, 1 H), 7.68-7.66 (m, 2 H), 6.73 (d, J = 6.2 Hz, 1 H), 4.73 (dd, J = 12.9, 1.5 Hz, 1 H), 4.66-4.55 (m, 1 H), 3.70 (s, 3 H), 3.29-3.23 (m, 1 H), 1.15-1.05 (m, 1 H), 0.75-0.65 (m, 1 H), 0.65-0.60 (m, 1 H), 0.60-0.52 (m, 1 H), 0.43 (ddd, J = 10.4, 9.4, 5.0 Hz, 1 H); LCMS (Method T4) RT 2.47 min; m/z calcd for $C_{22}H_{19}ClN_5O_3^+$ [M + H]$^+$: 436.1171, Found: 436.1157. | Intermediate B1c: 10-amino-2-cyclopropyl-7-methyl-2,3-dihydro-[1,4]oxazepino[6,5-c]quinoline-5,6(1H,7H)-dione |
| Example 6d: 2-chloro-4-((2,3,7-trimethyl-5,6-dioxo-1,2,3,5,6,7-hexahydro-[1,4]oxazepino[6,5-c]quinolin-10-yl)amino)nicotinonitrile | Compound isolated as a mixture of diastereoisomers (d.r. 2:1, diastereoisomer A: diastereoisomer B): Diastereoisomer A: $^1$H NMR (500 MHz, Methanol-$d_4$) δ 8.08 (d, J = 1.9 Hz, 1 H), 8.01 (d, J = 6.2 Hz, 1 H), 7.67-7.64 (m, 2 H), 6.74 (d, J = 6.2 Hz, 1 H), 5.13-5.07 (m, 1 H), 3.94-3.88 (m, 1 H), 3.69 (s, 3 H), 1.45 (d, J = 6.4 Hz, 3 H), 1.36 (d, J = 6.6 Hz, 3 H); Diastereomer B: $^1$H NMR (500 MHz, Methanol-$d_4$) δ 8.03 (d, J = 6.2 Hz, 1 H), 8.02-8.01 (m, 1 H), 7.67-7.64 (m, 2 H), 6.72 (d, J = 6.2 Hz, 1 H), 3.94-3.88 (m, 1 H), 3.88-3.82 (m, 1 H), 3.68 (s, 3 H), 1.44 (d, J = 6.4 Hz, 3 H), 1.32 (d, J = 6.6 Hz, 3 H); LCMS (Method T4) RT 2.44 min; m/z calcd for $C_{21}H_{19}ClN_5O_3^+$ [M + H]$^+$: 424.1171, Found: 424.1158. | Intermediate B1d: 10-amino-2,3,7-trimethyl-2,3-dihydro-[1,4]oxazepino[6,5-c]quinoline-5,6(1H,7H)-dione |

Example 7a: (S)-10-((5-chloro-2-((tetrahydro-2H-pyran-4-yl)oxy)pyridin-4-yl)amino)-2,7-dimethyl-2,3-dihydro-[1,4]oxazepino[6,5-c]quinoline-5,6(1H,7H)-dione

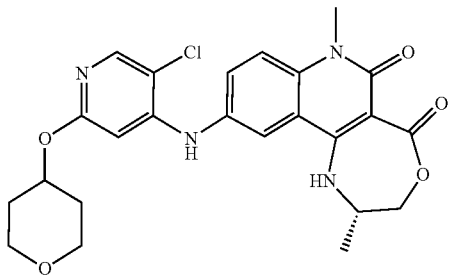 [SMILES: C[C@H]1COC(=O)c2c(c3cc(Nc4cc(OC5CCOCC5)ncc4Cl)ccc3n(C)c2=O)N1]

A mixture of cesium carbonate (95 mg, 0.293 mmol), Xantphos (13 mg, 0.022 mmol), (S)-10-amino-2,7-dimethyl-2,3-dihydro-[1,4]oxazepino[6,5-c]quinoline-5,6(1H, 7H)-dione (Intermediate B1a, 10 mg, 0.037 mmol), 5-chloro-4-iodo-2-((tetrahydro-2H-pyran-4-yl)oxy)pyridine (Intermediate H1.12 mg, 0.037 mmol) and $Pd_2(dba)_3$ (3 mg, 0.004 mmol) was suspended in a mixture of toluene (3 mL) and DMF (0.5 mL). The resulting suspension was stirred under microwave irradiation at 140° C. for 1 h. The reaction mixture was allowed to cool to rt. The suspension was filtered, and the filtrated was diluted with water and extracted with EtOAc. The organic extracts were combined, dried ($Na_2SO_4$) and concentrated in vacuo. Purification by preparative HPLC (15 min gradient of 60:40 to 0:100 $H_2O$:MeOH (both modified with 0.1% formic acid); flow rate 20 mL.min$^{-1}$) afforded the title compound (4 mg, 23%) as a light yellow solid. $^1$H NMR (600 MHz, DMF-$d_7$) δ 8.50 (s, 1H), 8.38 (d, J=2.2 Hz, 1H), 8.19 (s, 1H), 7.85 (dd, J=8.9, 2.2 Hz, 1H), 7.77 (d, J=8.9 Hz, 1H), 7.75 (br s, 1H), 6.20 (s, 1H), 5.28 (tt, J=8.6, 4.1 Hz, 1H), 4.81 (dd, J=12.9, 1.6 Hz, 1H), 4.65 (dd, J=12.9, 5.6 Hz, 1H), 4.32-4.23 (m, 1H), 4.02 (dt, J=11.5, 4.4 Hz, 2H), 3.81 (s, 3H), 3.67 (ddd, J=11.5, 9.4, 2.8 Hz, 2H), 2.21-2.07 (m, 2H), 1.83-1.70 (m, 2H), 1.54 (d, J=6.6 Hz, 3H); LCMS (Method X4) RT 2.49 min; m/z calcd for $C_{24}H_{26}ClN_4O_5^+$ [M+H]$^+$: 485.1586, Found: 485.1542.

Example 8a: (S)-10-((5-chloro-2-((2S,6R)-2,6-dimethylmorpholino)pyrimidin-4-yl)amino)-2,7-dimethyl-2,3-dihydro-[1,4]oxazepino[6,5-c]quinoline-5,6(1H,7H)-dione

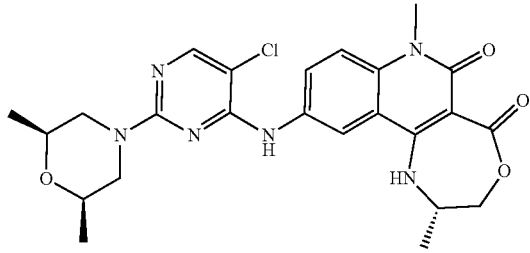 [SMILES: C[C@@H]1CN(c2ncc(Cl)c(Nc3ccc4c(c3)c3c(c(=O)n4C)C(=O)OC[C@H](C)N3)n2)C[C@H](C)O1]

Step 1; (S)-10-((2,5-dichloropyrimidin-4-yl)amino)-2,7-dimethyl-2,3-dihydro-[1,4]oxazepino-[6,5-c]quinoline-5,6(1H, 7H)-dione A suspension of 2,4,5-trichloropyrimidine (12 mg, 0.066 mmol), (S)-10-amino-2,7-dimethyl-2,3-dihydro-[1,4]oxazepino[6,5-c]quinoline-5,6(1H,7H)-dione (Intermediate B1a, 20 mg, 0.073 mmol) and DIPEA (20 uL, 0.110 mmol) in NMP (1.5 mL) was stirred under microwave irradiation at 140° C. for 1 h. The reaction mixture containing (S)-10-((2,5-dichloropyrimidin-4-yl)amino)-2,7-dimethyl-2,3-dihydro-[1,4]oxazepino[6,5-c]quinoline-5,6(1H,7H)-dione was divided into aliquots to be used in the next step without further purification. LCMS (Method T2) RT 1.27 min; m/z 420.1 [M+H]$^+$.

Step 2; (S)-10-((5-chloro-2-((2S,6R)-2,6-dimethylmorpholino)pyrimidin-4-yl)amino)-2,7-dimethyl-2,3-dihydro-[1,4]oxazepino[6,5-c]quinoline-5,6(1H, 7H)-dione A mixture of crude (S)-10-((2,5-dichloropyrimidin-4-yl)amino)-2,7-dimethyl-2,3-dihydro-[1,4]oxazepino[6,5-c]quinoline-5,6(1H,7H)-dione (from step 1; 5 mg, 0.012 mmol), (2R,6S)-2,6-dimethylmorpholine (7 mg, 0.060 mmol) and DIPEA (6 uL, 0.036 mmol) in NMP (1.5 mL) was stirred under microwave irradiation at 140° C. for 1 h. The crude reaction mixture was directly purified by preparative HPLC (3 runs; 15 min gradient of 60:40 to 0:100 $H_2O$:MeOH (both modified with 0.1% formic acid); flow rate 20 mL.min$^{-1}$) affording the title compound (2 mg, 34% over 2 steps) as a brown oil. $^1$H NMR (600 MHz, Methanol-$d_4$) δ 8.20 (d, J=2.4 Hz, 1H), 7.98 (s, 1H), 7.88 (dd, J=9.0, 2.4 Hz, 1H), 7.54 (d, J=9.0 Hz, 1H), 4.66 (d, J=12.8 Hz, 1H), 4.44 (dd, J=12.8, 5.0 Hz, 1H), 4.34 (d, J=13.1 Hz, 2H), 4.14-3.98 (m, 1H), 3.67 (s, 3H), 3.61-3.51 (m, 2H), 2.49 (dt, J=13.7, 10.2 Hz, 2H), 1.41 (d, J=6.7 Hz, 3H), 1.15 (m, 6H); LCMS (Method T4) RT 2.55 min; m/z calcd for $C_{24}H_{28}ClN_6O_4^+$ [M+H]$^+$: 499.1855, Found: 499.1827.

The following tabulated examples were prepared by a method analogous to that used for the preparation of Example 8a, starting from the intermediate(s) shown in the table and appropriate amine.

| Example | Data and comments | Intermediate |
|---|---|---|
| Example 8b: (2S)-10-((2-(8-azabicyclo[3.2.1]octan-8-yl)-5-chloropyrimidin-4-yl)amino)-2,7-dimethyl-2,3-dihydro-[1,4]oxazepino[6,5-c]quinoline-5,6(1H,7H)-dione | $^1$H NMR (500 MHz, Methanol-$d_4$) δ 8.18 (s, 1 H), 8.01 (dd, J = 9.1, 2.2 Hz, 1 H), 7.95 (s, 1 H), 7.54 (d, J = 9.1 Hz, 1 H), 4.65 (d, J = 12.8 Hz, 1 H), 4.52-4.45 (m, 2 H), 4.44 (dd, J = 12.8, 5.2 Hz, 1 H), 4.10-4.02 (m, 1 H), 3.67 (s, 3 H), 2.05-1.98 (m, 2 H), 1.95-1.85 (m, 1 H), 1.85-1.75 (m, 5 H), 1.59-1.51 (m, 1 H), 1.48-1.42 (m, 1 H), 1.40 (d, J = 6.7 Hz, 3 H); LCMS (Method T4) RT 2.30 min; m/z calcd for $C_{25}H_{28}ClN_6O_3^+$ [M + H]$^+$: 495.1906, Found: 495.1889. | Intermediate B1a: (S)-10-amino-2,7-dimethyl-2,3-dihydro-[1,4]oxazepino[6,5-c]quinoline-5,6(1H,7H)-dione |
| Example 8c: (S)-10-((5-chloro-2-((3S,5R)-4,4-difluoro-3,5-dimethylpiperidin-1-yl)pyrimidin-4-yl)amino)-2,7-dimethyl-2,3-dihydro-[1,4]oxazepino[6,5-c]quinoline-5,6(1H,7H)-dione | $^1$H NMR (600 MHz, Methanol-$d_4$) δ 8.18 (d, J = 2.4 Hz, 1 H), 7.99 (d, J = 2.0 Hz, 1 H), 7.87 (dd, J = 9.0, 2.4 Hz, 1 H), 7.55 (d, J = 9.0 Hz, 1 H), 4.66 (d, J = 13.0 Hz, 1 H), 4.55-4.47 (m, 2 H), 4.44 (dd, J = 13.0, 5.0 Hz, 1 H), 4.10-4.02 (m, 1 H), 3.67 (s, 3 H), 2.78-2.58 (m, 2 H), 2.01-1.83 (m, 2 H), 1.41 (d, J = 6.7 Hz, 3 H), 0.98 (d, J = 6.6 Hz, 3 H), 0.96 (d, J = 6.6, 3 H); LCMS (Method T4) RT 2.97 min; m/z calcd for $C_{25}H_{28}ClF_2N_6O_3^+$ [M + H]$^+$: 533.1874, Found: 533.1857. | Intermediate B1a: (S)-10-amino-2,7-dimethyl-2,3-dihydro-[1,4]oxazepino[6,5-c]quinoline-5,6(1H,7H)-dione |
| Example 8d: (S)-1-(5-chloro-4-((2,7-dimethyl-5,6-dioxo-1,2,3,5,6,7-hexahydro-[1,4]oxazepino[6,5-c]quinolin-10-yl)amino)pyrimidin-2-yl)-N,N-dimethylpiperidine-4-carboxamide | $^1$H NMR (500 MHz, Methanol-$d_4$) δ 8.19 (d, J = 2.2 Hz, 1 H), 7.96 (s, 1 H), 7.87 (dd, J = 9.0, 2.2 Hz, 1 H), 7.53 (d, J = 9.0 Hz, 1 H), 4.64 (d, J = 13.0 Hz, 1 H), 4.60-4.54 (m, 2 H), 4.42 (dd, J = 13.0, 5.0 Hz, 1 H), 4.10-4.02 (m, 1 H), 3.66 (s, 3 H), 3.14 (s, 3 H), 3.02-2.94 (m, 2 H), 2.93 (s, 3 H), 2.91-2.87 (m, 1 H), 1.75-1.55 (m, 4 H), 1.38 (d, J = 6.7 Hz, 3 H); LCMS (Method T4) RT 2.15 min; m/z calcd for $C_{26}H_{31}ClN_7O_4^+$ [M + H]$^+$: 540.2121, Found: 540.2098. | Intermediate B1a: (S)-10-amino-2,7-dimethyl-2,3-dihydro-[1,4]oxazepino[6,5-c]quinoline-5,6(1H,7H)-dione |
| Example 8e: (S)-10-((5-chloro-2-(2-methyl-1-oxo-2,9-diazaspiro[5.5]undecan-9-yl)pyrimidin-4-yl)amino)-2,7-dimethyl-2,3-dihydro-[1,4]oxazepino[6,5-c]quinoline-5,6(1H,7H)-dione | $^1$H NMR (500 MHz, Methanol-$d_4$) δ 8.19 (d, J = 2.2 Hz, 1 H), 7.93 (s, 1 H), 7.89 (dd, J = 9.0, 2.2 Hz, 1 H), 7.50 (d, J = 9.0 Hz, 1 H), 4.62 (dd, J = 12.9, 1.4 Hz, 1 H), 4.40 (dd, J = 12.9, 5.1 Hz, 1 H), 4.25-4.18 (m, 2 H), 4.07-4.00 (m, 1 H), 3.64 (s, 3 H), 3.35 (app. t, J = 5.9 Hz, 1 H), 3.38-3.34 (m, 2 H), 3.24-3.16 (m, 2 H), 2.90 (s, 3 H), 2.37 (app. t, J = 8.1 Hz, 1 H), 2.13-1.97 (m, 2 H), 1.95-1.80 (m, 2 H), 1.52-1.42 (m, 2 H), 1.38 (d, J = 6.7 Hz, 3 H); LCMS (Method T4) RT 2.28 min; m/z calcd for $C_{28}H_{33}ClN_7O_4^+$ [M + H]$^+$: 566.2277, Found: 566.2258. | Intermediate B1a: (S)-10-amino-2,7-dimethyl-2,3-dihydro-[1,4]oxazepino[6,5-c]quinoline-5,6(1H,7H)-dione |

-continued

| Example | Data and comments | Intermediate |
|---|---|---|
| Example 8f: (2S)-10-((5-chloro-2-(3,3-difluoro-8-azabicyclo[3.2.1]octan-8-yl)pyrimidin-4-yl)amino)-2,7-dimethyl-2,3-dihydro-[1,4]oxazepino[6,5-c]quinoline-5,6(1H,7H)-dione | $^1$H NMR (600 MHz, Methanol-$d_4$) δ 8.13 (d, J = 2.2 Hz, 1 H), 8.02 (s, 1 H), 7.95 (dd, J = 9.0, 2.2 Hz, 1 H), 7.56 (d, J = 9.0 Hz, 1 H), 4.64 (d, J = 13.0 Hz, 1 H), 4.62-4.55 (m, 2 H), 4.45 (dd, J = 13.0, 5.2 Hz, 1 H), 4.10-4.02 (m, 1 H), 3.67 (s, 3 H), 2.24-1.95 (m, 8 H), 1.40 (d, J = 6.7 Hz, 3 H); LCMS (Method T4) RT 2.71 min; m/z calcd for $C_{25}H_{26}ClF_2N_6O_3^+$ [M + H]$^+$: 531.1717, Found: 531.1694. | Intermediate B1a: (S)-10-amino-2,7-dimethyl-2,3-dihydro-[1,4]oxazepino[6,5-c]quinoline-5,6(1H,7H)-dione |
| Example 8g: (S)-10-((5-chloro-2-((3R,5S)-3,5-dimethylpiperidin-1-yl)pyrimidin-4-yl)amino)-2,7-dimethyl-2,3-dihydro-[1,4]oxazepino[6,5-c]quinoline-5,6(1H,7H)-dione | $^1$H NMR (500 MHz, Methanol-$d_4$) δ 8.18 (d, J = 2.3 Hz, 1 H), 7.91 (s, 1 H), 7.89 (dd, J = 9.1, 2.3 Hz, 1 H), 7.50 (d, J = 9.1 Hz, 1 H), 4.64 (dd, J = 12.9, 1.4 Hz, 1 H), 4.52-4.44 (m, 2 H), 4.41 (dd, J = 12.9, 5.1 Hz, 1 H), 4.13-4.00 (m, 1 H), 3.64 (s, 3 H), 2.25 (ddd, J = 13.0, 11.3, 8.2 Hz, 2 H), 1.86-1.73 (m, 1 H), 1.58-1.45 (m, 2 H), 1.40 (d, J = 6.7 Hz, 3 H), 0.86 (d, J = 6.6 Hz, 3 H), 0.85 (d, J = 6.6, 3 H), 0.78 (q, J = 12.1 Hz, 1 H); LCMS (Method T4) RT 2.67 min; m/z calcd for $C_{25}H_{30}ClN_6O_3^+$ [M + H]$^+$: 497.2062, Found: 497.2080. | Intermediate B1a: (S)-10-amino-2,7-dimethyl-2,3-dihydro-[1,4]oxazepino[6,5-c]quinoline-5,6(1H,7H)-dione |
| Example 8h: (2S)-10-((2-(3-azabicyclo[3.2.1]octan-3-yl)-5-chloropyrimidin-4-yl)amino)-2,7-dimethyl-2,3-dihydro-[1,4]oxazepino[6,5-c]quinoline-5,6(1H,7H)-dione | $^1$H NMR (600 MHz, Methanol-$d_4$) δ 8.23 (d, J = 2.2 Hz, 1 H), 7.96 (dd, J = 9.0, 2.2 Hz, 1 H), 7.94 (s, 1 H), 7.54 (d, J = 9.0 Hz, 1 H), 4.66 (dd, J = 13.0, 1.4 Hz, 1 H), 4.45 (dd, J = 13.0, 5.2 Hz, 1 H), 4.19-4.12 (m, 2 H), 4.07 (ddd, J = 6.8, 5.2, 1.4 Hz, 1 H), 3.67 (s, 3 H), 2.91 (tt, J = 13.6, 1.7 Hz, 2 H), 2.30-2.22 (m, 2 H), 1.79-1.65 (m, 2 H), 1.64-1.61 (m, 2 H), 1.56-1.48 (m, 2 H), 1.41 (d, J = 6.7 Hz, 3 H); LCMS (Method T4) RT 2.47 min; m/z calcd for $C_{25}H_{28}ClN_6O_3^+$ [M + H]$^+$: 495.1906, Found: 495.1885. | Intermediate B1a: (S)-10-amino-2,7-dimethyl-2,3-dihydro-[1,4]oxazepino[6,5-c]quinoline-5,6(1H,7H)-dione |
| Example 8i: (S)-10-((5-chloro-2-(2-oxopyrrolidin-1-yl)pyrimidin-4-yl)amino)-2,7-dimethyl-2,3-dihydro-[1,4]oxazepino[6,5-c]quinoline-5,6(1H,7H)-dione | $^1$H NMR (500 MHz, DMF-$d_7$) δ 9.77 (d, J = 2.4 Hz, 1 H), 9.40 (br s, 1 H), 8.62 (s, 1 H), 8.26 (dd, J = 9.1, 2.4 Hz, 1 H), 7.96-7.94 (br s, 1H), 7.71 (d, J = 9.1 Hz, 1 H), 4.93 (dd, J = 12.9, 1.4 Hz, 1 H), 4.57 (dd, J = 12.9, 4.5 Hz, 1H), 4.46-4.34 (m, 1 H), 4.30-4.21 (m, 2 H), 3.78 (s, 3 H), 2.45-2.40 (m, 1 H), 2.39-2.27 (m, 2 H), 2.16-2.04 (m, 1 H), 1.61 (d, J = 6.7 Hz, 3H); LCMS (Method T4) RT 2.62 min; m/z calcd for $C_{22}H_{22}ClN_6O_4^+$ [M + H]$^+$: 469.1386, Found: 469.1383. | Intermediate B1a: (S)-10-amino-2,7-dimethyl-2,3-dihydro-[1,4]oxazepino[6,5-c]quinoline-5,6(1H,7H)-dione |

| Example | Data and comments | Intermediate |
| --- | --- | --- |
| Example 8j: (2S)-10-((2-(8-azabicyclo[3.2.1]octan-8-yl)-5-chloropyrimidin-4-yl)amino)-2-cyclopropyl-7-methyl-2,3-dihydro-[1,4]oxazepino[6,5-c]quinoline-5,6(1H,7H)-dione 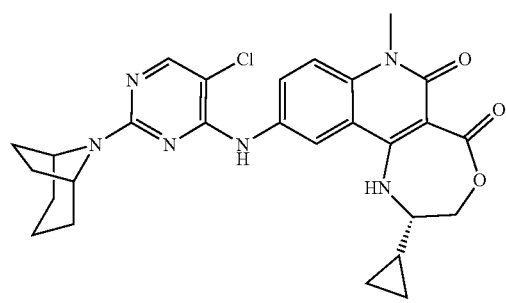 [SMILES: Cn1c(=O)c2c(c3cc(Nc4nc(N5C6CCCC5CC6)ncc4Cl)ccc31)N[C@@H](C1CC1)COC2=O] | $^1$H NMR (600 MHz, Methanol-$d_4$) δ 8.14-8.11 (m, 2 H), 7.95 (s, 1 H), 7.54 (d, J = 9.0 Hz, 1 H), 4.72 (dd, J = 12.9, 1.4 Hz, 1 H), 4.60 (dd, J = 12.9, 5.5 Hz, 1 H), 4.52-4.43 (m, 2 H), 3.68 (s, 3 H), 3.28-3.22 (m, 1 H), 2.04-1.98 (m, 2 H), 1.96-1.88 (m, 1 H), 1.88-1.78 (m, 4 H), 1.61-1.50 (m, 1 H), 1.50-1.37 (m, 2 H), 1.20-1.07 (m, 1 H), 0.76-0.70 (m, 1 H), 0.69-0.62 (m, 1 H), 0.62-0.55 (m, 1 H), 0.47-0.42 (m, 1 H); LCMS (Method T4) RT 2.44 min; m/z calcd for $C_{27}H_{30}ClN_6O_3^+$ [M + H]$^+$: 521.2062, Found: 521.2046. | Intermediate B1b: (S)-10-amino-2-cyclopropyl-7-methyl-2,3-dihydro-[1,4]oxazepino[6,5-c]quinoline-5,6(1H,7H)-dione |
| Example 8k: (S)-10-((5-chloro-2-((3S,5R)-4,4-difluoro-3,5-dimethylpiperidin-1-yl)pyrimidin-4-yl)amino)-2-cyclopropyl-7-methyl-2,3-dihydro-[1,4]oxazepino[6,5-c]quinoline-5,6(1H,7H)-dione 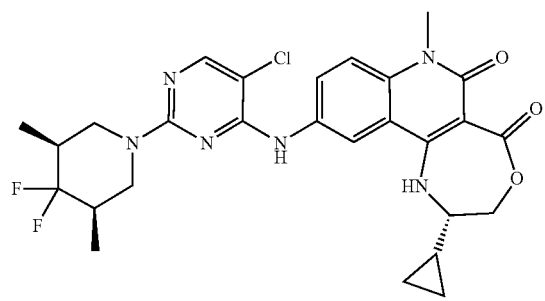 [SMILES: C[C@@H]1CN(c2ncc(Cl)c(Nc3ccc4c(c3)c3c(c(=O)n4C)C(=O)OC[C@H](C4CC4)N3)n2)C[C@H](C)C1(F)F] | $^1$H NMR (600 MHz, Methanol-$d_4$) δ 8.21 (d, J = 2.2 Hz, 1H), 8.00 (s, 1 H), 7.93 (dd, J = 9.1, 2.2 Hz, 1 H), 7.56 (d, J = 9.1 Hz, 1 H), 4.74 (dd, J = 12.9, 1.4 Hz, 1 H), 4.59 (dd, J = 12.9, 5.2 Hz, 1 H), 4.55-4.47 (m, 2 H), 3.68 (s, 3 H), 3.27-3.16 (m, 1 H), 2.75-2.65 (m, 2 H), 2.06-1.84 (m, 2 H), 1.20-1.12 (m, 1 H), 1.00 (d, J = 6.7 Hz, 3 H), 0.97 (d, J = 6.7 Hz, 3 H), 0.77-0.70 (m, 1 H), 0.70-0.64 (m, 1 H), 0.64-0.57 (m, 1 H), 0.50-0.40 (m, 1 H); LCMS (Method T4) RT 3.06 min; m/z calcd for $C_{27}H_{30}ClF_2N_6O_3^+$ [M + H]$^+$: 559.2030, Found: 559.2012. | Intermediate B1b: (S)-10-amino-2-cyclopropyl-7-methyl-2,3-dihydro-[1,4]oxazepino[6,5-c]quinoline-5,6(1H,7H)-dione |
| Example 8l: (S)-10-((5-chloro-2-((3R,5S)-3,5-dimethylpiperidin-1-yl)pyrimidin-4-yl)amino)-2-cyclopropyl-7-methyl-2,3-dihydro-[1,4]oxazepino[6,5-c]quinoline-5,6(1H,7H)-dione 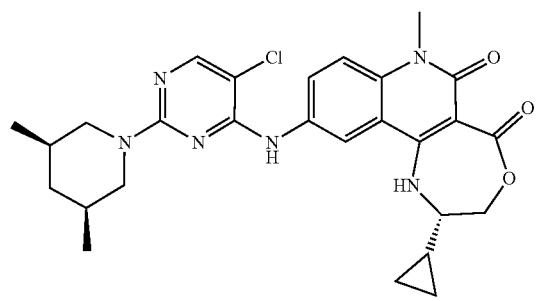 [SMILES: C[C@@H]1C[C@H](C)CN(c2ncc(Cl)c(Nc3ccc4c(c3)c3c(c(=O)n4C)C(=O)OC[C@H](C4CC4)N3)n2)C1] | $^1$H NMR (600 MHz, Methanol-$d_4$) δ 8.22 (d, J = 2.2 Hz, 1 H), 7.97 (dd, J = 9.0, 2.2 Hz, 1 H), 7.94 (s, 1 H), 7.54 (d, J = 9.0 Hz, 1 H), 4.73 (d, J = 12.9 Hz, 1 H), 4.62-4.56 (m, 2 H), 4.57-4.45 (m, 2 H), 2.96 (s, 3 H), 3.25-3.14 (m, 1 H), 2.32-2.20 (m, 2 H), 1.62-1.48 (m, 2H), 1.20-1.12 (m, 1 H), 0.88 (d, J = 6.6 Hz, 3 H), 0.86 (d, J = 6.6, 3 H), 0.79 (q, J = 12.1 Hz, 1 H), 0.75-0.70 (m, 1 H), 0.70-0.64 (m, 1 H), 0.64-0.58 (m, 1 H), 0.48-0.42 (m, 1 H); LCMS (Method T4) RT 2.80 min; m/z calcd for $C_{27}H_{32}ClN_6O_3^+$ [M + H]$^+$: 523.2219, Found: 523.2200. | Intermediate B1b: (S)-10-amino-2-cyclopropyl-7-methyl-2,3-dihydro-[1,4]oxazepino[6,5-c]quinoline-5,6(1H,7H)-dione |

| Example | Data and comments | Intermediate |
|---|---|---|
| Example 8m: (S)-1-(5-chloro-4-((2-cyclopropyl-7-methyl-5,6-dioxo-1,2,3,5,6,7-hexahydro-[1,4]oxazepino[6,5-c]quinolin-10-yl)amino)pyrimidin-2-yl)-N,N-dimethylpiperidine-4-carboxamide | $^1$H NMR (600 MHz, Methanol-d$_4$) δ 8.19 (d, J = 2.2 Hz, 1 H), 8.00-7.95 (m, 2 H), 7.55 (d, J = 9.0 Hz, 1 H), 4.71 (d, J = 12.8 Hz, 1 H), 4.62-4.53 (m, 3 H), 3.68 (s, 3 H), 3.30-3.20 (m, 1 H), 3.15 (s, 3 H), 3.02-2.86 (m, 3 H), overlapping with 2.93 (s, 3 H), 1.77-1.54 (m, 4 H), 1.16-1.07 (m, 1 H), 0.76-0.70 (m, 1 H), 0.69-0.62 (m, 1 H), 0.62-0.58 (m, 1 H), 0.48-0.42 (m, 1H); LCMS (Method T4) RT 2.29 min; m/z calcd for $C_{28}H_{33}ClN_7O_4^+$ [M + H]$^+$: 566.2277, Found: 566.2263. | Intermediate B1b: (S)-10-amino-2-cyclopropyl-7-methyl-2,3-dihydro-[1,4]oxazepino[6,5-c]quinoline-5,6(1H,7H)-dione |
| Example 8n: (S)-10-((5-chloro-2-((2S,6R)-2,6-dimethylmorpholino)pyrimidin-4-yl)amino)-2-cyclopropyl-7-methyl-2,3-dihydro-[1,4]oxazepino[6,5-c]quinoline-5,6(1H,7H)-dione | $^1$H NMR (600 MHz, Methanol-d$_4$) δ 8.21 (d, J = 2.2 Hz, 1 H), 7.99 (s, 1 H), 7.95 (dd, J = 9.1, 2.2 Hz, 1 H), 7.56 (d, J = 9.1 Hz, 1 H), 4.74 (dd, J = 13.0, 1.4 Hz, 1 H), 4.59 (dd, J = 12.9, 5.2 Hz, 2 H), 4.35 (d, J = 12.8 Hz, 2 H), 3.68 (s, 3 H), 3.62-3.52 (m, 2 H), 3.27-3.18 (m, 1 H), 2.51 (ddd, J = 24.3, 13.2, 10.6 Hz, 2 H), 1.15 (m, 6 H), 0.77-0.72 (m, 1 H), 0.70-0.64 (m, 1 H), 0.64-0.57 (m, 1 H), 0.48-0.43 (m, 1 H); LCMS (Method T4) RT 2.68 min; m/z calcd for $C_{26}H_{30}ClN_6O_4^+$ [M + H]$^+$: 525.2012, Found: 525.1997. | Intermediate B1b: (S)-10-amino-2-cyclopropyl-7-methyl-2,3-dihydro-[1,4]oxazepino[6,5-c]quinoline-5,6(1H,7H)-dione |
| Example 8o: 10-((5-chloro-2-(4,4-difluoropiperidin-1-yl)pyrimidin-4-yl)amino)-2-cyclopropyl-7-methyl-2,3-dihydro-[1,4]oxazepino[6,5-c]quinoline-5,6(1H,7H)-dione | $^1$H NMR (500 MHz, DMF-d$_7$) δ 9.25 (s, 1 H), 8.67 (d, J = 2.2 Hz, 1 H), 8.31 (s, 1 H), 8.11 (dd, J = 9.1, 2.2 Hz, 1 H), 7.77 (br d, J = 4.8 Hz, 1 H), 7.70 (d, J = 9.1 Hz, 1 H), 4.96 (dd, J = 12.9, 1.2 Hz, 1 H), 4.70 (dd, J = 12.9, 4.7 Hz, 1 H), 4.06-3.96 (m, 4 H), 3.78 (s, 3 H), 3.46 (dt, J = 9.0, 4.7 Hz, 1 H), 2.25-2.12 (m, 4 H), 1.40-1.26 (m, 1 H), 0.86-0.78 (m, 2 H), 0.76-0.70 (m, 1 H), 0.66-0.60 (m, 1 H); LCMS (Method T4) RT 2.82 min; m/z calcd for $C_{25}H_{26}ClF_2N_6O_3^+$ [M + H]$^+$: 531.1717, Found: 531.1702. | Intermediate B1c: 10-amino-2-cyclopropyl-7-methyl-2,3-dihydro-[1,4]oxazepino[6,5-c]quinoline-5,6(1H,7H)-dione |

The following tabulated examples were prepared by an analogous method to that used for the preparation of Example 8a. Example 8p and Example 8q represent a pair of diastereoisomers where one is cis- and one is trans-across the oxazepinone ring. The compounds were separated by preparative HPLC (15 min gradient of 60:40 to 0:100 H$_2$O:MeOH (both modified with 0.1% formic acid); flow rate 20 mLmin$^{-1}$) with Example 8p eluting first followed by Example 8q. It has not been unambiguously determined which is the cis- and which is the trans-structure. Both compounds are racemic.

| Example | Data and comments | Intermediate |
| --- | --- | --- |
| Example 8p: rac-(2S,3R)-10-((5-chloro-2-((3S,5R)-3,5-dimethylpiperidin-1-yl)pyrimidin-4-yl)amino)-2,3,7-trimethyl-2,3-dihydro-[1,4]oxazepino[6,5-c]quinoline-5,6(1H,7H)-dione or rac-(2S,3S)-10-((5-chloro-2-((3S,5R)-3,5-dimethylpiperidin-1-yl)pyrimidin-4-yl)amino)-2,3,7-trimethyl-2,3-dihydro-[1,4]oxazepino[6,5-c]quinoline-5,6(1H,7H)-dione | $^1$H NMR (500 MHz, Methanol-$d_4$) δ 8.23 (d, J = 2.2 Hz, 1 H), 7.93 (s, 1 H), 7.83 (dd, J = 9.1, 2.2 Hz, 1 H), 7.53 (d, J = 9.1 Hz, 1H), 5.11-5.05 (m, 1H), 4.52-4.44 (m, 2 H), 3.87-3.81 (m, 1 H), 3.66 (s 3 H), 2.25 (q, J = 12.7 Hz, 2 H), 1.85-1.75 (m, 1 H), 1.60-1.48 (m, 2 H), 1.42 (d, J = 6.6 Hz, 3 H), 1.34 (d, J = 6.6 Hz, 3 H), 0.85 (d, J = 6.6, Hz, 3 H), 0.84 (d, J = 6.6, Hz, 3 H), 0.83-0.74 (m, 1 H); LCMS (Method T4) RT 2.72 min; m/z calcd for $C_{26}H_{32}ClN_6O_3^+$ [M + H]$^+$: 511.2219, Found: 511.2208. | Intermediate B1d: 10-amino-2,3,7-trimethyl-2,3-dihydro-[1,4]oxazepino[6,5-c]quinoline-5,6(1H,7H)-dione |
| Example 8q: rac-(2S,3R)-10-((5-chloro-2-((3S,5R)-3,5-dimethylpiperidin-1-yl)pyrimidin-4-yl)amino)-2,3,7-trimethyl-2,3-dihydro-[1,4]oxazepino[6,5-c]quinoline-5,6(1H,7H)-dione or rac-(2S,3S)-10-((5-chloro-2-((3S,5R)-3,5-dimethylpiperidin-1-yl)pyrimidin-4-yl)amino)-2,3,7-trimethyl-2,3-dihydro-[1,4]oxazepino[6,5-c]quinoline-5,6(1H,7H)-dione | $^1$H NMR (500 MHz, Methanol-$d_4$) δ 8.12 (d, J = 2.2 Hz, 1 H), 8.02 (dd, J = 9.1, 2.2 Hz, 1 H), 7.93 (s, 1 H), 7.53 (d, J = 9.1 Hz, 1 H), 4.85 (m, 1 H), 4.55-4.41 (m, 2 H), 3.94-3.86 (m, 1 H), 3.66 (s, 3 H) 2.30-2.22 (m, 2 H), 1.85-1.78 (m, 1 H), 1.61-1.47 (m, 2 H), 1.44 (d, J = 6.6 Hz, 3 H), 1.38 (d, J = 6.6 Hz, 3 H), 0.89 (d, J = 6.6 Hz, 3 H), 0.86 (d, J = 6.6 Hz, 3 H), 0.84-0.75 (m, 1 H); LCMS (Method T4) RT 2.81 min; m/z calcd for $C_{26}H_{32}ClN_6O_3^+$ [M + H]$^+$: 511.2219, Found: 511.2225. | Intermediate B1d: 10-amino-2,3,7-trimethyl-2,3-dihydro-[1,4]oxazepino[6,5-c]quinoline-5,6(1H,7H)-dione |

Example 9a: (S)-2-chloro-4-((2,7-dimethyl-6-oxo-1,2,3,5,6,7-hexahydro-[1,4]oxazepino[6,5-c]quinolin-10-yl)amino)nicotinonitrile

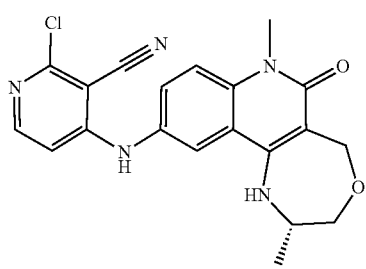 [SMILES: C[C@H]1COCc2c(c3cc(Nc4ccnc(Cl)c4C#N)ccc3n(C)c2=O)N1]

A suspension of DIPEA (7 uL, 0.041 mmol), 2,4-dichloropyridine-3-carbonitrile (3 mg, 0.019 mmol) and (S)-10-amino-2,7-dimethyl-2,3,5,7-tetrahydro-[1,4]oxazepino[6,5-c]quinolin-6(1H)-one (Intermediate B2a, 4 mg, 0.014 mmol) in NMP (1.5 mL) was stirred under microwave irradiation at 160° C. for 1 h. The crude reaction mixture was directly purified by preparative HPLC (15 min gradient of 60:40 to 0:100 H$_2$O:MeOH (both modified with 0.1% formic acid); flow rate 20 mLmin$^{-1}$) affording the title compound (1 mg, 19%) as a yellow solid. $^1$H NMR (600 MHz, Methanol-$d_4$) δ 8.06 (d, J=2.2 Hz, 1H), 8.00 (d, J=6.2 Hz, 1H), 7.65 (d, J=8.9 Hz, 1H), 7.58 (dd, J=8.9, 2.2 Hz, 1H), 6.71 (d, J=6.2 Hz, 1H), 4.94 (d, J=14.4 Hz, 1H), 4.84 (d, J=14.4 Hz, 1H), 3.96 (ddd, J=9.2, 6.5, 3.0 Hz, 1H), 3.93 (dd, J=11.1, 3.0 Hz, 1H), 3.72 (s, 3H), 3.64 (dd, J=11.1, 8.9 Hz, 1H), 1.27 (d, J=6.6 Hz, 3H). LCMS (Method T4) RT 2.53 min; m/z calcd for $C_{20}H_{19}ClN_5O_2$+[M+H]$^+$: 396.1222, Found: 396.1214.

The following tabulated examples were prepared by a method analogous to that used for the preparation of Example 9a, starting from the intermediate(s) shown in the table and appropriate amine.

| Example | Data and comments | Intermediate |
|---|---|---|
| Example 9b: (S)-2-chloro-4-((2-cyclopropyl-7-methyl-6-oxo-1,2,3,5,6,7-hexahydro-[1,4]oxazepino[6,5-c]quinolin-10-yl)amino)nicotinonitrile 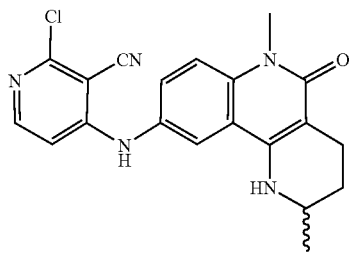 | $^1$H NMR (600 MHz, methanol-$d_4$) δ 8.09 (d, J = 2.3 Hz, 1 H), 8.02 (d, J = 6.2 Hz, 1 H), 7.65 (d, J = 9.0 Hz, 1 H), 7.59 (dd, J = 8.9, 2.3 Hz, 1 H), 6.77 (d, J = 6.2 Hz, 1 H), 4.89-4.88 (m, 2 H; underneath $H_2O$ peak) 4.00 (dd, J = 11.4, 3.1 Hz, 1 H), 3.86 (dd, J = 11.4, 8.1 Hz, 1 H), 3.72 (s, 3H), 2.80 (ddd, J = 10.0, 8.1, 3.1 Hz, 1 H), 1.12-1.02 (m, 1 H), 0.70-0.50 (m, 2 H), 0.46-0.28 (m, 2 H); LCMS (Method T4) RT 2.67 min; m/z calcd for $C_{22}H_{21}ClN_5O_2^+$ [M + H]$^+$: 422.1378, Found: 422.1367. | Intermediate B2b: (S)-10-amino-2-cyclopropyl-7-methyl-2,3,5,7-tetrahydro-[1,4]oxazepino[6,5-c]quinolin-6(1H)-one |

Example 10a: 2-chloro-4-((2,6-dimethyl-5-oxo-1,2,3,4,5,6-hexahydrobenzo[h][1,6]-naphthyridin-9-yl)amino)nicotinonitrile

Example 11a: 10-((5-chloro-2-((1R,5S,7s)-7-hydroxy-3-oxa-9-azabicyclo[3.3.1]nonan-9-yl)pyrimidin-4-yl)amino)-2-cyclopropyl-3,3-difluoro-7-methyl-1,2,3,4-tetrahydro-[1,4]oxazepino[2,3-c]quinolin-6(7H)-one

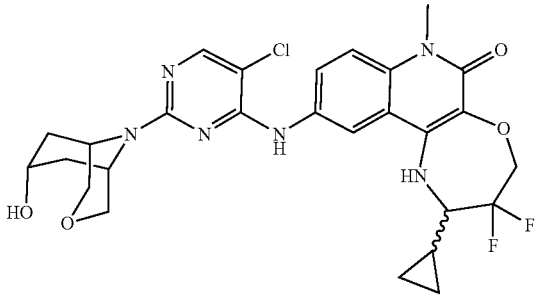 [SMILES: Cn1c(=O)c2c(c3cc(Nc4nc(N5C6COCC5CC(O)C6)ncc4Cl)ccc31)NC(C1CC1)C(F)(F)CO2]

To a microwave vial (0.5-2.0 mL volume) containing 9-amino-2,6-dimethyl-2,3,4,6-tetrahydrobenzo[/7][1,6]naphthyridin-5(1H)-one (Intermediate C1; 12 mg, 0.05 mmol) was added 2,4-dichloropyridine-3-carbonitrile (11 mg, 0.06 mmol), NMP (0.51 mL) and triethylamine (14 uL, 0.10 mmol). The vial was sealed and purged with argon for 5 min. The vial was then heated at 160° C. under microwave irradiation for 1 h. The reaction mixture was allowed to cool to rt. The reaction mixture was diluted with MeCN and directly purified by preparative HPLC (15 min gradient of 60:40 to 0:100 $H_2O$:MeOH (both modified with 0.1% formic acid); flow rate 20 mLmin$^{-1}$) affording the title compound (10 mg, 51%) as an off-white solid. $^1$H NMR (500 MHz, CDCl$_3$) δ 8.04 (d, J=6.1 Hz, 1H), 7.44-7.37 (m, 3H), 6.92 (s, 1H), 6.59 (d, J=6.1 Hz, 1H), 4.51 (s, 1H), 3.70 (s, 3H), 3.58-3.47 (m, 1H), 2.86 (ddd, J=17.6, 5.3, 3.9 Hz, 1H), 2.60 (ddd, J=17.6, 10.5, 5.9 Hz, 1H), 2.09-2.00 (m, 1H), 1.69-1.52 (m, 1H), 1.34 (d, J=6.4 Hz, 3H); LCMS (Method X4) RT 2.60 min; m/z calcd for $C_{20}H_{19}ClN_5O^+$ [M+H]$^+$: 380.1278, Found: 380.1280.

A microwave vial (0.5-2.0 mL volume) was charged with 10-amino-2-cyclopropyl-3,3-difluoro-7-methyl-1,2,3,4-tetrahydro-[1,4]oxazepino[2,3-c]quinolin-6(7H)-one (Intermediate A1l; 15 mg, 0.047 mmol) and (1R,5S,7s)-9-(5-chloro-4-(methylsulfonyl)-pyrimidin-2-yl)-3-oxa-9-azabicyclo[3.3.1]nonan-7-ol (Intermediate J2; 17 mg, 0.050 mmol). 2,2,2-Trifluoroethanol (1.0 mL) was added followed by trifluoroacetic acid (4.00 uL, 0.052 mmol). The reaction vial was flushed with Ar and sealed with a cap. The reaction mixture was heated at 70° C. in a heating block for 18 h. The reaction mixture was cooled to rt and concentrated in vacuo. The residue was re-dissolved in DMSO (1 mL) and directly purified by reverse-phase chromatography (Biotage reverse-phase 12 g C-18 column; 10-100% MeOH in $H_2O$ (containing 0.1% formic acid)), affording the title compound (7 mg, 27%) as an off-white solid. $^1$H NMR (600 MHz, methanol-$d_4$) δ 8.02-7.99 (m, 2H), 7.88 (dd, J=9.1, 1.7 Hz, 1H), 7.54 (d, J=9.1 Hz, 1H), 4.62-4.37 (m, 4H), 3.94-3.84 (m, 3H), 3.79-3.73 (m, 2H), 3.71 (s, 3H), 3.30-3.26 (m, 1H), 2.24-2.14 (m, 2H), 1.83-1.73 (m, 2H), 1.43-1.36 (m, 1H), 0.82-0.76 (m, 1H), 0.69-0.63 (m, 1H), 0.63-0.57 (m, 1H), 0.37-0.31 (m, 1H); LCMS (Method X4) RT 2.95 min; m/z calcd for $C_{27}H_{30}ClF_2N_6O_4^+$ [M+H]$^+$: 575.1985, Found: 575.1973.

The following tabulated examples were prepared by a method analogous to that used for the preparation of Example 11a, starting from the intermediate(s) shown in the table and appropriate amine.

| Example | Data and comments | Intermediate |
|---|---|---|
| Example 11b: (R)-10-((5-chloro-2-((1R,5S,7S)-7-hydroxy-3-oxa-9-azabicyclo[3.3.1]nonan-9-yl)pyrimidin-4-yl)amino)-2-cyclopropyl-7-methyl-1,2,3,4-tetrahydro-[1,4]oxazepino[2,3-c][1,8]naphthyridin-6(7H)-one | $^1$H NMR (600 MHz, methanol-$d_4$) δ 8.80 (d, J = 2.3 Hz, 1 H), 8.38 (d, J = 2.3 Hz, 1 H), 8.03 (s, 1 H), 4.68-4.33 (m, 3 H), 4.25-4.19 (m, 1 H), 3.94-3.85 (m, 3 H), 3.79-3.72 (m, 5 H), 2.95 (dt, J = 9.4, 3.5 Hz, 1 H), 2.38-2.31 (m, 1 H), 2.23-2.15 (m, 2 H), 2.14-2.07 (m, 1 H), 1.83-1.73 (m, 2 H), 1.25-1.18 (m, 1 H), 0.68-0.61 (m, 2 H), 0.44-0.38 (m, 1 H), 0.35-0.30 (m, 1 H); LCMS (Method X4) RT 2.94 min; m/z calcd for $C_{26}H_{31}ClN_7O_4^+$ [M + H]$^+$: 540.2126, Found: 540.2137. | Intermediate A7a: (R)-10-amino-2-cyclopropyl-7-methyl-1,2,3,4-tetrahydro-[1,4]oxazepino[2,3-c][1,8]naphthyridin-6(7H)-one and Intermediate J2: (1R,5S,7s)-9-(5-chloro-4-(methylsulfonyl)pyrimidin-2-yl)-3-oxa-9-azabicyclo[3.3.1]nonan-7-ol |

Example 11c: (S)-10-((5-chloro-2-((1R,5S,7R)-7-hydroxy-3-oxa-9-azabicyclo[3.3.1]-nonan-9-yl)pyrimidin-4-yl)amino)-2-cyclopropyl-3,3-difluoro-7-methyl-1,2,3,4-tetrahydro-[1,4]oxazepino[2,3-c]quinolin-6(7H)-one

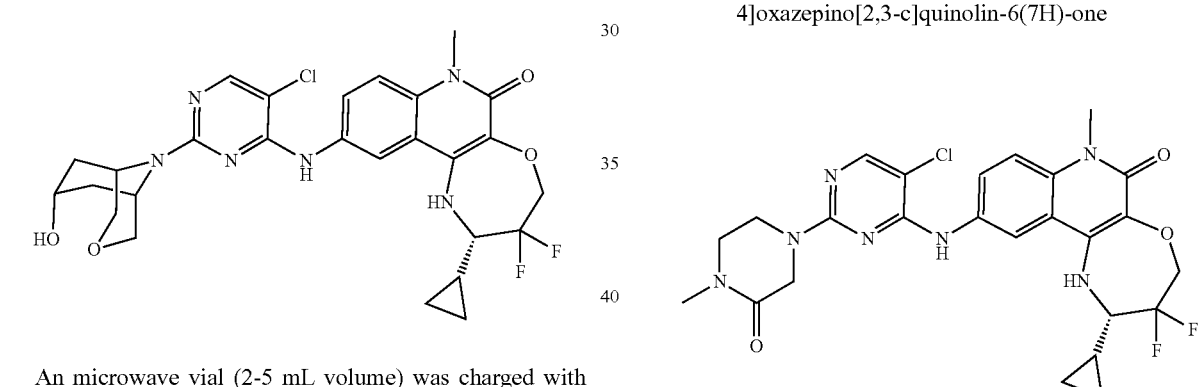

An microwave vial (2-5 mL volume) was charged with (S)-10-amino-2-cyclopropyl-3,3-difluoro-7-methyl-1,2,3,4-tetrahydro-[1,4]oxazepino[2,3-c]quinolin-6(7H)-one (Intermediate A1m; 29 mg, 0.09 mmol) and (1R,5S,7s)-9-(5-chloro-4-(methylsulfonyl)-pyrimidin-2-yl)-3-oxa-9-azabicyclo[3.3.1]nonan-7-ol (Intermediate J2; 36 mg, 0.11 mmol). Trifluoroethanol (1.0 mL) was added followed by trifluoroacetic acid (7.7 uL, 0.10 mmol). The reaction vial was flushed with Ar and sealed with a cap. The reaction mixture was heated at 70° C. in a heating block for 20 h. The reaction mixture was cooled to rt and concentrated in vacuo. The residue was re-dissolved in DMSO (1 mL) and directly purified by reverse-phase chromatography (Biotage reverse-phase 12 g C-18 column; 10-100% MeOH in H$_2$O (containing 0.1% formic acid)). The product-containing fractions were passed through an SCX-2 (2 g) column, eluting with MeOH (15 mL) followed by 2 N methanolic ammonia (30 mL). The basic fraction was concentrated in vacuo affording the title compound (16 mg, 31%) as an off-white solid. $^1$H NMR (600 MHz, methanol-$d_4$) δ 8.02-7.99 (m, 2H), 7.88 (dd, J=9.1, 1.7 Hz, 1H), 7.54 (d, J=9.1 Hz, 1H), 4.62-4.37 (m, 4H), 3.94-3.84 (m, 3H), 3.79-3.73 (m, 2H), 3.71 (s, 3H), 3.30-3.26 (m, 1H), 2.24-2.14 (m, 2H), 1.83-1.73 (m, 2H), 1.43-1.36 (m, 1H), 0.82-0.76 (m, 1H), 0.69-0.63 (m, 1H), 0.63-0.57 (m, 1H), 0.37-0.31 (m, 1H); LCMS (Method X4) RT 2.98 min; m/z calcd for $C_{27}H_{30}ClF_2N_6O_4^+$ [M+H]$^+$: 575.1985, Found: 575.1987.

Example 12a: (S)-10-((5-chloro-2-(4-methyl-3-oxopiperazin-1-yl)pyrimidin-4-yl)amino)-2-cyclopropyl-3,3-difluoro-7-methyl-1,2,3,4-tetrahydro-[1,4]oxazepino[2,3-c]quinolin-6(7H)-one An oven-dried microwave vial (0.5-2.0 mL volume) was charged with (S)-2-cyclopropyl-10-((2,5-dichloropyrimidin-4-yl)amino)-3,3-difluoro-7-methyl-1,2,3,4-tetrahydro-[1,4]oxazepino[2,3-c]quinolin-6(7H)-one (Intermediate A10a; 7 mg, 0.015 mmol), 1-methylpiperazin-2-one (4 mg, 0.037 mmol) and DIPEA (13 uL, 0.075 mmol). The reaction vial was flushed with Ar and sealed with a cap. NMP (0.65 mL) was added and the reaction mixture was heated at 140° C. under microwave irradiation for 1 h. The reaction mixture was dissolved in DMSO (0.8 mL) and directly purified by reverse-phase chromatography (Biotage reverse-phase 12 g Ultra C-18 column; 10-60-80-100% MeOH in H$_2$O (containing 0.1% formic acid)). The product-containing fractions were combined, passed through an SCX-2 (1 g), additional MeOH (10 mL) was passed through and the product was eluted with 2 N methanolic ammonia (25 mL). The solvent was removed in vacuo affording the title compound (5 mg, 57%) as an off-white solid. $^1$H NMR (600 MHz, methanol-$d_4$) δ 8.04 (d, J=2.2 Hz, 1H), 8.01 (s, 1H), 7.92 (dd, J=9.1, 2.2 Hz, 1H), 7.57 (d, J=9.1 Hz, 1H), 4.53-4.38 (m, 2H), 4.24 (d, J=18.2 Hz, 1H), 4.18 (d, J=18.2 Hz, 1H), 3.98-3.92 (m, 1H), 3.92-3.87 (m, 1H), 3.73 (s, 3H), 3.47-3.39 (m, 2H), 3.35-3.28 (m, 1H), 2.98 (s, 3H), 1.42-1.37 (m, 1H), 0.82-0.75 (m, 1H) 0.68-0.57 (m, 2H), 0.37-0.31 (m, 1H); LCMS (Method X4) RT 2.85 min; m/z calcd for $C_{25}H_{27}ClF_2N_7O_3^+$ [M+H]$^+$: 546.1832, Found: 546.18342.

The following tabulated examples were prepared by a method analogous to that used for the preparation of Example 12a, starting from the intermediate(s) shown in the table and appropriate amine. For Example 12c, Example 12d, Example 12e and Example 12u, reactions were heated at 140° C. in a heating block for 2-3 h. For Example 12f, Example 12i, Example 12p, Example 12s, Example 12t and Example 12x, reactions were heated at 140° C. under microwave irradiation for 90 min-3 h. For Example 12n and Example 12o, reactions were heated at 140° C. under microwave irradiation for 1 h followed by 140° C. in a heating block for 4 h. For Example 12v, the reaction was heated at 140° C. in a heating block for 6 h. For Example 12h the reaction was heated at 160° C. in a heating block overnight. For Example 12j and Example 12w, reactions were heated at 160° C. under microwave irradiation for 10-12 h. For Example 12c and Example 12d, the SCX-2 purification step was not conducted. An additional purification step by normal-phase chromatography was required for Example 12h and Example 12x.

| Example | Data and comments | Intermediate |
| --- | --- | --- |
| Example 12b: (R)-10-((5-chloro-2-(4-methyl-3-oxopiperazin-1-yl)pyrimidin-4-yl)amino)-2-cyclopropyl-7-methyl-1,2,3,4-tetrahydro-[1,4]oxazepino[2,3-c]quinolin-6(7H)-one | $^1$H NMR (600 MHz, methanol-d$_4$) δ 8.00 (s, 1 H), 7.98 (d, J = 2.3 Hz, 1 H), 7.92 (dd, J = 9.1, 2.3 Hz, 1 H), 7.53 (d, J = 9.1 Hz, 1 H), 4.42-4.36 (m, 1 H), 4.27-4.15 (m, 3 H), 3.98-3.88 (m, 2 H), 3.71 (s, 3 H), 3.43 (t, J = 5.5 Hz, 2 H), 2.98 (s, 3 H), 2.94 (dt, J = 9.5, 3.5 Hz, 1 H), 2.36-2.29 (m, 1 H), 2.14-2.07 (m, 1 H), 1.25-1.19 (m, 1 H), 0.67-0.60 (m, 2H), 0.42-0.37 (m, 1 H), 0.35-0.30 (m, 1 H); LCMS (Method X4) RT 2.78 min; m/z calcd for $C_{25}H_{29}ClN_7O_3^+$ [M + H]$^+$: 510.2020, Found: 510.2023. | Intermediate A10b: (R)-2-cyclopropyl-10-((2,5-dichloropyrimidin-4-yl)amino)-7-methyl-1,2,3,4-tetrahydro-[1,4]oxazepino[2,3-c]quinolin-6(7H)-one |
| Example 12c: (R)-10-((5-chloro-2-((3R,5S)-3-hydroxy-5-methylpiperidin-1-yl)pyrimidin-4-yl)amino)-2-cyclopropyl-7-methyl-1,2,3,4-tetrahydro-[1,4]oxazepino[2,3-c]quinolin-6(7H)-one or (R)-10-((5-chloro-2-((3S,5R)-3-hydroxy-5-methylpiperidin-1-yl)pyrimidin-4-yl)amino)-2-cyclopropyl-7-methyl-1,2,3,4-tetrahydro-[1,4]oxazepino[2,3-c]quinolin-6(7H)-one: formic acid (1:2) | $^1$H NMR (600 MHz, methanol-d$_4$) δ 8.13 (s, 2 H), 8.02 (s, 1 H), 7.99-7.90 (m, 2 H), 7.52 (dd, J = 9.2, 2.4 Hz, 1 H), 4.72 (dd, J = 12.5, 4.8 Hz, 1 H), 4.53-4.47 (m, 1 H), 4.43-4.37 (m, 1 H), 4.22-4.16 (m, 1 H), 3.72 (s, 3 H), 3.57-3.50 (m, 1 H), 2.96 (td, J = 9.6, 3.4 Hz, 1 H), 2.47 (dd, J = 12.5, 10.5 Hz, 1 H), 2.39-2.27 (m, 2 H), 2.16-2.05 (m, 2 H), 1.62 (ddt, J = 15.0, 11.6, 5.2 Hz, 1 H), 1.24 (dtd, J = 17.3, 8.3, 7.8, 3.7 Hz, 1 H), 1.08 (q, J = 11.7 Hz, 1 H), 0.95 (d, J = 6.6 Hz, 3 H), 0.68-0.63 (m, 2 H), 0.46-0.41 (m, 1 H), 0.38-0.32 (m, 1H); LCMS (Method T4) RT 2.70 min; m/z calcd for $C_{26}H_{32}ClN_6O_3^+$ [M + H]$^+$: 511.2219, Found: 511.2219. | Intermediate A10b: (R)-2-cyclopropyl-10-((2,5-dichloropyrimidin-4-yl)amino)-7-methyl-1,2,3,4-tetrahydro-[1,4]oxazepino[2,3-c]quinolin-6(7H)-one and Intermediate M2a: (3R,5S)-5-methylpiperidin-3-ol or (3S,5R)-5-methylpiperidin-3-ol |

| Example | Data and comments | Intermediate |
| --- | --- | --- |
| Example 12d: (R)-10-((5-chloro-2-((3S,5R)-3-hydroxy-5-methylpiperidin-1-yl)pyrimidin-4-yl)amino)-2-cyclopropyl-7-methyl-1,2,3,4-tetrahydro-[1,4]oxazepino[2,3-c]quinolin-6(7H)-one or (R)-10-((5-chloro-2-((3R,5S)-3-hydroxy-5-methylpiperidin-1-yl)pyrimidin-4-yl)amino)-2-cyclopropyl-7-methyl-1,2,3,4-tetrahydro-[1,4]oxazepino[2,3-c]quinolin-6(7H)-one: formic acid (1:1) 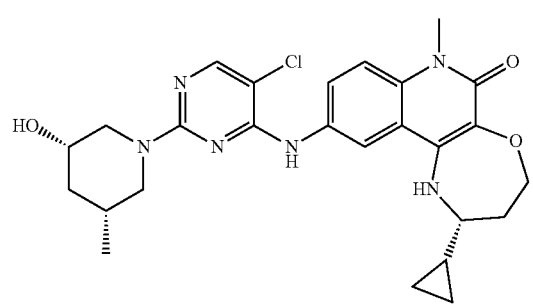 [SMILES: C[C@@H]1C[C@H](O)CN(c2ncc(Cl)c(Nc3ccc4c(c3)c3c(c(=O)n4C)OCC[C@H](C4CC4)N3)n2)C1] or 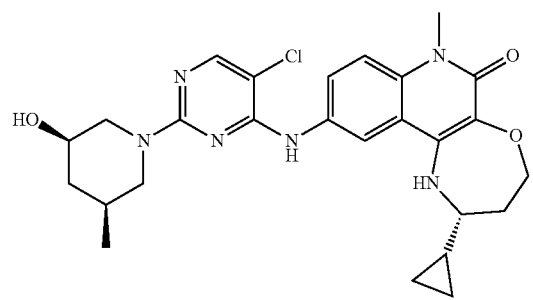 [SMILES: C[C@H]1C[C@@H](O)CN(c2ncc(Cl)c(Nc3ccc4c(c3)c3c(c(=O)n4C)OCC[C@H](C4CC4)N3)n2)C1] | $^1$H NMR (600 MHz, methanol-$d_4$) δ 8.18 (s, 1 H), 8.00 (d, J = 2.2 Hz, 1 H), 7.98-7.92 (m, 2 H), 7.51 (d, J = 9.0 Hz, 1 H), 4.76-4.69 (m, 1 H), 4.51-4.46 (m, 1 H), 4.43-4.37 (m, 1 H), 4.22-4.15 (m, 1 H), 3.71 (s, 3 H), 3.53 (tt, J = 10.9, 4.6 Hz, 1 H), 2.95 (td, J = 9.6, 3.5 Hz, 1 H), 2.47 (dd, J = 12.4, 10.5 Hz, 1 H), 2.40-2.24 (m, 2 H), 2.15-2.03 (m, 2 H), 1.67-1.57 (m, 1 H), 1.28-1.20 (m, 1 H), 1.07 (q, J = 11.8 Hz, 1 H), 0.95 (d, J = 6.6 Hz, 3 H), 0.69-0.62 (m, 2 H), 0.45-0.40 (m, 1 H), 0.34 dd, J = 9.9, 4.4 Hz, 1 H); LCMS (Method T4) RT 2.70 min; m/z calcd for $C_{26}H_{32}ClN_6O_3^+$ [M + H]$^+$: 511.2219, Found: 511.2230. | Intermediate A10b: (R)-2-cyclopropyl-10-((2,5-dichloropyrimidin-4-yl)amino)-7-methyl-1,2,3,4-tetrahydro-[1,4]oxazepino[2,3-c]quinolin-6(7H)-one and Intermediate M2b: (3S,5R)-5-methylpiperidin-3-ol or (3R,5S)-5-methylpiperidin-3-ol |
| Example 12e: (R)-10-((5-chloro-2-((3S,4R,5R)-4-fluoro-3,5-dimethylpiperidin-1-yl)pyrimidin-4-yl)amino)-2-cyclopropyl-7-methyl-1,2,3,4-tetrahydro-[1,4]oxazepino[2,3-c]quinolin-6(7H)-one 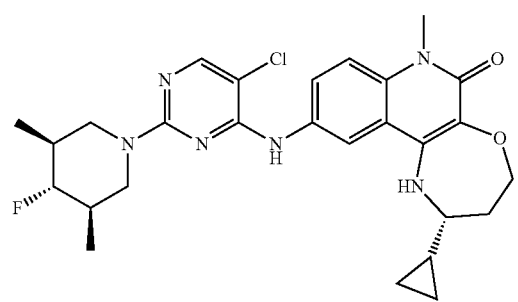 [SMILES: C[C@@H]1CN(c2ncc(Cl)c(Nc3ccc4c(c3)c3c(c(=O)n4C)OCC[C@H](C4CC4)N3)n2)C[C@H](C)[C@H]1F] | $^1$H NMR (600 MHz, methanol-$d_4$) δ 8.05 (d, J = 2.2 Hz, 1 H), 7.97 (s, 1 H), 7.87 (dd, J = 9.1, 2.2 Hz, 1 H), 7.53 (d, J = 9.1 Hz, 1 H), 4.58-4.50 (m, 2 H), 4.44-4.38 (m, 1 H), 4.23-4.17 (m, 1 H), 3.84 (dt, J = 49.9, 9.9 Hz, 1 H), 3.73 (s, 3 H), 2.96 (td, J = 9.5, 3.6 Hz, 1 H), 2.57-2.48 (m, 2 H), 2.38-2.31 (m, 1 H), 2.15-2.08 (m, 1 H), 1.75-1.65 (m, 2 H), 1.28-1.20 (m, 1 H), 1.03 (d, J = 6.5 Hz, 6 H), 0.69-0.63 (m, 2 H), 0.45-0.40 (m, 1 H), 0.38-0.32 (m, 1H); LCMS (Method T4) RT 3.13 min; m/z calcd for $C_{27}H_{33}ClFN_6O_2^+$ [M + H]$^+$: 527.2332, Found: 527.2320. | Intermediate A10b: (R)-2-cyclopropyl-10-((2,5-dichloropyrimidin-4-yl)amino)-7-methyl-1,2,3,4-tetrahydro-[1,4]oxazepino[2,3-c]quinolin-6(7H)-one and Intermediate O1: (3S,4r,5R)-4-fluoro-3,5-dimethylpiperidine hydrochloride |

-continued

| Example | Data and comments | Intermediate |
|---|---|---|
| Example 12f: (R)-10-((5-chloro-2-((1R,3R,5S)-3-hydroxy-8-azabicyclo[3.2.1]octan-8-yl)pyrimidin-4-yl)amino)-2-cyclopropyl-7-methyl-1,2,3,4-tetrahydro-[1,4]oxazepino[2,3-c]quinolin-6(7H)-one<br>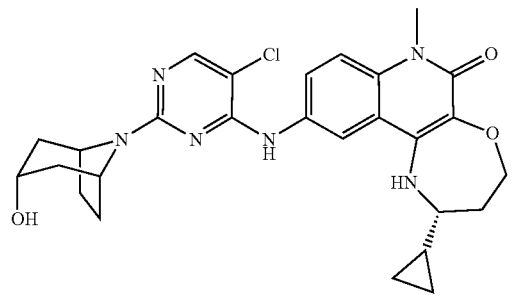 [SMILES: Cn1c(=O)c2c(c3cc(Nc4nc(N5C6CCC5CC(O)C6)ncc4Cl)ccc31)N[C@@H](C1CC1)CCO2] | $^1$H NMR (600 MHz, methanol-d$_4$) δ 8.01 (br s, 1 H), 7.98 (dd, J = 9.1, 2.2 Hz, 1 H), 7.93 (s, 1 H), 7.51 (d, J = 9.1 Hz, 1 H), 4.51-4.44 (m, 2 H), 4.42-4.36 (m, 1 H), 4.21-4.15 (m, 1 H), 4.01-3.98 (m, 1 H), 3.78 (s, 3 H), 2.93 (dt, J = 9.5, 3.4 Hz, 1 H), 2.36-2.25 (m, 3 H), 2.14-2.06 (m, 3 H), 1.98-1.91 (m, 2 H), 1.72 (dd, J = 14.4, 6.2 Hz, 2 H), 1.24-1.18 (m, 1 H), 0.68-0.62 (m, 2 H), 0.43-0.38 (m, 1 H), 0.38-0.30 (m, 1 H); LCMS (Method X4) RT 2.43 min; m/z calcd for $C_{27}H_{32}ClN_6O_3^+$ [M + H]$^+$: 523.2224, Found: 523.2228. | Intermediate A10b: (R)-2-cyclopropyl-10-((2,5-dichloropyrimidin-4-yl)amino)-7-methyl-1,2,3,4-tetrahydro-[1,4]oxazepino[2,3-c]quinolin-6(7H)-one |
| Example 12g: (R)-10-((2-(8-oxa-3-azabicyclo[3.2.1]octan-3-yl)-5-chloropyrimidin-4-yl)amino)-2-cyclopropyl-7-methyl-1,2,3,4-tetrahydro-[1,4]oxazepino[2,3-c]quinolin-6(7H)-one<br>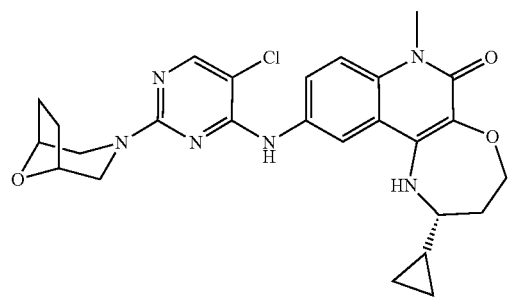 [SMILES: Cn1c(=O)c2c(c3cc(Nc4nc(N5CC6CCC(C5)O6)ncc4Cl)ccc31)N[C@@H](C1CC1)CCO2] | $^1$H NMR (600 MHz, methanol-d$_4$) δ 8.02 (d, J = 2.2 Hz, 1 H), 7.96 (s, 1 H), 7.91 (dd, J = 9.1, 2.2 Hz, 1 H), 7.51 (d, J = 9.1 Hz, 1 H), 4.41-4.36 (m, 3 H), 4.22-4.16 (m, 1 H), 4.07 (dd, J = 12.8, 6.3 Hz, 2 H), 3.71 (s, 3 H), 3.12-3.05 (m, 2 H), 2.95 (dt, J = 9.6, 3.5 Hz, 1 H), 2.37-2.30 (m, 1 H), 2.14-2.06 (m, 1 H), 1.92-1.85 (m, 2 H), 1.79-1.72 (m, 2 H), 1.25-1.19 (m, 1 H), 0.69-0.62 (m, 2 H), 0.44-0.39 (m, 1 H), 0.36-0.31 (m, 1 H); LCMS (Method X4) RT 2.93 min; m/z calcd for $C_{26}H_{30}ClN_6O_3^+$ [M + H]$^+$: 509.2068, Found: 509.2073. | Intermediate A10b: (R)-2-cyclopropyl-10-((2,5-dichloropyrimidin-4-yl)amino)-7-methyl-1,2,3,4-tetrahydro-[1,4]oxazepino[2,3-c]quinolin-6(7H)-one |
| Example 12h: (R)-10-((5-chloro-2-((1R,5S,7S)-7-hydroxy-7-methyl-3-oxa-9-azabicyclo[3.3.1]nonan-9-yl)pyrimidin-4-yl)amino)-2-cyclopropyl-7-methyl-1,2,3,4-tetrahydro-[1,4]oxazepino[2,3-c]quinolin-6(7H)-one<br>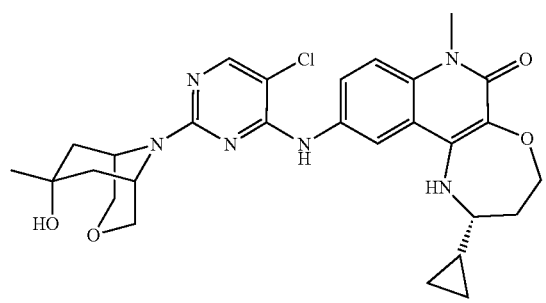 [SMILES: Cn1c(=O)c2c(c3cc(Nc4nc(N5C6COCC5CC(C)(O)C6)ncc4Cl)ccc31)N[C@@H](C1CC1)CCO2] | $^1$H NMR (600 MHz, methanol-d$_4$) δ 7.99 (s, 1 H), 7.92 (d, J = 2.3 Hz, 1 H), 7.88-7.85 (m, 1 H), 7.50 (d, J = 9.1 Hz, 1 H), 4.55 (br s, 2 H), 4.41-4.35 (m, 1 H), 4.22-4.16 (m, 1 H), 3.96-3.90 (m, 2 H), 3.81-3.76 (m, 2 H), 3.69 (s, 3 H), 2.92 (td, J = 9.5, 3.6 Hz, 1 H), 2.36-2.28 (m, 1 H), 2.12-2.05 (m, 1 H), 2.03-1.95 (m, 2 H), 1.84-1.76 (m, 2 H), 1.25-1.17 (m, 1 H), 1.16 (s, 3 H), 0.67-0.60 (m, 2 H), 0.42-0.37 (m, 1 H), 0.34-0.28 (m, 1 H); LCMS (Method T4) RT 2.90 min; m/z calcd for $C_{28}H_{34}ClN_6O_4^+$ [M + H]$^+$: 553.2325, Found: 553.2332. | Intermediate A10b: (R)-2-cyclopropyl-10-((2,5-dichloropyrimidin-4-yl)amino)-7-methyl-1,2,3,4-tetrahydro-[1,4]oxazepino[2,3-c]quinolin-6(7H)-one and Intermediate P1: (1R,5S,7s)-7-methyl-3-oxa-9-azabicyclo[3.3.1]nonan-7-ol |

| Example | Data and comments | Intermediate |
|---|---|---|
| Example 12i: (R)-10-((5-chloro-2-(3-methyl-3,8-diazabicyclo[3.2.1]octan-8-yl)pyrimidin-4-yl)amino)-2-cyclopropyl-7-methyl-1,2,3,4-tetrahydro-[1,4]oxazepino[2,3-c]quinolin-6(7H)-one | $^1$H NMR (600 MHz, methanol-d$_4$) δ 7.99-7.94 (m, 3 H), 7.52 (d, J = 9.1 Hz, 1 H), 4.56-4.49 (m, 2 H), 4.42-4.36 (m, 1 H), 4.22-4.15 (m, 1 H), 3.71 (s, 3 H), 2.93 (dt, J = 9.5, 3.5 Hz, 1 H), 2.73-2.67 (m, 2 H), 2.37-2.29 (m, 3 H), 2.20 (s, 3 H), 2.13-2.06 (m, 1 H), 1.98-1.89 (m, 4 H), 1.25-1.19 (m, 1 H), 0.68-0.62 (m, 2 H), 0.44-0.38 (m, 1 H), 0.36-0.30 (m, 1 H); LCMS (Method T4) RT 2.43 min; m/z calcd for C$_{27}$H$_{33}$ClN$_7$O$_2^+$ [M + H]$^+$: 522.2379, Found: 522.2360. | Intermediate A10b: (R)-2-cyclopropyl-10-((2,5-dichloropyrimidin-4-yl)amino)-7-methyl-1,2,3,4-tetrahydro-[1,4]oxazepino[2,3-c]quinolin-6(7H)-one |
| Example 12j: (R)-10-((5-chloro-2-(3,3-dioxido-3-thia-8-azabicyclo[3.2.1]octan-8-yl)pyrimidin-4-yl)amino)-2-cyclopropyl-7-methyl-1,2,3,4-tetrahydro-[1,4]oxazepino[2,3-c]quinolin-6(7H)-one | $^1$H NMR (600 MHz, methanol-d$_4$) δ 8.07 (s, 1 H), 7.97 (d, J = 2.1 Hz, 1 H), 7.86 (dd, J = 9.1, 2.1 Hz, 1 H), 7.54 (d, J = 9.1 Hz, 1 H), 4.92-4.87 (m, 1 H), 4.84-4.82 (m, 1 H; under H$_2$O peak), 4.42-4.36 (m, 1 H), 4.23-4.18 (m, 1 H), 3.71 (s, 3 H), 3.45 (dt, J = 13.8, 3.3 Hz, 2 H), 3.19 (d, J = 13.8 Hz, 2 H), 2.95 (dt, J = 9.5, 3.5 Hz, 1 H), 2.45-2.38 (m, 2 H), 2.36-2.30 (m, 1 H), 2.19-2.14 (m, 2 H), 2.13-2.07 (m, 1 H), 1.27-1.20 (m, 1 H), 0.68-0.61 (m, 2 H), 0.42-0.38 (m, 1 H), 0.34-0.30 (m, 1 H); LCMS (Method T4) RT 2.82 min; m/z calcd for C$_{26}$H$_{30}$ClN$_6$O$_4$S$^+$ [M + H]$^+$: 557.1732, Found: 557.1729. | Intermediate A10b: (R)-2-cyclopropyl-10-((2,5-dichloropyrimidin-4-yl)amino)-7-methyl-1,2,3,4-tetrahydro-[1,4]oxazepino[2,3-c]quinolin-6(7H)-one |
| Example 12k: (S)-10-((5-chloro-2-((3R,5S)-3-hydroxy-5-methylpiperidin-1-yl)pyrimidin-4-yl)amino)-2,7-dimethyl-1,2,3,4-tetrahydro-[1,4]oxazepino[2,3-c]quinolin-6(7H)-one or (S)-10-((5-chloro-2-((3S,5R)-3-hydroxy-5-methylpiperidin-1-yl)pyrimidin-4-yl)amino)-2,7-dimethyl-1,2,3,4-tetrahydro-[1,4]oxazepino[2,3-c]quinolin-6(7H)-one 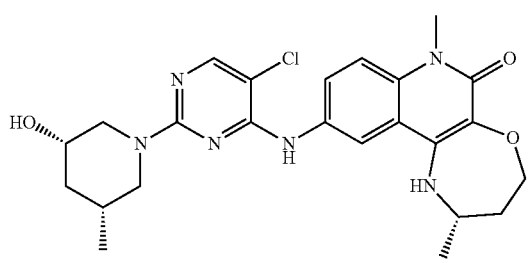 [SMILES: C[C@@H]1C[C@H](O)CN(c2ncc(Cl)c(Nc3ccc4c(c3)c3c(c(=O)n4C)OCC[C@H](C)N3)n2)C1] or | $^1$H NMR (500 MHz, DMSO-d$_6$) δ 8.74 (s, 1 H), 8.14 (d, J = 2.2 Hz, 1 H), 8.01 (s, 1 H), 7.69 (d, J = 9.1 Hz, 1 H), 7.37 (d, J = 9.1 Hz, 1 H), 5.48 (s, 1 H), 4.85 (s, 1 H), 4.59 (br s, 1 H), 4.36 (br s, 1 H), 4.18-4.06 (m, 2 H), 3.93-3.88 (m, 1 H), 3.55 (s, 3 H), 3.34 (tt, J = 10.5, 4.6 Hz, 1 H), 2.33 (dd, J = 12.3, 10.5 Hz, 1 H), 2.18 (t, J = 12.3 Hz, 1 H), 2.14-2.02 (m, 1 H), 1.95-1.88 (m, 1 H), 1.79-1.75 (m, 1 H), 1.53-1.45 (m, 1 H), 1.32 (d, J = 6.5 Hz, 3 H), 0.95 (q, J = 11.8 Hz, 1 H), 0.83 (d, J = 6.5 Hz, 3 H); LCMS (Method T4) RT 2.53 min; m/z calcd for C$_{24}$H$_{30}$ClN$_6$O$_3^+$ [M + H]$^+$: 485.2062, Found: 485.2056. | Intermediate A10d: (S)-10-((2,5-dichloropyrimidin-4-yl)amino)-2,7-dimethyl-1,2,3,4-tetrahydro-[1,4]oxazepino[2,3-c]quinolin-6(7H)-one and Intermediate M2a: (3R,5S)-5-methylpiperidin-3-ol or (3S,5R)-5-methylpiperidin-3-ol |

| Example | Data and comments | Intermediate |
| --- | --- | --- |
| Example 12l: (S)-10-((5-chloro-2-((3S,5R)-3-hydroxy-5-methylpiperidin-1-yl)pyrimidin-4-yl)amino)-2,7-dimethyl-1,2,3,4-tetrahydro-[1,4]oxazepino[2,3-c]quinolin-6(7H)-one or (S)-10-((5-chloro-2-((3R,5S)-3-hydroxy-5-methylpiperidin-1-yl)pyrimidin-4-yl)amino)-2,7-dimethyl-1,2,3,4-tetrahydro-[1,4]oxazepino[2,3-c]quinolin-6(7H)-one 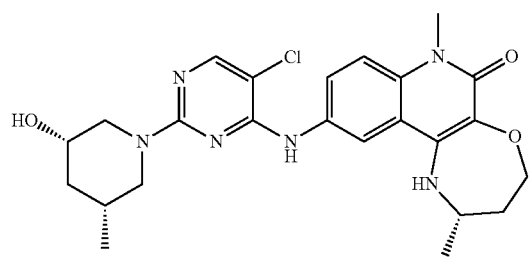 [SMILES: C[C@@H]1C[C@H](O)CN(c2ncc(Cl)c(Nc3ccc4c(c3)c3c(c(=O)n4C)OCC[C@H](C)N3)n2)C1] or 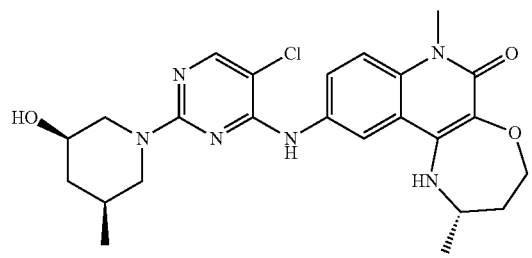 [SMILES: C[C@H]1C[C@@H](O)CN(c2ncc(Cl)c(Nc3ccc4c(c3)c3c(c(=O)n4C)OCC[C@H](C)N3)n2)C1] | $^1$H NMR (600 MHz, DMSO-d$_6$) δ 8.73 (s, 1 H), 8.14 (d, J = 2.3 Hz, 1 H), 8.02 (s, 1 H), 7.70 (d, J = 9.0 Hz, 1 H), 7.38 (d, J = 9.0 Hz, 1 H), 5.47 (brs, 1 H), 4.93 (s, 1 H), 4.60 (s, 1 H), 4.37 (s, 1 H), 4.23-4.03 (m, 2 H), 3.93-3.86 (m, 1 H), 3.55 (s, 3 H), 3.36-3.32 (m, 1 H), 2.33 (dd, J = 12.3, 10.4 Hz, 1 H), 2.19 (t, J = 12.1 Hz, 1 H), 2.14-2.05 (m, 1 H), 1.97-1.90 (m, 1 H), 1.80-1.75 (m, 1 H), 1.59-1.46 (m, 1 H), 1.34 (d, J = 6.6 Hz, 3 H), 0.96 (q, J = 11.8 Hz, 1 H), 0.84 (d, J = 6.6 Hz, 3 H); LCMS (Method T4) RT 2.53 min; m/z calcd for C$_{24}$H$_{30}$ClN$_6$O$_3^+$ [M + H]$^+$: 485.2062, Found: 485.2064. | Intermediate A10d: (S)-10-((2,5-dichloropyrimidin-4-yl)amino)-2,7-dimethyl-1,2,3,4-tetrahydro-[1,4]oxazepino[2,3-c]quinolin-6(7H)-one and and Intermediate M2b: (3S,5R)-5-methylpiperidin-3-ol or (3R,5S)-5-methylpiperidin-3-ol |
| Example 12m: (R)-10-((5-chloro-2-((3S,5R)-4,4-difluoro-3,5-dimethylpiperidin-1-yl)pyrimidin-4-yl)amino)-2-cyclopropyl-7-methyl-1,2,3,4-tetrahydro-[1,4]thiazepino[2,3-c]quinolin-6(7H)-one 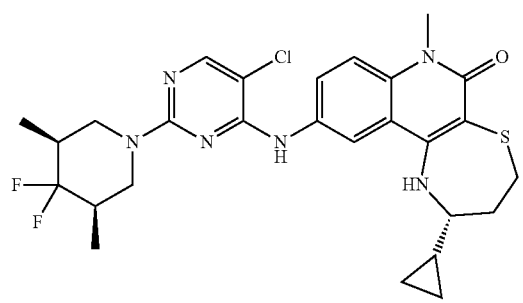 [SMILES: C[C@@H]1CN(c2ncc(Cl)c(Nc3ccc4c(c3)c3c(c(=O)n4C)SCC[C@H](C4CC4)N3)n2)C[C@H](C)C1(F)F] | $^1$H NMR (500 MHz, CDCl$_3$) δ 8.01 (s, 1 H), 7.76-7.64 (m, 2 H), 7.30 (d, J = 9.1 Hz, 1 H), 7.08 (s, 1 H), 4.65-4.56 (m, 2 H), 4.39 (s, 1 H), 3.98-3.90 (m, 1 H), 3.77-3.66 (m, 4 H), 2.98-2.89 (m, 1 H), 2.79-2.68 (m, 2 H), 2.26-2.15 (m, 1 H), 2.06-1.87 (m, 3 H), 1.07 (d, J = 6.7 Hz, 6 H), 1.05-0.95 (m, 1 H), 0.73-0.64 (m, 1 H), 0.62-0.53 (m, 1 H), 0.43-0.35 (m, 1 H), 0.30-0.21 (m, 1 H); LCMS (Method T4) RT 3.35 min; m/z calcd for C$_{27}$H$_{32}$ClF$_2$N$_6$OS$^+$ [M + H]$^+$: 561.2009, Found: 561.1998. | Intermediate A10c: (R)-2-cyclopropyl-10-((2,5-dichloropyrimidin-4-yl)amino)-7-methyl-1,2,3,4-tetrahydro-[1,4]thiazepino[2,3-c]quinolin-6(7H)-one |

| Example | Data and comments | Intermediate |
| --- | --- | --- |
| Example 12n: (S)-10-((5-chloro-2-(4,4-difluoropiperidin-1-yl)pyrimidin-4-yl)amino)-2-cyclopropyl-3,3-difluoro-7-methyl-1,2,3,4-tetrahydro-[1,4]oxazepino[2,3-c]quinolin-6(7H)-one | $^1$H NMR (600 MHz, methanol-$d_4$) δ 8.07 (d, J = 2.1 Hz, 1 H), 7.99 (s, 1 H), 7.89 (dd, J = 9.2, 2.1 Hz, 1 H), 7.56 (d, J = 9.2 Hz, 1 H), 4.56-4.46 (m, 1 H), 4.46-4.37 (m, 1 H), 3.85-3.80 (m, 4 H), 3.72 (s, 3 H), 3.34-3.28 (m, 1 H), 1.98-1.90 (m, 4 H), 1.42-1.36 (m, 1 H), 0.82-0.76 (m, 1 H), 0.69-0.63 (m, 1 H), 0.63-0.58 (m, 1 H), 0.38-0.32 (m, 1 H); LCMS (Method X4) RT 3.33 min; m/z calcd for $C_{25}H_{26}ClF_4N_6O_2^+$ [M + H]$^+$: 553.1742, Found: 553.1738. | Intermediate A10a: (S)-2-cyclopropyl-10-((2,5-dichloropyrimidin-4-yl)amino)-3,3-difluoro-7-methyl-1,2,3,4-tetrahydro-[1,4]oxazepino[2,3-c]quinolin-6(7H)-one |
| Example 12o: (S)-10-((5-chloro-2-((3S,5R)-4,4-difluoro-3,5-dimethylpiperidin-1-yl)pyrimidin-4-yl)amino)-2-cyclopropyl-3,3-difluoro-7-methyl-1,2,3,4-tetrahydro-[1,4]oxazepino[2,3-c]quinolin-6(7H)-one | $^1$H NMR (600 MHz, methanol-$d_4$) δ 8.04 (d, J = 2.2 Hz, 1 H), 7.98 (s, 1 H), 7.88 (dd, J = 9.1, 2.2 Hz, 1 H), 7.55 (d, J = 9.1 Hz, 1 H), 4.53-4.36 (m, 4 H), 3.72 (s, 3 H), 3.33-3.27 (m, 1 H), 2.72-2.65 (m, 2 H), 1.98-1.88 (m, 2 H), 1.43-1.37 (m, 1 H), 0.99 (d, J = 6.6 Hz, 3 H), 0.98 (d, J = 6.6 Hz, 3 H), 0.82-0.76 (m, 1 H), 0.68-0.57 (m, 2 H), 0.37-0.31 (m, 1 H); LCMS (Method X4) RT 3.61 min; m/z calcd for $C_{27}H_{30}ClF_4N_6O_2^+$ [M + H]$^+$: 581.2055, Found: 581.2065. | Intermediate A10a: (S)-2-cyclopropyl-10-((2,5-dichloropyrimidin-4-yl)amino)-3,3-difluoro-7-methyl-1,2,3,4-tetrahydro-[1,4]oxazepino[2,3-c]quinolin-6(7H)-one |
| Example 12p: (S)-10-((5-chloro-2-((R)-4,4-difluoro-3-(hydroxymethyl)piperidin-1-yl)pyrimidin-4-yl)amino)-2-cyclopropyl-3,3-difluoro-7-methyl-1,2,3,4-tetrahydro-[1,4]oxazepino[2,3-c]quinolin-6(7H)-one or (S)-10-((5-chloro-2-((S)-4,4-difluoro-3-(hydroxymethyl)piperidin-1-yl)pyrimidin-4-yl)amino)-2-cyclopropyl-3,3-difluoro-7-methyl-1,2,3,4-tetrahydro-[1,4]oxazepino[2,3-c]quinolin-6(7H)-one | $^1$H NMR (600 MHz, methanol-$d_4$) δ 8.07-8.00 (m, 3 H), 7.56 (d, J = 9.1 Hz, 1 H), 4.58-4.39 (m, 3 H), 4.30 (d, J = 14.2 Hz, 1 H), 3.91 (dd, J = 11.2, 3.9 Hz, 1 H), 3.74 (s, 3 H), 3.52-3.46 (m, 1 H), 3.46-3.40 (m, 1 H), 3.32-3.25 (m, 2 H), 2.18-2.08 (m, 1 H), 2.08-1.97 (m, 1 H), 1.97-1.84 (m, 1 H), 1.46-1.37 (m, 1 H), 0.85-0.78 (m, 1 H), 0.72-0.66 (m, 1 H), 0.65-0.59 (m, 1 H), 0.40-0.33 (m, 1 H); LCMS (Method T4) RT 2.96 min; m/z calcd for $C_{26}H_{28}ClF_4N_6O_3^+$ [M + H]$^+$: 583.1842, Found: 583.1832. | Intermediate A10a: (S)-2-cyclopropyl-10-((2,5-dichloropyrimidin-4-yl)amino)-3,3-difluoro-7-methyl-1,2,3,4-tetrahydro-[1,4]oxazepino[2,3-c]quinolin-6(7H)-one and Intermediate N2a: (R)-(4,4-difluoropiperidin-3-yl)methanol or (S)-(4,4-difluoropiperidin-3-yl)methanol | or

| Example | Data and comments | Intermediate |
|---|---|---|
| 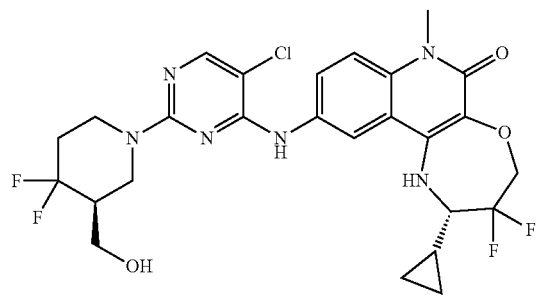 [SMILES: Cn1c(=O)c2c(c3cc(Nc4nc(N5CCC(F)(F)[C@H](CO)C5)ncc4Cl)ccc31)N[C@@H](C1CC1)C(F)(F)CO2]<br><br>Example 12q: (S)-10-((5-chloro-2-((S)-4,4-difluoro-3-(hydroxymethyl)piperidin-1-yl)pyrimidin-4-yl)amino)-2-cyclopropyl-3,3-difluoro-7-methyl-1,2,3,4-tetrahydro-[1,4]oxazepino[2,3-c]quinolin-6(7H)-one or (S)-10-((5-chloro-2-((R)-4,4-difluoro-3-(hydroxymethyl)piperidin-1-yl)pyrimidin-4-yl)amino)-2-cyclopropyl-3,3-difluoro-7-methyl-1,2,3,4-tetrahydro-[1,4]oxazepino[2,3-c]quinolin-6(7H)-one<br><br>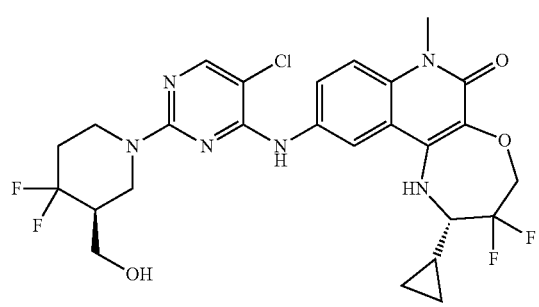 [SMILES: Cn1c(=O)c2c(c3cc(Nc4nc(N5CCC(F)(F)[C@H](CO)C5)ncc4Cl)ccc31)N[C@@H](C1CC1)C(F)(F)CO2]<br><br>or | $^1$H NMR (600 MHz, methanol-$d_4$) δ 8.08-8.00 (m, 3 H), 7.56 (d, J = 9.0 Hz, 1 H), 4.55-4.40 (m, 3 H), 4.27 (d, J = 13.9 Hz, 1 H), 3.90 (dd, J = 11.1, 4.0 Hz, 1 H), 3.74 (s, 3 H), 3.53-3.44 (m, 2 H), 3.31-3.27 (m, 2 H), 2.19-2.07 (m, 1 H), 2.06-1.97 (m, 1 H), 1.97-1.84 (m, 1 H), 1.48-1.38 (m, 1 H), 0.85-0.77 (m, 1 H), 0.71-0.59 (m, 2 H), 0.40-0.33 (m, 1 H);<br>LCMS (Method T4) RT 2.96 min; m/z calcd for $C_{26}H_{28}ClF_4N_6O_3^+$ [M + H]$^+$: 583.1842, Found: 583.1835. | Intermediate A10a: (S)-2-cyclopropyl-10-((2,5-dichloropyrimidin-4-yl)amino)-3,3-difluoro-7-methyl-1,2,3,4-tetrahydro-[1,4]oxazepino[2,3-c]quinolin-6(7H)-one and Intermediate N2b: (S)-(4,4-difluoropiperidin-3-yl)methanol or (R)-(4,4-difluoropiperidin-3-yl)methanol |
| 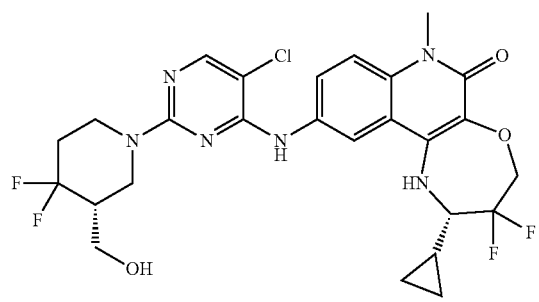<br><br>Example 12r: (S)-10-((5-chloro-2-morpholinopyrimidin-4-yl)amino)-2-cyclopropyl-3,3-difluoro-7-methyl-1,2,3,4-tetrahydro-[1,4]oxazepino[2,3-c]quinolin-6(7H)-one<br><br>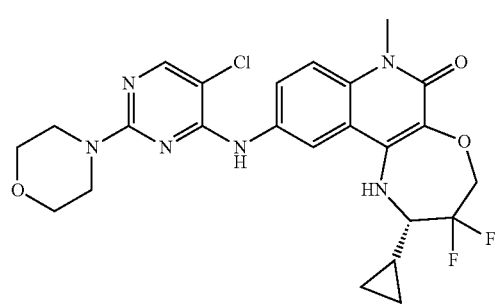 [SMILES: Cn1c(=O)c2c(c3cc(Nc4nc(N5CCOCC5)ncc4Cl)ccc31)N[C@@H](C1CC1)C(F)(F)CO2] | $^1$H NMR (600 MHz, methanol-$d_4$) δ 8.08 (d, J = 2.2 Hz, 1 H), 7.98 (s, 1 H), 7.91 (dd, J = 9.1, 2.2 Hz, 1 H), 7.55 (d, J = 9.1 Hz, 1 H), 4.52-4.36 (m, 2 H), 3.71 (s, 3 H), 3.69-3.66 (m, 4 H), 3.65-3.62 (m, 4 H), 3.35-3.28 (m, 1 H), 1.44-1.37 (m, 1 H), 0.83-0.75 (m, 1 H), 0.70-0.64 (m, 1 H), 0.64-0.58 (m, 1 H), 0.38-0.32 (m, 1 H);<br>LCMS (Method T4) RT 2.84 min; m/z calcd for $C_{24}H_{26}ClF_2N_6O_3^+$ [M + H]$^+$: 519.1717, Found: 517.1720. | Intermediate A10a: (S)-2-cyclopropyl-10-((2,5-dichloropyrimidin-4-yl)amino)-3,3-difluoro-7-methyl-1,2,3,4-tetrahydro-[1,4]oxazepino[2,3-c]quinolin-6(7H)-one |

| Example | Data and comments | Intermediate |
|---|---|---|
| Example 12s: (S)-10-((5-chloro-2-((R)-2-methylmorpholino)pyrimidin-4-yl)amino)-2-cyclopropyl-3,3-difluoro-7-methyl-1,2,3,4-tetrahydro-[1,4]oxazepino[2,3-c]quinolin-6(7H)-one<br>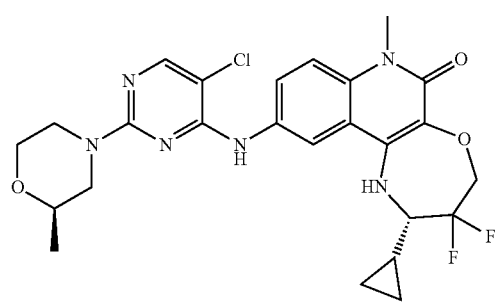 [SMILES: C[C@@H]1CN(c2ncc(Cl)c(Nc3ccc4c(c3)c3c(c(=O)n4C)OCC(F)(F)[C@H](C4CC4)N3)n2)CCO1] | $^1$H NMR (600 MHz, methanol-$d_4$) δ 8.07 (d, J = 2.2 Hz, 1 H), 7.97 (s, 1 H), 7.89 (dd, J = 9.1, 2.2 Hz, 1 H), 7.53 (d, J = 9.1 Hz, 1 H), 4.52-4.36 (m, 2 H), 4.34 (app. d, J = 13.0 Hz, 1 H), 4.26 (app. d, J = 13.3 Hz, 1 H), 3.87 (dd, J = 11.6, 2.5 Hz, 1 H), 3.71 (s, 3 H), 3.57-3.49 (m, 2 H), 3.34-3.27 (m, 1 H), 2.96-2.90 (m, 1 H), 2.59 (dd, J = 13.0, 10.5 Hz, 1 H), 1.44-1.36 (m, 1 H), 1.15 (d, J = 6.2 Hz, 3 H), 0.82-0.76 (m, 1 H), 0.70-0.64 (m, 1 H), 0.63-0.58 (m, 1 H), 0.38-0.32 (m, 1 H); LCMS (Method T4) RT 2.95 min; m/z calcd for $C_{25}H_{28}ClF_2N_6O_3^+$ [M + H]$^+$: 533.1874, Found: 533.1874. | Intermediate A10a: (S)-2-cyclopropyl-10-((2,5-dichloropyrimidin-4-yl)amino)-3,3-difluoro-7-methyl-1,2,3,4-tetrahydro-[1,4]oxazepino[2,3-c]quinolin-6(7H)-one |
| Example 12t: (S)-10-((5-chloro-2-((S)-2-methylmorpholino)pyrimidin-4-yl)amino)-2-cyclopropyl-3,3-difluoro-7-methyl-1,2,3,4-tetrahydro-[1,4]oxazepino[2,3-c]quinolin-6(7H)-one<br>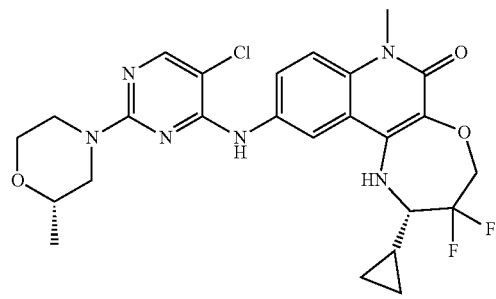 [SMILES: C[C@H]1CN(c2ncc(Cl)c(Nc3ccc4c(c3)c3c(c(=O)n4C)OCC(F)(F)[C@H](C4CC4)N3)n2)CCO1] | $^1$H NMR (600 MHz, methanol-$d_4$) δ 8.06 (d, J = 2.1 Hz, 1 H), 7.97 (s, 1 H), 7.91 (dd, J = 9.1, 2.1 Hz, 1 H), 7.54 (d, J = 9.1 Hz, 1 H), 4.52-4.37 (m, 2 H), 4.33 (app. d, J = 13.0 Hz, 1 H), 4.27 (app. d, J = 13.3 Hz, 1 H), 3.88 (dd, J = 11.5, 2.7 Hz, 1 H), 3.71 (s, 3 H), 3.58-3.50 (m, 2 H), 3.31-3.26 (m, 1 H), 2.96-2.90 (m, 1 H), 2.58 (dd, J = 13.1, 10.5 Hz, 1 H), 1.44-1.37 (m, 1 H), 1.15 (d, J = 6.2 Hz, 3 H), 0.83-0.76 (m, 1 H), 0.69-0.63 (m, 1 H), 0.63-0.57 (m, 1 H), 0.38-0.32 (m, 1 H); LCMS (Method T4) RT 2.95 min; m/z calcd for $C_{25}H_{28}ClF_2N_6O_3^+$ [M + H]$^+$: 533.1874, Found: 533.1879. | Intermediate A10a: (S)-2-cyclopropyl-10-((2,5-dichloropyrimidin-4-yl)amino)-3,3-difluoro-7-methyl-1,2,3,4-tetrahydro-[1,4]oxazepino[2,3-c]quinolin-6(7H)-one |
| Example 12u: (S)-10-((2-(8-oxa-3-azabicyclo[3.2.1]octan-3-yl)-5-chloropyrimidin-4-yl)amino)-2-cyclopropyl-3,3-difluoro-7-methyl-1,2,3,4-tetrahydro-[1,4]oxazepino[2,3-c]quinolin-6(7H)-one<br>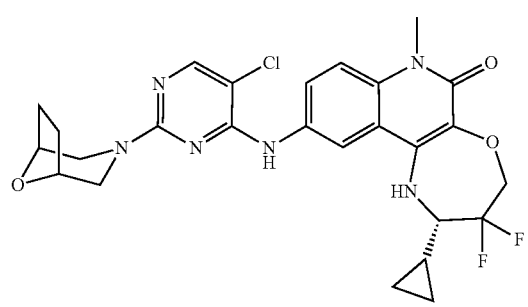 [SMILES: Cn1c(=O)c2c(c3cc(Nc4nc(N5CC6CCC(C5)O6)ncc4Cl)ccc31)N[C@@H](C1CC1)C(F)(F)CO2] | $^1$H NMR (600 MHz, methanol-$d_4$) δ 8.08 (d, J = 2.2 Hz, 1 H), 7.95 (s, 1 H), 7.91 (dd, J = 9.1, 2.2 Hz, 1 H), 7.54 (d, J = 9.1 Hz, 1 H), 4.53-4.39 (m, 2 H), 4.39-4.35 (m, 2 H), 4.09-4.03 (m, 2 H), 3.71 (s, 3 H), 3.35-3.28 (m, 1 H), 3.10-3.05 (m, 2 H), 1.92-1.85 (m, 2 H), 1.78-1.72 (m, 2 H), 1.43-1.36 (m, 1 H), 0.83-0.76 (m, 1 H), 0.70-0.64 (m, 1 H), 0.63-0.57 (m, 1 H), 0.39-0.33 (m, 1 H); LCMS (Method T4) RT 2.87 min; m/z calcd for $C_{26}H_{28}ClF_2N_6O_3^+$ [M + H]$^+$: 545.1874, Found: 545.1874. | Intermediate A10a: (S)-2-cyclopropyl-10-((2,5-dichloropyrimidin-4-yl)amino)-3,3-difluoro-7-methyl-1,2,3,4-tetrahydro-[1,4]oxazepino[2,3-c]quinolin-6(7H)-one |

| Example | Data and comments | Intermediate |
|---|---|---|
| Example 12v: (S)-10-((2-(3-oxa-8-azabicyclo[3.2.1]octan-8-yl)-5-chloropyrimidin-4-yl)amino)-2-cyclopropyl-3,3-difluoro-7-methyl-1,2,3,4-tetrahydro-[1,4]oxazepino[2,3-c]quinolin-6(7H)-one | $^1$H NMR (600 MHz, methanol-$d_4$) δ 8.03 (d, J = 2.1 Hz, 1 H), 7.97 (s, 1 H), 7.93 (dd, J = 9.1, 2.1 Hz, 1 H), 7.54 (d, J = 9.1 Hz, 1 H), 4.52-4.36 (m, 4 H), 3.74-3.70 (m, 5 H), 3.58-3.54 (m, 2H), 3.34-3.27 (m, 1 H), 2.04-1.97 (m, 2 H), 1.97-1.91 (m, 2 H), 1.43-1.35 (m, 1 H), 0.82-0.76 (m, 1 H), 0.69-0.63 (m, 1 H), 0.63-0.57 (m, 1 H), 0.38-0.32 (m, 1 H); LCMS (Method T4) RT 2.80 min; m/z calcd for $C_{26}H_{28}ClF_2N_6O_3^+$ [M + H]$^+$: 545.1874, Found: 545.1880. | Intermediate A10a: (S)-2-cyclopropyl-10-((2,5-dichloropyrimidin-4-yl)amino)-3,3-difluoro-7-methyl-1,2,3,4-tetrahydro-[1,4]oxazepino[2,3-c]quinolin-6(7H)-one |
| Example 12w: (S)-10-((5-chloro-2-(3,3-dioxido-3-thia-8-azabicyclo[3.2.1]octan-8-yl)pyrimidin-4-yl)amino)-2-cyclopropyl-3,3-difluoro-7-methyl-1,2,3,4-tetrahydro-[1,4]oxazepino[2,3-c]quinolin-6(7H)-one | $^1$H NMR (600 MHz, methanol-$d_4$) δ 8.06 (s, 1 H, Ar-H), 8.04 (d, J = 2.1 Hz, 1 H, Ar-H), 7.87 (dd, J = 9.1, 2.1 Hz, 1 H), 7.57 (d, J = 9.1 Hz, 1 H), 4.92-4.83 (m, 2 H), 4.53-4.38 (m, 2 H), 3.72 (s, 3 H), 3.45 (dt, J = 13.8, 3.4 Hz, 2 H), 3.35-3.27 (m, 1 H), 3.21-3.15 (m, 2 H), 2.44-2.37 (m, 2 H), 2.20-2.13 (m, 2 H), 1.44-1.37 (m, 1 H), 0.82-0.75 (m, 1 H), 0.69-0.63 (m, 1 H), 0.63-0.57 (m, 1 H), 0.38-0.31 (m, 1 H); LCMS (Method T4) RT 2.90 min; m/z calcd for $C_{26}H_{28}ClF_2N_6O_4S^+$ [M + H]$^+$: 593.1544, Found: 593.1543. | Intermediate A10a: (S)-2-cyclopropyl-10-((2,5-dichloropyrimidin-4-yl)amino)-3,3-difluoro-7-methyl-1,2,3,4-tetrahydro-[1,4]oxazepino[2,3-c]quinolin-6(7H)-one |
| Example 12x: (S)-10-((5-chloro-2-((R)-4,4-difluoro-2-(hydroxymethyl)pyrrolidin-1-yl)pyrimidin-4-yl)amino)-2-cyclopropyl-3,3-difluoro-7-methyl-1,2,3,4-tetrahydro-[1,4]oxazepino[2,3-c]quinolin-6(7H)-one | $^1$H NMR (600 MHz, methanol-$d_4$) δ 8.08 (d, J = 2.2 Hz, 1 H), 8.00 (s, 1 H), 7.94 (app. d, J = 9.1 Hz, 1 H), 7.56 (d, J = 9.1 Hz, 1 H), 4.53-4.37 (m, 2 H), 4.38-4.31 (m, 1 H), 4.03 (app. q, J = 12.4 Hz, 1 H), 3.80-3.73 (m, 1 H), 3.72 (s, 3 H), 3.70-3.64 (m, 2 H), 3.35-3.27 (m, 1 H), 2.60-2.43 (m, 2 H), 1.45-1.37 (m, 1 H), 0.81-0.75 (m, 1 H), 0.69-0.63 (m, 1 H), 0.63-0.57 (m, 1 H), 0.37-0.30 (m, 1 H); LCMS (Method T4) RT 2.95 min; m/z calcd for $C_{25}H_{26}ClF_2N_6O_3$ [M + H]$^+$: 569.1686, Found: 569.1679. | Intermediate A10a: (S)-2-cyclopropyl-10-((2,5-dichloropyrimidin-4-yl)amino)-3,3-difluoro-7-methyl-1,2,3,4-tetrahydro-[1,4]oxazepino[2,3-c]quinolin-6(7H)-one |

The following tabulated examples were prepared by an analogous method to that used for the preparation of Example 12a starting from Intermediate A10b: (R)-2-cyclopropyl-10-((2,5-dichloropyrimidin-4-yl)amino)-7-methyl-1,2,3,4-tetrahydro-[1,4]ox-azepino[2,3-c]quinolin-6(7H)-one and rac-4,4-difluoropiperidin-3-ol hydrochloride. Example 12y and Example 12z represent a pair of enantiomers where one is the (R)- and the other is the (S)-piperidinol. It has not been determined which is the (R)- and which is the (S)-enantiomer. The compounds were separated by preparative chiral SFC using the following method. The racemic mixture was dissolved to 9 mg/mL in EtOH:CH$_2$Cl$_2$ (5:4) and was then purified by SFC (Lux A1 (21.2 mm×250 mm, 5 μm), 40:60 EtOH:CO$_2$ (0.2% v/v NH$_3$); flow rate 50 mLmin$^{-1}$). The earlier eluting enantiomer was identified as Example 12y and the later eluting enantiomer was identified as Example 12z. Combined fractions of each were then concentrated in vacuo before being stored in a vacuum oven at 35° C. and 5 mbar affording Example 12y (19 mg) and Example 12z (17 mg) as white solids. Chiral purity analysis was determined by SFC (Amy-C (4.6 mm×250 mm, 5 μm), 40:60 EtOH:CO$_2$ (0.2% v/v NH$_3$); flow rate 4 mLmin$^{-1}$).

| Example | Data and comments |
|---|---|
| Example 12y: (R)-10-((5-chloro-2-((R)-4,4-difluoro-3-hydroxypiperidin-1-yl)pyrimidin-4-yl)amino)-2-cyclopropyl-7-methyl-1,2,3,4-tetrahydro-[1,4]oxazepino[2,3-c]quinolin-6(7H)-one or (R)-10-((5-chloro-2((S)-4,4-difluoro-3-hydroxypiperidin-1-yl)pyrimidin-4-yl)amino)-2-cyclopropyl-7-methyl-1,2,3,4-tetrahydro-[1,4]oxazepino[2,3-c]quinolin-6(7H)-one 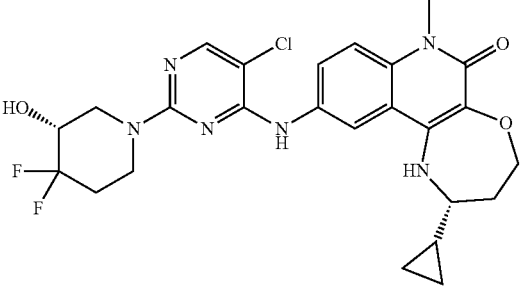 [SMILES: Cn1c(=O)c2c(c3cc(Nc4nc(N5CCC(F)(F)[C@H](O)C5)ncc4Cl)ccc31)N[C@@H](C1CC1)CCO2] or 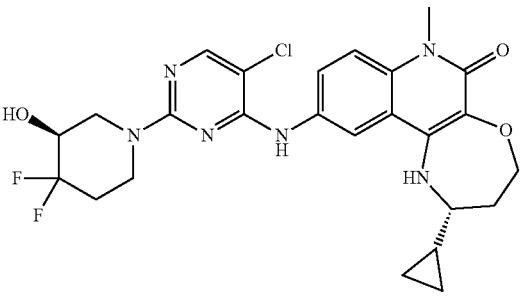 [SMILES: Cn1c(=O)c2c(c3cc(Nc4nc(N5CCC(F)(F)[C@@H](O)C5)ncc4Cl)ccc31)N[C@@H](C1CC1)CCO2] | $^1$H NMR (600 MHz, methanol-d$_4$) δ 8.01 (d, J = 2.1 Hz, 1 H), 7.98 (s, 1 H), 7.91 (dd, J = 9.1, 2.1 Hz, 1 H), 7.53 (d, J = 9.1 Hz, 1 H), 4.42-4.36 (m, 1 H), 4.23-4.17 (m, 1 H), 3.95-3.89 (m, 1 H), 3.84-3.78 (m, 3 H), 3.77-3.73 (m, 1 H), 3.72 (s, 3 H), 2.95 (dt, J = 9.4, 3.4 Hz, 1 H), 2.37-2.30 (m, 1 H), 2.24-2.14 (m, 1 H), 2.14-2.07 (m, 1 H), 1.93-1.83 (m, 1 H), 1.26-1.19 (m, 1 H), 0.68-0.61 (m, 2 H), 0.45-0.38 (m, 1 H), 0.37-0.29 (m, 1 H); LCMS (Method T4) RT 2.84 min; m/z calcd for C$_{25}$H$_{28}$ClF$_2$N$_6$O$_3^+$ [M + H]$^+$: 533.1874, Found: 533.1877; ee = 99.6%; RT 3.19 min. |
| Example 12z: (R)-10-((5-chloro-2-((S)-4,4-difluoro-3-hydroxypiperidin-1-yl)pyrimidin-4-yl)amino)-2-cyclopropyl-7-methyl-1,2,3,4-tetrahydro-[1,4]oxazepino[2,3-c]quinolin-6(7H)-one or (R)-10-((5-chloro-2((R)-4,4-difluoro-3-hydroxypiperidin-1-yl)pyrimidin-4-yl)amino)-2-cyclopropyl-7-methyl-1,2,3,4-tetrahydro-[1,4]oxazepino[2,3-c]quinolin-6(7H)-one 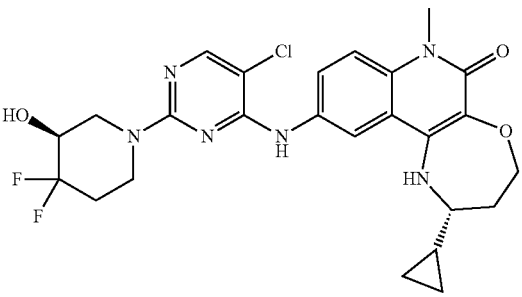 [SMILES: Cn1c(=O)c2c(c3cc(Nc4nc(N5CCC(F)(F)[C@@H](O)C5)ncc4Cl)ccc31)N[C@@H](C1CC1)CCO2] or | $^1$H NMR (600 MHz, methanol-d$_4$) δ 8.00 (d, J = 2.2 Hz, 1 H), 7.98 (s, 1 H), 7.91 (dd, J = 9.1, 2.2 Hz, 1 H), 7.53 (d, J = 9.1 Hz, 1 H), 4.42-4.36 (m, 1 H), 4.23-4.17 (m, 1 H), 3.99-3.92 (m, 1 H), 3.87-3.81 (m, 1 H), 3.80-3.73 (m, 3 H), 3.72 (s, 3 H), 2.95 (dt, J = 9.5, 3.5 Hz, 1 H), 2.37-2.30 (m, 1 H), 2.22-2.07 (m, 2 H), 1.93-1.83 (m, 1 H), 1.26-1.21 (m, 1 H), 0.68-0.61 (m, 2 H), 0.44-0.38 (m, 1 H), 0.36-0.31 (m, 1 H); LCMS (Method T4) RT 2.85 min; m/z calcd for C$_{25}$H$_{28}$ClF$_2$N$_6$O$_3^+$ [M + H]$^+$: 533.1874, Found: 533.1861; ee = 99.4%; RT 3.75 min. |

| Example | Data and comments |
|---|---|
| 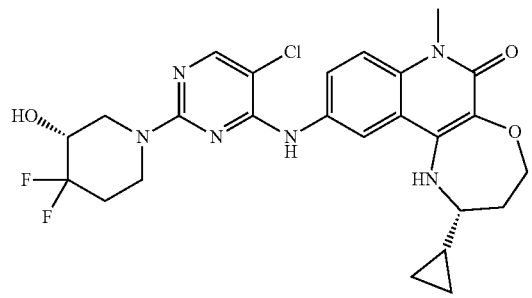 [SMILES: Cn1c(=O)c2c(c3cc(Nc4nc(N5CCC(F)(F)[C@H](O)C5)ncc4Cl)ccc31)N[C@@H](C1CC1)CCO2] | |

The following tabulated examples were prepared by a method analogous to that used for the preparation of Example 12a, starting from the intermediate(s) shown in the table and appropriate amine. For Example 13a, the reaction was heated at 140° C. under microwave irradiation for 8 h. For Example 13b and Example 13c, the reactions were heated at 160° C. under microwave irradiation for 8 h and 12 h respectively. For Example 13f, the reaction was heated at 120° C. under microwave irradiation for 1 h. For Example 13g and Example 13h, acetonitrile was used instead of NMP and the reactions were heated at 80° C. in a heating block for 1 h and 12 h respectively. For Example 13i, the reaction was heated at 140° C. under microwave irradiation for 10 h. For Example 13j, the reaction was heated at 140° C. in a heating block for 46 h. For Example 13a-Example 13c, purification was conducted using preparative HPLC. Example 13b was isolated as a mixture of diastereoisomers. Example 13c was isolated as a mixture of endo- and exo-isomers. For Example 13g and Example 13h, the SCX-2 purification step was not conducted. PGP-220 IRE M

| Example | Data and comments | Intermediate |
|---|---|---|
| Example 13a: (S)-10-((5-chloro-2-(4-hydroxy-7,8-dihydropyrido[4,3-d]pyrimidin-6(5H)-yl)pyrimidin-4-yl)amino)-2-cyclopropyl-3,3-difluoro-7-methyl-1,2,3,4-tetrahydro-[1,4]oxazepino[2,3-c]quinolin-6(7H)-one<br>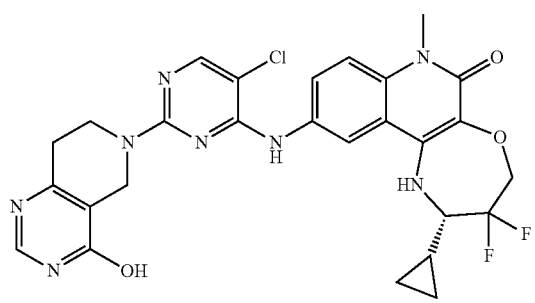 [SMILES: Cn1c(=O)c2c(c3cc(Nc4nc(N5CCc6ncnc(O)c6C5)ncc4Cl)ccc31)N[C@@H](C1CC1)C(F)(F)CO2] | $^1$H NMR (600 MHz, methanol-$d_4$) δ 8.08-8.06 (m, 2 H), 8.03 (s, 1 H), 7.99 (dd, J = 9.1, 2.3 Hz, 1 H), 7.60 (d, J = 9.1 Hz, 1 H), 4.57 (s, 2 H), 4.52-4.45 (m, 2 H), 4.04-3.94 (m, 2 H), 3.76 (s, 3 H), 3.32-2.28 (m, 1 H), 2.78-2.71 (m, 2 H), 1.43-1.35 (m, 1 H), 0.82-0.73 (m, 1 H), 0.68-0.56 (m, 2 H), 0.38-0.30 (m, 1 H); LCMS (Method X4) RT 2.91 min; m/z calcd for $C_{27}H_{26}ClF_2N_8O_3^+$ [M + H]$^+$: 583.1784, Found: 583.1786. | Intermediate A10a: (S)-2-cyclopropyl-10-((2,5-dichloropyrimidin-4-yl)amino)-3,3-difluoro-7-methyl-1,2,3,4-tetrahydro-[1,4]oxazepino[2,3-c]quinolin-6(7H)-one |
| Example 13b: (S)-10-((5-chloro-2-((1S,5R)-3-methyl-2-oxo-3,8-diazabicyclo[3.2.1]octan-8-yl)pyrimidin-4-yl)amino)-2-cyclopropyl-3,3-difluoro-7-methyl-1,2,3,4-tetrahydro-[1,4]oxazepino[2,3-c]quinolin-6(7H)-one and (S)-10-((5-chloro-2-((1R,5S)-3-methyl-2-oxo-3,8-diazabicyclo[3.2.1]octan-8-yl) pyrimidin-4-yl)amino)-2-cyclopropyl-3,3-difluoro-7-methyl-1,2,3,4-tetrahydro-[1,4]oxazepino[2,3-c]quinolin-6(7H)-one | Compound isolated as a mixture of diastereoisomers (d.r. 1:1, diastereoisomer A:diastereoisomer B): Diastereoisomer A: $^1$H NMR (600 MHz, methanol-$d_4$) δ 8.08-8.03 (m, 2 H), 7.92-7.84 (m, 1 H), 7.59 (d, J = 9.1 Hz, 1 H), 4.68 (d, J = 7.1 Hz, 1 H), 4.51 (d, J = 6.6 Hz, 2 H), 4.49-4.45 (m, 1 H), 3.79-3.76 (m, 1 H), 3.74 | Intermediate A10a: (S)-2-cyclopropyl-10-((2,5-dichloropyrimidin-4-yl)amino)-3,3-difluoro-7-methyl-1,2,3,4-tetrahydro-[1,4]oxazepino |

| Example | Data and comments | Intermediate |
|---|---|---|
| 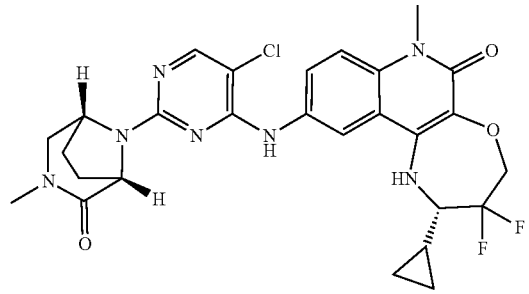 [SMILES: CN1C[C@H]2CC[C@@H](C1=O)N2c1ncc(Cl)c(Nc2ccc3c(c2)c2c(c(=O)n3C)OCC(F)(F)[C@H](C3CC3)N2)n1]<br><br>and<br><br>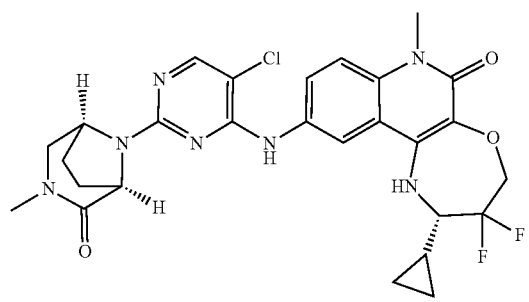 [SMILES: CN1C[C@@H]2CC[C@H](C1=O)N2c1ncc(Cl)c(Nc2ccc3c(c2)c2c(c(=O)n3C)OCC(F)(F)[C@H](C3CC3)N2)n1] | (s, 3 H), 3.32-3.27 (m, 1 H), 3.08 (dd, J = 12.0, 2.1 Hz, 1 H), 2.81 (s, 3 H), 2.26-2.19 (m, 2 H), 2.00-1.92 (m, 2 H), 1.55 1.42 (m, 1 H), 0.85-0.76 (m, 1 H), 0.69-0.56 (m, 2 H), 0.40-0.32 (m, 1 H);<br>Diastereoisomer B: $^1$H NMR (600 MHz, methanol-$d_4$) δ 8.23 (br s, 1 H), 8.08-8.03 (m, 1 H), 7.92-7.84 (m, 1 H), 7.60 (d, J = 9.1 Hz, 1 H), 4.76-4.71 (m, 3 H), 4.49-4.45 (m, 1 H), 3.82-3.79 (m, 1 H), 3.75 (s, 3 H), 3.32-3.27 (m, 1 H), 3.08 (dd, J = 12.0, 2.1 Hz, 1 H), 2.81 (s, 3 H), 2.36-2.27 (m, 2 H), 2.10-2.03 (m, 2 H), 1.55-1.42 (m, 1 H), 0.85-0.76 (m, 1 H), 0.69-0.56 (m, 2 H), 0.47-0.40 (m, 1 H);<br>LCMS (Method X4) RT 3.29 min; m/z calcd for $C_{27}H_{29}ClF_2N_7O_3^+$ [M + H]$^+$: 572.1989, Found: 572.1986. | [2,3-c]quinolin-6(7H)-one and Intermediate P2: rac-methyl-3,8-diazabicyclo[3.2.1]octan-2-one |
| Example 13c: (1R,5S,7S)-9-(5-chloro-4-(((S)-2-cyclopropyl-3,3-difluoro-7-methyl-6-oxo-1,2,3,4,6,7-hexahydro-[1,4]oxazepino[2,3-c]quinolin-10-yl)amino)pyrimidin-2-yl)-N,N-dimethyl-3-oxa-9-azabicyclo[3.3.1]nonane-7-carboxamide and (1R,5S,7R)-9-(5-chloro-4-(((S)-2-cyclopropyl-3,3-difluoro-7-methyl-6-oxo-1,2,3,4,6,7-hexahydro-[1,4]oxazepino[2,3-c]quinolin-10-yl)amino)pyrimidin-2-yl)-N,N-dimethyl-3-oxa-9-azabicyclo[3.3.1]nonane-7-carboxamide<br><br>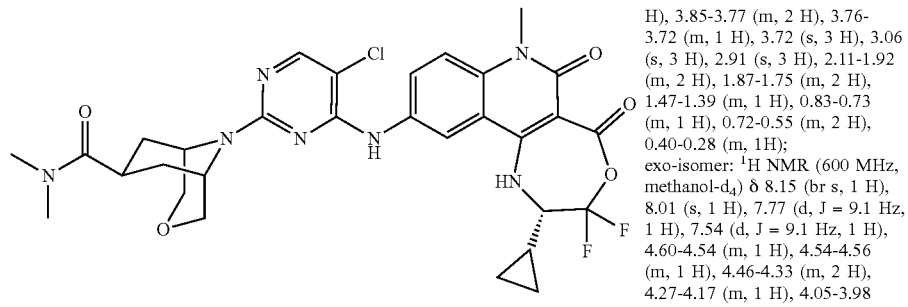<br><br>and<br><br>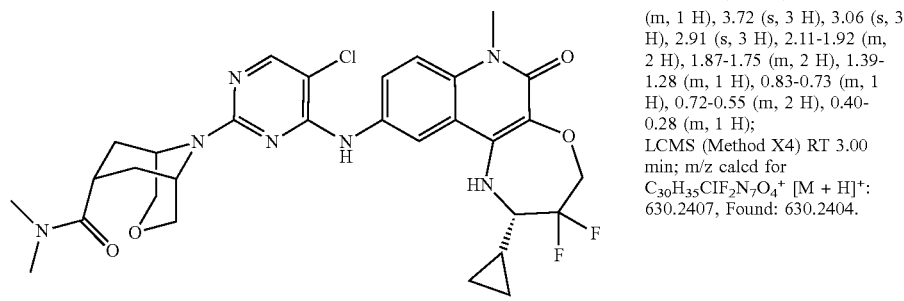 | Compound isolated as a mixture of endo- and exo-isomers (ratio 1.0:1.3, endo-:exo-):<br>endo-isomer: $^1$H NMR (600 MHz, methanol-$d_4$) δ 8.06 (br s, 1 H), 8.01 (s, 1 H), 7.88 (d, J = 9.1 Hz, 1 H), 7.54 (d, J = 9.1 Hz, 1 H), 4.60-4.54 (m, 1 H), 4.54-4.56 (m, 1 H), 4.46-4.33 (m, 2 H), 4.27-4.17 (m, 1 H), 4.05-3.98 (m, 1 H), 3.98-3.88 (m, 1 H), 3.85-3.77 (m, 2 H), 3.76-3.72 (m, 1 H), 3.72 (s, 3 H), 3.06 (s, 3 H), 2.91 (s, 3 H), 2.11-1.92 (m, 2 H), 1.87-1.75 (m, 2 H), 1.47-1.39 (m, 1 H), 0.83-0.73 (m, 1 H), 0.72-0.55 (m, 2 H), 0.40-0.28 (m, 1H);<br>exo-isomer: $^1$H NMR (600 MHz, methanol-$d_4$) δ 8.15 (br s, 1 H), 8.01 (s, 1 H), 7.77 (d, J = 9.1 Hz, 1 H), 7.54 (d, J = 9.1 Hz, 1 H), 4.60-4.54 (m, 1 H), 4.54-4.56 (m, 1 H), 4.46-4.33 (m, 2 H), 4.27-4.17 (m, 1 H), 4.05-3.98 (m, 1 H), 3.98-3.88 (m, 1 H), 3.85-3.77 (m, 2 H), 3.76-3.72 (m, 1 H), 3.72 (s, 3 H), 3.06 (s, 3 H), 2.91 (s, 3 H), 2.11-1.92 (m, 2 H), 1.87-1.75 (m, 2 H), 1.39-1.28 (m, 1 H), 0.83-0.73 (m, 1 H), 0.72-0.55 (m, 2 H), 0.40-0.28 (m, 1 H);<br>LCMS (Method X4) RT 3.00 min; m/z calcd for $C_{30}H_{35}ClF_2N_7O_4^+$ [M + H]$^+$: 630.2407, Found: 630.2404. | Intermediate A10a: (S)-2-cyclopropyl-10-((2,5-dichloropyrimidin-4-yl)amino)-3,3-difluoro-7-methyl-1,2,3,4-tetrahydro-[1,4]oxazepino[2,3-c]quinolin-6(7H)-one and Intermediate P3: (1R,5S)-N,N-dimethyl-3-oxa-9-azabicyclo[3.3.1]nonane-7-carboxamide |

| Example | Data and comments | Intermediate |
|---|---|---|
| Example 13d: (S)-10-((5-chloro-2-((3R,5S)-3-hydroxy-5-methylpiperidin-1-yl)pyrimidin-4-yl)amino)-2-cyclopropyl-3,3-difluoro-7-methyl-1,2,3,4-tetrahydro-[1,4]oxazepino[2,3-c]quinolin-6(7H)-one or (S)-10-((5-chloro-2-((3S,5R)-3-hydroxy-5-methylpiperidin-1-yl)pyrimidin-4-yl)amino)-2-cyclopropyl-3,3-difluoro-7-methyl-1,2,3,4-tetrahydro-[1,4]oxazepino[2,3-c]quinolin-6(7H)-one<br>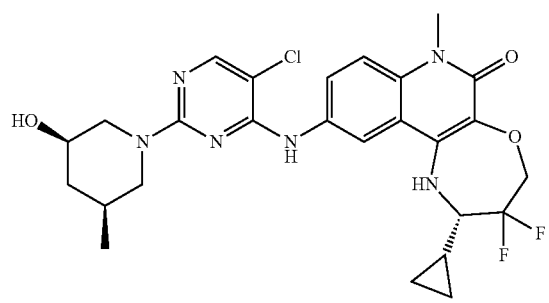 [SMILES: C[C@H]1C[C@@H](O)CN(c2ncc(Cl)c(Nc3ccc4c(c3)c3c(c(=O)n4C)OCC(F)(F)[C@H](C4CC4)N3)n2)C1]<br>or<br>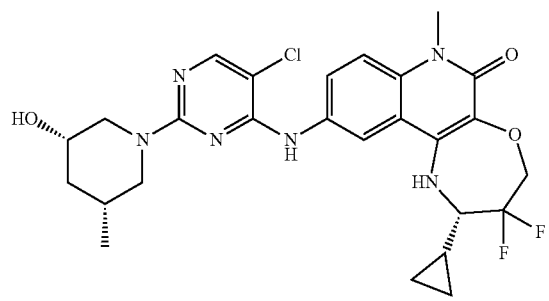 [SMILES: C[C@@H]1C[C@H](O)CN(c2ncc(Cl)c(Nc3ccc4c(c3)c3c(c(=O)n4C)OCC(F)(F)[C@H](C4CC4)N3)n2)C1] | $^1$H NMR (600 MHz, DMSO-d$_6$) δ 8.80 (s, 1 H), 8.09 (d, J = 2.3 Hz, 1 H), 8.02 (s, 1 H), 7.75 (d, J = 8.9 Hz, 1 H), 7.44 (d, J = 9.1 Hz, 1 H), 6.20 (d, J = 4.4 Hz, 1 H), 4.84 (s, 1 H), 4.56 (s, 1 H), 4.49-4.30 (m, 3 H), 3.57 (s, 3 H), 3.36-3.18 (m, 2 H), 2.33 (dd, J = 12.4, 10.4 Hz, 1 H), 2.18 (t, J = 12.1 Hz, 1 H), 1.91 (t, J = 6.3 Hz, 1 H), 1.55-1.45 (m, 1 H), 1.37-1.29 (m, 1 H), 0.95 (q, J = 11.8 Hz, 1 H), 0.83 (d, J = 6.7 Hz, 3 H), 0.75-0.68 (m, 1 H), 0.55-0.47 (m, 2 H), 0.38-0.32 (m, 1 H); LCMS (Method T4) RT 2.77 min; m/z calcd for C$_{26}$H$_{30}$ClF$_2$N$_6$O$_3^+$ [M + H]$^+$: 547.2030, Found: 547.2004. | Intermediate A10a: (S)-2-cyclopropyl-10-((2,5-dichloropyrimidin-4-yl)amino)-3,3-difluoro-7-methyl-1,2,3,4-tetrahydro-[1,4]oxazepino[2,3-c]quinolin-6(7H)-one |
| Example 13e: (S)-10-((5-chloro-2-((3S,5R)-3-hydroxy-5-methylpiperidin-1-yl)pyrimidin-4-yl)amino)-2-cyclopropyl-3,3-difluoro-7-methyl-1,2,3,4-tetrahydro-[1,4]oxazepino[2,3-c]quinolin-6(7H)-one or (S)-10-((5-chloro-2-((3R,5S)-3-hydroxy-5-methylpiperidin-1-yl)pyrimidin-4-yl)amino)-2-cyclopropyl-3,3-difluoro-7-methyl-1,2,3,4-tetrahydro-[1,4]oxazepino[2,3-c]quinolin-6(7H)-one<br>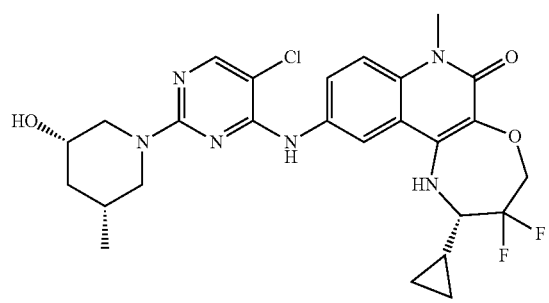 [SMILES: C[C@@H]1C[C@H](O)CN(c2ncc(Cl)c(Nc3ccc4c(c3)c3c(c(=O)n4C)OCC(F)(F)[C@H](C4CC4)N3)n2)C1]<br>or | $^1$H NMR (600 MHz, DMSO-d$_6$) δ 8.78 (s, 1 H), 8.11 (s, 1 H), 8.02 (s, 1 H), 7.75 (d, J = 9.0 Hz, 1 H), 7.44 (d, J = 9.0 Hz, 1 H), 10-6.20 (d, J = 4.2 Hz, 1 H), 4.88-4.80 (m, 1 H), 4.57 (s, 1 H), 4.50-4.25 (m, 3 H), 3.57 (s, 3 H), 3.36-3.18 (m, 2 H), 2.32 (dd, J = 12.3, 10.4 Hz, 1 H), 2.18 (t, J = 12.1 Hz, 1 H), 1.91 (q, J = 5.7, 5.0 Hz, 1 H), 1.55-1.44 (m, 1 H), 1.36-1.28 (m, 1 H), 0.94 (q, J = 11.8 Hz, 1 H), 0.81 (d, J = 6.7 Hz, 3 H), 0.74-0.67 (m, 1 H), 0.56-0.47 (m, 2 H), 0.38-0.30 (m, 1 H); LCMS (Method T4) RT 2.77 min; m/z calcd for C$_{26}$H$_{30}$ClF$_2$N$_6$O$_3^+$ [M + H]$^+$: 547.2030, Found: 547.2014. | Intermediate A10a: (S)-2-cyclopropyl-10-((2,5-dichloropyrimidin-4-yl)amino)-3,3-difluoro-7-methyl-1,2,3,4-tetrahydro-[1,4]oxazepino[2,3-c]quinolin-6(7H)-one |

| Example | Data and comments | Intermediate |
|---|---|---|
| 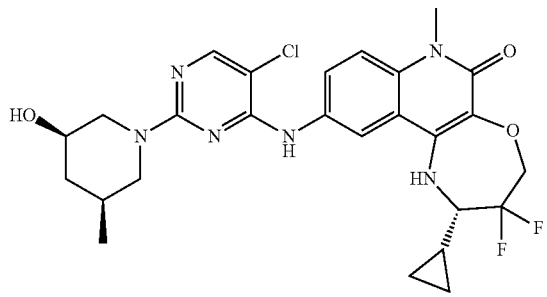<br>Example 13f: (S)-3-(4-(5-chloro-4-((2-cyclopropyl-3,3-difluoro-7-methyl-6-oxo-1,2,3,4,6,7-hexahydro-[1,4]oxazepino[2,3-c]quinolin-10-yl)amino)pyrimidin-2-yl)piperazin-1-yl)propanenitrile | $^1$H NMR (600 MHz, methanol-$d_4$) δ 8.10 (d, J = 2.2 Hz, 1 H), 7.96 (s, 1 H), 7.90 (dd, J = 9.1, 2.2 Hz, 1 H), 7.54 (d, J = 9.1 Hz, 1 H), 4.53-4.37 (m, 2 H), 3.73-3.68 (m, 7 H), 3.35-3.28 (m, 1 H), 2.70-2.66 (m, 2 H), 2.66-2.62 (m, 2 H), 2.54-2.50 (m, 4 H), 1.44-1.36 (m, 1 H), 0.83-0.76 (m, 1 H), 0.70-0.64 (m, 1 H), 0.64-0.57 (m, 1 H), 0.38-0.32 (m, 1 H); LCMS (Method T4) RT 2.51 min; m/z calcd for $C_{27}H_{30}ClF_2N_8O_2^+$ [M + H]$^+$: 571.2143, Found: 571.2129. | Intermediate A10a: (S)-2-cyclopropyl-10-((2,5-dichloropyrimidin-4-yl)amino)-3,3-difluoro-7-methyl-1,2,3,4-tetrahydro-[1,4]oxazepino[2,3-c]quinolin-6(7H)-one |
| 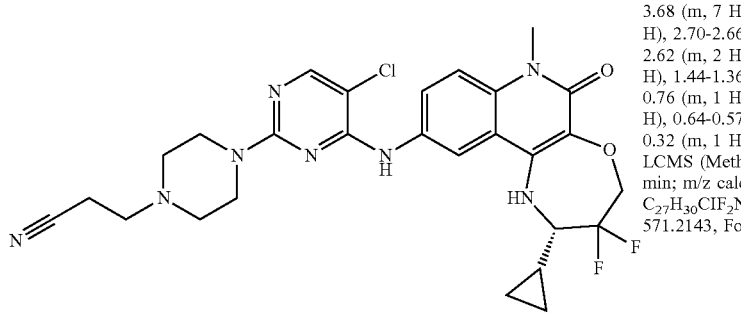<br>Example 13g: (S)-10-((5-chloro-2-(6-methyl-2,6-diazaspiro[3.3]heptan-2-yl)pyrimidin-4-yl)amino)-2-cyclopropyl-3,3-difluoro-7-methyl-1,2,3,4-tetrahydro-[1,4]oxazepino[2,3-c]quinolin-6(7H)-one:formic acid (1:2) | $^1$H NMR (600 MHz, methanol-$d_4$) δ 8.49 (br s, 2 H), 8.05 (dd, J = 9.1 Hz, 1 H), 8.02 (d, J = 2.1 Hz, 1 H), 7.96 (s, 1 H), 7.52 (d, J = 9.1 Hz, 1 H), 4.54-4.38 (m, 2 H), 4.25-4.16 (m, 8 H), 3.72 (s, 3 H), 3.36-3.32 (m, 1 H), 2.82 (s, 3 H), 1.45-1.38 (m, 1 H), 0.84-0.77 (m, 1 H), 0.71-0.65 (m, 1 H), 0.65-0.59 (m, 1 H), 0.39-0.33 (m, 1 H); LCMS (Method T4) RT 2.25 min; m/z calcd for $C_{26}H_{29}ClF_2N_7O_2^+$ [M + H]$^+$: 544.2034, Found: 544.2020. | Intermediate A10a: (S)-2-cyclopropyl-10-((2,5-dichloropyrimidin-4-yl)amino)-3,3-difluoro-7-methyl-1,2,3,4-tetrahydro-[1,4]oxazepino[2,3-c]quinolin-6(7H)-one |
| 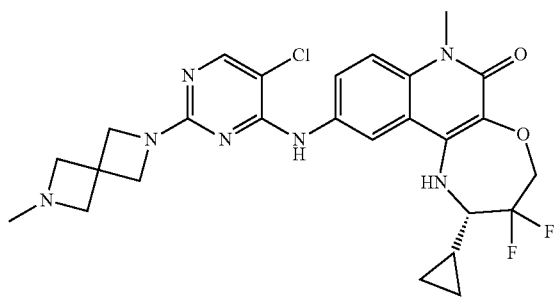 [SMILES: CN1CC2(C1)CN(c1ncc(Cl)c(Nc3ccc4c(c3)c3c(c(=O)n4C)OCC(F)(F)[C@H](C4CC4)N3)n1)C2]<br>Example 13h: (2S)-10-((5-chloro-2-(3-methyl-3,6-diazabicyclo[3.1.1]heptan-6-yl)pyrimidin-4-yl)amino)-2-cyclopropyl-3,3-difluoro-7-methyl-1,2,3,4-tetrahydro-[1,4]oxazepino[2,3-c]quinolin-6(7H)-one: formic acid (1:1)<br>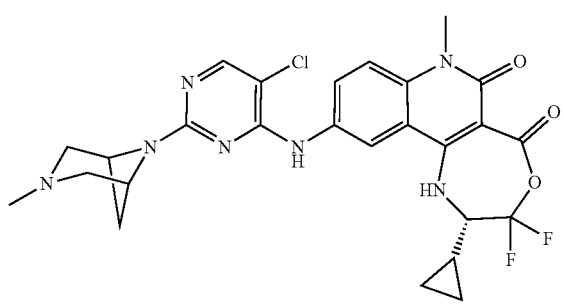 | $^1$H NMR (600 MHz, MeOD-$d_4$) δ 8.39 (br s, 1 H), 8.07 (d, J = 2.1 Hz, 1 H), 8.04 (s, 1 H), 7.94 (dd, J = 9.1, 2.1 Hz, 1 H), 7.54 (d, J = 9.1 Hz, 1 H), 4.53-4.37 (m, 2 H), 4.36-4.30 (m, 2 H), 3.71 (s, 3 H), 3.41-3.36 (m, 2 H), 3.36-3.32 (m, 1 H), 3.30-3.25 (m, 2 H), 2.74-2.68 (m, 1 H), 2.53 (s, 3 H), 1.91 (d, J = 9.2 Hz, 1 H), 1.43-1.35 (m, 1 H), 0.84-0.77 (m, 1 H), 0.71-0.65 (m, 1 H), 0.65-0.58 (m, 1 H), 0.39-0.32 (m, 1 H); LCMS (Method T4) RT 2.43 min; m/z calcd for $C_{26}H_{29}ClF_2N_7O_2^+$ [M + H]$^+$: 544.2034, Found: 544.2018. | Intermediate A10a: (S)-2-cyclopropyl-10-((2,5-dichloropyrimidin-4-yl)amino)-3,3-difluoro-7-methyl-1,2,3,4-tetrahydro-[1,4]oxazepino[2,3-c]quinolin-6(7H)-one |

| Example | Data and comments | Intermediate |
|---|---|---|
| Example 13i: (S)-2-cyclopropyl-3,3-difluoro-10-((5-fluoro-2-(4-methyl-3-oxopiperazin-1-yl)pyrimidin-4-yl)amino)-7-methyl-1,2,3,4-tetrahydro-[1,4]oxazepino[2,3-c]quinolin-6(7H)-one 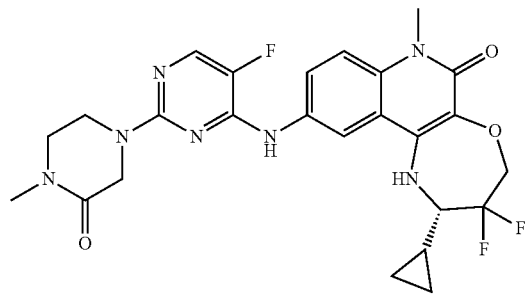 [SMILES: CN1CCN(c2ncc(F)c(Nc3ccc4c(c3)c3c(c(=O)n4C)OCC(F)(F)[C@H](C4CC4)N3)n2)CC1=O] | $^1$H NMR (600 MHz, methanol-$d_4$) δ 8.01 (d, J = 2.1 Hz, 1 H), 7.98 (dd, J = 9.1, 2.1 Hz, 1 H), 7.92 (d, J = 3.6 Hz, 1 H), 7.57 (d, J = 9.1 Hz, 1 H), 4.53-4.38 (m, 2 H), 4.25 (d, J = 18.1 Hz, 1 H), 4.19 (d, J = 18.1 Hz, 1 H), 3.98-3.93 (m, 1 H), 3.93-3.87 (m, 1 H), 3.72 (s, 3 H), 3.45 (app. t, J = 5.4 Hz, 2 H), 3.36-3.28 (m, 1 H), 2.98 (s, 3 H), 1.45-1.37 (m, 1 H), 0.81-0.76 (m, 1 H) 0.67-0.57 (m, 2 H), 0.38-0.32 (m, 1 H); LCMS (Method T4) RT 2.64 min; m/z calcd for $C_{25}H_{27}F_3N_7O_3^+$ [M + H]$^+$: 530.2122, Found: 530.2107. | Intermediate A10e: (S)-10-((2-chloro-5-fluoropyrimidin-4-yl)amino)-2-cyclopropyl-3,3-difluoro-7-methyl-1,2,3,4-tetrahydro-[1,4]oxazepino[2,3-c]quinolin-6(7H)-one |
| Example 13j: (S)-10-((2-(3-oxa-8-azabicyclo[3.2.1]octan-8-yl)-5-fluoropyrimidin-4-yl)amino)-2-cyclopropyl-3,3-difluoro-7-methyl-1,2,3,4-tetrahydro-[1,4]oxazepino[2,3-c]quinolin-6(7H)-one 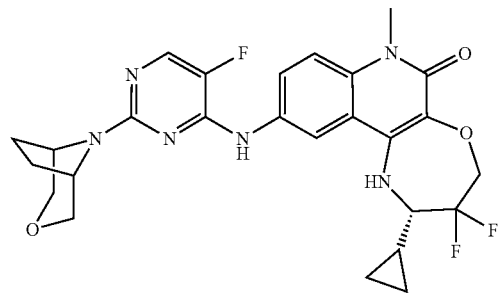 | $^1$H NMR (600 MHz, MeOD-$d_4$) δ 8.02 (d, J = 2.2 Hz, 1 H), 7.98 (dd, J = 9.1, 2.2 Hz, 1 H), 7.89 (d, J = 3.8 Hz, 1 H), 7.54 (d, J = 9.1 Hz, 1 H), 4.53-4.37 (m, 4 H), 3.75 (app.d, J = 10.8 Hz, 2 H), 3.71 (s, 3 H), 3.59-3.55 (m, 2H), 3.34-3.27 (m, 1 H), 2.04-1.98 (m, 2 H), 1.97-1.90 (m, 2 H), 1.42-1.36 (m, 1 H), 0.83-0.76 (m, 1 H), 0.69-0.58 (m, 2 H), 0.39-0.33 (m, 1 H); LCMS (Method T4) RT 2.58 min; m/z calcd for $C_{26}H_{28}F_3N_6O_3^+$ [M + H]$^+$: 529.2169, Found: 529.2151. | Intermediate A10e: (S)-10-((2-chloro-5-fluoropyrimidin-4-yl)amino)-2-cyclopropyl-3,3-difluoro-7-methyl-1,2,3,4-tetrahydro-[1,4]oxazepino[2,3-c]quinolin-6(7H)-one |

Example 14a: (R)-10-((5-chloro-2-((S)-4,4-difluoro-3-methylpiperidin-1-yl)pyrimidin-4-yl)amino)-2-cyclopropyl-7-methyl-1,2,3,4-tetrahydro-[1,4]oxazepino[2,3-c]quinolin-6(7H)-one or (R)-10-((5-chloro-2-((R)-4,4-difluoro-3-methylpiperidin-1-yl)pyrimidin-4-yl)amino)-2-cyclopropyl-7-methyl-1,2,3,4-tetrahydro-[1,4]oxazepino[2,3-c]quinolin-6(7H)-one

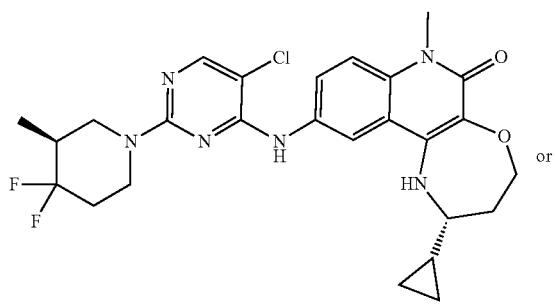

or

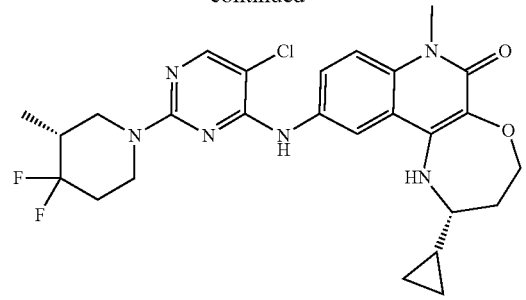

A vial containing (S)-4,5-dichloro-2-(4,4-difluoro-3-methylpiperidin-1-yl)pyrimidine or (R)-4,5-dichloro-2-(4,4-difluoro-3-methylpiperidin-1-yl)pyrimidine (Intermediate L2a; 10 mg, 0.035 mmol), DIPEA (20 uL, 0.089 mmol), and (R)-10-amino-2-cyclopropyl-7-methyl-1,2,3,4-tetrahydro-

[1,4]oxazepino[2,3-c]quinolin-6(7H)-one (Intermediate A1d; 10 mg, 0.035 mmol) in NMP (0.56 mL) was heated at 140° C. under microwave irradiation for 3 h. The reaction mixture was directly purified by reverse-phase chromatography (Biotage reverse-phase 12 g Ultra C-18 column; 45-100% MeOH in $H_2O$ (containing 0.1% formic acid)). To the resulting mixture was added (R)-10-amino-2-cyclopropyl-7-methyl-1,2,3,4-tetrahydro-[1,4]oxazepino[2,3-c]quinolin-6(7H)-one (Intermediate A1d; 10 mg, 0.035 mmol), NMP (0.56 mL) and 3 M aq HCl (0.1 mL) and the reaction was heated in a heating block at 80° C. for 22 h. The reaction mixture was directly purified by reverse-phase chromatography (Biotage reverse-phase 12 g Ultra C-18 column; 45-100% MeOH in $H_2O$ (containing 0.1% formic acid)) affording the title compound (4 mg, 21%) as a grey solid. $^1$H NMR (600 MHz, methanol-$d_4$) δ 8.34 (s, 1H), 8.18 (s, 1H), 7.91 (dd, J=9.2, 2.0 Hz, 1H), 7.84 (dd, J=9.2, 2.0 Hz, 1H), 4.52-4.44 (m, 1H), 4.41-4.34 (m, 1H), 4.20 (d, J=13.9 Hz, 1H), 4.10 (d, J=13.0 Hz, 1H), 3.89 (d, J=1.5 Hz, 3H), 3.47-3.39 (m, 1H), 3.20-3.13 (m, 2H), 2.48-2.40 (m, 1H), 2.29-2.14 (m, 3H), 2.13-2.01 (m, 1H), 1.37-1.29 (m, 1H), 1.04 (d, J=6.7 Hz, 3H), 0.73-0.64 (m, 2H), 0.51-0.45 (m, 1H), 0.40-0.34 (m, 1H); LCMS (Method X4) RT 3.47 min; m/z calcd for $C_{26}H_{30}ClF_2N_6O_2^+$ [M+H]$^+$: 531.2087, Found: 531.2091.

The following tabulated examples were prepared by a method analogous to that used for the preparation of Example 14a, starting from the intermediate(s) shown in the table.

| Example | Data and comments | Intermediate |
| --- | --- | --- |
| Example 14b: (R)-10-((5-chloro-2-((R)-4,4-difluoro-3-methylpiperidin-1-yl)pyrimidin-4-yl)amino)-2-cyclopropyl-7-methyl-1,2,3,4-tetrahydro-[1,4]oxazepino[2,3-c]quinolin-6(7H)-one or (R)-10-((5-chloro-2-((S)-4,4-difluoro-3-methylpiperidin-1-yl)pyrimidin-4-yl)amino)-2-cyclopropyl-7-methyl-1,2,3,4-tetrahydro-[1,4]oxazepino[2,3-c]quinolin-6(7H)-one | $^1$H NMR (600 MHz, methanol-$d_4$) δ 8.10 (d, J = 6.1 Hz, 1 H), 8.06 (d, J = 2.3 Hz, 1H), 7.83 (d, J = 9.0, 2.3 Hz, 1 H), 7.60 (d, J = 9.2 Hz, 1 H), 4.45-4.38 (m, 1 H), 4.31-4.21 (m, 2 H), 4.17 (d, J = 13.9 Hz, 1 H), 3.74 (s, 3 H), 3.38 (td, J = 12.8, 11.5, 3.1 Hz, 1 H), 3.08 (dd, J = 13.7, 10.6 Hz, 1 H), 2.98 (td, J = 9.4, 3.3 Hz, 1 H), 2.40-2.31 (m, 1 H), 2.19-2.08 (m, 3 H), 2.03-1.90 (m, 1 H), 1.28-1.20 (m, 1 H), 1.02 (d, J = 6.8 Hz, 3 H), 0.66 (d, J = 7.9 Hz, 2 H), 0.44-0.39 (m, 1 H), 0.37-0.32 (m, 1 H); LCMS (Method X4) RT 3.47 min; m/z calcd for $C_{26}H_{30}ClF_2N_6O_2^+$ [M + H]$^+$: 531.2087, Found: 531.2084. | Intermediate A1d: (R)-10-amino-2-cyclopropyl-7-methyl-1,2,3,4-tetrahydro-[1,4]oxazepino[2,3-c]quinolin-6(7H)-one and Intermediate L2b: (R)-4,5-dichloro-2-(4,4-difluoro-3-methylpiperidin-1-yl)pyrimidine or (S)-4,5-dichloro-2-(4,4-difluoro-3-methylpiperidin-1-yl)pyrimidine |

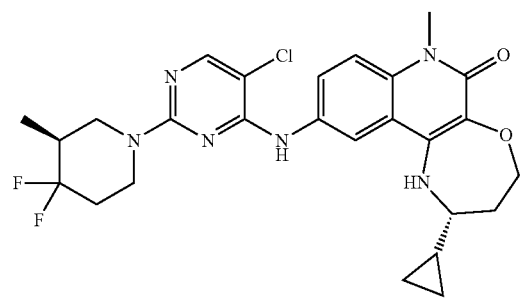 [SMILES: C[C@H]1CN(c2ncc(Cl)c(Nc3ccc4c(c3)c3c(c(=O)n4C)OCC[C@H](C4CC4)N3)n2)CCC1(F)F]

or

Example 15a: (R)-10-((5-chloro-2-((1R,5S,7S)-7-hydroxy-3-oxa-9-azabicyclo[3.3.1]-nonan-9-yl)pyrimidin-4-yl)amino)-2-cyclopropyl-7-methyl-1,2,3,4-tetrahydro-[1,4]thiazepino[2,3-c]quinolin-6(7H)-one

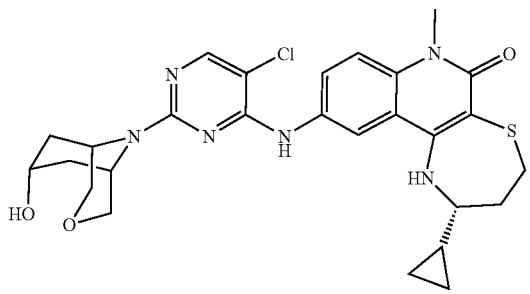 [SMILES: Cn1c(=O)c2c(c3cc(Nc4nc(N5C6COCC5CC(O)C6)ncc4Cl)ccc31)N[C@@H](C1CC1)CCS2]

To a solution of (R)—N-(2-cyclopropyl-7-methyl-6-oxo-1,2,3,4,6,7-hexahydro-[1,4]thiazepino[2,3-c]quinolin-10-yl)formamide (Intermediate A8c; 5 mg, 0.015 mmol) in THF (0.30 mL) was added sodium hydride (60% dispersion in mineral oil; 10 mg, 0.25 mmol). The mixture was stirred for 15 min then cooled to 0° C. and (1R,5S,7s)-9-(5-chloro-4-(methylsulfonyl)pyrimidin-2-yl)-3-oxa-9-azabicyclo[3.3.1]-nonan-7-ol (Intermediate J2; 15 mg, 0.045 mmol) was added. The mixture was stirred at 0° C. for 1 h. Further THF (0.3 mL) and sodium hydride (60% dispersion in mineral oil; 10 mg, 0.25 mmol) was added and the mixture was warmed to rt and stirred overnight. The mixture was then heated in a sealed vial to 60° C. for 3 h. The reaction mixture was cooled to rt, water was added with care to the mixture which was then concentrated to remove the THF. The residue was diluted with DMSO (1.2 mL) and directly purified by reverse-phase chromatography (Biotage reverse-phase 12 g Ultra C-18 column; 10-100% MeOH in H$_2$O (containing 0.1% formic acid)). The product-containing fractions were combined, passed through an SCX-2 (2 g), and the product was eluted with 2 N methanolic ammonia. The solvent was removed in vacuo affording the title compound (3 mg, 36%) as a pale yellow solid. $^1$H NMR (600 MHz, CDCl$_3$) δ 8.03 (s, 1H), 7.74-7.61 (m, 1H), 7.56 (s, 1H), 7.30 (d, J=9.0 Hz, 1H), 7.06 (s, 1H), 5.67-5.53 (m, 1H), 4.74-4.65 (m, 1H), 4.54-4.46 (m, 1H), 4.33-4.29 (m, 1H), 3.98-3.89 (m, 4H), 3.83-3.78 (m, 2H), 3.75-3.69 (m, 1H), 3.69 (s, 3H), 2.95 (dd, J=14.6, 6.2 Hz, 1H), 2.27-2.15 (m, 3H), 2.06-1.98 (m, 1H), 1.92-1.83 (m, 2H), 1.03-0.94 (m, 1H), 0.75-0.66 (m, 1H), 0.62-0.54 (m, 1H), 0.44-0.37 (m, 1H), 0.31-0.22 (m, 1H). LCMS (Method T4) RT 2.93 min; m/z calcd for C$_{27}$H$_{32}$ClN$_6$O$_3$S$^+$ [M+H]$^+$: 555.1940, Found: 555.1931.

The following tabulated examples were prepared by a method analogous to that used for the preparation of Example 15a, starting from the intermediate(s) shown in the table and appropriate substituted pyrimidine. For Example 15b and Example 15c, the reactions were stirred at 60° C. immediately after the addition of the sulfone. Additionally, due to hydrolysis of the sulfone starting material under the reaction conditions, additional equivalents of sulfone were added sequentially to achieve higher conversions to the desired products.

| Example | Data and comments | Intermediate |
| --- | --- | --- |
| Example 15b: (R)-10-((5-chloro-2-((R)-4,4-difluoro-3-(hydroxymethyl)piperidin-1-yl)pyrimidin-4-yl)amino)-2-cyclopropyl-7-methyl-1,2,3,4-tetrahydro-[1,4]oxazepino[2,3-c]quinolin-6(7H)-one or (R)-10-((5-chloro-2-((S)-4,4-difluoro-3-(hydroxymethyl)piperidin-1-yl)pyrimidin-4-yl)amino)-2-cyclopropyl-7-methyl-1,2,3,4-tetrahydro-[1,4]oxazepino[2,3-c]quinolin-6(7H)-one | $^1$H NMR (600 MHz, methanol-d$_4$) δ 8.03 (dd, J = 9.1, 2.2 Hz, 1 H), 7.99 (s, 1 H), 7.95 (d, J = 2.2 Hz, 1 H), 7.52 (d, J = 9.1 Hz, 1 H), 4.59-4.53 (m, 1 H), 4.42-4.36 (m, 1 H), 4.34-4.29 (m, 1 H), 4.22-4.16 (m, 1 H), 3.90 (dd, J = 11.2, 4.0 Hz, 1 H), 3.71 (s, 3 H), 3.52-3.47 (m, 1 H), 3.42-3.36 (m, 1 H), 3.24 (dd, J = 13.5, 10.0 Hz, 1 H), 2.95 (dt, J = 9.6, 3.6 Hz, 1 H), 2.37-2.30 (m, 1 H), 2.16-2.06 (m, 2 H), 2.05-1.96 (m, 1 H), 1.95-1.84 (m, 1 H), 1.26-1.18 (m, 1 H), 0.69-0.61 (m, 2 H), 0.44-0.38 (m, 1 H), 0.37-0.31 (m, 1 H); LCMS (Method X4) RT 3.08 min; m/z calcd for C$_{26}$H$_{30}$ClF$_2$N$_6$O$_3$$^+$ [M + H]$^+$: 547.2036, Found: 547.2029. | Intermediate A11a: (R)-N-(2-cyclopropyl-7-methyl-6-oxo-1,2,3,4,6,7-hexahydro-[1,4]oxazepino[2,3-c]quinolin-10-yl)formamide and Intermediate K2b: (R)-(1-(5-chloro-4-(methylsulfonyl)pyrimidin-2-yl)-4,4-difluoropiperidin-3-yl)methanol or (S)-(1-(5-chloro-4-(methylsulfonyl)pyrimidin-2-yl)-4,4-difluoropiperidin-3-yl)methanol | or

| Example | Data and comments | Intermediate |
|---|---|---|
| Example 15c: (R)-10-((5-chloro-2-((S)-4,4-difluoro-3-(hydroxymethyl)piperidin-1-yl)pyrimidin-4-yl)amino)-2-cyclopropyl-7-methyl-1,2,3,4-tetrahydro-[1,4]oxazepino[2,3-c]quinolin-6(7H)-one or (R)-10-((5-chloro-2-((R)-4,4-difluoro-3-(hydroxymethyl)piperidin-1-yl)pyrimidin-4-yl)amino)-2-cyclopropyl-7-methyl-1,2,3,4-tetrahydro-[1,4]oxazepino[2,3-c]quinolin-6(7H)-one | $^1$H NMR (600 MHz, methanol-$d_4$) δ 8.04 (dd, J = 9.1, 2.2 Hz, 1 H), 7.99 (s, 1 H), 7.95 (d, J = 2.2 Hz, 1 H), 7.52 (d, J = 9.1 Hz, 1 H), 4.55-4.49 (m, 1 H), 4.42-4.37 (m, 1 H), 4.32-4.26 (m, 1 H), 4.21-4.16 (m, 1 H), 3.89 (dd, J = 11.2, 4.0 Hz, 1 H), 3.71 (s, 3 H), 3.51-3.47 (m, 1 H), 3.45-3.40 (m, 1 H), 3.29-3.25 (m, 1 H), 2.94 (dt, J = 9.4, 3.6 Hz, 1 H), 2.37-2.29 (m, 1 H), 2.16-2.08 (m, 2 H), 2.05-1.96 (m, 1 H), 1.95-1.84 (m, 1 H), 1.26-1.19 (m, 1 H), 0.69-0.61 (m, 2 H), 0.45-0.39 (m, 1 H), 0.36-0.30 (m, 1 H); LCMS (Method X4) RT 3.08 min; m/z calcd for $C_{26}H_{30}ClF_2N_6O_3^+$ [M + H]$^+$: 547.2036, Found: 547.2042. | Intermediate A11a: (R)-N-(2-cyclopropyl-7-methyl-6-oxo-1,2,3,4,6,7-hexahydro-[1,4]oxazepino[2,3-c]quinolin-10-yl)formamide and Intermediate K2a: (S)-(1-(5-chloro-4-(methylsulfonyl)pyrimidin-2-yl)-4,4-difluoropiperidin-3-yl)methanol or (R)-(1-(5-chloro-4-(methylsulfonyl)pyrimidin-2-yl)-4,4-difluoropiperidin-3-yl)methanol | or

Example 16a: (R)-10-((5-chloro-2-((3S,5R)-4,4-difluoro-3,5-dimethylpiperidin-1-yl)pyrimidin-4-yl)amino)-2-cyclopropyl-7-(2-hydroxyethyl)-1,2,3,4-tetrahydro-[1,4]oxazepino[2,3-c]quinolin-6(7H)-one

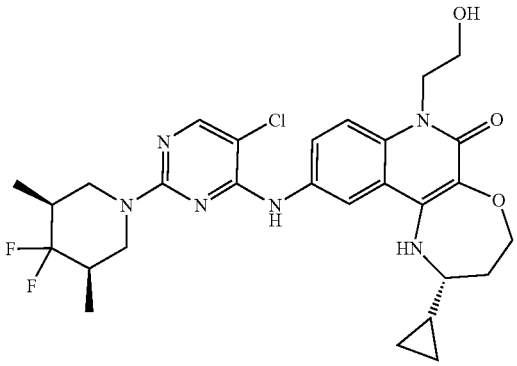 [SMILES: C[C@@H]1CN(c2ncc(Cl)c(Nc3ccc4c(c3)c3c(c(=O)n4CCO)OCC[C@H](C4CC4)N3)n2)C[C@H](C)C1(F)F]

Sodium borohydride (1.4 mg, 0.037 mmol) was added to a stirred solution of 2-((R)-10-((5-chloro-2-((3S,5R)-4,4-difluoro-3,5-dimethylpiperidin-1-yl)pyrimidin-4-yl)amino)-2-cyclopropyl-6-oxo-1,3,4,6-tetrahydro-[1,4]oxazepino[2,3-c]quinolin-7(2H)-yl)acetaldehyde (Intermediate A12a; 5.4 mg, 0.009 mmol) in anhydrous methanol (0.5 mL) at 0° C. under Ar. The reaction mixture was stirred at 0° C. for 2 h. The reaction mixture was quenched with saturated aq. NaHCO$_3$ (0.1 mL) and stirred for 15 min. DMSO (0.5 mL) was added and the reaction mixture was concentrated in vacuo to remove the MeOH. The crude reaction mixture in DMSO (additional 0.6 mL of DMSO used to wash out vial) was directly purified by reverse-phase chromatography (Biotage reverse-phase 12 g C-18 column; 10-30-100% MeOH in H$_2$O (containing 0.1% formic acid)), affording the title compound (4 mg, 76%) as an off-white solid. $^1$H NMR (600 MHz, methanol-d$_4$) δ 8.01 (d, J=2.2 Hz, 1H), 7.98 (s, 1H), 7.82 (dd, J=9.1, 2.2 Hz, 1H), 7.64 (d, J=9.1 Hz, 1H), 4.58-4.49 (m, 2H), 4.46 (t, J=6.3 Hz, 2H), 4.42-4.37 (m, 1H), 4.24-4.18 (m, 1H), 3.85 (t, J=6.3 Hz, 2H), 2.95 (dt, J=9.5, 3.5 Hz, 1H), 2.74-2.65 (m, 2H), 2.37-2.30 (m, 1H), 2.14-2.06 (m, 1H), 2.01-1.88 (m, 2H), 1.25-1.19 (m, 1H), 1.00 (d, J=6.7 Hz, 6H), 0.68-0.60 (m, 2H), 0.43-0.37 (m, 1H), 0.35-0.29 (m, 1H); LCMS (Method X4) RT 3.46 min; m/z calcd for C$_{28}$H$_{34}$ClF$_2$N$_6$O$_3$$^+$ [M+H]$^+$: 575.2349, Found: 575.2351.

Example 17a: (R)-10-((5-chloro-2-((3S,5R)-4,4-difluoro-3,5-dimethylpiperidin-1-yl)pyrimidin-4-yl)amino)-2-cyclopropyl-7-(2-(methylamino)ethyl)-1,2,3,4-tetrahydro-[1,4]oxazepino[2,3-c]quinolin-6(7H)-one

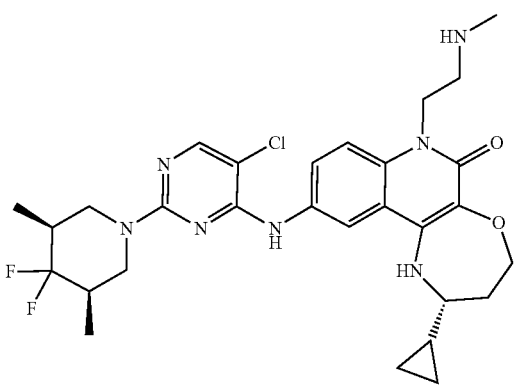 [SMILES: CNCCn1c(=O)c2c(c3cc(Nc4nc(N5C[C@@H](C)C(F)(F)[C@@H](C)C5)ncc4Cl)ccc31)N[C@@H](C1CC1)CCO2]

Methylamine (2 M in THF; 0.20 mL, 0.400 mmol) was added to a stirred solution of 2-((R)-10-((5-chloro-2-((3S,5R)-4,4-difluoro-3,5-dimethylpiperidin-1-yl)pyrimidin-4-yl)amino)-2-cyclopropyl-6-oxo-1,3,4,6-tetrahydro-[1,4]oxazepino[2,3-c]quinolin-7(2H)-yl)acetaldehyde (Intermediate A12a; 6.5 mg, 0.011 mmol) in THF (0.2 mL) under Ar. The reaction mixture was stirred at rt for 5 min. Sodium triacetoxyborohydride (6.0 mg, 0.028 mmol) was added and the reaction mixture was stirred at 25° C. for 3 d. After this time, DCE (0.5 mL) was added as well as additional methyamine (2 M in THF; 1.5 mL) and sodium triacetoxyborohydride (22 mg, 0.1 mmol). The reaction mixture was stirred at 25° C. for an additional 18 h. After this time additional methylamine (2 M in THF; 0.5 mL) added followed by sodium acetate (12 mg) and sodium triacetoxyborohydride (19 mg). The reaction mixture was stirred at 45° C. for 24 h. After this time, a few drops of water were added and the reaction mixture was concentrated in vacuo. The crude reaction mixture was re-dissolved in DMSO (0.8 mL) and directly purified by reverse-phase chromatography (Biotage reverse-phase 12 g C-18 column; 10-30-100% MeOH in H$_2$O (containing 0.1% formic acid)), affording a mixture of products. The product-containing fractions were combined, concentrated in vacuo and re-purified by flash chromatography (pipette column, 0%-5%-10%-25% MeOH in CH$_2$Cl$_2$) affording the title compound (1 mg, 13%) as an off white solid. $^1$H NMR (600 MHz, methanol-d$_4$) δ 8.11 (d, J=2.1 Hz, 1H), 8.00 (s, 1H), 7.86 (dd, J=9.2, 2.1 Hz, 1H), 7.53 (d, J=9.2 Hz, 1H), 4.63-4.59 (m, 2H), 4.56-4.51 (m, 2H), 4.44-4.38 (m, 1H), 4.27-4.22 (m, 1H), 3.29-3.25 (m, 2H), 2.99 (dt, J=9.4, 3.5 Hz, 1H), 2.73-2.66 (m, 5H), 2.39-2.32 (m, 1H), 2.16-2.09 (m, 1H), 2.00-1.91 (m, 2H), 1.27-1.22 (m, 1H), 1.01 (d, J=6.7 Hz, 6H), 0.69-0.61 (m, 2H), 0.42-0.37 (m, 1H), 0.36-0.31 (m, 1H); LCMS (Method T4) RT 2.85 min; m/z calcd for C$_{29}$H$_{37}$ClF$_2$N$_7$O$_2$$^+$ [M+H]$^+$: 588.2660, Found: 588.2671.

Example 18a: 2-chloro-4-((2,7-dimethyl-5,6-dioxo-2,3,4,5,6,7-hexahydro-1H-[1,4]diazepino[6,5-c]quinolin-10-yl)amino)nicotinonitrile

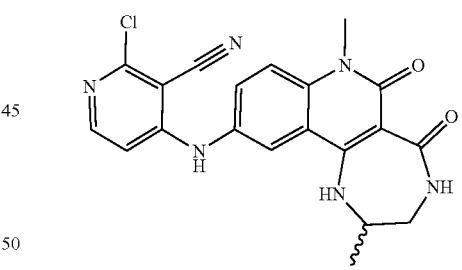

To a solution of ethyl 4-((1-((tert-butoxycarbonyl)amino)propan-2-yl)amino)-6-((2-chloro-3-cyanopyridin-4-yl)amino)-1-methyl-2-oxo-1,2-dihydroquinoline-3-carboxylate (Intermediate B3a; 62 mg, 0.11 mmol) in THF (2 mL) was added 4 M HCl in dioxane (279 uL, 1.12 mmol) and the reaction mixture was heated to 70° C. for 15 min. Further 4 M HCl in dioxane (279 uL, 1.12 mmol) was added and heating was continued for 90 min. The acidic reaction mixture was quenched with triethylamine (389 uL, 2.79 mmol) and heated at 70° C. overnight. The reaction mixture was cooled to rt and diluted with water. The organic solvents were removed in vacuo and the reaction mixture was purified by reverse-phase chromatography (Biotage reverse-phase 12 g C-18 column; 5-50% MeOH in H$_2$O (containing 0.1% formic acid)) affording the title compound (9 mg, 18%) as an off-white solid. ¹H NMR (500 MHz, methanol-d₄) δ 8.03-8.01 (m, 1H), 8.00 (d, J=6.2 Hz, 1H), 7.62-7.61 (m, 2H), 6.71 (d, J=6.2 Hz, 1H), 3.97-3.93 (m, 1H), 3.67 (s, 3H), 3.58 (dd, J=13.4, 1.7 Hz, 1H), 3.39-3.27 (m, 1H), 1.32 (d, J=6.5 Hz, 3H); LCMS (Method X4) RT 2.01 min; m/z calcd for C₂₀H₁₈ClN₆O₂⁺ [M+H]⁺: 409.1180, Found: 409.1088.

Intermediate Compounds

Intermediate A1a: (S)-10-amino-2,7-dimethyl-1,2,3,4-tetrahydro-[1,4]oxazepino[2,3-c]quinolin-6(7H)-one

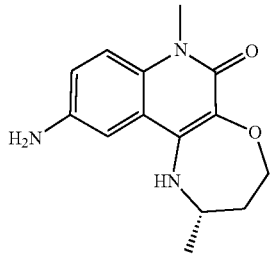 [SMILES: C[C@H]1CCOc2c(c3cc(N)ccc3n(C)c2=O)N1]

Step 1; (S)-4-((4-hydroxybutan-2-yl)amino)-1-methyl-6-nitroquinolin-2(1H)-one

An oven-dried microwave vial (10-20 mL volume) was charged with 4-chloro-1-methyl-6-nitroquinolin-2(1H)-one (Intermediate F1; 800 mg, 3.4 mmol) and (S)-3-aminobutan-1-ol (446 mg, 5.0 mmol). The reaction vial was flushed with Ar, sealed with a cap and then further flushed with Ar. Anhydrous NMP (10 mL) was added followed by DIPEA (1.2 mL, 6.9 mmol). The reaction mixture was heated at 160° C. in a heating block for 20 h. The reaction mixture was allowed to cool to rt. The reaction mixture was diluted with water (100 mL), and the aqueous mixture was extracted with EtOAc (100 mL). The organic extract was washed with water (2×25 mL). The aqueous washings were combined and further extracted with EtOAc (3×50 mL). The organic extracts were combined, dried (Na₂SO₄) and concentrated in vacuo. The crude reaction mixture was dry-loaded onto silica and purified by flash chromatography (50 g KP-sil; 0% to 10% MeOH in CH₂Cl₂) affording (S)-4-((4-hydroxybutan-2-yl)amino)-1-methyl-6-nitroquinolin-2(1H)-one (547 mg, 56%) as a yellow solid. ¹H NMR (500 MHz, DMSO-d₆) δ 9.11 (d, J=2.5 Hz, 1H), 8.37 (dd, J=9.4, 2.5 Hz, 1H), 7.60 (d, J=9.4 Hz, 1H), 7.11 (d, J=7.9 Hz, 1H), 5.59 (s, 1H), 4.57 (t, J=5.0 Hz, 1H), 3.80-3.71 (m, 1H), 3.55 (s, 3H), 3.53-3.48 (m, 2H), 1.94-1.87 (m, 1H), 1.67-1.60 (m, 1H), 1.23 (d, J=6.4 Hz, 3H).

Step 2; (S)-3-bromo-4-((4-hydroxybutan-2-yl)amino)-1-methyl-6-nitroquinolin-2(1H)-one Trifluoroacetic acid (0.72 mL, 9.4 mmol) was added to a stirred mixture of N-bromosuccinimide (509 mg, 2.9 mmol) and (S)-4-((4-hydroxybutan-2-yl)amino)-1-methyl-6-nitroquinolin-2(1H)-one (from step 1; 547 mg, 1.9 mmol) in anhydrous CH₂Cl₂ (10 mL) at 0° C. under Ar. The reaction mixture was stirred at 0° C. for 10 min then at rt for 30 min. The reaction mixture was diluted with EtOAc (100 mL) and washed with water (30 mL) followed by saturated aq. NaHCO₃ (3×30 mL). The aqueous washings were combined and further extracted with EtOAc (30 mL). The organic extracts were combined, dried (Na₂SO₄) and concentrated in vacuo. The crude reaction mixture was dry-loaded onto silica and purified by flash chromatography (25 g KP-sil; 0% to 10% MeOH in CH₂Cl₂) affording (S)-3-bromo-4-((4-hydroxybutan-2-yl)amino)-1-methyl-6-nitroquinolin-2(1H)-one (532 mg, 77%) as a yellow solid. ¹H NMR (500 MHz, DMSO-d₆) δ 8.89 (d, J=2.6 Hz, 1H), 8.42 (dd, J=9.4, 2.6 Hz, 1H), 7.72 (d, J=9.4 Hz, 1H), 5.82 (d, J=9.8 Hz, 1H), 4.51 (t, J=4.7 Hz, 1H), 4.28-4.19 (m, 1H), 3.69 (s, 3H), 3.51-3.46 (m, 2H), 1.90-1.82 (m, 1H), 1.79-1.71 (m, 1H), 1.29 (d, J=6.5 Hz, 3H).

Step 3; (S)-2,7-dimethyl-10-nitro-1,2,3,4-tetrahydro-[1,4]oxazepino[2,3-c]quinolin-6(7H)-one An oven-dried microwave vial (2.0-5.0 mL volume) was charged with (S)-3-bromo-4-((4-hydroxybutan-2-yl)amino)-1-methyl-6-nitroquinolin-2(1H)-one (from step 2; 111 mg, 0.30 mmol). The reaction vial was flushed with Ar, sealed with a cap and then further flushed with Ar. Anhydrous DMSO (4 mL) was added followed by potassium tert-butoxide (1 M in THF; 0.54 mL, 0.54 mmol). The reaction mixture was heated at 60° C. under microwave irradiation for 50 min. The reaction mixture was allowed to cool to rt. Water (10 mL) was added followed by EtOAc (10 mL). The layers were separated and the aqueous layer was further extracted with EtOAc (10 mL). The organic extracts were combined and concentrated in vacuo. The crude product was dissolved in DMSO (1.2 mL) and directly purified by reverse-phase chromatography (Biotage reverse-phase 12 g C-18 column; 45-75% MeOH in H₂O (containing 0.1% formic acid)), affording (S)-2,7-dimethyl-10-nitro-1,2,3,4-tetrahydro-[1,4]oxazepino[2,3-c]quinolin-6(7H)-one (36 mg, 41%) as a dark yellow solid. ¹H NMR (600 MHz, CDCl₃) δ 8.93 (d, J=2.1 Hz, 1H), 8.33 (dd, J=9.2, 2.1 Hz, 1H), 7.40 (d, J=9.2 Hz, 1H), 4.49-4.38 (m, 2H), 4.14-4.08 (m, 1H), 4.01 (brs, 1H), 3.76 (s, 3H), 2.23-2.26 (m, 1H), 1.91-1.84 (m, 1H), 1.47 (d, J=6.3 Hz, 3H).

Step 4; (S)-10-amino-2,7-dimethyl-1,2,3,4-tetrahydro-[1,4]oxazepino[2,3-c]quinolin-6(7H)-one A microwave vial (0.5-2.0 mL volume) was charged with (S)-2,7-dimethyl-10-nitro-1,2,3,4-tetrahydro-[1,4]oxazepino[2,3-c]quinolin-6(7H)-one (from step 3; 356 mg, 0.12 mmol), Pd/C (10 wt %, 6.3 mg) and ammonium formate (53 mg, 0.85 mmol). The reaction vial was flushed with Ar, sealed with a cap and then further flushed with Ar. Anhydrous methanol (1.2 mL) was added. The reaction mixture was stirred at 80° C. for 20 min. The reaction mixture was cooled to rt, the cap removed and additional ammonium formate (33 mg, 0.52 mmol) and Pd/C (10 wt %, 2.6 mg) were added. The reaction vial was re-sealed and heated at 80° C. for a further 10 min. The reaction mixture was allowed to cool to rt, filtered through Celite™, and the solids washed with MeOH (40 mL). The filtrate was concentrated in vacuo, re-dissolved in MeOH and passed through an SCX-2 (2 g) column, eluting with MeOH (40 mL) followed by 2 N methanolic ammonia (40 mL). The methanolic ammonia fraction was concentrated in vacuo affording the title compound (22 mg, 67%) as a dark yellow solid which was used without further purification. LCMS (Method T2) RT 0.41 min; m/z 260.1382 [M+H]⁺.

The following tabulated examples were prepared by a method analogous to that used for the preparation of Intermediate A1a, starting from the amino-alcohols shown in the table. An alternative procedure for Step 1 was conducted for the preparation of Intermediate A1I. Details of this procedure are described below for the preparation of Intermediate A1d.

| Intermediate | Data and comments | Amino-alcohol/intermediate |
|---|---|---|
| Intermediate A1b: (R)-10-amino-2,7-dimethyl-1,2,3,4-tetrahydro-[1,4]oxazepino[2,3-c]quinolin-6(7H)-one | LCMS (Method T2) RT 0.41 min; m/z 260.1362 [M + H]$^+$. | (R)-3-aminobutan-1-ol |

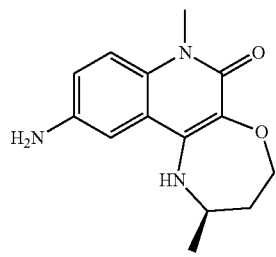 [SMILES: C[C@@H]1CCOc2c(c3cc(N)ccc3n(C)c2=O)N1]

| Intermediate A1c: 10-amino-2-ethyl-7-methyl-1,2,3,4-tetrahydro-[1,4]oxazepino[2,3-c]quinolin-6(7H)-one | LCMS (Method T2) RT 0.84 min; m/z 274.2 [M + H]$^+$. | 3-aminopentan-1-ol |

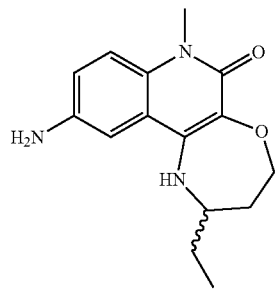 [SMILES: CCC1CCOc2c(c3cc(N)ccc3n(C)c2=O)N1]

| Intermediate A1d: (R)-10-amino-2-cyclopropyl-7-methyl-1,2,3,4-tetrahydro-[1,4]oxazepino[2,3-c]quinolin-6(7H)-one | LCMS (Method T2) RT 0.92 min; m/z 286.1516 [M + H]$^+$. | Intermediate D1a: (R)-3-amino-3-cyclopropylpropan-1-ol |

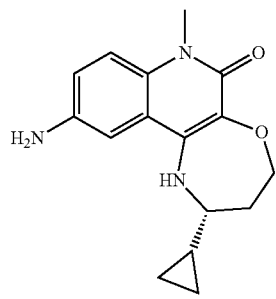 [SMILES: Cn1c(=O)c2c(c3cc(N)ccc31)N[C@@H](C1CC1)CCO2]

| Intermediate A1e: (S)-10-amino-2-cyclopropyl-7-methyl-1,2,3,4-tetrahydro-[1,4]oxazepino[2,3-c]quinolin-6(7H)-one | LCMS (Method T2) RT 0.92 min; m/z 286.1510 [M + H]$^+$. | Intermediate D1b: (S)-3-amino-3-cyclopropylpropan-1-ol |

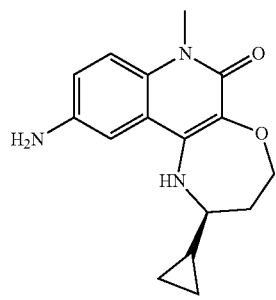 [SMILES: Cn1c(=O)c2c(c3cc(N)ccc31)N[C@H](C1CC1)CCO2]

-continued

| Intermediate | Data and comments | Amino-alcohol/intermediate |
|---|---|---|
| Intermediate A1f: 10-amino-2,3,3,7-tetramethyl-1,2,3,4-tetrahydro-[1,4]oxazepino[2,3-c]quinolin-6(7H)-one | LCMS (Method T2) RT 0.96 min; m/z 288.1674 [M + H]+. | 3-amino-2,2-dimethylbutan-1-ol |

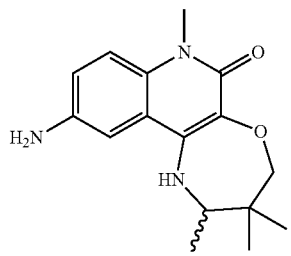 [SMILES: CC1Nc2c(c(=O)n(C)c3ccc(N)cc23)OCC1(C)C]

| Intermediate A1g: 10'-amino-2',7'-dimethyl-1',2'-dihydro-4'H-spiro[cyclopropane-1,3'-[1,4]oxazepino[2,3-c]quinolin]-6'(7'H)-one | LCMS (Method T2) RT 0.74 min; m/z 286.1518 [M + H]+. | (1-(1-aminoethyl)cyclopropyl)methanol |

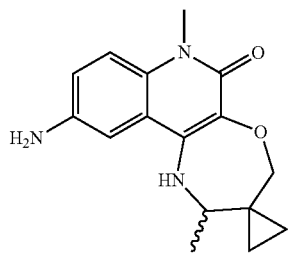 [SMILES: CC1Nc2c(c(=O)n(C)c3ccc(N)cc23)OCC12CC2]

| Intermediate A1h: (2S,4S)-10-amino-2,4,7-trimethyl-1,2,3,4-tetrahydro-[1,4]oxazepino[2,3-c]quinolin-6(7H)-one | LCMS (Method T2) RT 0.79 min; m/z 274.1519 [M + H]+. | Intermediate E1: (2S,4S)-4-aminopentan-2-ol |

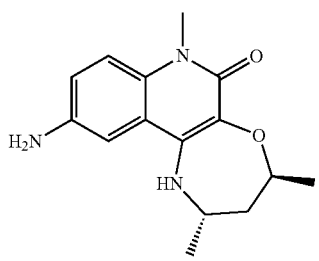 [SMILES: C[C@H]1C[C@H](C)Oc2c(c3cc(N)ccc3n(C)c2=O)N1]

| Intermediate A1i: 9-amino-2-ethyl-6-methyl-2,3-dihydro-1H-[1,4]oxazino[2,3-c]quinolin-5(6H)-one | LCMS (Method T2) RT 0.44 min; m/z 260.1362 [M + H]+. | 2-aminobutan-1-ol |

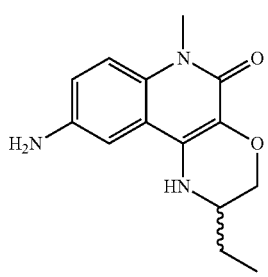 [SMILES: CCC1COc2c(c3cc(N)ccc3n(C)c2=O)N1]

-continued

| Intermediate | Data and comments | Amino-alcohol/intermediate |
|---|---|---|
| Intermediate A1j: 9-amino-2-cyclopropyl-6-methyl-2,3-dihydro-1H-[1,4]oxazino[2,3-c]quinolin-5(6H)-one | LCMS (Method T2) RT 0.57 min; m/z 272.1359 [M + H]$^+$. | 2-amino-2-cyclopropylethan-1-ol |

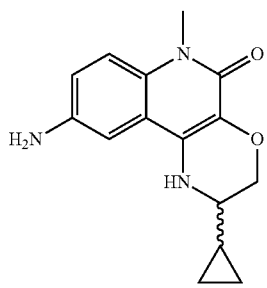 [SMILES: Cn1c(=O)c2c(c3cc(N)ccc31)NC(C1CC1)CO2]

| | | |
|---|---|---|
| Intermediate A1k: 9-amino-2-cyclobutyl-6-methyl-2,3-dihydro-1H-[1,4]oxazino[2,3-c]quinolin-5(6H)-one | LCMS (Method T2) RT 0.95 min; m/z 286.1514 [M + H]$^+$. | 2-amino-2-cyclobutylethan-1-ol |

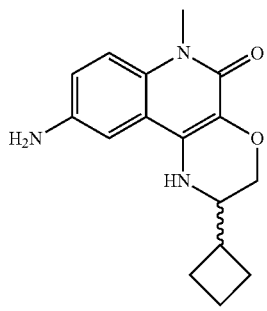 [SMILES: Cn1c(=O)c2c(c3cc(N)ccc31)NC(C1CCC1)CO2]

| | | |
|---|---|---|
| Intermediate A1l: 10-amino-2-cyclopropyl-3,3-difluoro-7-methyl-1,2,3,4-tetrahydro-[1,4]oxazepino[2,3-c]quinolin-6(7H)-one | LCMS (Method T2) RT 1.00 min; m/z 322.1454 [M + H]$^+$. | 3-amino-3-cyclopropyl-2,2-difluoropropan-1-ol |

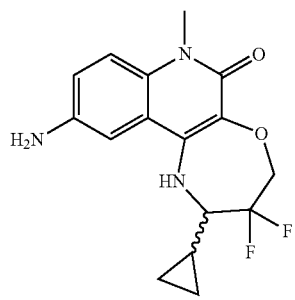 [SMILES: Cn1c(=O)c2c(c3cc(N)ccc31)NC(C1CC1)C(F)(F)CO2]

Intermediate A1m: (S)-10-amino-2-cyclopropyl-3,3-difluoro-7-methyl-1,2,3,4-tetrahydro-[1,4]oxazepino[2,3-c]quinolin-6(7H)-one

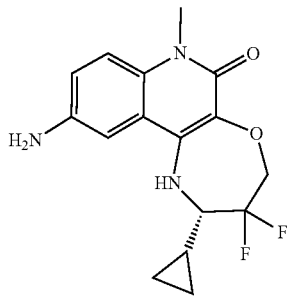 [SMILES: Cn1c(=O)c2c(c3cc(N)ccc31)N[C@@H](C1CC1)C(F)(F)CO2]

Step 1; (S)-4-((1-cyclopropyl-2,2-difluoro-3-hydroxypropyl)amino)-1-methyl-6-nitroquinolin-2(1H)-one An oven-dried microwave vial (10-20 mL volume) was charged with (S)-3-amino-3-cyclopropyl-2,2-difluoropropan-1-ol hydrochloride (1.02 g, 5.43 mmol) and ethyl 4-chloro-1-methyl-6-nitro-2-oxo-1,2-dihydroquinoline-3-carboxylate (Intermediate F2; 1.41 g, 4.52 mmol). The reaction vial was flushed with Ar and sealed with a cap. Anhydrous acetonitrile (15 mL) was added followed by DIPEA (2 mL, 11.48 mmol). The reaction mixture was heated at 160° C. under microwave irradiation for 12 h. The reaction mixture was transferred to a flask and 2 M sodium hydroxide (13.5 mL, 27 mmol) was added. A reflux condenser was attached and the reaction mixture was heated at 85° C. for 2 h. The reaction mixture was cooled to rt. Water (40 mL) was added and the reaction mixture was acidified to pH 5 with 3 M HCl. The resulting precipitate was filtered, washed with $H_2O$ (150 mL) and dried affording (S)-4-((1-cyclopropyl-2,2-difluoro-3-hydroxypropyl)amino)-1-methyl-6-nitroquinolin-2(1H)-one (1.41 g, 88%) as an off-white solid which was used without further purification. $^1$H NMR (500 MHz, DMSO-$d_6$) δ 9.31 (d, J=2.5 Hz, 1H), 8.40 (dd, J=9.4, 2.5 Hz, 1H), 7.62 (d, J=9.4 Hz, 1H), 7.48 (d, J=8.7 Hz, 1H), 5.72 (s, 1H), 5.60 (t, J=6.1 Hz, 1H), 3.90-3.71 (m, 2H), 3.57-3.45 (m, 4H), 1.38-1.29 (m, 1H), 0.71-0.64 (m, 1H), 0.63-0.56 (m, 1H), 0.53-0.46 (m, 1H), 0.27-0.20 (m, 1H); LCMS (Method X2) RT 1.15 min; m/z 354.1270 [M+H]$^+$.

Step 2; (S)-3-bromo-4-((1-cyclopropyl-2,2-difluoro-3-hydroxypropyl)amino)-1-methyl-6-nitroquinolin-2(1H)-one Trifluoroacetic acid (1.2 mL, 15.67 mmol) was added to a stirred mixture of (S)-4-((1-cyclopropyl-2,2-difluoro-3-hydroxypropyl)amino)-1-methyl-6-nitroquinolin-2(1H)-one (from step 1; 1.14 g, 3.21 mmol) and freshly recrystallised N-bromosuccinimide (572 mg, 3.21 mmol) in anhydrous $CH_2Cl_2$ (21 mL) at 0° C. under Ar. The reaction mixture was stirred at 0° C. for 15 min. The reaction mixture was diluted with $CH_2Cl_2$ (60 mL) and washed with saturated aq. $NaHCO_3$ (3×30 mL). The aqueous washings were further extracted with $CH_2Cl_2$ (60 mL). The organic extracts were combined, washed with brine (30 mL), dried ($Na_2SO_4$) and concentrated in vacuo affording (S)-3-bromo-4-((1-cyclopropyl-2,2-difluoro-3-hydroxypropyl)amino)-1-methyl-6-nitroquinolin-2(1H)-one (1.39 g, 100%) as a yellow solid which was used without further purification. $^1$H NMR (500 MHz, DMSO-$d_6$) δ 8.95 (d, J=2.5 Hz, 1H), 8.43 (dd, J=9.4, 2.5 Hz, 1H), 7.75 (d, J=9.4 Hz, 1H), 5.86 (d, J=11.1 Hz, 1H), 5.63 (t, J=5.9 Hz, 1H), 4.05-3.95 (m, 1H), 3.89-3.74 (m, 2H), 3.71 (s, 3H), 1.29-1.21 (m, 1H), 0.68-0.62 (m, 1H), 0.62-0.51 (m, 2H), 0.50-0.44 (m, 1H); LCMS (Method X2) RT 1.31 min; m/z 432.0369 [M+H]$^+$.

Step 3; (S)-2-cyclopropyl-3,3-difluoro-7-methyl-10-nitro-1,2,3,4-tetrahydro-[1,4]oxazepino-[2,3-c]quinolin-6(7H)-one Lithium tert-butoxide (1 M in THF; 5.14 mL, 5.14 mmol) was added to a suspension of (S)-3-bromo-4-((1-cyclopropyl-2,2-difluoro-3-hydroxypropyl)amino)-1-methyl-6-nitro-quinolin-2(1H)-one (from step 2; 1.39 g, 3.21 mmol) in THF (32 mL) under Ar. A reflux condenser and Ar balloon were fitted and the reaction mixture was heated at 60° C. for 15 min. The reaction mixture was cooled to rt. Water (40 mL) was added and the aqueous mixture was extracted with $CH_2Cl_2$ (3×40 mL). The organic extracts were combined, washed with brine (2×40 mL), dried ($Na_2SO_4$) and concentrated in vacuo affording (S)-2-cyclopropyl-3,3-difluoro-7-methyl-10-nitro-1,2,3,4-tetrahydro-[1,4]oxazepino[2,3-c]quinolin-6(7H)-one (1.08 g, 96%) as a yellow solid which was used without further purification. $^1$H NMR (500 MHz, DMSO-$d_6$) δ 9.12 (d, J=2.5 Hz, 1H), 8.35 (dd, J=9.4, 2.5 Hz, 1H), 7.66 (d, J=9.4 Hz, 1H), 7.01 (d, J=4.4 Hz, 1H), 4.54-4.37 (m, 2H), 3.62 (s, 3H, $NCH_3$), 3.29-3.22 (m, 1H), 1.39-1.31 (m, 1H), 0.76-0.69 (m, 1H), 0.58-0.49 (m, 2H), 0.37-0.30 (m, 1H); LCMS (Method X2) RT 1.29 min; m/z 352.1105 [M+H]$^+$.

Step 4; (S)-10-amino-2-cyclopropyl-3,3-difluoro-7-methyl-1,2,3,4-tetrahydro-[1,4]oxazepino[2,3-c]quinolin-6(7H)-one A 100 mL flask was charged with (S)-2-cyclopropyl-3,3-difluoro-7-methyl-10-nitro-1,2,3,4-tetrahydro-[1,4]oxazepino[2,3-c]quinolin-6(7H)-one (from step 3; 1.08 g, 3.09 mmol) and 10 wt % Pd/C (108 mg). The reaction vial was flushed with Ar, and ethanol (15 mL) was added. The reaction mixture was stirred at 60° C. under an atmosphere of $H_2$ for 1 h. The reaction mixture was allowed to cool to rt. The reaction mixture was filtered through celite, the solids washed with EtOH (60 mL). The filtrate was concentrated in vacuo affording the title compound (1.03 g, 100%) as an orange solid which was used without further purification. LCMS (Method X2) RT 0.89 min; m/z 322.1370 [M+H]⁺.

This alternative synthesis has also been used for the larger scale synthesis of Intermediate A1a and Intermediate A1d.

Intermediate A2a: 10-amino-2,2,7-trimethyl-1,2,3,4-tetrahydro-[1,4]oxazepino[2,3-c]quinolin-6(7H)-one

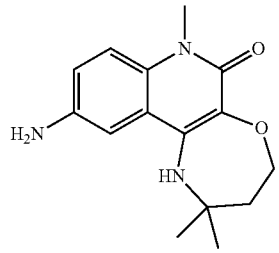 [SMILES: Cn1c(=O)c2c(c3cc(N)ccc31)NC(C)(C)CCO2]

Step 1; 4-((4-hydroxy-2-methylbutan-2-yl)amino)-1-methyl-6-nitroquinolin-2(1H)-one An oven-dried microwave vial (2.0-5.0 mL volume) was charged with ethyl 4-chloro-1-methyl-6-nitro-2-oxo-1,2-dihydroquinoline-3-carboxylate (Intermediate F2; 310 mg, 1.0 mmol) and 3-amino-3-methylbutan-1-ol (178 mg, 1.7 mmol). The reaction vial was flushed with Ar, sealed with a cap and then further flushed with Ar. Anhydrous NMP (3.5 mL) was added followed by DIPEA (0.52 mL, 2.9855 mmol). The reaction mixture was heated at 160° C. under microwave irradiation for 1 h. The reaction was allowed to cool to rt. The cap was removed and lithium chloride (239 mg, 5.6 mmol) was added. The reaction vial was re-sealed with a cap and heated at 160° C. in a heating block for 3 h. The reaction mixture was allowed to cool to rt. The reaction mixture was then added dropwise to water (25 mL). The aqueous mixture was extracted with EtOAc (3×30 mL). The organic extracts were combined, dried (Na$_2$SO$_4$) and concentrated in vacuo. The crude product was dissolved in DMSO (1.5 mL) and directly purified by reverse-phase chromatography (2 runs; Biotage reverse-phase 12 g C-18 column; 10-100% MeOH in H$_2$O (containing 0.1% formic acid)). The fractions containing the impure product were combined and concentrated in vacuo and dissolved in DMF (1.5 mL). The DMF mixture was added dropwise to stirred water (10 mL). The aqueous mixture was stirred for 30 min. The resulting suspension was filtered and the solid was washed with water (50 mL) and dried affording 4-((4-hydroxy-2-methylbutan-2-yl)amino)-1-methyl-6-nitroquinolin-2(1H)-one (29 mg, 10%) as a cream solid. ¹H NMR (500 MHz, DMSO-d$_6$) δ 8.83 (d, J=2.5 Hz, 1H), 8.37 (dd, J=9.3, 2.5 Hz, 1H), 7.61 (d, J=9.3 Hz, 1H), 7.07 (s, 1H), 5.74 (s, 1H), 5.12 (t, J=4.5 Hz, 1H), 3.66-3.62 (m, 2H), 3.55 (s, 3H), 1.93 (t, J=6.3 Hz, 2H), 1.44 (s, 6H).

Step 2; 3-bromo-4-((4-hydroxy-2-methylbutan-2-yl)amino)-1-methyl-6-nitroquinolin-2(1H)-one Trifluoroacetic acid (15 uL, 0.20 mmol) was added to a stirred mixture of N-bromosuccinimide (22 mg, 0.13 mmol) and 4-((4-hydroxy-2-methylbutan-2-yl)amino)-1-methyl-6-nitroquinolin-2(1H)-one (from step 1; 29 mg, 0.10 mmol) in anhydrous CH$_2$Cl$_2$ (0.5 mL) at 0° C. under Ar. The reaction mixture was stirred at 0° C. for 20 min. The reaction mixture was diluted with EtOAc (20 mL) and washed with saturated aq. NaHCO$_3$ (2×20 mL). The aqueous washings were combined and extracted with EtOAc (20 mL). The organic extracts were combined, dried (Na$_2$SO$_4$) and concentrated in vacuo. The crude reaction mixture was dry-loaded onto silica and purified by flash chromatography (10 g KP-sil; 0% to 10% MeOH in CH$_2$Cl$_2$) affording 3-bromo-4-((4-hydroxy-2-methylbutan-2-yl)amino)-1-methyl-6-nitroquinolin-2(1H)-one (20 mg, 53%) as a yellow solid. ¹H NMR (500 MHz, DMSO-d$_6$) δ 8.86 (d, J=2.7 Hz, 1H), 8.42 (dd, J=9.4, 2.7 Hz, 1H), 7.75 (d, J=9.4 Hz, 1H), 5.05 (br s, 1H), 3.75-3.73 (m, 2H), 3.72 (s, 3H), 1.90 (t, J=6.7 Hz, 2H), 1.22 (s, 6H).

Step 3; 2,2,7-trimethyl-10-nitro-1,2,3,4-tetrahydro-[1,4]oxazepino[2,3-c]quinolin-6(7H)-one A microwave vial (0.5-2.0 mL volume) was charged with 3-bromo-4-((4-hydroxy-2-methylbutan-2-yl)amino)-1-methyl-6-nitroquinolin-2(1H)-one (from step 2; 20 mg, 0.05 mmol). The reaction vial was flushed with Ar, sealed with a cap and then further flushed with Ar. Anhydrous DMSO (0.68 mL) was added followed by potassium tert-butoxide (1 M in THF; 92 uL, 0.09 mmol). The reaction mixture was heated at 60° C. under microwave irradiation for 50 min. The reaction mixture was allowed to cool to rt. Water (10 mL) was added followed by EtOAc (10 mL). The layers were separated and the aqueous layer was further extracted with EtOAc (2×10 mL). The organic extracts were combined and concentrated in vacuo. The crude product was dissolved in DMSO (1 mL) and directly purified by reverse-phase chromatography (Biotage reverse-phase 12 g C-18 column; 45-65% MeOH in H$_2$O (containing 0.1% formic acid)), affording 2,2,7-trimethyl-10-nitro-1,2,3,4-tetrahydro-[1,4]oxazepino[2,3-c]quinolin-6(7H)-one (5 mg, 29%) as a yellow solid. ¹H NMR (500 MHz, DMSO-d$_6$) δ 8.99 (d, J=2.5 Hz, 1H), 8.31 (dd, J=9.3, 2.5 Hz, 1H), 7.61 (d, J=9.3 Hz, 1H), 6.01 (s, 1H), 4.13 (t, J=6.1 Hz, 2H), 3.62 (s, 3H), 1.92 (t, J=6.1 Hz, 2H), 1.41 (s, 6H).

Step 4; 10-amino-2,2,7-trimethyl-1,2,3,4-tetrahydro-[1,4]oxazepino[2,3-c]quinolin-6(7H)-one A microwave vial (0.5-2.0 mL volume) was charged with 2,2,7-trimethyl-10-nitro-1,2,3,4-tetrahydro-[1,4]oxazepino[2,3-c]quinolin-6(7H)-one (from step 3; 5 mg, 0.015 mmol), Pd/C (10 wt %, 0.5 mg) and ammonium formate (8 mg, 0.13 mmol). The reaction vial was flushed with Ar, sealed with a cap and then further flushed with Ar. Anhydrous methanol (0.5 mL) was added. The reaction mixture was stirred at 80° C. for 10 min. The reaction mixture was cooled to rt, the cap removed and additional ammonium formate (5 mg, 0.08 mmol) and Pd/C (10 wt %, 0.5 mg) were added. The reaction vial was re-sealed with a cap, and heated at 80° C. for a further 10 min. The reaction mixture was allowed to cool to rt, filtered through Celite™ and the solids washed with MeOH (30 mL). The filtrate was concentrated in vacuo, re-dissolved in MeOH and passed through an SCX-2 (1 g) column, eluting with MeOH (20 mL) followed by 2 N methanolic ammonia (30 mL). The methanolic ammonia fraction was concentrated in vacuo affording the title compound (4 mg, 99%) as a yellow solid which was used without further purification. LCMS (Method T2) RT 0.72 min; m/z 274.1538 [M+H]⁺.

The following tabulated example was prepared by a method analogous to that used for the preparation of Intermediate A2a, starting from the amino-alcohol shown in the table.

| Intermediate | Data & comments | Amino-alcohol |
|---|---|---|
| Intermediate A2b: 10-amino-2-(methoxymethyl)-2,7-dimethyl-1,2,3,4-tetrahydro-[1,4]oxazepino[2,3-c]quinolin-6(7H)-one | LCMS (Method T2) RT 0.81 min; m/z 304.1625 [M + H]⁺. | 3-amino-4-methoxy-3-methylbutan-1-ol |
| Intermediate A2c: 10'-amino-7'-methyl-3',4,4',5-tetrahydro-1'H,2H-spiro[furan-3,2'-[1,4]oxazepino[2,3-c]quinolin-6'(7'H)-one | LCMS (Method T2) RT 0.34 min; m/z 302.1487 [M + H]⁺. | 2-(3-aminotetrahydrofuran-3-yl)ethan-1-ol |
| Intermediate A2d: 10-amino-2-(difluoromethyl)-7-methyl-1,2,3,4-tetrahydro-[1,4]oxazepino[2,3-c]quinolin-6(7H)-one | LCMS (Method X2) RT 0.61 min; m/z 296.1224 [M + H]⁺. | 3-amino-4,4-difluorobutan-1-ol |

Intermediate A3: 9-amino-2,6-dimethyl-2,3-dihydro-1H-[1,4]oxazino[2,3-c]quinolin-5(6H)-one

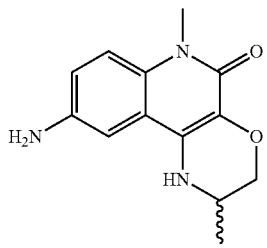

Step 1: 4-((1-hydroxypropan-2-yl)amino-1-methyl-6-nitroquinolin-2(1H)-one

A suspension of 4-chloro-1-methyl-6-nitroquinolin-2(1H)-one (Intermediate F1; 250 mg, 1.05 mmol), 2-aminopropan-1-ol (236 mg, 3.14 mmol) and DIPEA (0.36 mL, 2.10 mmol) in NMP (4.19 mL) was heated to 160° C. in a heating block for 24 h. The reaction mixture was allowed to cool to rt. Water (3 mL) was added to the reaction mixture and after 5 min a yellow precipitate formed. The aqueous mixture was added to water (20 mL). After 15 min, the precipitate was filtered, washed with water (100 mL) and dried affording 4-((1-hydroxypropan-2-yl)amino)-1-methyl-6-nitroquinolin-2(1H)-one as a yellow solid. $^1$H NMR (500 MHz, DMSO-$d_6$) δ 9.12 (d, J=2.5 Hz, 1H), 8.37 (dd, J=9.4, 2.5 Hz, 1H), 7.60 (d, J=9.4 Hz, 1H), 7.02 (d, J=7.4 Hz, 1H), 5.62 (s, 1H), 4.82 (t, J=5.8 Hz, 1H), 3.66-3.52 (m, 5H), 3.43-3.36 (m, 1H), 1.22 (d, J=6.4 Hz, 3H).

Step 2; 4-((1-hydroxypropan-2-yl)amino)-3-iodo-1-methyl-6-nitroquinolin-2(1H)-one A microwave vial (0.5-2.0 mL volume) was charged with 4-((1-hydroxypropan-2-yl)amino)-1-methyl-6-nitroquinolin-2(1H)-one (from step 1; 52 mg, 0.19 mmol) and iodine (145 mg, 0.57 mmol). The reaction vial was flushed with Ar, sealed with a cap and then further flushed with Ar. Anhydrous methanol (1.2 mL) was added and the reaction mixture was heated at 60° C. under microwave irradiation for 30 min. Water (0.6 mL) was added the reaction mixture was heated at 60° C. under microwave irradiation for a further 90 min. The reaction mixture was allowed to cool to rt, diluted with MeOH and directly dry-loaded onto silica. Purification by flash chromatography (10 g KP-sil; 0% to 15% MeOH in $CH_2Cl_2$) afforded 4-((1-hydroxypropan-2-yl)amino)-3-iodo-1-methyl-6-nitroquinolin-2(1H)-one (29 mg, 38%) as a yellow solid. $^1$H NMR (500 MHz, $CDCl_3$) δ 8.92 (d, J=2.6 Hz, 1H), 8.40 (dd, J=9.3, 2.6 Hz, 1H), 7.46 (d, J=9.3 Hz, 1H), 4.62 (d, J=10.6 Hz, 1H), 3.99-3.90 (m, 1H), 3.86-3.76 (m, 5H), 3.71 (dd, J=11.2, 5.9 Hz, 1H), 1.37 (d, J=6.6 Hz, 3H).

Step 3: 2,6-dimethyl-9-nitro-2,3-dihydro-1H-[1,4]oxazino[2,3-c]quinolin-5(6H)-one A microwave vial (2.0-5.0 mL volume) was charged with 4-((1-hydroxypropan-2-yl)amino)-3-iodo-1-methyl-6-nitroquinolin-2(1H)-one (from step 2; 29 mg, 0.07 mmol), 1,10-phenanthroline (6 mg, 0.03 mmol), copper(I) iodide (3 mg, 0.02 mmol) and cesium carbonate (46 mg, 0.14 mmol). The reaction vial was evacuated under reduced pressure for 30 min. The reaction vial was flushed with Ar, sealed with a cap and then further flushed with Ar. Anhydrous NMP (2.4 mL) was added. The reaction mixture was heated at 120° C. under microwave irradiation for 1 h. The reaction mixture was cooled to rt. Water (5 mL) was added and the aqueous mixture was extracted with $CH_2Cl_2$ (3×15 mL). The organic extracts were combined, dried ($Na_2SO_4$) and concentrated in vacuo. The crude product was purified by flash chromatography (10 g KP-sil; 0% to 15% MeOH in $CH_2Cl_2$). The product-containing fractions was combined, concentrated in vacuo and passed through an SCX-2 column (5 g), eluting with MeOH (50 mL) followed by 2 N methanolic ammonia (50 mL). The MeOH fraction was collected and concentrated in vacuo. The impure product was diluted with DMSO (0.8 mL) and purified by reverse-phase chromatography (Biotage reverse-phase 12 g C-18 column; 10-100% MeOH in $H_2O$ (containing 0.1% formic acid) affording 2,6-dimethyl-9-nitro-2,3-dihydro-1H-[1,4]oxazino[2,3-c]quinolin-5(6H)-one (8 mg, 41%) as a yellow solid. $^1$H NMR (500 MHz, $CDCl_3$) δ 8.45 (d, J=2.2 Hz, 1H), 8.32 (dd, J=9.3, 2.2 Hz, 1H), 7.43 (d, J=9.3 Hz, 1H), 4.43 (brs, 1H), 4.39 (dd, J=10.5, 2.7 Hz, 1H), 3.82 (dd, J=10.5, 7.3 Hz, 1H), 3.79 (s, 3H), 3.76-3.72 (m, 1H), 1.39 (d, J=6.4 Hz, 3H).

Step 4; 9-amino-2,6-dimethyl-2,3-dihydro-1H-[1,4]oxazino[2,3-c]quinolin-5(6H)-one A microwave vial (0.5-2.0 mL volume) was charged with 2,6-dimethyl-9-nitro-2,3-dihydro-1H-[1,4]oxazino[2,3-c]quinolin-5(6H)-one (from step 3; 11 mg, 0.0392 mmol), Pd/C (10 wt %, 2 mg) and ammonium formate (13 mg, 0.20 mmol). The reaction vial was flushed with Ar, sealed with a cap and then further flushed with Ar. Anhydrous methanol (0.4 mL) was added and the reaction mixture was stirred at 80° C. for 90 min. The reaction mixture was allowed to cool to rt, filtered through Celite™, and the solids washed with MeOH (20 mL). The filtrate was concentrated in vacuo, re-dissolved in MeOH and passed through an SCX-2 (2 g) column, eluting with MeOH (30 mL) followed by 2 N methanolic ammonia (30 mL). The methanolic ammonia fraction was concentrated in vacuo affording the title compound (8 mg, 81%) as an off-white solid which was used without further purification. LCMS (Method T2) RT 0.21 min; m/z 246.1253 $[M+H]^+$.

Intermediate A4: (R)-2-cyclopropyl-10-nitro-1,2,3,4-tetrahydro-[1,4]oxazepino[2,3-c]quinolin-6(7H)-one

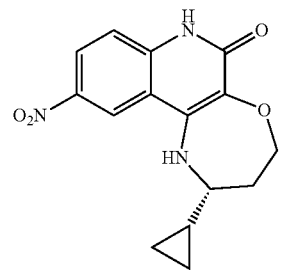

Step 1: (R)-4-((1-cyclopropyl-3-hydroxypropyl)amino)-6-nitroquinolin-2(1H)-one A mixture of ethyl 4-chloro-6-nitro-2-oxo-1,2-dihydroquinoline-3-carboxylate (Intermediate F3; 2.0 g, 6.74 mmol), (R)-3-amino-3-cyclopropylpropan-1-ol (Intermediate D1a; 1.09 g, 9.44 mmol), and DIPEA (2.94 mL, 16.9 mmol) in acetonitrile (13.5 mL) was heated at 80° C. overnight. The reaction mixture was cooled to rt, and 2 M sodium hydroxide (16.9 mL, 33.7 mmol) was added and the reaction mixture was stirred at 80° C. for 13 h. Additional 2 M sodium hydroxide (16.9 mL, 33.7 mmol) was added and stirring at 80° C. was continued for a further 16 h. The organic solvent was removed in vacuo and the aqueous mixture was acidified to pH 4 using 2 M aq. HCl. The aqueous suspension was then washed with EtOAc (10×200 mL). The organic solvent was removed under vacuum and the crude product purified by flash chromatography (25 g KP-sil; 0%-20% MeOH in EtOAc) to afford crude product as a yellow solid (1.7 g). The crude product was suspended in water and filtered, washed further with 100 mL of water and dried overnight in air affording (R)-4-((1-cyclopropyl-3-hydroxypropyl)amino)-6-nitroquinolin-2(1H)-one (1.14 g, 56%) as a yellow solid. LCMS (Method T2) RT 1.19 min; m/z 304.13 [M+H]$^+$.

Step 2: (R)-3-bromo-4-((1-cyclopropyl-3-hydroxypropyl)amino)-6-nitroquinolin-2(1H)-one Trifluoroacetic acid (1.44 mL, 18.74 mmol) was added to a stirred mixture of N-bromosuccinimide (1.01 g, 5.67 mmol) and (R)-4-((1-cyclopropyl-3-hydroxypropyl)amino)-6-nitroquinolin-2(1H)-one (from step 1; 1.14 g, 3.76 mmol) in anhydrous CH$_2$Cl$_2$ (38 mL) at 0° C. The reaction mixture was stirred at 0° C. for 10 min. The reaction mixture was partitioned between EtOAc (50 mL) and water (75 mL). The aqueous layer was extracted twice with EtOAc (50 mL) and the organics were combined, washed with saturated aq. NaHCO$_3$, dried (MgSO$_4$) and concentrated in vacuo affording (R)-3-bromo-4-((1-cyclopropyl-3-hydroxypropyl)amino)-6-nitroquinolin-2(1H)-one (1.69 g) as a dark green solid containing 0.5 equiv. of succinimide by NMR which was used without further purification. LCMS (Method T2) RT 1.33 min; m/z 384.04 [M+H]$^+$.

Step 3: (R)-2-cyclopropyl-10-nitro-1,2,3,4-tetrahydro-[1,4]oxazepino[2,3-c]quinolin-6(7H)-one A microwave vial (0.5-2.0 mL volume) was charged with (R)-3-bromo-4-((1-cyclopropyl-3-hydroxypropyl)amino)-6-nitroquinolin-2(1H)-one (100 mg, 0.26 mmol) and DMSO (1.0 mL), evacuated, and backfilled with argon. Potassium tert-butoxide (1M in THF; 0.47 mL, 0.47 mmol) was then added and the reaction mixture was heated to 65° C. under microwave irradiation for 1 h.

4 batches repeated as above. One batch conducted using 67 mg of (R)-3-bromo-4-((1-cyclopropyl-3-hydroxypropyl)amino)-6-nitroquinolin-2(1H)-one and 0.32 mL of potassium tert-butoxide (1M in THF) and 1.00 mL of DMSO. All batches combined for purification. Purification by reverse-phase chromatography (Biotage reverse-phase 12 g C-18 column; 30-70% MeOH in H$_2$O (containing 0.1% formic acid) afforded the title compound as a brown solid (110 mg, 38% over 2 steps). LCMS (Method T2) RT 1.28 min; m/z 302.12 [M+H]$^+$.

Intermediate A5a: (R)-10-amino-2-cyclopropyl-7-(cyclopropylmethyl)-1,2,3,4-tetrahydro[1,4]oxazepino[2,3-c]quinolin-6(7H)-one

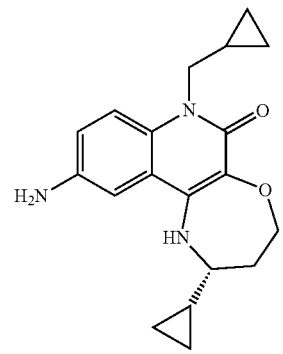 [SMILES: Nc1ccc2c(c1)c1c(c(=O)n2CC2CC2)OCC[C@H](C2CC2)N1]

Step 1: (R)-2-cyclopropyl-7-(cyclopropylmethyl)-10-nitro-1,2,3,4-tetrahydro-[1,4]oxazepino-[2,3-c]quinolin-6(7H)-one A suspension of (R)-2-cyclopropyl-10-nitro-1,2,3,4-tetrahydro-[1,4]oxazepino[2,3-c]quinolin-6(7H)-one (Intermediate A4) (46 mg, 0.15 mmol) and cesium carbonate (74 mg, 0.23 mmol) in DMF (1.4 mL) was stirred at rt for 15 min under argon. To this was added bromomethyl cyclopropane (29 uL, 0.30 mmol) and the reaction mixture was stirred at rt overnight. Water was added and the aqueous mixture was extracted with EtOAc (4×10 mL). The combined organic layers were dried (Na$_2$SO$_4$) and concentrated in vacuo. Purification flash chromatography (10 g, KP-Sil, 30%-80% EtOAc in cyclohexane) afforded (R)-4-((1-cyclopropyl-3-hydroxypropyl)amino)-6-nitroquinolin-2(1H)-one (30 mg, 56%) as a yellow oil. $^1$H NNMR (500 MHz, CDCl$_3$) δ 8.50 (d, J=2.4 Hz, 1H), 8.33 (dd, J=9.3, 2.4 Hz, 1H), 7.55 (d, J=9.4 Hz, 1H), 4.49 (ddd, J=12.0, 8.8, 5.3 Hz, 1H), 4.38-4.32 (m, 1H), 4.27 (dd, J=6.9, 4.5 Hz, 2H), 3.09-2.99 (m, 1H), 2.40 (ddt, J=19.6, 6.8, 3.8 Hz, 1H), 1.43 (s, 5H), 1.23-1.11 (m, 2H), 0.80-0.69 (m, 2H), 0.64-0.48 (m, 4H), 0.42-0.34 (m, 2H); LCMS (Method T2) RT 1.50 min; m/z 356 [M+H]$^+$.

Step 2: (R)-10-amino-2-cyclopropyl-7-(cyclopropylmethyl)-1,2,3,4-tetrahydro-[1,4]oxazepino-[2,3-c]quinolin-6(7H)-one To a suspension of (R)-4-((1-cyclopropyl-3-hydroxypropyl)amino)-6-nitroquinolin-2(1H)-one (from step 1; 30 mg, 0.08 mmol) in ethanol (8.0 mL) was added ammonium formate (53 mg, 0.84 mmol) and Pd/C (10 wt %, 9 mg). The flask was flushed with nitrogen and heated to 80° C. for 30 min. The product was directly loaded onto a SCX-2 (2 g) column and washed with methanol. The product was eluted with 2 M methanolic ammonia, and concentrated in vacuo affording the title compound (12 mg, 42%) as a brown solid. $^1$H NMR (500 MHz, methanol-$d_4$) δ 7.43 (d, J=9.0 Hz, 1H), 7.14 (d, J=2.4 Hz, 1H), 7.04 (dd, J=9.0, 2.5 Hz, 1H), 4.38 (ddd, J=11.8, 7.5, 5.4 Hz, 1H), 4.21 (dd, J=6.9, 1.4 Hz, 2H), 4.13 (dt, J=11.8, 5.9 Hz, 1H), 2.86 (td, J=9.6, 3.6 Hz, 1H), 2.31 (dddd, J=13.6, 7.5, 5.9, 3.6 Hz, 1H), 2.08 (ddt, J=13.8, 9.6, 5.6 Hz, 1H), 1.32-1.17 (m, 2H), 0.70-0.61 (m, 2H), 0.52-0.45 (m, 4H), 0.45-0.36 (m, 1H), 0.36-0.31 (m, 1H); LCMS (Method T2) RT 1.09 min; m/z 326 [M+H]$^+$.

The following tabulated example was prepared by a method analogous to that used for the preparation of Intermediate A5a, starting from the intermediate(s) shown in the table. For Intermediate A5b, reverse-phase chromatography was conducted after the reduction step.

Intermediate A7a: (R)-10-amino-2-cyclopropyl-7-methyl-1,2,3,4-tetrahydro-[1,4]oxazepino[2,3-c][1,8]naphthyridin-6(7H)-one

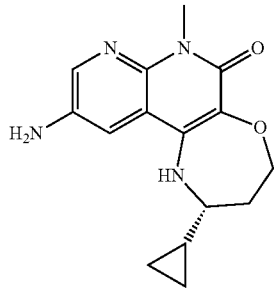 [SMILES: Cn1c(=O)c2c(c3cc(N)cnc31)N[C@@H](C1CC1)CCO2]

| Intermediate | Data and comments | Intermediate |
| --- | --- | --- |
| Intermediate A5b: (R)-10-amino-2-cyclopropyl-7-((3,3-difluorocyclobutyl)methyl)-1,2,3,4-tetrahydro-[1,4]oxazepino[2,3-c]quinolin-6(7H)-one | LCMS (Method T2) RT 1.21 min; m/z 376.1937 [M + H]$^+$. | Intermediate A4: (R)-2-cyclopropyl-10-nitro-1,2,3,4-tetrahydro-[1,4]oxazepino[2,3-c]quinolin-6(7H)-one and 3-(bromomethyl)-1,1-difluorocyclobutane |

Intermediate A6a: (R)-10-amino-2-cyclopropyl-1,2,3,4-tetrahydro-[1,4]oxazepino[2,3-c]quinolin-6(7H)-one

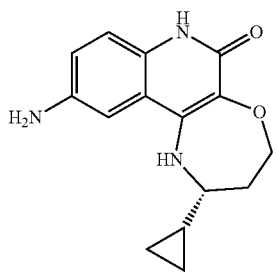

A mixture of (R)-2-cyclopropyl-10-nitro-1,2,3,4-tetrahydro-[1,4]oxazepino[2,3-c]quinolin-6(7H)-one (Intermediate A4; 12 mg, 0.04 mmol) and tin(II) chloride (30 mg, 0.16 mmol) were suspended in ethanol (0.23 mL) and trifluoroethanol (0.08 mL) and heated at 120° C. under microwave irradiation for 1 h. The crude mixture was carried forward without any purification. LCMS (Method T2) RT 0.50 min; m/z 272.14 [M+H]$^+$.

Step 1: (R)-6-chloro-4-((1-cyclopropyl-3-hydroxypropyl)amino)-1-methyl-1,8-naphthyridin-2(1H)-one A microwave vial (2.0-5.0 mL volume) was charged with (R)-3-amino-3-cyclopropylpropan-1-ol (Intermediate D1a; 139 mg, 1.2 mmol), ethyl 4,6-dichloro-1-methyl-2-oxo-1,2-dihydro-1,8-naphthyridine-3-carboxylate (Intermediate F4; 201 mg, 0.67 mmol), DIPEA (0.30 mL, 1.7 mmol) and MeCN (2.7 mL). The reaction vial was flushed with Ar and sealed with a cap. The reaction mixture was heated at 90° C. under microwave irradiation for 2 h. The reaction mixture was transferred to a flask and 2 M sodium hydroxide (2.0 mL, 4.0 mmol) was added. The reaction mixture was heated at 95° C. for 1 h. The reaction mixture was cooled to rt and the resulting precipitate was filtered, washed with water (10 mL) and dried affording (R)-6-chloro-4-((1-cyclopropyl-3-hydroxypropyl)amino)-1-methyl-1,8-naphthyridin-2(1H)-one (136 mg, 66%) as an off-white solid. $^1$H NMR (500 MHz, DMSO-$d_6$) δ 8.75 (d, J=2.3 Hz, 1H), 8.62 (d, J=2.3 Hz, 1H), 6.77 (d, J=8.3 Hz, 1H), 5.54 (s, 1H), 4.49 (t, J=4.9 Hz, 1H), 3.57-3.50 (m, 4H), 3.50-3.44 (m, 1H), 3.27-3.20 (m, 1H), 1.89-1.82 (m, 1H), 1.82-1.73 (m, 1H), 1.08-1.00

(m, 1H), 0.52-0.47 (m, 1H), 0.41-0.36 (m, 1H), 0.28-0.21 (m, 2H); LCMS (Method T2) RT 1.40 min; m/z 308.116 [M+H]+

Step 2: (R)-3-bromo-6-chloro-4-((1-cyclopropyl-3-hydroxypropyl)amino)-1-methyl-1,8-naphthyridin-2(1H)-one Trifluoroacetic acid (0.17 mL, 2.2 mmol) was added was added to a stirred mixture of N-bromosuccinimide (117 mg, 0.66 mmol) and (R)-6-chloro-4-((1-cyclopropyl-3-hydroxypropyl)amino)-1-methyl-1,8-naphthyridin-2(1H)-one (from step 1; 135 mg, 0.44 mmol) in anhydrous CH$_2$Cl$_2$ (3.0 mL) at 0° C. under Ar. The reaction mixture was stirred at 0° C. for 25 min. The reaction mixture was diluted with EtOAc (20 mL) and washed with saturated aq. NaHCO$_3$ (2×10 mL). The aqueous washings were combined and extracted with EtOAc (20 mL). The organic extracts were combined, dried (Na$_2$SO$_4$) and concentrated in vacuo. Purification by flash chromatography (10 g KP-sil; 0% to 10% MeOH in CH$_2$Cl$_2$) afforded (R)-3-bromo-6-chloro-4-((1-cyclopropyl-3-hydroxypropyl)amino)-1-methyl-1,8-naphthyridin-2(1H)-one (137 mg, 81%) as an off-white solid. $^1$H NMR (500 MHz, DMSO-d$_6$) δ 8.72 (d, J=2.4 Hz, 1H), 8.69 (d, J=2.4 Hz, 1H), 5.57 (d, J=10.4 Hz, 1H), 4.62 (dd, J=5.1, 4.3 Hz, 1H), 3.69-3.63 (m, 4H), 3.63-3.57 (m, 1H), 3.57-3.51 (m, 1H), 1.98-1.91 (m, 1H), 1.91-1.82 (m, 1H), 1.08-1.00 (m, 1H), 0.44-0.36 (m, 1H), 0.31-0.24 (m, 1H), 0.19-0.11 (m, 1H), −0.01--0.07 (m, 1H); LCMS (Method T2) RT 1.45 min; m/z 386.025 [M+H]+

Step 3: (R)-10-chloro-2-cyclopropyl-7-methyl-1,2,3,4-tetrahydro-[1,4]oxazepino[2,3-c][1,8]-naphthyridin-6(7H)-one A microwave vial (2-5 mL volume) was charged with (R)-3-bromo-6-chloro-4-((1-cyclopropyl-3-hydroxypropyl)amino)-1-methyl-1,8-naphthyridin-2(1H)-one (from step 2; 137 mg, 0.35 mmol). The reaction vial was flushed with Ar, sealed with a cap and then further flushed with Ar. Anhydrous DMSO (4.71 mL) was added followed by potassium tert-butoxide (1 M in THF; 0.64 mL, 0.64 mmol). The reaction mixture was heated at 60° C. under microwave irradiation for 80 min. The reaction mixture was allowed to cool to rt. Water (20 mL) was added followed by EtOAc (20 mL). The layers were separated and the aqueous layer was further extracted with EtOAc (2×20 mL). The organic extracts were combined, washed with brine (10 mL) and concentrated in vacuo. The crude product was dissolved in DMSO (1 mL) and directly purified by reverse-phase chromatography (Biotage reverse-phase 12 g C-18 column; 60-84% MeOH in H$_2$O (containing 0.1% formic acid)) affording (R)-10-chloro-2-cyclopropyl-7-methyl-1,2,3,4-tetrahydro-[1,4]oxazepino[2,3-c][1,8]naphthyridin-6(7H)-one (41 mg, 38%) as an off-white solid. $^1$H NMR (500 MHz, DMSO-d$_6$) δ 8.69 (d, J=2.4 Hz, 1H), 8.55 (d, J=2.4 Hz, 1H), 6.22 (d, J=3.6 Hz, 1H), 4.27-4.15 (m, 2H), 3.57 (s, 3H), 2.93-2.86 (m, 1H), 2.24-2.16 (m, 1H), 2.03-1.95 (m, 1H), 1.22-1.14 (m, 1H), 0.57-0.48 (m, 2H), 0.38-0.33 (m, 1H), 0.29-0.23 (m, 1H); LCMS (Method T2) RT 1.45 min; m/z 306.117 [M+H]+

Step 4: (R)-10-amino-2-cyclopropyl-7-methyl-1,2,3,4-tetrahydro-[1,4]oxazepino[2,3-c][1,8]-naphthyridin-6(7H)-one An oven dried microwave vial (0.5-2.0 mL volume) was charged with (R)-10-chloro-2-cyclopropyl-7-methyl-1,2,3,4-tetrahydro-[1,4]oxazepino[2,3-c][1,8]naphthyridin-6(7H)-one (from step 3; 32 mg, 0.10 mmol), benzophenone imine (27 mg, 0.15 mmol), sodium tert-butoxide (15 mg, 0.15 mmol), palladium(II) acetate (2.3 mg, 0.010 mmol) and Josiphos (5.7 mg, 0.010 mmol). Anhydrous 1,2-dimethoxyethane (0.40 mL) was added and the vial was sealed with a cap and Ar was bubbled through the reaction mixture. The reaction mixture was heated at 70° C. in a heating block for 2 h. The reaction mixture was cooled to rt and 3 M HCl (0.9 mL) was added for imine hydrolysis. The mixture was stirred at rt for 2 h. The reaction mixture was directly passed through an SCX-2 (2 g) column, eluting with water (10 mL), MeOH (20 mL) and 2 N methanolic ammonia (20 mL). The basic fraction was concentrated in vacuo affording the title compound (30 mg, 99%, 0.12 mmol) as a dark yellow solid which was used without further purification. LCMS (Method T2) RT 1.10 min; m/z 287.139 [M+H]+.

Intermediate A8a: (R)-10-amino-2-cyclopropyl-7-methyl-1,2,3,4-tetrahydro[1,4]thiazepino[2,3-c]quinolin-6(7H)-one

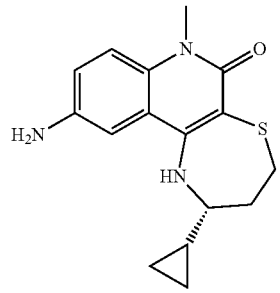 [SMILES: Cn1c(=O)c2c(c3cc(N)ccc31)N[C@@H](C1CC1)CCS2]

Step 1: (R)-3-((3-bromo-1-methyl-6-nitro-2-oxo-1,2-dihydroquinolin-4-yl)amino)-3-cyclopropylpropyl 4-methylbenzenesulfonate The starting material: (R)-3-bromo-4-((1-cyclopropyl-3-hydroxypropyl)amino)-1-methyl-6-nitroquinolin-2(1H)-one was prepared using steps 1-2 as shown for Intermediate Aid.

To a solution of (R)-3-bromo-4-((1-cyclopropyl-3-hydroxypropyl)amino)-1-methyl-6-nitroquinolin-2(1H)-one (200 mg, 0.50 mmol) in pyridine (5.0 mL) cooled to 0° C. was added tosyl chloride (289 mg, 1.51 mmol). The mixture was stirred with warming to rt for 2 h. Additional tosyl chloride (289 mg, 1.51 mmol) was added and the mixture stirred overnight at rt. The reaction mixture was poured into 5% aq. HCl then extracted with CH$_2$Cl$_2$. The organic extracts were combined, washed with 5% aq. HCl, dried (MgSO$_4$) and concentrated in vacuo. The residue was purified by flash chromatography (25 g KP-sil; 20%-75% EtOAc in cyclohexane) affording (R)-3-((3-bromo-1-methyl-6-nitro-2-oxo-1,2-dihydroquinolin-4-yl)amino)-3-cyclopropylpropyl 4-methylbenzenesulfonate (127 mg, 46%) as a yellow solid. LCMS (Method T2) RT 1.56 min; m/z 550.06 [M+H]+.

Step 2: (R)—S-(3-((3-bromo-1-methyl-6-nitro-2-oxo-1,2-dihydroquinolin-4-yl)amino)-3-cyclopropylpropyl) ethanethioate To a solution of (R)-3-((3-bromo-1-methyl-6-nitro-2-oxo-1,2-dihydroquinolin-4-yl)amino)-3-cyclopropylpropyl 4-methylbenzenesulfonate (from step 1; 60 mg, 0.11 mmol) in DMF (1.1 mL) was added potassium thioacetate (25 mg, 0.22 mmol) followed by sodium iodide (1.6 mg, 0.01 mmol). The solution was heated to 50° C. and stirred for 4 h. The mixture was cooled to rt and quenched by the addition of water. The mixture was extracted with EtOAc. The combined organic extracts were washed with water, brine, dried (MgSO$_4$) and concentrated in vacuo. The residue (diluted in DMSO (1 mL)) was purified using reverse-phase flash chromatography (Biotage 12g SNAP Ultra C-18, 30-100% MeOH in H$_2$O (containing 0.1% formic acid)) affording (R)—S-(3-((3-bromo-1-methyl-6-nitro-2-oxo-1,2-dihydroquinolin-4-yl)amino)-3-cyclopropylpropyl) ethanethioate (38 mg, 77%) as a brown oil. LCMS (Method T2) RT 1.56 min; m/z 456.04 [M+H]$^+$.

Step 3: (R)-2-cyclopropyl-7-methyl-10-nitro-1,2,3,4-tetrahydro-[1,4]thiazepino[2,3-c]quinolin-6(7H)-one To a suspension of (R)—S-(3-((3-bromo-1-methyl-6-nitro-2-oxo-1,2-dihydroquinolin-4-yl)amino)-3-cyclopropylpropyl) ethanethioate (from step 2; 38 mg, 0.084 mmol) in methanol (0.84 mL), cooled to 0° C. under an atmosphere of air was added 15% aq. NaOH (0.50 mL, 0.084 mmol). Stirring was continued with warming to rt overnight. The mixture was concentrated in vacuo to remove the methanol. DMSO (1.5 mL) and couple of drops of water were then added. The solution was purified using reverse-phase flash chromatography (Biotage 12g SNAP Ultra C-18, 30-100% MeOH in H$_2$O (containing 0.1% formic acid)) affording (R)-2-cyclopropyl-7-methyl-10-nitro-1,2,3,4-tetrahydro-[1,4]thiazepino[2,3-c]quinolin-6(7H)-one (17 mg, 61%) as a yellow oil. LCMS (Method T2) RT 1.45 min; m/z 332.11 [M+H]$^+$.

Step 4: (R)-10-amino-2-cyclopropyl-7-methyl-1,2,3,4-tetrahydro-[1,4]thiazepino[2,3-c]quinolin-6(7H)-one To a suspension of (R)-2-cyclopropyl-7-methyl-10-nitro-1,2,3,4-tetrahydro-[1,4]thiazepino[2,3-c]quinolin-6(7H)-one (from step 3; 17 mg, 0.051 mmol) in ethanol (1.0 mL) was added ammonium formate (32 mg, 0.51 mmol) and Pd/C (10 wt %, 10). The vial was sealed and evacuated then refilled with argon three times. The vial was then placed into a drysyn block preheated to 60° C. and stirred for 1 hour. The reaction mixture was directly passed through an SCX-2 (2 g) column, and the title compound product eluted with methanolic ammonia. (R)-10-Amino-2-cyclopropyl-7-methyl-1,2,3,4-tetrahydro-[1,4]thiaze-pino[2,3-c]quinolin-6(7H)-one (6 mg, 39%) was obtained as a yellow solid. LCMS (Method T2) RT 1.07 min; m/z 302.13 [M+H]$^+$.

The following tabulated example was prepared by a method analogous to that used for the preparation of Intermediate A8a, starting from the amino-alcohol shown in the table.

| Intermediate | Data & comments | Amino-alcohol |
|---|---|---|
| Intermediate A8b: 9-amino-2,6-dimethyl-2,3-dihydro-1H-[1,4]thiazino[2,3-c]quinolin-5(6H)-one | LCMS (Method T2) RT 0.48 min; m/z 262.1034 [M + H]$^+$. | 2-aminopropan-1-ol |

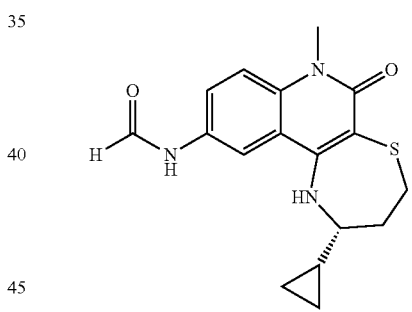

Intermediate A8c: (R)—N-(2-cyclopropyl-7-methyl-6-oxo-1,2,3,4,6,7-hexahydro-[1,4]thiazepino[2,3-c]quinolin-10-yl)formamide

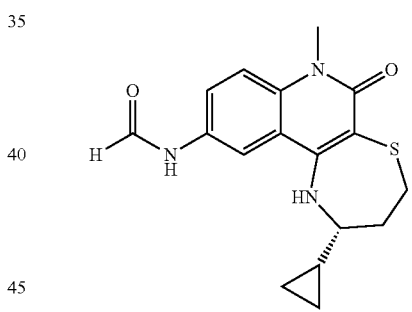

Step 1 is analogous to that used for the preparation of Intermediate A8a.

Step 2: (R)-2-cyclopropyl-7-methyl-10-nitro-1,2,3,4-tetrahydro-[1,4]thiazepino[2,3-c]quinolin-6(7H)-one To a solution of (R)-3-((3-bromo-1-methyl-6-nitro-2-oxo-1,2-dihydroquinolin-4-yl)amino)-3-cyclopropylpropyl 4-methylbenzenesulfonate (from step 1; 176 mg, 0.32 mmol) in DMF (3.2 mL) was added potassium thioacetate (73 mg, 0.64 mmol) followed by sodium iodide (5 mg, 0.032 mmol). The solution was heated to 50° C. and stirred for 3 h. Once cooled to rt, 15% aq. sodium hydroxide (1.00 mL, 0.32 mmol) was added via syringe. The mixture was allowed to stir at rt overnight. Water (5 mL) was added to the mixture, forming a precipitate which was collected under vacuum filtration and further washed with water and dried in vacuo affording (R)-2-cyclopropyl-7-methyl-10-nitro-1,2,3,4-tetrahydro-[1,4]thiazepino[2,3-c]quinolin-6(7H)-one which was used without further purification. LCMS (Method X2) RT 1.35 min; m/z 354.09 [M+H]+.

Step 3: (R)—N-(2-cyclopropyl-7-methyl-6-oxo-1,2,3,4,6,7-hexahydro-[1,4]thiazepino[2,3-c]quinolin-10-yl)formamide To a suspension of (R)-2-cyclopropyl-7-methyl-10-nitro-1,2,3,4-tetrahydro-[1,4]thiazepino[2,3-c]quinolin-6(7H)-one (from step 2; 106 mg, 0.32 mmol) in ethanol (3.2 mL) was added ammonium formate (202 mg, 3.20 mmol) and 10 wt % Pd/C (34 mg). The vial was sealed and evacuated then refilled with argon three times. The vial was then placed into a drysyn block preheated to 60° C. After stirring for 1 h additional Pd/C and ammonium formate (same quantities as above) were added and stirring continued at 60° C. for a further 2 h. The mixture was filtered through a pad of Celite and concentrated in vacuo. The residue was taken up in ethanol (4 mL) and tin(II) chloride (243 mg, 1.28 mmol) was added. The mixture was heated at 120° C. under microwave irradiation for a total of 9 h 30 min. The reaction mixture was cooled to rt, and 15% aq. NaOH (2 mL) was added and the reaction mixture was stirred at 60° C. overnight. Once cooled, the mixture was concentrated then the residue taken up in $CH_2Cl_2$ and washed with water. The organic extracts were dried ($MgSO_4$) and concentrated in vacuo. Purification by flash chromatography (Biotage KP-Sil 25 g; 0-10% MeOH in $CH_2Cl_2$). The product-containing fractions were combined, concentrated in vacuo and further purified by reverse-phase chromatography (Biotage reverse-phase 12 g C-18 column; 10-100% MeOH in $H_2O$ (containing 0.1% formic acid)) affording the title compound (5 mg, 5% over 2 steps) as a yellow oil. LCMS (Method T2) RT 1.31 min; m/z 330.12 [M+H]+. N.B. Intermediate A8a: (R)-10-amino-2-cyclopropyl-7-methyl-1,2,3,4-tetrahydro[1,4]thiaze-pino[2,3-c]quinolin-6(7H)-one (13 mg, 13% over 2 steps) was also isolated during this reaction.

Intermediate A9a: (R)-10-amino-2-cyclopropyl-7-methyl-1,2,3,4-tetrahydro-[1,4]thiazepino[2,3-c]quinolin-6(7H)-one 5,5-dioxide

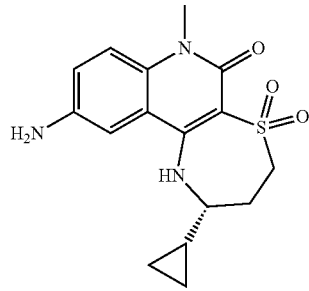 [SMILES: Cn1c(=O)c2c(c3cc(N)ccc31)N[C@@H](C1CC1)CCS2(=O)=O]

Steps 1-3 are analogous to those used for the preparation of Intermediate A8a.

Step 4: (R)-2-cyclopropyl-7-methyl-10-nitro-1,2,3,4-tetrahydro-[1,4]thiazepino[2,3-c]quinolin-6(7H)-one 5,5-dioxide 3-Chloroperoxybenzoic acid (126 mg, 0.56 mmol) was added portionwise to a solution of (R)-2-cyclopropyl-7-methyl-10-nitro-1,2,3,4-tetrahydro-[1,4]thiazepino[2,3-c]quinolin-6(7H)-one (62 mg, 0.19 mmol) in a mixture of $CH_2Cl_2$ (1.87 mL) and acetonitrile (1.87 mL) cooled to 0° C. After 15 min the mixture was allowed to warm to rt and stirred for 24 h. The mixture was quenched by addition of 10% aq. $NaHCO_3$ and sat. aq. $Na_2S_2O_3$. The mixture was then extracted 3 times with EtOAc. The combined organic extracts were combined, washed with 10% aq. $Na_2CO_3$, brine, dried ($MgSO_4$) and concentrated in vacuo affording (R)-2-cyclopropyl-7-methyl-10-nitro-1,2,3,4-tetrahydro-[1,4]thiazepino[2,3-c]quinolin-6(7H)-one 5,5-dioxide (45 mg, 66%) as a yellow solid which was used without further purification. LCMS (Method T2) RT 1.20 min; m/z 364.0943 [M+H]+.

Step 5: (R)-10-amino-2-cyclopropyl-7-methyl-1,2,3,4-tetrahydro-[1,4]thiazepino[2,3-c]quinolin-6(7H)-one 5,5-dioxide A mixture of (R)-2-cyclopropyl-7-methyl-10-nitro-1,2,3,4-tetrahydro-[1,4]thiazepino-[2,3-c]quinolin-6(7H)-one 5,5-dioxide (from step 4; 20 mg, 0.055 mmol) and tin(II) chloride (42 mg, 0.22 mmol) in ethanol (0.67 mL) and trifluoroethanol (0.22 mL) was heated at 70° C. for 1 h. The reaction mixture was loaded onto an SCX-2 cartridge in 1:1 1 M HCl:MeOH, flushed with MeOH, then eluted with 2 M $NH_3$ in MeOH, affording the title compound (16 mg, 87%) as a yellow glass which was used without further purification. LCMS (Method X2); RT 1.54 min; m/z 334.1224 [M+H]+.

Intermediate A10a: (S)-2-cyclopropyl-10-((2,5-dichloropyrimidin-4-yl)amino)-3,3-difluoro-7-methyl-1,2,3,4-tetrahydro-[1,4]oxazepino[2,3-c]quinolin-6(7H)-one

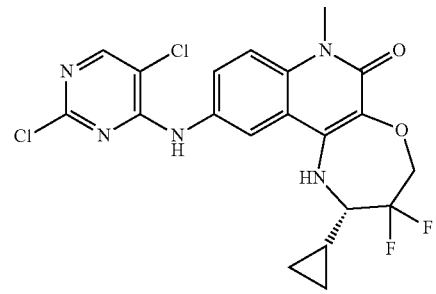 [SMILES: Cn1c(=O)c2c(c3cc(Nc4nc(Cl)ncc4Cl)ccc31)N[C@@H](C1CC1)C(F)(F)CO2]

A microwave vial (0.5-2.0 mL volume) was charged with (S)-10-amino-2-cyclopropyl-3,3-difluoro-7-methyl-1,2,3,4-tetrahydro-[1,4]oxazepino[2,3-c]quinolin-6(7H)-one (Intermediate A1m; 800 mg, 2.49 mmol) and 2,4,5-trichloropyrimidine (531 mg, 2.89 mmol). The reaction vial was flushed with Ar, sealed with a cap and then further flushed with Ar. NMP (3 mL) was added followed by DIPEA (1.7 mL, 9.76 mmol). The reaction mixture was heated at 140° C. under microwave irradiation for 1 h. The reaction mixture was cooled to rt. The reaction mixture was added to water (10 mL) and a beige precipitate formed. Additional water (10 mL) was added and the aq. mixture was stirred for 5 min. The precipitate was filtered, washed with water (25 mL) and dried affording the title compound (1.16 g, 100%) as a beige solid which was used without further purification. $^1$H NMR (600 MHz, DMSO-$d_6$) δ 9.74 (s, 1H), 8.39 (s, 1H), 8.15 (d, J=2.1 Hz, 1H), 7.61 (dd, J=9.0, 2.1 Hz, 1H), 7.50 (d, J=9.0 Hz, 1H), 6.25 (d, J=2.7 Hz, 1H), 4.52-4.44 (m, 1H), 4.43-4.34 (m, 1H), 3.58 (s, 3H), 3.28-3.23 (m, 1H), 1.35-1.27 (m, 1H), 0.77-0.67 (m, 1H), 0.56-0.49 (m, 2H), 0.36-0.30 (m, 1H); LCMS (Method X2); RT 1.60 min; m/z 468.0796 [M+H]+.

The following tabulated example was prepared by a method analogous to that used for the preparation of Intermediate A10a, starting from the intermediate(s) shown in the table. For Intermediate A10b and Intermediate A10c; instead of precipitation, the crude reaction mixtures were directly purified by reverse-phase chromatography using the conditions shown in the table to afford the title compounds. For Intermediate A10d; instead of precipitation, the crude reaction mixture was directly purified by preparative HPLC using the conditions shown in the table.

| Intermediate | Data and comments | Intermediate | Purification conditions |
|---|---|---|---|
| Intermediate A10b: (R)-2-cyclopropyl-10-((2,5-dichloropyrimidin-4-yl)amino)-7-methyl-1,2,3,4-tetrahydro-[1,4]oxazepino[2,3-c]quinolin-6(7H)-one | LCMS (Method X2) RT 1.39 min; m/z 432.1075 [M + H]+. | Intermediate A1d: (R)-10-amino-2-cyclopropyl-7-methyl-1,2,3,4-tetrahydro-[1,4]oxazepino[2,3-c]quinolin-6(7H)-one | Biotage 30 g C-18 column; 20-90% MeOH in H₂O (containing 0.1% formic acid) |
| Intermediate A10c: (R)-2-cyclopropyl-10-((2,5-dichloropyrimidin-4-yl)amino)-7-methyl-1,2,3,4-tetrahydro-[1,4]thiazepino[2,3-c]quinolin-6(7H)-one | LCMS (Method T2) RT 1.57 min; m/z 448.0739 [M + H]+. | Intermediate A8a: (R)-10-amino-2-cyclopropyl-7-methyl-1,2,3,4-tetrahydro[1,4]thiazepino[2,3-c]quinolin-6(7H)-one | Biotage 12 g Ultra C-18 column; 10-100% MeOH in H₂O (containing 0.1% formic acid) |
| Intermediate A10d: (S)-10-((2,5-dichloropyrimidin-4-yl)amino)-2,7-dimethyl-1,2,3,4-tetrahydro-[1,4]oxazepino[2,3-c]quinolin-6(7H)-one | LCMS (Method X2) RT 1.32 min; m/z 406.0842 [M + H]+. | Intermediate A1a: (S)-10-amino-2,7-dimethyl-1,2,3,4-tetrahydro-[1,4]oxazepino[2,3-c]quinolin-6(7H)-one | 15 min gradient of 60:40 to 0:100 H₂O:MeOH (both modified with 0.1% formic acid); flow rate 20 mLmin⁻¹ |
| Intermediate A10e: (S)-10-((2-chloro-5-fluoropyrimidin-4-yl)amino)-2-cyclopropyl-3,3-difluoro-7-methyl-1,2,3,4-tetrahydro-[1,4]oxazepino[2,3-c]quinolin-6(7H)-one | LCMS (Method X2) RT 1.59 min; m/z 452.1104 [M + H]+. | Intermediate A1m: (S)-10-amino-2-cyclopropyl-3,3-difluoro-7-methyl-1,2,3,4-tetrahydro-[1,4]oxazepino[2,3-c]quinolin-6(7H)-one | n/a |

| Intermediate | Data and comments | Intermediate | Purification conditions |
|---|---|---|---|

Intermediate A11a: (R)—N-(2-cyclopropyl-7-methyl-6-oxo-1,2,3,4,6,7-hexahydro-[1,4]oxazepino[2,3-c]quinolin-10-yl)formamide

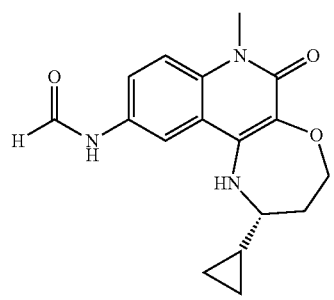 [SMILES: Cn1c(=O)c2c(c3cc(NC=O)ccc31)N[C@@H](C1CC1)CCO2]

A mixture of (R)-10-amino-2-cyclopropyl-7-methyl-1,2,3,4-tetrahydro-[1,4]oxazepino[2,3-c]quinolin-6(7H)-one (Intermediate A1d; 61 mg, 0.21 mmol) and phenyl formate (25 uL, 0.23 mmol) in anhydrous $CH_2Cl_2$ (0.60 mL) was stirred at rt for 1 h. The reaction mixture was concentrated in vacuo. Purification by flash chromatography (10 g KP-sil; 0% to 10% MeOH in $CH_2Cl_2$) afforded the title compound (32 mg, 48%) as a yellow solid. LCMS (Method X2) RT 1.00 min; m/z 314.1499 [M+H]+

Intermediate A12a: 2-((R)-10-((5-chloro-2-((3S,5R)-4,4-difluoro-3,5-dimethylpiperidin-1-yl)pyrimidin-4-yl)amino)-2-cyclopropyl-6-oxo-1,3,4,6-tetrahydro-[1,4]oxazepino[2,3-c]quinolin-7(2H)-yl)acetaldehyde

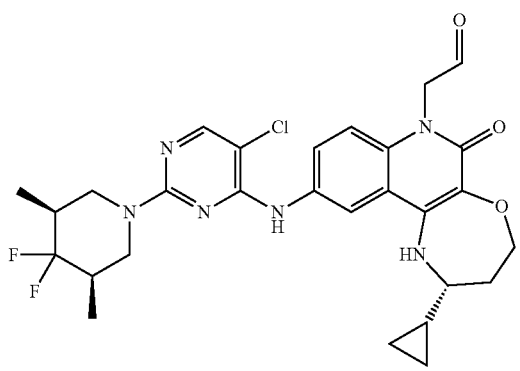 [SMILES: C[C@@H]1CN(c2ncc(Cl)c(Nc3ccc4c(c3)c3c(c(=O)n4CC=O)OCC[C@H](C4CC4)N3)n2)C[C@H](C)C1(F)F]

Step 1: (R)-2-cyclopropyl-7-(2,2-dimethoxyethyl)-10-nitro-1,2,3,4-tetrahydro-[1,4]oxazepino[2,3-c]quinolin-6(7H)-one A microwave vial (2.0-5.0 mL volume) was charged with (R)-2-cyclopropyl-10-nitro-1,2,3,4-tetrahydro-[1,4]oxazepino[2,3-c]quinolin-6(7H)-one (Intermediate A4; 69 mg, 0.23 mmol) and cesium carbonate (82 mg, 0.25 mmol). The reaction vial was flushed with Ar, sealed with a cap and then further flushed with Ar. DMF (1.5 mL) was added and the mixture was stirred at rt for 30 min. 2-bromo-1,1-dimethoxyethane (82 uL, 0.69 mmol) was added and the reaction mixture was heated at 100° C. for 3 h. After this time, additional 2-bromo-1,1-dimethoxyethan (40 uL, 0.34 mmol) was added and the reaction mixture was heated at 100° C. for a further 2 h. The reaction mixture was cooled to rt, diluted with EtOAc (15 mL) and water (10 mL) was added. The layers were separated and the aqueous mixture was extracted with EtOAc (2×15 mL). The organic extracts were combined, washed with brine (10 mL), dried ($Na_2SO_4$) and concentrated in vacuo. Purification by flash chromatography (10 g KP-sil; 60% to 100% EtOAc in cyclohexane (5 CV) followed by 0% to 3% MeOH in EtOAc (10 CV)) afforded (R)-2-cyclopropyl-7-(2,2-dimethoxyethyl)-10-nitro-1,2,3,4-tetrahydro-[1,4]oxazepino[2,3-c]quinolin-6(7H)-one (42 mg, 47%) as a dark yellow solid. $^1H$ NMR (500 MHz, methanol-$d_4$) δ 8.96 (d, J=2.5 Hz, 1H), 8.34 (dd, J=9.5, 2.5 Hz, 1H), 7.84 (d, J=9.5 Hz, 1H), 4.69 (t, J=5.3 Hz, 1H), 4.54-4.45 (m, 2H), 4.45-4.38 (m, 1H), 4.33-4.26 (m, 1H), 3.41 (s, 3H), 3.40 (s, 3H), 3.02 (dt, J=9.1, 3.9 Hz, 1H), 2.41-2.33 (m, 1H), 2.20-2.11 (m, 1H), 1.34-1.28 (m, 1H), 0.77-0.63 (m, 2H), 0.48-0.43 (m, 1H), 0.36-0.31 (m, 1H); LCMS (Method X2) RT 1.34 min; m/z 358.1378 [M−MeOH+H]+

Step 2: (R)-10-amino-2-cyclopropyl-7-(2,2-dimethoxyethyl)-1,2,3,4-tetrahydro-[1,4]oxazepino[2,3-c]quinolin-6(7H)-one A microwave vial (2.0-5.0 mL volume) was charged with (R)-2-cyclopropyl-7-(2,2-dimethoxyethyl)-10-nitro-1,2,3,4- tetrahydro-[1,4]oxazepino[2,3-c]quinolin-6(7H)-one (from step 1; 42 mg, 0.11 mmol) and 10 wt % Pd/C (5 mg). The reaction vial was flushed with Ar, sealed with a cap and then further flushed with Ar. Ethanol (1 mL) was added. The reaction mixture was stirred at 60° C. under an atmosphere of $H_2$ for 1 h. The reaction mixture was allowed to cool to rt. The reaction mixture was filtered through celite, the solids washed with EtOH (25 mL). The filtrate was concentrated in vacuo affording (R)-10-amino-2-cyclopropyl-7-(2,2-dimethoxyethyl)-1,2,3,4-tetrahydro-[1,4]oxazepino[2,3-c]quinolin-6(7H)-one (38 mg, 99%) as a yellow solid that was used without further purification. LCMS (Method X2) RT 0.89 min; m/z 328.1776 [M-MeOH+H]$^+$.

Step 3: 2-((R)-10-((5-chloro-2-((3S,5R)-4,4-difluoro-3,5-dimethylpiperidin-1-yl)pyrimidin-4-yl)amino)-2-cyclopropyl-6-oxo-1,3,4,6-tetrahydro-[1,4]oxazepino[2,3-c]quinolin-7(2H)-yl) acetaldehyde A microwave vial (0.5-2.0 mL volume) was charged with (R)-10-amino-2-cyclopropyl-7-(2,2-dimethoxyethyl)-1,2,3,4-tetrahydro-[1,4]oxazepino[2,3-c]quinolin-6(7H)-one (from step 2; 36 mg, 0.10 mmol) and 5-chloro-2-((3S,5R)-4,4-difluoro-3,5-dimethylpiperidin-1-yl)-4-(methylsulfonyl)pyrimidine (Intermediate J3; 70 mg, 0.21 mmol). Trifluoroethanol (1 mL) was added followed by trifluoroacetic acid (8.4 uL, 0.11 mmol). The reaction vial was flushed with Ar, with Ar bubbling through the reaction mixture, and sealed with a cap. The reaction mixture was heated at 60° C. in a heating block for 2 h 30 min. After this time, the cap was removed and additional 5-chloro-2-((3S,5R)-4,4-difluoro-3,5-dimethylpiperidin-1-yl)-4-(methylsulfonyl)pyrimidine (Intermediate J3; 41 mg, 0.12 mmol) and trifluoroacetic acid (8.4 uL, 0.11 mmol) were added. The vial was re-sealed and heated at 60° C. for an additional 16 h. The reaction mixture was cooled to rt, and the resulting precipitate was filtered and washed with $Et_2O$. The precipitate was identified as hydrolysed Intermediate J3. The filtrate was transferred using methanol to a microwave vial (0.5-2.0 mL volume). Trifluoroacetic acid (0.3 mL) and water (0.5 mL) were added to facilitate acetal de-protection. The reaction vial was re-sealed with a cap and heated at 60° C. in a heating block for 1 h followed by 80° C. for 1 h. The reaction mixture was cooled to rt, and concentrated in vacuo. The crude aqueous mixture was diluted with DMSO (0.8 mL) and directly purified by reverse-phase chromatography (Biotage reverse-phase 12 g C-18 column; 10-30-100% MeOH in $H_2O$ (containing 0.1% formic acid)), affording the title compound (7 mg, 11%) as an off-white solid. LCMS (Method X2) RT 1.62 min; m/z 605.2466 [M+MeOH+H]$^+$.

Intermediate B1a: (S)-10-amino-2,7-dimethyl-2,3-dihydro-[1,4]oxazepino[6,5-c]quinoline-5,6(1H,7H)-dione

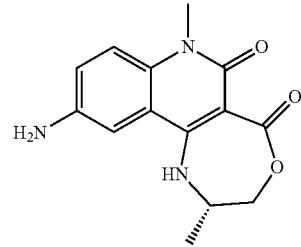

Step 1; (S)-2,7-dimethyl-10-nitro-2,3-dihydro-[1,4]oxazepino[6,5-c]quinoline-5,6(1H,7H)-dione A suspension of ethyl 4-chloro-1-methyl-6-nitro-2-oxo-1,2-dihydroquinoline-3-carboxylate (Intermediate F2; 132 mg, 0.43 mmol), (S)-2-aminopropan-1-ol (64 mg, 0.85 mmol) and DIPEA (0.15 mL, 0.85 mmol) in NMP (1.5 mL) was stirred under microwave irradiation at 160° C. for 1 h. The reaction mixture was allowed to cool to rt. The cap was removed and lithium chloride (108 mg, 2.55 mmol) was then added. The reaction vial was re-sealed with a cap and the mixture was further stirred under microwave irradiation at 160° C. for 1 h. The crude reaction mixture was directly purified by preparative HPLC (15 min gradient of 60:40 to 0:100 $H_2O$:MeOH (both modified with 0.1% formic acid); flow rate 20 mL·min$^{-1}$) affording (S)-2,7-dimethyl-10-nitro-2,3-dihydro-[1,4]oxazepino[6,5-c]quinoline-5,6(1H,7H)-dione (48 mg, 37%) as a light brown solid. $^1$H NMR (500 MHz, DMF-$d_7$) δ 9.20 (d, J=2.4 Hz, 1H), 8.48 (dd, J=9.4, 2.4 Hz, 1H), 8.20 (br s, 1H), 7.72 (d, J=9.4 Hz, 1H), 4.72 (dd, J=13.0, 1.2 Hz, 1H), 4.49 (dd, J=13.0, 5.1 Hz, 1H), 4.20 (q, J=6.4 Hz, 1H), 3.66 (s, 3H), 1.42 (d, J=6.4 Hz, 3H).

Step 2; (S)-10-amino-2,7-dimethyl-2,3-dihydro-[1,4]oxazepino[6,5-c]quinoline-5,6(1H,7H)-dione (S)-2,7-dimethyl-10-nitro-2,3-dihydro-[1,4]oxazepino[6,5-c]quinoline-5,6(1H,7H)-dione (from step 1; 48 mg, 0.16 mmol) and Pd/C (10 wt %, 3 mg) were suspended in EtOH (4 mL) under Ar. The mixture evacuated and filled with $H_2$ 3 times. The reaction mixture was stirred under an atmosphere of $H_2$ for 16 h. The reaction mixture was filtered through Celite™ and the solids washed with MeOH. The filtrate was concentrated in vacuo affording the title compound (40 mg, 92%) as a yellow oil which was used without further purification. LCMS (Method T2) RT 0.19 min; m/z 274.1 [M+H]$^+$.

The following tabulated examples were prepared by a method analogous to that used for the preparation of Intermediate B1a, starting from the amino-alcohols shown in the table.

| Intermediate | Data and comments | Amino-alcohol |
|---|---|---|
| Intermediate B1b: (S)-10-amino-2-cyclopropyl-7-methyl-2,3-dihydro-[1,4]oxazepino[6,5-c]quinoline-5,6(1H,7H)-dione | LCMS (Method T2) RT 0.53 min; m/z 300.1 [M + H]$^+$. | (S)-2-amino-2-cyclopropylethan-1-ol hydrochloride |
| Intermediate B1c: 10-amino-2-cyclopropyl-7-methyl-2,3-dihydro-[1,4]oxazepino[6,5-c]quinoline-5,6(1H,7H)-dione | LCMS (Method T2) RT 0.53 min; m/z 300.1 [M + H]$^+$. | 2-amino-2-cyclopropylethan-1-ol hydrochloride |
| Intermediate B1d: 10-amino-2,3,7-trimethyl-2,3-dihydro-[1,4]oxazepino[6,5-c]quinoline-5,6(1H,7H)-dione | LCMS (Method T2) RT 0.52 min; m/z 288.1 [M + H]$^+$. | 3-aminobutan-2-ol |

Intermediate B2a: (S)-10-amino-2,7-dimethyl-2,3,5,7-tetrahydro-[1,4]oxazepino[6,5-c]quinolin-6(1H)-one

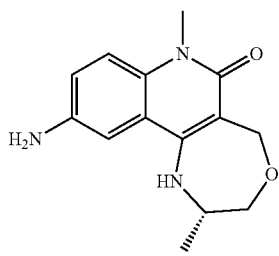 [SMILES: C[C@H]1COCc2c(c3cc(N)ccc3n(C)c2=O)N1]

Boron trifluoride diethyl etherate (~50% BF$_3$; 0.1 mL, 0.41 mmol) was added to a stirred suspension of (S)-10-amino-2,7-dimethyl-2,3-dihydro-[1,4]oxazepino[6,5-c]quinoline-5,6(1H,7H)-dione (Intermediate B1a; 12 mg, 0.042 mmol) in THF (4 mL) at 0° C. The reaction mixture was stirred at 0° C. for 15 min, after which sodium borohydride (5 mg, 0.127 mmol) was added. The reaction mixture was stirred at 0° C. for a further 2 h. The reaction was quenched with the addition of methanol. The reaction mixture was concentrated in vacuo. Brine was added to the residue and the aqueous mixture was extracted with EtOAc. The organic layer was dried (Na$_2$SO$_4$) and concentrated in vacuo. Purification by flash chromatography (10 g KP-sil; 5% MeOH in EtOAc) afforded the title compound (4 mg, 32%) as a yellow solid. $^1$H NMR (500 MHz, Methanol-d$_4$) δ 7.34 (dd, J=9.0, 1.4 Hz, 1H), 7.23 (dd, J=2.4, 1.4 Hz, 1H), 7.10 (dd, J=9.0, 2.4 Hz, 1H), 4.96 (d, J=14.4 Hz, 1H), 4.77 (d, J=14.4 Hz, 1H), 3.92 (dt, J=11.2, 2.9 Hz, 1H), 3.86 (ddt, J=12.1, 6.6, 3.0 Hz, 1H), 3.60 (s, 3H), 3.60 (ddd, J=11.2, 8.8, 2.0 Hz, 1H), 1.29 (d, J=6.6 Hz, 3H).

Intermediate B3a: ethyl 4-((1-((tert-butoxycarbonyl)amino)propan-2-yl)amino)-6-((2-chloro-3-cyanopyridin-4-yl)amino)-1-methyl-2-oxo-1,2-dihydroquinoline-3-carboxylate

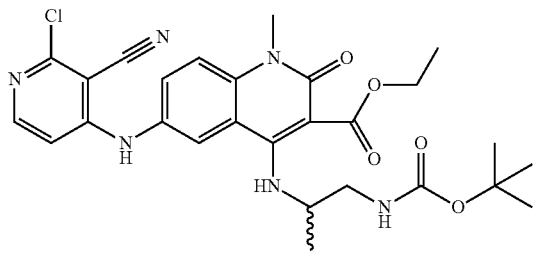 [SMILES: CCOC(=O)c1c(NC(C)CNC(=O)OC(C)(C)C)c2cc(Nc3ccnc(Cl)c3C#N)ccc2n(C)c1=O]

Step 1; ethyl 4-((1-((tert-butoxycarbonyl)amino)propan-2-yl)amino)-1-methyl-6-nitro-2-oxo-1,2-dihydroquinoline-3-carboxylate Ethyl 4-chloro-1-methyl-6-nitro-2-oxo-1,2-dihydroquinoline-3-carboxylate (Intermediate F2; 325 mg, 1.05 mmol), tert-butyl (2-aminopropyl)carbamate (200 mg, 1.15 mmol) and DIPEA (0.2 mL, 1.15 mmol) were combined in a microwave vial and dissolved in THF (5.2 mL). The reaction mixture was then heated to 100° C. for 16 h. Excess amine was added in 1 mL of THF followed by DIPEA (50 uL) and heating was continued for 2 h. The reaction mixture was cooled to rt, partitioned between EtOAC (25 mL) and water (25 mL). The aqueous layer was further extracted with EtOAc (25 mL) and the organic extracts were combined, washed with brine (50 mL), dried (MgSO$_4$) and concentrated in vacuo affording ethyl 4-((1-((tert-butoxycarbonyl)amino)propan-2-yl)amino)-1-methyl-6-nitro-2-oxo-1,2-dihydroquinoline-3-carboxylate (606 mg, 129%) as a yellow solid that was used without further purification. LCMS (Method T4); RT 2.87 min; m/z 449.2078 [M+H]$^+$. Note; The LCMS showed a mixture of the desired product and amine starting material. This mixture was carried forward assuming 100% conversion.

Step 2; ethyl 6-amino-4-((1-((tert-butoxycarbonyl)amino)propan-2-yl)amino)-1-methyl-2-oxo-1,2-dihydroquinoline-3-carboxylate Ethyl 4-((1-((tert-butoxycarbonyl)amino)propan-2-yl)amino)-1-methyl-6-nitro-2-oxo-1,2-dihydroquinoline-3-carboxylate (from step 1; 50 mg, 0.11 mmol), Pd/C (10 wt %; 1.2 mg) and ammonium formate (70 mg, 1.11 mmol) were combined in a microwave vial which was sealed and placed under an argon atmosphere by alternating vacuum and argon three times. Ethanol (0.64 mL) was then added and the reaction mixture heated to 70° C. for 2 h. The reaction mixture was filtered over Celite and the solvent removed in vacuo. The crude product was partitioned between EtOAc (20 mL) and water (20 mL). The organic layer was washed with further water (2×20 mL), then dried (MgSO$_4$) and filtered over a hydrophobic frit. The solvent was removed in vacuo affording ethyl 6-amino-4-((1-((tert-butoxycarbonyl)amino)propan-2-yl)amino)-1-methyl-2-oxo-1,2-dihydroquinoline-3-carboxylate (44 mg, 94%) as a green oil which was used without further purification. LCMS (Method T2); RT 1.23 min; m/z 419.2728 [M+H]$^+$.

Step 3; ethyl 4-((1-((tert-butoxycarbonyl)amino)propan-2-yl)amino)-6-((2-chloro-3-cyanopyridin-4-yl)amino)-1-methyl-2-oxo-1,2-dihydroquinoline-3-carboxylate Ethyl 6-amino-4-((1-((tert-butoxycarbonyl)amino)propan-2-yl)amino)-1-methyl-2-oxo-1,2-dihydroquinoline-3-carboxylate (from step 2; 50 mg, 0.12 mmol), 2,4-dichloronicotinonitrile (21 mg, 0.12 mmol) and DIPEA (62 uL, 0.36 mmol) were combined in a microwave vial and dissolved in NMP (1 mL). The reaction mixture was heated at 110° C. under microwave irradiation for 90 min, followed by heating at 110° C. in a heating block for a further 8 h. The reaction mixture was cooled to rt, and trifluoroacetic acid (183 uL, 2.39 mmol) was added and the reaction mixture was stirred at 70° C. for 30 min. The reaction mixture was cooled to rt, and DIPEA (0.5 mL) was added. The reaction mixture was stirred at 70° C. for 4 h. The reaction mixture was cooled to rt and partitioned between EtOAc (20 mL) and water (20 mL). The aqueous layer was extracted once with EtOAc (20 mL) and the organic extracts were combined, washed twice with brine, dried (MgSO$_4$), and concentrated in vacuo affording the title compound (62 mg, 94%) as a brown oil which was used without further purification. LCMS (Method T4); RT 2.91 min; m/z 555.211 [M+H]$^+$.

Intermediate C1: 9-amino-2,6-dimethyl-2,3,4,6-tetrahydrobenzo[h][1,6]naphthyridin-5(1H)-one

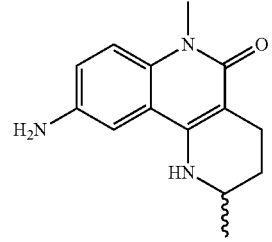 [SMILES: CC1CCc2c(c3cc(N)ccc3n(C)c2=O)N1]

Step 1; 4-((4-hydroxybutan-2-yl)amino)-1-methyl-6-nitroquinolin-2(1H)-one

A mixture of 4-chloro-1-methyl-6-nitroquinolin-2(1H)-one (Intermediate F1; 250 mg, 1.05 mmol) and 3-aminobutan-1-ol (280 mg, 3.14 mmol) and DIPEA (0.36 mL, 2.10 mmol) in NMP (1.9 mL) was stirred at 160° C. for 20 h. The reaction mixture was allowed to cool to rt. The reaction mixture was diluted with water and extracted with EtOAc. The organic extracts were combined, washed with water and brine, dried (Na$_2$SO$_4$) and concentrated in vacuo. Purification by flash chromatography (50 g KP-sil; 0% to 10% MeOH in CH$_2$Cl$_2$, afforded 4-((4-hydroxybutan-2-yl)amino)-1-methyl-6-nitroquinolin-2(1H)-one (200 mg, 66%). $^1$H NMR (500 MHz, CDCl$_3$) δ 8.48 (d, J=2.5 Hz, 1H), 8.36 (dd, J=9.3, 2.5 Hz, 1H), 7.38 (d, J=9.3 Hz, 1H), 6.05 (d, J=6.6 Hz, 1H), 5.80 (s, 1H), 4.10-3.97 (m, 1H), 3.96-3.82 (m, 2H), 3.68 (s, 3H), 2.08-1.95 (m, 2H), 1.89 (dtd, J=14.8, 6.3, 3.5 Hz, 1H), 1.35 (d, J=6.4 Hz, 3H). LCMS (Method T2) RT 1.21 min, m/z 292.13 [M+H]$^+$.

Step 2; 3-((1-methyl-6-nitro-2-oxo-1,2-dihydroquinolin-4-yl)amino)butyl 4-methylbenzenesulfonate Tosyl chloride (61 mg, 0.32 mmol) was added to a stirred solution of 4-((4-hydroxybutan-2-yl)amino)-1-methyl-6-nitroquinolin-2(1H)-one (from step 1; 100 mg, 0.34 mmol) and pyridine (3 mL, 37.2 mmol) in CH₂Cl₂ (3.43 mL) at 0° C. The reaction mixture was warmed to rt and stirred at that temperature for 20 h. The mixture was diluted with water and extracted with CH₂Cl₂. The organic extracts were combined, washed with 10% citric acid solution, dried (MgSO₄) and concentrated in vacuo. Purification by flash chromatography (25 g KP-sil; 60% to 80% EtOAc in cyclohexane) afforded 3-((1-methyl-6-nitro-2-oxo-1,2-dihydroquinolin-4-yl)amino)butyl 4-methylbenzenesulfonate (68 mg, 44%) as a yellow solid. ¹H NMR (500 MHz, CDCl₃) δ 8.43 (d, J=2.4 Hz, 1H), 8.39 (dd, J=9.3, 2.4 Hz, 1H), 7.77 (d, J=8.2 Hz, 2H), 7.41 (d, J=9.3 Hz, 1H), 7.28 (d, J=8.2 Hz, 2H), 5.74 (s, 1H), 4.77 (d, J=7.8 Hz, 1H), 4.22 (t, J=5.9 Hz, 2H), 3.77 (app. hept, J=6.7 Hz, 1H), 3.69 (s, 3H), 2.38 (s, 3H), 2.09-2.02 (m, 2H), 1.32 (d, J=6.5 Hz, 3H). LCMS (Method T2) RT 1.42 min, m/z 446.14 [M+H]⁺.

Step 3; 2,6-dimethyl-9-nitro-2,3,4,6-tetrahydrobenzo[h][1,6]naphthyridin-5(1H)-one A mixture of 3-[(1-methyl-6-nitro-2-oxo-4-quinolyl)amino]butyl 4-methylbenzenesulfonate (from step 2; 34 mg, 0.076 mmol) and DIPEA (40 uL, 0.23 mmol) in NMP (0.76 mL) was heated at 160° C. under microwave irradiation for 1 h. The reaction mixture was allowed to cool to rt. The reaction mixture was diluted with water and extracted with EtOAc. The organic extracts were combined, washed with water and brine, dried (MgSO₄), and concentrated in vacuo. Purification by flash chromatography (10 g KP-sil; 0% to 10% MeOH in CH₂Cl₂) afforded 2,6-dimethyl-9-nitro-2,3,4,6-tetrahydrobenzo[h][1,6]naphthyridin-5(1H)-one (14 mg, 67%) as an orange solid. LCMS (Method T2) RT 1.36 min, m/z 274.12 [M+H]⁺.

Step 4; 9-amino-2,6-dimethyl-2,3,4,6-tetrahydrobenzo[h][1,6]naphthyridin-5(1H)-one To a solution of 2,6-dimethyl-9-nitro-2,3,4,6-tetrahydrobenzo[h][1,6]naphthyridin-5(1H)-one (from step 3; 14 mg, 0.051 mmol) in ethanol (1 mL) and NMP (0.2 mL) in a 0.5-2.0 mL microwave vial was added Pd/C (10 wt %, 2.7 mg) followed by ammonium formate (32 mg, 0.51 mmol). The vial was sealed with a cap and evacuated then refilled with Ar three times. The reaction mixture was heated at 60° C. in a heating block for 30 min. The reaction mixture was allowed to cool to rt, filtered through Celite™ loaded onto an SCX-2 (2 g) column, eluting with MeOH (20 mL) followed by 2 N methanolic ammonia (20 mL). The methanolic ammonia fraction was concentrated in vacuo affording the title compound (16 mg, 100%) as a yellow oil (some residual NMP was present). LCMS (Method T2) RT 0.62 min, m/z 244.1443 [M+H]⁺.

Intermediate D1a: (R)-3-amino-3-cyclopropylpropan-1-ol

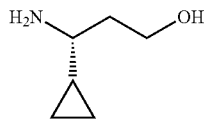

Lithium aluminium hydride (1 M in THF; 18.6 mL, 18.6 mmol) was added dropwise to a stirred suspension of ethyl (R)-3-amino-3-cyclopropylpropanoate hydrochloride (3.00 g, 15.5 mmol) in diethyl ether (50 mL) at 0° C. under Ar. The reaction mixture was stirred at 0° C. for 90 min. The reaction mixture was quenched with the addition of water (0.7 mL) followed by 15% aq. sodium hydroxide (0.7 mL) and water (2.1 mL). The quenched reaction mixture was stirred at rt for 1 h. The resulting aluminium precipitates were filtered through Celite™, and the solid was washed with Et₂O (200 mL). The filtrate was concentrated in vacuo affording the title compound (1.78 g, 100%) as a yellow oil that was used without further purification. ¹H NMR (500 MHz, MeOD-d₄) δ 3.75-3.66 (m, 2H), 2.10-2.04 (m, 1H), 1.84-1.76 (m, 1H), 1.73-1.65 (m, 1H), 0.79-0.71 (m, 1H), 0.53-0.44 (m, 2H), 0.25-0.18 (m, 2H).

The following tabulated examples were prepared by a method analogous to that used for the preparation of Intermediate D1a, starting from the amines shown in the table.

| Intermediate | Data and comments | Amine |
|---|---|---|
| Intermediate D1b: (S)-3-amino-3-cyclopropylpropan-1-ol 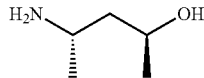 | ¹H NMR (500 MHz, DMSO-d₆) δ 3.56-3.50 (m, 2 H), 3.32 (br s, 2 H), 2.09-2.04 (m, 1 H), 1.62-1.56 (m, 2 H), 1.50-1.42 (m, 1 H), 0.70-0.64 (m, 1 H), 0.37-0.29 (m, 2 H), 0.15-0.10 (m, 2 H). | ethyl (S)-3-amino-3-cyclopropylpropanoate hydrochloride |

Intermediate E1: (2S,4S)-4-aminopentan-2-ol

Step 1; tert-butyl (S)-(4-(methoxy(methyl)amino)-4-oxobutan-2-yl)carbamate

DIPEA (0.76 mL, 4.36 mmol) followed by T3P (50 wt % in EtOAc, 1.17 g, 1.845 mmol) and N,O-dimethylhydroxylamine hydrochloride (214 mg, 2.20 mmol) were added sequentially to a solution of Boc-L-β-homoalanine (296 mg, 1.45 mmol) in DMF under Ar. The reaction mixture was stirred at rt for 68 h. Water (20 mL) was added and the aqueous mixture was stirred for 1 h, then extracted with EtOAc (3×5 mL). The organic extracts were combined, dried (Na₂SO₄) and concentrated in vacuo. Purification by flash chromatography (25 g KP-sil; 10% to 80% EtOAc in cyclohexane) afforded tert-butyl (S)-(4-(methoxy(methyl)amino)-4-oxobutan-2-yl)carbamate (341 mg, 95%) as a pale yellow oil. $R_f$=0.24 (50% EtOAc in cyclohexane); $^1$H NMR (500 MHz, CDCl$_3$) δ 5.32 (br s, 1H), 4.10-4.02 (m, 1H), 3.69 (s, 3H), 3.18 (s, 3H), 2.71 (dd, J=15.6, 4.8 Hz, 1H), 2.55 (dd, J=15.6, 4.4 Hz, 1H), 1.44 (s, 9H), 1.25 (d, J=6.7 Hz, 3H).

Step 2; tert-butyl (S)-(4-oxopentan-2-yl)carbamate

Methylmagnesium bromide (3 M in Et$_2$O; 0.46 mL, 1.38 mmol) was added dropwise to a stirred solution of tert-butyl (S)-(4-(methoxy(methyl)amino)-4-oxobutan-2-yl)carbamate (from step 1; 341 mg, 1.38 mmol) in THF (4.5 mL) at −15° C. under Ar. After stirring at this temperature for 15 min, additional methylmagnesium bromide (3 M in Et$_2$O; 0.57 mL, 1.71 mmol) was added dropwise to the reaction mixture at −15° C. The reaction mixture was then allowed to warm to rt and stirred at that temperature for 2 h. The reaction mixture was cooled to 0° C. and saturated aq. NH$_4$Cl (10 mL) was added. The aqueous mixture was extracted with EtOAc (3×15 mL). The organic extracts were combined, dried (Na$_2$SO$_4$) and concentrated in vacuo. Purification by flash chromatography (10 g KP-sil; 0% to 70% EtOAc in cyclohexane) afforded tert-butyl (S)-(4-oxopentan-2-yl)carbamate (149 mg, 54%) as a white solid. $R_f$=0.58 (70% EtOAc in cyclohexane); $^1$H NMR (500 MHz, CDCl$_3$) δ 4.84 (br s, 1H), 4.07-3.97 (m, 1H), 2.70 (dd, J=16.5, 5.3 Hz, 1H), 2.57 (dd, J=16.5, 6.3 Hz, 1H), 2.16 (s, 3H), 1.44 (s, 9H), 1.20 (d, J=6.7 Hz, 3H).

Step 3; tert-butyl ((2S,4S)-4-hydroxypentan-2-yl) carbamate and tert-butyl ((2S,4R)-4-hydroxypentan-2-yl)carbamate Sodium borohydride (36 mg, 0.96 mmol) was added portionwise to a stirred solution of tert-butyl (S)-(4-oxopentan-2-yl)carbamate (from step 2; 149 mg, 0.74 mmol) in anhydrous ethanol (5 mL) at 0° C. under Ar. The reaction mixture was stirred at 0° C. for 5 min, then warmed to rt and stirred for 2 h. Additional sodium borohydride (40 mg, 1.06 mmol) was added and the reaction mixture was stirred at rt for a further 20 min. Saturated aq. NH$_4$Cl (10 mL) was added. The aqueous mixture was extracted with EtOAc (3×15 mL). The organic extracts were combined, dried (Na$_2$SO$_4$) and concentrated in vacuo. The crude reaction mixture was dry-loaded onto silica and purified by flash chromatography (10 g KP-sil; 30% to 80% EtOAc in cyclohexane) affording tert-butyl ((2S,4S)-4-hydroxypentan-2-yl)carbamate (82 mg, 55%) as a white crystalline solid followed by tert-butyl ((2S,4R)-4-hydroxypentan-2-yl)carbamate (68 mg, 45%) as a white crystalline solid. (2S,4S)-4-hydroxypentan-2-yl)carbamate; $R_f$=0.66 (70% EtOAc in cyclohexane); $^1$H NMR (500 MHz, CDCl$_3$) δ 4.51 (br s, 1H), 3.92 (br s, 1H), 3.86-3.75 (m, 1H), 3.74-3.40 (br s, 1H), 1.57-1.50 (m, 1H), 1.46 (s, 9H), 1.35-1.28 (m, 1 H), 1.19 (d, J=6.0 Hz, 3H), 1.18 (d, J=6.4 Hz, 3H); tert-butyl ((2S,4R)-4-hydroxypentan-2-yl)carbamate; $R_f$=0.51 (70% EtOAc in cyclohexane)$^1$H NMR (500 MHz, CDCl$_3$) δ 3.96-3.88 (m, 1H), 3.82-3.72 (m, 1H), 1.63-1.57 (m, 1H), 1.55-1.49 (m, 1H), 1.45 (s, 9H), 1.22 (d, J=6.3 Hz, 3H), 1.18 (d, J=6.6 Hz, 3H).

Step 4; (2S,4S)-4-aminopentan-2-ol

Trifluoroacetic acid (1 mL, 13 mmol) was added dropwise to a solution of tert-butyl ((2S,4S)-4-hydroxypentan-2-yl) carbamate (from step 3; 82 mg, 0.40 mmol) in anhydrous CH$_2$Cl$_2$ (4 mL) at 0° C. under Ar. The reaction mixture was allowed to warm to rt over 2 h. The reaction mixture was concentrated in vacuo and the resulting residue was diluted with CH$_2$Cl$_2$ (10 mL) and concentrated in vacuo. The crude product was passed through an SCX-2 column (2 g), eluting with MeOH (20 mL) followed by 2 M methanolic ammonia (30 mL). The ammonia fractions were collected and concentrated in vacuo affording the title compound (31 mg, 74%) as a pale yellow oil that was used without further purification. LCMS (Method T4) RT 0.20 min; m/z 104.1080 [M+H]$^+$.

Intermediate F1:
4-chloro-1-methyl-6-nitroquinolin-2(1H)-one

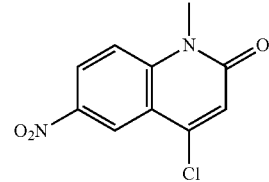 [SMILES: Cn1c(=O)cc(Cl)c2cc([N+](=O)[O-])ccc21]

Step 1; 4-chloroquinolin-2(1H)-one

To a stirred solution of 2,4-dichloroquinoline (24.9 g, 126 mmol) in 1,4-dioxane (126 mL) was added conc. HCl (83.8 mL, 1.01 mol) dropwise. The reaction mixture was refluxed for 18 h. The mixture was cooled to room temperature, poured into excess ice water and allowed to stir for 1 h. The precipitate was filtered and dried under vacuum to afford 4-chloroquinolin-2(1H)-one (19.2 g, 85%) as an off-white solid. LCMS (Method T2) RT 1.25 min; m/z 180.03 [M+H]$^+$.

Step 2; 4-chloro-6-nitroquinolin-2(1H)-one

A mixture of 4-chloro-1H-quinolin-2-one (from step 1; 17.8 g, 98.9 mmol) in sulfuric acid (52.7 mL, 989 mmol) was cooled to 0° C. Nitric acid (70%) (9.9 mL, 109 mmol) was added dropwise. The solution was stirred at 0° C. for 1 h and then poured onto ice water. The yellow precipitate that formed was filtered and washed with water, methanol, ethyl acetate and diethyl ether before being stirred under vacuum at 120° C. for approx. 10 min affording 4-chloro-6-nitroquinolin-2(1H)-one (21.5 g, 97%) as a pale yellow solid. LCMS (Method T2) RT 1.27 min; m/z 225.01 [M+H]$^+$.

Step 3;
4-chloro-1-methyl-6-nitroquinolin-2(1H)-one

Sodium hydride (60% in mineral oil; 2.6 g, 63.9 mmol) was added portionwise to a stirred solution of 4-chloro-6-nitroquinolin-2(1H)-one (from step 2; 7.1 g, 31.7 mmol) in DMF (60 mL) at 0° C. The reaction mixture was stirred at 0° C. for 10 min, after which iodomethane (3 mL, 48.2 mmol) was added dropwise. The reaction mixture was stirred at rt for 75 min. Water (80 mL) was added and the aqueous mixture was stirred for 20 min. The resulting yellow precipitate was filtered, washed with water (2×100 mL), Et$_2$O (2×50 mL) and dried affording the title compound (6.1 g, 81%) as a yellow solid. LCMS (Method T2) RT 1.30 min; m/z 239.02 [M+H]$^+$.

Intermediate F2: ethyl 4-chloro-1-methyl-6-nitro-2-oxo-1,2-dihydroquinoline-3-carboxylate

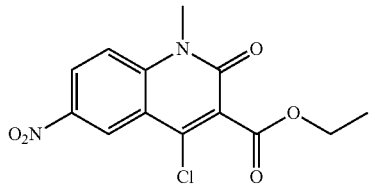 [SMILES: CCOC(=O)c1c(Cl)c2cc([N+](=O)[O-])ccc2n(C)c1=O]

Step 1; 1-methyl-6-nitro-2H-benzo[d][1,3]oxazine-2,4(1H)-dione

To a solution of 5-nitro-isatoic anhydride (25.1 g, 120.6 mmol) in DMF (241 mL) at rt was added sodium hydride (60% in mineral oil; 7.24 g, 180.9 mmol). The solution was allowed to stir for 15 min with warming to RT. Iodomethane (18.8 mL, 301.5 mmol) was added and the mixture was stirred at rt for 4 h. The reaction mixture was poured onto ice, the resulting precipitate filtered and washed with water (5 litres). The solid was collected and dried under vacuum overnight affording 1-methyl-6-nitro-2H-benzo[d][1,3]oxazine-2,4(1H)-dione (19.7 g, 73%) as an orange powder. LCMS (Method T2) RT 1.35 min, m/z 211.069 [M+MeOH—$CO_2$]$^+$.

Step 2; ethyl 4-hydroxy-1-methyl-6-nitro-2-oxo-1,2-dihydroquinoline-3-carboxylate To a solution of 1-methyl-6-nitro-2H-benzo[d][1,3]oxazine-2,4(1H)-dione (from step 1; 19.6 g, 88.2 mmol) in DMF (177 mL) was added diethyl malonate (40.4 mL, 264.7 mmol). The solution was cooled to 0° C., then Sodium hydride (60% in mineral oil) (7.06 g, 176.46 mmol) was added in 4 portions over 30 min. The solution was allowed to warm to rt and stirred at that temperature for 3 h. Water was added with care to the reaction mixture followed by 10% aq. HCl until the pH of the mixture was pH5. The resulting precipitate was filtered through a sinter funnel and washed with water (5 litres). The resulting solid was transferred to a round bottom flask and dried under vacuum affording ethyl 4-hydroxy-1-methyl-6-nitro-2-oxo-1,2-dihydroquinoline-3-carboxylate (24.2 g, 94%) as a pale yellow solid. LCMS (Method T2) RT 1.45 min; m/z 293.074 [M+H]$^+$.

Step 3; ethyl 4-chloro-1-methyl-6-nitro-2-oxo-1,2-dihydroquinoline-3-carboxylate Phosphorus oxychloride (250 mL, 2700 mmol) was added to a flask containing ethyl 4-hydroxy-1-methyl-6-nitro-2-oxo-1,2-dihydroquinoline-3-carboxylate (24.1 g, 82.5 mmol). The flask was fitted with a suba-seal and an argon balloon then heated to 80° C. with stirring for 2.5 h. The mixture was concentrated in vacuo. The residue was diluted with water and extracted with EtOAc. The combined organic extracts were washed with brine, dried (MgSO4) and concentrated in vacuo. Purification by flash chromatography (340 g KP-sil; 0% to 10% MeOH in $CH_2Cl_2$) afforded the title compound (14.5 g, 57%) as a dark orange solid. $^1$H NMR (500 MHz, CDCl$_3$) δ 8.95 (d, J=2.5 Hz, 1H), 8.50 (dd, J=9.3, 2.5 Hz, 1H), 7.53 (d, J=9.3 Hz, 1H), 4.48 (q, J=7.1 Hz, 2H), 3.78 (s, 3H), 1.42 (t, J=7.1 Hz, 3H); LCMS (Method T2) RT 1.42 min; m/z 311.043 [M+H]$^+$.

Intermediate F3: ethyl 4-chloro-6-nitro-2-oxo-1,2-dihydroquinoline-3-carboxylate

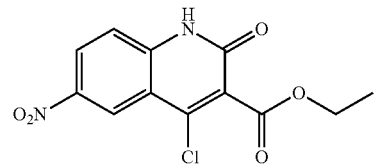 [SMILES: CCOC(=O)c1c(Cl)c2cc([N+](=O)[O-])ccc2[nH]c1=O]

Step 1; ethyl 4-hydroxy-6-nitro-2-oxo-1,2-dihydroquinoline-3-carboxylate

Sodium hydride (60 wt % in mineral oil; 1.93 g, 48.2 mmol) was added in 3 portions over 30 min to a solution of diethyl malonate (11.0 mL, 72.5 mmol) and 5-nitro-isatoic anhydride (5.03 g, 24.2 mmol) in DMF (80.0 mL) at 0° C. under Ar. The reaction mixture was allowed to warm to 25° C. and stirred for 3 d. The reaction mixture was cooled to 0° C. and water (150 mL) was added. The aqueous mixture was neutralised to pH 7 using 10% HCl and the resulting mixture was stirred at rt for 30 min. The resulting yellow precipitate was filtered and washed with water (200 mL). The filtrate was further acidified to pH 5 using 10% HCl and more precipitate formed. The additional yellow precipitate was filtered and dried under vacuum affording ethyl 4-hydroxy-6-nitro-2-oxo-1,2-dihydroquinoline-3-carboxylate (6.29 g, 93%) as a pale yellow solid. LCMS (Method T2) RT 1.42 min; m/z 279.061 [M+H]$^+$.

Step 2; ethyl 2,4-dichloro-6-nitroquinoline-3-carboxylate

Phosphorus oxychloride (50 mL, 534.8 mmol) was added to a flask containing ethyl 4-hydroxy-6-nitro-2-oxo-1,2-dihydroquinoline-3-carboxylate (from step 1; 6.29 g, 22.6 mmol). The flask was fitted with a reflux condenser, suba-seal and an argon balloon then heated to 80° C. with stirring for 4 h. The reaction mixture was cooled to rt and concentrated in vacuo. The crude reaction mixture was dissolved in EtOAc (100 mL) and washed with water (2×50 mL) and saturated aq. NaHCO$_3$ (50 mL). The organic layer was dried (Na$_2$SO$_4$) and concentrated in vacuo affording ethyl 2,4-dichloro-6-nitroquinoline-3-carboxylate (5.12 g, 72%) as a yellow solid which was used without further purification. LCMS (Method T2) RT 1.58 min; m/z 314.995 [M+H]$^+$.

Step 3; ethyl 4-chloro-6-nitro-2-oxo-1,2-dihydroquinoline-3-carboxylate

A mixture of ethyl 2,4-dichloro-6-nitroquinoline-3-carboxylate (from step 2; 5.12 g, 16.3 mmol) and sodium acetate (1.48 g, 18.0 mmol) in acetic acid (30 mL) was heated at 120° C. for 8 h. The reaction mixture was cooled to rt and water (100 mL) was added. The precipitate was filtered, washed with water (200 mL) and dried, affording the title compound (4.02 g, 83%) as a pale yellow solid. $^1$H NMR (500 MHz, DMSO-d$_6$) δ 13.00 (s, 1H), 8.67 (d, J=2.5 Hz, 1H), 8.50 (dd, J=9.1, 2.5 Hz, 1H), 7.56 (d, J=9.1 Hz, 1H), 4.38 (q, J=7.1 Hz, 2H), 1.32 (t, J=7.1 Hz, 3H); LCMS (Method T2) RT 1.42 min; m/z 297.027 [M+H]⁺.

Intermediate F4: ethyl 4,6-dichloro-1-methyl-2-oxo-1,2-dihydro-1,8-naphthyridine-3-carboxylate

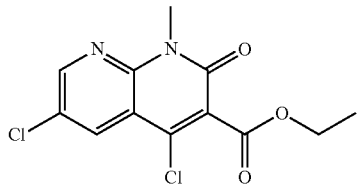 [SMILES: CCOC(=O)c1c(Cl)c2cc(Cl)cnc2n(C)c1=O]

Step 1; methyl 5-chloro-2-(methylamino)nicotinate

A microwave vial (10-20 mL volume) was charged with methyl 5-chloro-2-fluoronicotinate (404 mg, 2.1 mmol). The reaction vial was flushed with Ar, sealed with a cap and then further flushed with Ar. Anhydrous THF (6 mL) was added followed by methylamine (2 M in THF; 5 mL, 10 mmol). The reaction mixture was stirred at 40° C. for 5 h. The reaction mixture was concentrated in vacuo. The residue was diluted with water (10 mL) and extracted with EtOAc (2×15 mL). The organic extracts were combined, washed with brine (10 mL), dried (Na2SO4) and concentrated in vacuo. Purification by flash chromatography (10 g KP-sil; 0% to 30% EtOAc in cyclohexane) afforded methyl 5-chloro-2-(methylamino)nicotinate (378 mg, 88%) as a white solid. $^1$H NMR (500 MHz, CDCl$_3$) δ 8.25 (d, J=2.7 Hz, 1H), 8.07 (d, J=2.7 Hz, 1H), 7.87 (br s, 1H), 3.88 (s, 3H), 3.05 (d, J=4.9 Hz, 3H); LCMS (Method T2) RT 1.40 min; m/z 201.052 [M+H]⁺.

Step 2; ethyl 6-chloro-4-hydroxy-1-methyl-2-oxo-1,2-dihydro-1,8-naphthyridine-3-carboxylate A microwave vial (2.0-5.0 mL volume) was charged with methyl 5-chloro-2-(methylamino)nicotinate (from step 1; 378 mg, 1.9 mmol). The reaction vial was flushed with Ar, sealed with a cap and then further flushed with Ar. Anhydrous CH$_2$Cl$_2$ (7 mL) was added followed by ethyl 3-chloro-3-oxopropanoate (0.37 mL, 2.9 mmol) and triethylamine (0.53 mL, 3.8 mmol). The reaction mixture was heated at 60° C. in a heating block for 2 h. Additional ethyl 3-chloro-3-oxo-propanoate (0.37 mL, 2.9 mmol) and triethylamine (0.53 mL, 3.8 mmol) were added and the reaction mixture was stirred at 60° C. for a further 1 h. The reaction mixture was concentrated in vacuo. Water (20 mL) was added, followed by 10% aq. HCl (10 mL). The aqueous mixture was extracted with EtOAc (3×20 mL). The organic extracts were combined, washed with brine (10 mL), dried (Na$_2$SO$_4$) and concentrated in vacuo. Purification by flash chromatography (10 g KP-sil; 0% to 10% MeOH in CH$_2$Cl$_2$) afforded ethyl 6-chloro-4-hydroxy-1-methyl-2-oxo-1,2-dihydro-1,8-naphthyridine-3-carboxylate (378 mg, 71%) as a pale yellow solid. $^1$H NMR (500 MHz, DMSO-d$_6$) δ 8.77 (d, J=2.5 Hz, 1H), 8.42 (d, J=2.5 Hz, 1H), 4.30 (q, J=7.1 Hz, 2H), 3.58 (s, 3H), 1.29 (t, J=7.1 Hz, 3H); LCMS (Method T2) RT 1.53 min; m/z 283.057 [M+H]⁺

Step 3; ethyl A6-dichloro-1-methyl-2-oxo-1,2-dihydro-1,8-naphthyridine-3-carboxylate Phosphorus oxychloride (4 mL, 42.8 mmol) was added to a flask containing ethyl 6-chloro-4-hydroxy-1-methyl-2-oxo-1,2-dihydro-1,8-naphthyridine-3-carboxylate (from step 2; 378 mg, 1.3 mmol). The flash was fitted with a reflux condenser with a suba-seal and an argon balloon then heated to 80° C. with stirring for 1 h. The reaction mixture was cooled to rt and concentrated in vacuo. The crude reaction mixture was dissolved in EtOAc (20 mL) and washed with water (2×10 mL) and saturated aq. NaHCO$_3$ (10 mL). The aqueous washings were combined and extracted with EtOAc (20 mL). The organic extracts were combined, washed with brine (10 mL), dried (Na$_2$SO$_4$) and concentrated in vacuo. Purification by flash chromatography attempted (10 g KP-sil; 20-80% EtOAc in cyclohexane) afforded the title compound (207 mg, 51%) as a yellow solid. $^1$H NMR (500 MHz, DMSO-d$_6$) δ 8.87 (d, J=2.5 Hz, 1H), 8.46 (d, J=2.5 Hz, 1H), 4.38 (q, J=7.1 Hz, 2H), 3.67 (s, 3H), 1.31 (t, J=7.1 Hz, 3H); LCMS (Method T2) RT 1.48 min; m/z 302.020 [M+H]⁺

Intermediate G1: (S)-(4,5-dichloropyridin-2-yl)(2-(methoxymethyl)pyrrolidin-1-yl)-methanone

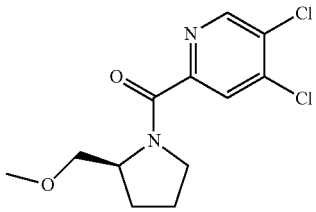 [SMILES: COC[C@@H]1CCCN1C(=O)c1cc(Cl)c(Cl)cn1]

A mixture of HATU (155 mg, 0.41 mmol), 4,5-dichloropicolinic acid (39 mg, 0.20 mmol) and (S)-2-(methoxymethyl)pyrrolidine (117 mg, 1.02 mmol) was stirred at 25° C. for 16 h. The crude reaction mixture was directly purified by preparative HPLC (15 min gradient of 60:40 to 0:100 H$_2$O:MeOH (both modified with 0.1% formic acid); flow rate 20 mLmin⁻¹) affording the title compound (39 mg, 66%) as a colourless oil that existed as a mixture of rotamers. Rotamer A $^1$H NMR (500 MHz, Methanol-d$_4$) δ 8.71 (s, 1H), 7.96 (s, 1H), 4.44-4.38 (m, 1H), 3.82-3.75 (m, 1H), 3.68-3.64 (m, 2H), 3.40 (s, 3H), 2.14-1.96 (m, 5H). Rotamer B: $^1$H NMR (500 MHz, Methanol-d$_4$) δ 8.69 (s, 1H), 7.95 (s, 1H), 4.85-4.78 (m, 1H), 3.75-3.69 (m, 1H), 3.63-3.58 (m, 2H), 3.17 (s, 3H), 2.14-1.96 (m, 4H), 1.94-1.80 (m, 1H). LCMS (Method T2) Rt=1.39 min; m/z 289.1 [M+H]⁺.

Intermediate H1: 5-chloro-4-iodo-2-((tetrahydro-2H-pyran-4-yl)oxy)pyridine

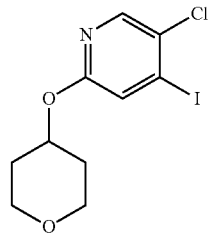 [SMILES: Clc1cnc(OC2CCOCC2)cc1I]

Sodium hydride (60% in mineral oil; 103 mg, 2.56 mmol) was added to a suspension of tetrahydro-2H-pyran-4-ol (262 mg, 2.56 mmol) in THF (10 mL) at 0° C. The reaction mixture was stirred at 0° C. for 10 min, then rt for 15 min, after which 5-chloro-2-fluoro-4-iodopyridine (550.0 mg, 2.137 mmol) was added. The resulting solution was stirred at rt for 16 h. The crude reaction mixture was concentrated in vacuo and a portion of this was purified by preparative HPLC (15 min gradient of 60:40 to 0:100 H₂O:MeOH (both modified with 0.1% formic acid); flow rate 20 mLmin⁻¹) affording the title compound (63 mg) as a white crystalline solid. ¹H NMR (500 MHz, Methanol-d₄) δ 8.13 (s, 1H), 7.39 (s, 1H), 5.18 (tt, J=8.5, 4.0 Hz, 1H), 3.95 (dt, J=11.8, 4.6 Hz, 2H), 3.60 (ddd, J=11.8, 9.0, 3.0 Hz, 2H), 2.22-1.97 (m, 2H), 1.74 (dtd, J=13.0, 8.5, 4.0 Hz, 2H). LCMS (Method T2) RT 1.60 min; m/z 340.0 [M+H]⁺.

Intermediate 11: (2S,6R)-2,6-dimethyl-4-(4,5,6-trichloropyrimidin-2-yl)morpholine

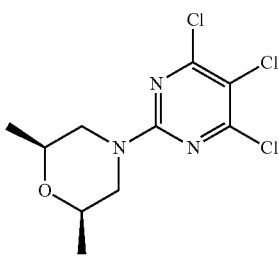 [SMILES: C[C@@H]1CN(c2nc(Cl)c(Cl)c(Cl)n2)C[C@H](C)O1]

Step 1; (2S,6R)-4-(5-chloro-4,6-dimethoxypyrimidin-2-yl)-2,6-dimethylmorpholine

A mixture of 2-chloro-4,6-dimethoxypyrimidine (1.05 g, 6.0 mmol), (2S,6R)-2,6-dimethylmorpholine (0.78 mL, 6.3 mmol) and triethylamine (0.84 mL, 6.0 mmol) in NMP (12.0 mL) was sealed in a vial then heated at 140° C. under microwave irradiation for 2 h. The reaction mixture was cooled to rt, and N-chlorosuccinimide (1.60 g, 12.0 mmol) was added and the mixture was stirred at 60° C. overnight. The mixture was poured into water forming a brown precipitate which was collected under vacuum filtration. The aqueous filtrate was extracted with EtOAc and combined with the solid obtained earlier. The mixture was loaded onto silica and purified by flash chromatograph (50 g KP-sil; 10-30% EtOAc in cyclohexane) afforded (2S,6R)-4-(5-chloro-4,6-dimethoxypyrimidin-2-yl)-2,6-dimethylmorpholine (916 mg, 53%) as a white solid. ¹H NMR (500 MHz, CDCl₃) δ 4.47-4.43 (m, 2H), 3.95 (s, 6H), 3.62 (dqd, J=10.6, 6.2, 2.5 Hz, 2H), 2.55 (dd, J=13.3, 10.6 Hz, 2H), 1.25 (d, J=6.2 Hz, 6H); LCMS (Method T2) RT 1.62 min; m/z 288.32 [M+H]⁺.

Step 2; 5-chloro-2-((2S,6R)-2,6-dimethylmorpholino)pyrimidine-4,6-diol

A mixture of (2S,6R)-4-(5-chloro-4,6-dimethoxypyrimidin-2-yl)-2,6-dimethylmorpholine (from step 1; 624 mg, 2.2 mmol) and HCl (32% aq. solution; 10.0 mL, 2.2 mmol) was stirred at 60° C. overnight. The suspension was diluted with water and filtered. A precipitate formed in the filtrate, so was passed though the filter pad once more affording 5-chloro-2-((2S,6R)-2,6-dimethylmorpholino)pyrimidine-4,6-diol (475 mg, 84%) as a white solid. LCMS (Method T2) RT 0.76 min; m/z 260.0848 [M+H]⁺.

Step 3: (2S,6R)-2,6-dimethyl-4-(4,5,6-trichloropyrimidin-2-yl)morpholine

Phosphorus oxychloride (2.0 mL, 21.4 mmol) was added to 5-chloro-2-((2S,6R)-2,6-dimethylmorpholino)pyrimidine-4,6-diol (from step 2; 200 mg, 0.77 mmol). The vial was sealed and heated to 90° C. for 2 h. The excess POCl₃ was removed in vacuo until a solid had crashed out. Water was added, forming a white precipitate which was collected under vacuum filtration, washed with water and dried affording the title compound (126 mg, 55%) as a white solid. ¹H NMR (500 MHz, CDCl₃) δ 4.47-4.40 (m, 2H), 3.64-3.56 (m, 2H), 2.62 (dd, J=13.3, 10.7 Hz, 2H), 1.25 (d, J=6.2 Hz, 6H); LCMS (Method T2) RT 1.72 min; m/z 296.01 [M+H]⁺.

Intermediate J1: (1R,5S,7s)-9-(5-chloro-4-(methylsulfinyl)pyrimidin-2-yl)-3-oxa-9-azabicyclo[3.3.1]nonan-7-ol

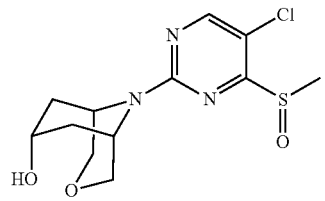

Step 1: 2,5-dichloro-4-(methylthio)pyrimidine 2,4,5-trichloropyrimidine (3.27 mL, 28.54 mmol) was dissolved in THF (29 mL) and water (29 mL) and chilled to 0° C. To this mixture was added sodium thiomethoxide (2.00 g, 28.54 mmol) and the reaction mixture was allowed to warm to room temperature and stirred for 4 h. EtOAc (50 mL) and water (50 mL) were added and the layers separated. The aqueous layer was extracted with a further 50 mL of EtOAc and the organic layers were combined, dried, and concentrated to afford a clear oil which rapidly crystallised to give 2,5-dichloro-4-methylsulfanyl-pyrimidine (5.5 g, 99%) as a white solid. LCMS (Method X2); RT 1.35 min; m/z 194.9542 [M+H]⁺

Step 2; (1R,5S,7s)-9-(5-chloro-4-(methylthio)pyrimidin-2-yl)-3-oxa-9-azabicyclo[3.3.1]nonan-7-ol An oven-dried microwave vial (2.0-5.0 mL volume) was charged with 2,5-dichloro-4-(methylthio)pyrimidine (from step 1; 234 mg, 1.20 mmol), endo-7-hydroxy-3-oxa-9-azabicyclo[3.3.1]nonane hydrochloride (238 mg, 1.32 mmol) and DIPEA (0.84 mL, 4.82 mmol). Isopropanol (3.4 mL) was added, the reaction vial was sealed with a cap and the reaction mixture was heated at 120° C. in a heating block for 24 h. The reaction mixture was cooled to rt and concentrated in vacuo. Purification by flash chromatography (10 g KP-sil; 0% to 70% EtOAc in cyclohexane) afforded (1R,5S,7s)-9-(5-chloro-4-(methylthio)pyrimidin-2-yl)-3-oxa-9-azabicyclo[3.3.1]nonan-7-ol (221 mg, 61%) as a colourless oil which solidified to an off-white solid when stored at 4° C. $^1$H NMR (500 MHz, CDCl$_3$) δ 7.97 (s, 1H), 5.63 (d, J=12.6 Hz, 1H), 4.80-4.65 (m, 2H), 4.00-3.92 (m, 3H), 3.87-3.82 (m, 2H), 2.48 (s, 3H), 2.26-2.15 (m, 2H), 1.89 (d, J=15.0 Hz, 2H); LCMS (2 min); RT 1.49 min; m/z 284.0726 [M−H$_2$O+H]$^+$ Step 3; (1R,5S,7s)-9-(5-chloro-4-(methylsulfinyl)pyrimidin-2-yl)-3-oxa-9-azabicyclo-[3.3.1]-nonan-7-ol (1R,5S,7s)-9-(5-Chloro-4-(methylthio)pyrimidin-2-yl)-3-oxa-9-azabicyclo[3.3.1]-nonan-7-ol (from step 2; 68 mg, 0.22 mmol) was dissolved in CH$_2$Cl$_2$ (1.1 mL) and MeCN (1.1 mL). 3-Chloroperoxybenzoic acid (53 mg, 0.24 mmol) was added and the reaction mixture was stirred for 1 h at room temperature. CH$_2$Cl$_2$ (20 mL) was added and the reaction mixture was extracted with saturated aq. NaHCO$_3$ (20 mL). The aqueous layer was extracted with CH$_2$Cl$_2$ (20 mL) and the organics combined, washed with brine, dried (MgSO$_4$) and concentrated in vacuo. Purification by flash chromatography (10 g KP-sil; 0% to 10% MeOH in CH$_2$Cl$_2$) afforded the title compound (48 mg, 67%) as a white solid. LCMS (Method X2); RT 0.98 min; m/z 300.0593 [M−H$_2$O+H]$^+$.

The following tabulated examples were prepared by a method analogous to that used for the preparation of Intermediate J1. The amine used in step 2 is shown in the table. For Intermediate J2 and Intermediate J3: during step 3, 2.5 equiv of 3-chloroperoxybenzoic acid (mCPBA) was used to fully oxidise the sulfide to the sulfone.

Intermediate K1a and Intermediate K1b represent a pair of enantiomers where one is the (R)- and the other is the (S)-(piperidin-3-yl)methanol. It has not been determined which is the (R)- and which is the (S)-enantiomer. The compounds were separated by preparative chiral SFC during Step 3 using the method described below.

Intermediate K1a and Intermediate K1b: (S)-(1-(5-chloro-4-(methylthio)pyrimidin-2-yl)-4,4-difluoropiperidin-3-yl)methanol and (R)-(1-(5-chloro-4-(methylthio)pyrimidin-2-yl)-4,4-difluoropiperidin-3-yl)methanol

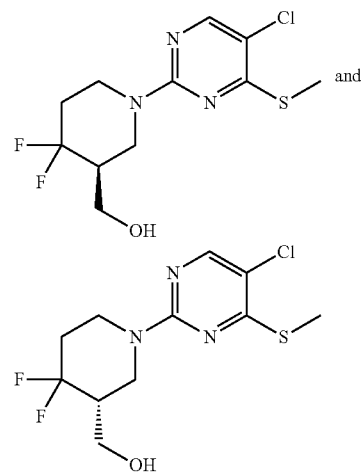

Step 1 is analogous to that used for the preparation of Intermediate J1.

| Intermediate | Data and comments | Amine |
|---|---|---|
| Intermediate J2: (1R,5S,7s)-9-(5-chloro-4-(methylsulfonyl)pyrimidin-2-yl)-3-oxa-9-azabicyclo[3.3.1]-nonan-7-ol | $^1$H NMR (500 MHz, methanol-d$_4$) δ 8.59 (s, 1 H), 4.83-4.77 (m, 1 H), 4.69-4.64 (m, 1 H), 4.01-3.99 (m, 1 H), 3.99-3.96 (m, 1 H), 3.94-3.89 (m, 1 H), 3.87-3.80 (m, 2 H), 3.35 (s, 3 H), 2.30-2.18 (m, 2 H), 1.94-1.86 (m, 2 H). LCMS (Method X2) RT 1.00; m/z 316.0537 [M-H$_2$O + H]$^+$. | endo-7-hydroxy-3-oxa-9-azabicyclo[3.3.1]-nonane hydrochloride |
| Intermediate J3: 5-chloro-2-((3S,5R)-4,4-difluoro-3,5-dimethylpiperidin-1-yl)-4-(methylsulfonyl)pyrimidine | $^1$H NMR (500 MHz, CDCl$_3$) δ 8.45 (s, 1 H), 4.61 (br s, 2 H), 3.32 (s, 3 H), 2.86 (app t, J = 12.7 Hz, 2 H), 2.08-1.93 (m, 2 H), 1.12 (d, J = 6.8 Hz, 6 H); LCMS (Method X2) RT 1.41 min; m/z 340.0818 [M + H]$^+$. | (3S,5R)-4,4-difluoro-3,5-dimethylpiperidine hydrochloride |

Step 2; rac-(1-(5-chloro-4-(methylsulfonyl)pyrimidin-2-yl)-4,4-difluoropiperidin-3-yl)methanol A mixture of rac-(1-benzyl-4,4-difluoropiperidin-3-yl)methanol (400 mg, 1.66 mmol) and palladium hydroxide (10 mg, 0.08 mmol) in EtOH (3.3 mL) was stirred at rt under a balloon of $H_2$ gas for 16 h. (Note; LCMS and NMR analysis showed approx. 3:1 ratio of product:starting material). The reaction mixture was concentrated in vacuo affording 287 mg of material. A microwave vial (2.0-5.0 mL volume) was charged with this crude mixture, 2,5-dichloro-4-methylsulfanyl-pyrimidine (217 mg, 1.11 mmol), and DIPEA (0.58 mL, 3.34 mmol). Isopropanol (3.4 mL) was added, the reaction vial was sealed with a cap and the reaction mixture was heated at 120° C. for 4 h. The reaction mixture was concentrated in vacuo and the crude product was loaded onto silica, and purified by normal-phase chromatography (Biotage 25 g KP-sil; 0% to 50% EtOAc in cyclohexane) to affording rac-(1-(5-chloro-4-(methylsulfonyl)pyrimidin-2-yl)-4,4-difluoropiperidin-3-yl)methanol (316 mg, 78%) as a clear oil, which slowly crystallised on standing. LCMS (Method T2); RT 1.54 min; m/z 310.0594 [M+H]$^+$.

Step 3; (S)-(1-(5-chloro-4-(methylsulfonyl)pyrimidin-2-yl)-4,4-difluoropiperidin-3-yl)methanol and (R)-(1-(5-chloro-4-(methylsulfonyl)pyrimidin-2-yl)-4,4-difluoropiperidin-3-yl)methanol rac-(1-(5-Chloro-4-(methylsulfonyl)pyrimidin-2-yl)-4,4-difluoropiperidin-3-yl)methanol (from Step 2; 256 mg) was dissolved to 25 mg/mL in 1:1 isopropanol:$CH_2Cl_2$ and was then purified by SFC (Lux C4 (21.2 mm×250 mm, 5 μm), 10:90 isopropanoi:$CO_2$; flow rate 50 mLmin$^{-1}$). The earlier eluting enantiomer was identified as Intermediate K1a and the later eluting enantiomer was identified as Intermediate K1 b. Combined fractions of each were then concentrated in vacuo before being stored in a vacuum oven at 35° C. and 5 mbar affording Intermediate K1a (101 mg) and Intermediate K1b (105 mg) as colourless gums.

Chiral purity analysis was determined by SFC (Lux C4 (4.6 mm×250 mm, 5 μm), 15:85 isopropanoi:$CO_2$; flow rate 4 mLmin$^{-1}$). Intermediate K1a: ee=98.4%; RT 2.17 min. Intermediate K1b: ee=98.4%; RT 2.52 min.

Intermediate K2a: (S)-(1-(5-chloro-4-(methylsulfonyl)pyrimidin-2-yl)-4,4-difluoropiperidin-3-yl)methanol or (R)-(1-(5-chloro-4-(methylsulfonyl)pyrimidin-2-yl)-4,4-difluoropiperidin-3-yl)methanol

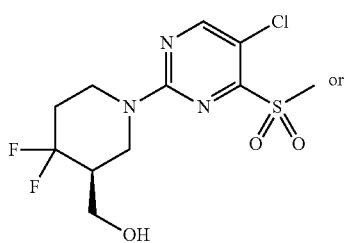

or

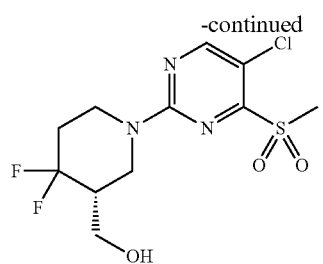

To a solution (S)-(1-(5-chloro-4-(methylthio)pyrimidin-2-yl)-4,4-difluoropiperidin-3-yl)methanol or (R)-(1-(5-chloro-4-(methylthio)pyrimidin-2-yl)-4,4-difluoropiperidin-3-yl)-methanol (Intermediate K1a; 50 mg, 0.16 mmol) in $CH_2Cl_2$ (0.85 mL) and MeCN (0.85 mL) at 0° C. was added 3-chloroperoxybenzoic acid (73 mg, 0.33 mmol) portion-wise. The reaction mixture was then warmed to room temperature and stirred for 16 h. The reaction mixture was diluted with $CH_2Cl_2$ (20 mL) and the reaction mixture was washed with sat. aq. sodium thiosulfate and sat. aq. NaHCO$_3$ (20 mL). The organic layer was separated, dried (MgSO$_4$) and concentrated in vacuo. To a solution (S)-(1-(5-chloro-4-(methylthio)pyrimidin-2-yl)-4,4-difluoropiperidin-3-yl)methanol or (R)-(1-(5-chloro-4-(methylthio)pyrimidin-2-yl)-4,4-difluoropiperidin-3-yl)methanol (Intermediate K1a; 50 mg, 0.16 mmol) in $CH_2Cl_2$ (0.85 mL) and MeCN (0.85 mL) at 0° C. was added 3-chloroperoxybenzoic acid (73 mg, 0.33 mmol) portion-wise. The reaction mixture was then warmed to room temperature and stirred for 16 h. The reaction mixture was diluted with $CH_2Cl_2$ (20 mL) and the reaction mixture was washed with sat. aq. sodium thiosulfate and sat. aq. NaHCO$_3$ (20 mL). The organic layer was separated, dried (MgSO$_4$) and concentrated in vacuo. The residue was purified by normal phase chromatography (Biotage 10 g KP-Sil; 0% to 5% MeOH in $CH_2Cl_2$) affording the title compound (40 mg, 73%) as an off-white solid. $^1$H NMR (600 MHz, CDCl$_3$) δ 8.48 (s, 1H), 4.37-4.25 (m, 1H), 4.22-4.10 (m, 1H), 3.98 (dd, J=11.4, 4.5 Hz, 1H), 3.86-3.79 (m, 1H), 3.79-3.72 (m, 1H), 3.60 (dd, J=11.4, 8.8 Hz, 1H), 3.33 (s, 3H), 2.34-2.23 (m, 1H), 2.14-2.04 (m, 1H), 2.06-1.90 (m, 1H); OH not observed; LCMS (Method T2); RT 1.20 min; m/z 342.04 [M+H]$^+$.

The following tabulated examples were prepared by a method analogous to that used for the preparation of Intermediate K2a, starting from the aryl sulfide shown in the table.

| Intermediate | Data and comments | Aryl sulfide |
|---|---|---|
| Intermediate K2b: (R)-(1-(5-chloro-4-(methylsulfonyl)pyrimidin-2-yl)-4,4-difluoropiperidin-3-yl)methanol or (S)-(1-(5-chloro-4-(methylsulfonyl)pyrimidin-2-yl)-4,4-difluoropiperidin-3-yl)methanol<br>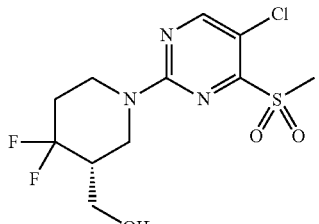<br>or<br>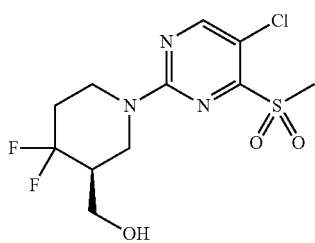 [SMILES: CS(=O)(=O)c1nc(N2CCC(F)(F)[C@H](CO)C2)ncc1Cl] | LCMS (Method T2); RT 1.25 min; m/z 342.0442 [M + H]$^+$. | Intermediate K1b: (R)-(1-(5-chloro-4-(methylthio)pyrimidin-2-yl)-4,4-difluoropiperidin-3-yl)methanol or (S)-1-(5-chloro-4-(methylthio)pyrimidin-2-yl)-4,4-difluoropiperidin-3-yl)methanol |

Intermediate L1a and Intermediate L1b represent a pair of enantiomers where one is the (R)- and the other is the (S)-methyl-piperidine. It has not been determined which is the (R)- and which is the (S)-enantiomer. The compounds were separated by preparative chiral SFC during Step 3 using the method described below.

Intermediate L1a and Intermediate L1b: (S)-5-chloro-2-(4,4-difluoro-3-methylpiperidin-1-yl)pyrimidin-4-ol and (R)-5-chloro-2-(4,4-difluoro-3-methylpiperidin-1-yl)pyrimidin-4-ol

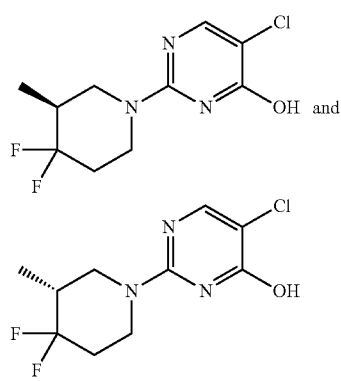

Step 1; 2,5-dichloropyrimidin-4-ol

2 M sodium hydroxide (6 mL, 12 mmol) was added to a stirred solution of 2,4,5-trichloropyrimidine (1.29 g, 7.0 mmol) in THF (4 mL). The reaction mixture was stirred at rt for 24 h. The reaction mixture was concentrated in vacuo and the aqueous mixture was neutralised with 3 M HCl. The aqueous mixture was extracted with Et$_2$O (2×10 mL) followed by EtOAc (2×10 mL). The organic extracts were combined, washed with brine (10 mL), dried (Na$_2$SO$_4$) and concentrated in vacuo affording 2,5-dichloropyrimidin-4-ol (923 mg, 80%) as a yellow solid which was used without further purification. $^1$H NMR (500 MHz, DMSO-d$_6$) δ 8.26 (s, 1H); LCMS (Method T2) RT 0.19 min; m/z 164.9602 [M+H]$^+$ Step 2; rac-5-chloro-2-(4,4-difluoro-3-methylpiperidin-1-yl)pyrimidin-4-ol A microwave vial (10-20 mL volume) was charged with 2,5-dichloropyrimidin-4-ol (from step 1; 502 mg, 3.0 mmol) and rac-4,4-difluoro-3-methylpiperidine hydrochloride (522 mg, 3.0 mmol). The reaction vial was flushed with Ar, sealed with a cap and then further flushed with Ar. Ethanol (5 mL) was added followed by DIPEA (1.4 mL, 8.0 mmol). The reaction mixture was heated at 80° C. in a heating block for 10 h. The reaction mixture was concentrated in vacuo. The residue was dissolved in DMSO (1 mL) and directly purified by reverse-phase chromatography (Biotage reverse-phase 12 g C-18 column; 25-80% MeOH in H$_2$O (containing 0.1% formic acid)) affording rac-5-chloro-2-(4,4-difluoro-3-methylpiperidin-1-yl)pyrimidin-4-ol (264 mg, 33%) as an off-white solid. $^1$H NMR (600 MHz, CDCl$_3$) δ 12.18 (brs, 1H), 7.89 (s, 1H), 4.49-4.41 (m, 1H), 4.34-4.27 (m, 1H), 3.37-3.30 (m, 1H), 3.08 (dd, J=13.8, 10.9 Hz, 1H), 2.26-2.17 (m, 1H), 2.17-2.08 (m, 1H), 2.02-1.89 (m, 1H), 1.16 (d, J=6.8 Hz, 3H); LCMS (Method T2) RT 1.21 min; m/z 264.0675 [M+H]$^+$

Step 3; (S)-5-chloro-2-(4,4-difluoro-3-methylpiperidin-1-yl)pyrimidin-4-ol and (R)-5-chloro-2-(4,4-difluoro-3-methylpiperidin-1-yl)pyrimidin-4-ol rac-5-Chloro-2-(4,4-difluoro-3-methylpiperidin-1-yl)pyrimidin-4-ol (250 mg) was dissolved to 25 mg/mL in MeOH:CH$_2$Cl$_2$ (4:1) (1% v/v NH$_3$) and was then purified by SFC (Amy-C (20 mm×250 mm, 5 μm), 10:90 MeOH:CO$_2$ (0.2% v/v NH$_3$); flow rate 50 mLmin$^{-1}$). The earlier eluting enantiomer was identified as Intermediate L1a and the later eluting enantiomer was identified as Intermediate L1b. Combined fractions of Intermediate L1a were concentrated in vacuo before being stored in a vacuum oven at 35° C. and 5 mbar affording Intermediate L1a (85 mg) as a white solid. Combined fractions of Intermediate L1b were concentrated in vacuo and re-purified and isolated as above to afford Intermediate L1b (68 mg) as a white solid.

Chiral purity analysis was determined by SFC (Amy-C (4.6 mm×250 mm, 5 μm), 10:90 MeOH:CO$_2$ (0.2% v/v NH$_3$); flow rate 4 mLmin$^{-1}$). Intermediate L1a: ee=99.2%; RT 3.58 min. Intermediate L1b: ee=99.0%; RT 3.83 min.

Intermediate L2a: (S)-4,5-dichloro-2-(4,4-difluoro-3-methylpiperidin-1-yl)pyrimidine or (R)-4,5-dichloro-2-(4,4-difluoro-3-methylpiperidin-1-yl)pyrimidine

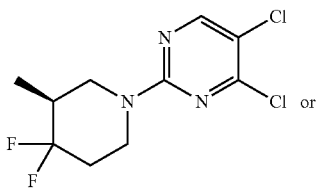

or

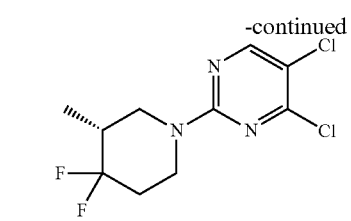

To a vial containing (S)-5-chloro-2-(4,4-difluoro-3-methylpiperidin-1-yl)pyrimidin-4-ol or (R)-5-chloro-2-(4,4-difluoro-3-methylpiperidin-1-yl)pyrimidin-4-ol (Intermediate L1a; 43 mg, 0.16 mmol) was added POCl$_3$ (0.6 mL, 6.4 mmol) and the vial was sealed and heated to 90° C. for 3 h. The excess POCl$_3$ was removed in vacuo, and the residue was partitioned between water and EtOAc. The layers were separated and the organic layer was dried (MgSO$_4$), and concentrated in vacuo to give the title compound (41 mg, 89%) as a colourless oil which was used without further purification. $^1$H NMR (500 MHz, CDCl$_3$) δ 8.22 (s, 1H), 4.56-4.50 (m, 1H), 4.47-4.41 (m, 1H), 3.40-3.33 (m, 1H), 3.11-3.04 (m, 1H), 2.21-2.11 (m, 1H), 2.11-1.98 (m, 1H), 1.96-1.82 (m, 1H), 1.09 (d, J=6.8 Hz, 3H); LCMS (Method T2); RT 1.71 min; m/z 282 [M+H]$^+$.

The following tabulated examples were prepared by a method analogous to that used for the preparation of Intermediate L2a, starting from the aryl sulfide shown in the table.

| Intermediate | Data and comments | Pyrimidin-4-ol |
|---|---|---|
| Intermediate L2b: (R)-4,5-dichloro-2-(4,4-difluoro-3-methylpiperidin-1-yl)pyrimidine or (S)-4,5-dichloro-2-(4,4-difluoro-3-methylpiperidin-1-yl)pyrimidine 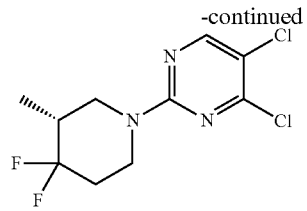 or 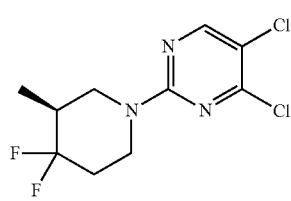 [SMILES: C[C@H]1CN(c2ncc(Cl)c(Cl)n2)CCC1(F)F] | LCMS (Method T2); RT 1.71 min; m/z 282 [M + H]$^+$. | Intermediate L1b: (R)-5-chloro-2-(4,4-difluoro-3-methylpiperidin-1-yl)pyrimidin-4-ol or (S)-5-chloro-2-(4,4-difluoro-3-methylpiperidin-1-yl)pyrimidin-4-ol |

Intermediate M1a and Intermediate M1b represent a pair of enantiomers where one is the (3R,5S)- and the other is the (3S,5R)-piperidinol. It has not been determined which is the (3R,5S)- and which is the (3S,5R)-enantiomer. The compounds were separated by preparative chiral using the method described below.

Intermediate M1a and Intermediate M1b: (3R,5S)-1-benzyl-5-methylpiperidin-3-ol and (3S,5R)-1-benzyl-5-methylpiperidin-3-ol

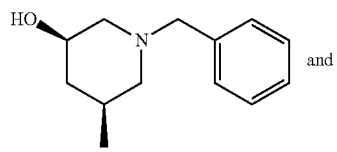
and

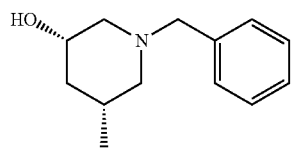

The commercially available rac-1-benzyl-5-methylpiperidin-3-ol (1 g) was dissolved to 50 mg/mL in MeOH and was then purified by SFC (Lux A1 (21.2 mm×250 mm, 5 μm), 15:85 MeOH:CO$_2$ (0.2% v/v DEA; flow rate 50 mlmin$^{-1}$). The earlier eluting enantiomer was identified as Intermediate M1a and the later eluting enantiomer was identified as Intermediate M1b. Combined fractions of Intermediate M1a were concentrated in vacuo before being stored in a vacuum oven at 35° C. and 5 mbar affording Intermediate M1a (369 mg) as a white solid. Combined fractions of Intermediate M1b were concentrated in vacuo and re-purified and isolated as above to afford Intermediate M1b (315 mg) as a white solid.

Chiral purity analysis was determined by SFC (Amy-C (4.6 mm×250 mm, 5 μm), 15:85 MeOH:CO$_2$ (0.2% v/v DEA); flow rate 4 mLmin$^{-1}$). Intermediate M1a: ee=98.4%; RT 1.47 min. Intermediate M1b: ee=99.4%; RT 1.84 min.

Intermediate M2a: (3R,5S)-5-methylpiperidin-3-ol or (3S,5R)-5-methylpiperidin-3-ol

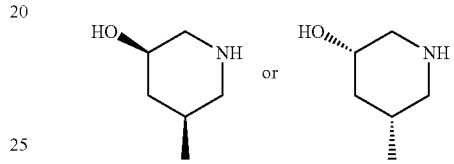

A flask containing (3R,5S)-1-benzyl-5-methylpiperidin-3-ol or (3S,5R)-1-benzyl-5-methylpiperidin-3-ol (Intermediate M1a; 200 mg, 0.97 mmol) in ethanol (10 mL) was degassed with argon for 5 min. Pd/C (10 wt %; 104 mg) was added and the suspension was degassed with argon for a further 10 min. The flask was evacuated and back-filled with hydrogen twice before being stirred at room temperature under a hydrogen balloon for 2 h. The reaction was filtered through celite (eluent methanol) and the filtrate was concentrated in vacuo to give the title compound (110 mg, 98%) as a white solid which was used without further purification. $^1$H NMR (500 MHz, methanol-d$_4$) δ 3.59-3.51 (m, 1H), 3.11-3.04 (m, 1 H), 2.90-2.81 (m, 1H), 2.20 (dd, J=11.8, 10.4 Hz, 1H), 2.07-1.98 (m, 2H), 1.67-1.54 (m, 1H), 1.01-0.86 (m, 4H).

The following tabulated examples were prepared by a method analogous to that used for the preparation of Intermediate M2a, starting from the amine shown in the table.

| Intermediate | | Data and comments | Pyrimidin-4-ol |
|---|---|---|---|
| Intermediate M2b: (3S,5R)-5-methylpiperidin-3-ol or (3R,5S)-5-methylpiperidin-3-ol | | $^1$H NMR (500 MHz, DMSO-d$_6$) δ 4.49 (d, J = 4.7 Hz, 1 H), 3.32-3.25 (m, 1 H), 2.90 (dddd, J = 11.4, 4.6, 2.1, 1.0 Hz, 1 H) 2.76-2.67 (m, 1 H), 2.19-2.03 (m, 1 H), 1.99 (dd, J = 11.5, 10.0 Hz, 1 H), 1.88-1.78 (m, 2 H), 1.48-1.35 (m, 1 H), 0.84-0.73 (m, 4 H). | Intermediate M1b: (3S,5R)-1-benzyl-5-methylpiperidin-3-ol or (3R,5S)-1-benzyl-5-methylpiperidin-3-ol |

Intermediate N1a and Intermediate N1b represent a pair of enantiomers where one is the (S)- and the other is the (R)-(piperidin-3-yl)methanol. It has not been determined which is the (S)- and which is the (R)-enantiomer. The compounds were separated by preparative chiral using the method described below.

Intermediate N1a and Intermediate N1b: (R)-(1-benzyl-4,4-difluoropiperidin-3-yl)methanol and (S)-(1-benzyl-4,4-difluoropiperidin-3-yl)methanol

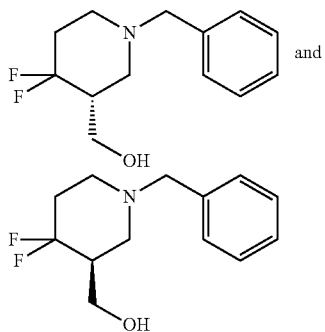

and

The commercially available rac-(1-benzyl-4,4-difluoropiperidin-3-yl)methanol (254 mg) was dissolved to 50 mg/mL in isopropanol and was then purified by SFC (Lux iC5 (21.2 mm×250 mm, 5 μm), 10:90 isopropanol:$CO_2$ (0.2% v/v $NH_3$; flow rate 21 mlmin$^{-1}$). The earlier eluting enantiomer was identified as Intermediate N1a and the later eluting enantiomer was identified as Intermediate N1b. Combined fractions of each were then concentrated in vacuo before being stored in a vacuum oven at 35° C. and 5 mbar affording Intermediate N1a (102 mg) and Intermediate N1b (100 mg) as clear gums.

Chiral purity analysis was determined by SFC (Lux iC5 (4.6 mm×250 mm, 5 μm), 10:90 isopropanoi:$CO_2$ (0.2% v/v DEA); flow rate 4 mLmin$^{-1}$). Intermediate N1a: ee=96.6%; RT 1.70 min. Intermediate N1b: ee=97.8%; RT 1.91 min.

Intermediate N2a: (R)-(4,4-difluoropiperidin-3-yl)methanol or (S)-(4,4-difluoropiperidin-3-yl)methanol

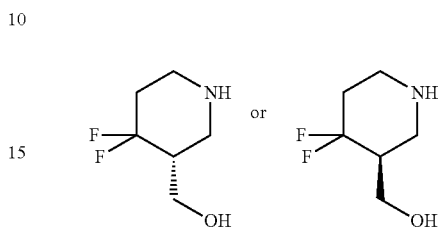

A flask containing (R)-(1-benzyl-4,4-difluoropiperidin-3-yl)methanol or (S)-(1-benzyl-4,4-difluoropiperidin-3-yl)methanol (Intermediate N1a; 102 mg, 0.42 mmol) in ethanol (8.0 mL) was degassed with argon for 2 min. Pd/C (10 wt %; 45 mg) was added and the suspension was degassed with argon for a further 10 min. The flask was evacuated and back-filled with hydrogen twice before being stirred at rt under a hydrogen balloon for 3 h. The reaction was filtered through celite (eluent methanol) and the filtrate was further filtered through cotton wool. The filtrate was concentrated in vacuo affording the title compound (64 mg, 100%) as a colourless oil which crystallised upon standing. $^1$H NMR (500 MHz, methanol-$d_4$) δ 3.92 (dd, J=11.2, 4.0 Hz, 1H), 3.51 (dd, J=11.2, 8.6 Hz, 1H), 3.27-3.21 (m, 1H), 3.07-3.00 (m, 1H), 2.82-2.74 (m, 1H), 2.61 (t, J=12.7, 10.3, 1.7 Hz, 1H), 2.12-1.96 (m, 2H), 1.92-1.78 (m, 1H).

The following tabulated examples were prepared by a method analogous to that used for the preparation of Intermediate N2a, starting from the amine shown in the table.

| Intermediate | Data and comments | Pyrimidin-4-ol |
| --- | --- | --- |
| Intermediate N2b: (S)-(4,4-difluoropiperidin-3-yl)methanol or (R)-(4,4-difluoropiperidin-3-yl)methanol<br><br>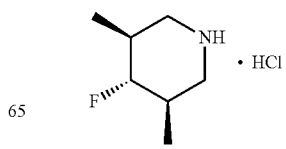 | $^1$H NMR (500 MHz, methanol-$d_4$) δ 3.92 (dd, J = 11.2, 4.0 Hz, 1 H), 3.51 (dd, J = 11.2, 8.7 Hz, 1 H), 3.27-3.20 (m, 1 H), 3.07-3.00 (m, 1 H), 2.82-2.74 (m, 1 H), 2.61 (t, J = 12.6, 10.2, 1.7 Hz, 1 H), 2.12-1.96 (m, 2 H), 1.92-1.78 (m, 1 H). | Intermediate N1b: (S)-(1-benzyl-4,4-difluoropiperidin-3-yl)methanol or (R)-(1-benzyl-4,4-difluoropiperidin-3-yl)methanol |

Intermediate O1: (3R,4r,5S)-4-fluoro-3,5-dimethylpiperidine hydrochloride

Step 1; (3R,4r,5S)-1-benzyl-3,5-dimethylpiperidin-4-ol and (3R,4s,5S)-1-benzyl-3,5-dimethylpiperidin-4-ol To a solution of (3R,5S)-1-benzyl-3,5-dimethylpiperidin-4-one (100 mg, 0.46 mmol) in methanol (1.0 mL) at 5° C. was added sodium borohydride (21 mg, 0.55 mmol) in two portions. The reaction was allowed to warm to room temperature and stirred for 16 h. The reaction was concentrated in vacuo, and the residue was partitioned between water and EtOAc. The organic layer was separated, dried (MgSO$_4$), and concentrated in vacuo to give a 1:1 mixture of (3R,4r,5S)-1-benzyl-3,5-dimethylpiperidin-4-ol and (3R,4s,5S)-1-benzyl-3,5-dimethylpiperidin-4-ol (98 mg, 97%) as a colourless oil. $^1$H NMR (500 MHz, CDCl$_3$) δ 7.36-7.31 (m, 8H), 7.30-7.25 (m, 2H), 3.60-3.56 (m, 1H), 3.52 (s, 2H), 3.49 (s, 2H), 2.87-2.79 (m, 2H), 2.72-2.66 (m, 1H), 2.56-2.49 (m, 2H), 1.98 (t, J=11.4 Hz, 2H), 1.94-1.83 (m, 2H), 1.75-1.65 (m, 4H), 0.97 (d, J=6.1 Hz, 6H), 0.94 (d, J=6.8 Hz, 6H); OH not observed.

Step 2; (3R,4r,5S)-1-benzyl-4-fluoro-3,5-dimethylpiperidine

To a solution of (3R,4r,5S)-1-benzyl-3,5-dimethylpiperidin-4-ol and (3R,4s,5S)-1-benzyl-3,5-dimethylpiperidin-4-ol (from step 1; 50 mg, 0.23 mmol) in CH$_2$Cl$_2$ (2 mL) at −78° C. was added DAST (60 uL, 0.46 mmol) and the reaction was allowed to warm to room temperature and stirred for 16 h. To the reaction mixture was added sat. aq. NaHCO$_3$ and the aqueous layer was extracted with CH$_2$Cl$_2$. The combined organic layers were dried (MgSO$_4$), and concentrated in vacuo to give (3R,4r,5S)-1-benzyl-4-fluoro-3,5-dimethylpiperidine (47 mg, 88%) as a yellow oil. 1H NMR analysis indicated that a single diastereoisomer was isolated. $^1$H NMR (500 MHz, CDCl$_3$) δ 7.39-7.26 (m, 5H), 3.64 (dt, J=50.2, 9.9 Hz, 1H), 3.51 (s, 2H), 2.86 (dtd, J=11.2, 4.5, 3.8, 2.0 Hz, 2H), 2.04-1.91 (m, 2H), 1.74 (td, J=11.7, 1.3 Hz, 2H), 0.99 (d, J=6.5 Hz, 6H).

Step 3; (3R,4r,5S)-4-fluoro-3,5-dimethylpiperidine hydrochloride

A flask containing (3R,4r,5S)-1-benzyl-4-fluoro-3,5-dimethylpiperidine (from step 2; 47 mg, 0.21 mmol) in ethanol (4 mL) was degassed with argon for 5 min. Pd/C (10 wt %; 23 mg) was added and the suspension was degassed with argon for a further 10 min. The flask was evacuated and back-filled with hydrogen twice before being stirred at room temperature under a hydrogen balloon for 5 h. A further sample of Pd/C (10 wt %; 23 mg) was added and the flask was evacuated and back-filled with hydrogen twice before being stirred at room temperature under a hydrogen balloon for 16 h. The reaction was filtered through celite (eluent methanol) and the filtrate was concentrated under 100 mbar pressure. A solution of 3 M HCl in 1,4-dioxane (0.6 mL) was added to this residue and the solution was stirred for 10 min, before being concentrated under reduced pressure to give the title compound (31 mg, 87%) as a white solid. $^1$H NMR (500 MHz, methanol-d$_4$) δ 3.98 (dtd, J=48.8, 10.0, 1.6 Hz, 1H), 3.42-3.30 (m, 2H), 2.81 (t, J=12.8 Hz, 2H), 2.14-2.02 (m, 2H), 1.11 (d, J=6.6 Hz, 6H); LCMS (Method T4); RT 0.16 min; m/z 132 [M+H]$^+$.

Intermediate P1: (1R,5S,7s)-7-methyl-3-oxa-9-azabicyclo[3.3.1]nonan-7-ol

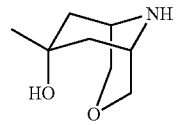

Step 1; (1R,5S,7s)-9-benzyl-7-methyl-3-oxa-9-azabicyclo[3.3.1]nonan-7-ol

Methylmagnesium bromide (3.0 M solution in Et$_2$O; 0.72 mL, 2.16 mmol) was added dropwise to a solution of 9-benzyl-3-oxa-9-azabicyclo[3.3.1]nonan-7-one (100 mg, 0.43 mmol) in THF (4.32 mL) at rt. The solution was then stirred at 60° C. overnight. After this time, the reaction mixture was cooled to rt and additional methylmagnesium bromide (3.0 M solution in Et$_2$O; 0.72 mL, 2.16 mmol) and THF (5 mL) was added. The reaction mixture was stirred at 60° C. for a further 3 d. The mixture was quenched by the careful and slow addition of water. The mixture was extracted with EtOAc and the organic extracts washed with brine then dried (MgSO$_4$) and concentrated in vacuo. The residue was purified by normal phase chromatography (Biotage 10 g KP-Sil; 20% to 100% EtOAc in cyclohexane affording (1R,5S,7s)-9-benzyl-7-methyl-3-oxa-9-azabicyclo[3.3.1]nonan-7-ol (77 mg, 72%) as a brown oil. $^1$H NMR (500 MHz, CDCl$_3$) δ 7.40-7.33 (m, 2H), 7.36-7.28 (m, 2H), 7.29-7.22 (m, 1H), 6.21 (s, 1H), 3.97-3.93 (m, 2H), 3.81-3.77 (m, 2H), 3.76 (s, 2H), 2.75-2.69 (m, 2H), 2.18 (dd, J=14.7, 5.4 Hz, 2H), 1.60 (d, J=14.9 Hz, 2H), 1.32 (d, J=1.3 Hz, 3H). A single diastereoisomer was observed. As such, it was assigned as methyl adding from exo face. NOESY NMR shows cross peaks between methyl and adjacent CH$_2$ protons (both the axial and equatorial protons) thus implying that the methyl has added from the top face as this result would not be possible with the methyl trans- to the axial CH$_2$ protons.

Step 2; (1R,5S,7s)-7-methyl-3-oxa-9-azabicyclo[3.3.1]nonan-7-ol

Pd/C (10 wt %) (25.00 mg, 0.0235 mmol) was added to a solution of (1R,5S,7s)-9-benzyl-7-methyl-3-oxa-9-azabicyclo[3.3.1]nonan-7-ol (from step 1; 61 mg, 0.23 mmol) in ethanol (2.3 mL) then placed under an atmosphere of hydrogen and stirred at 30° C. overnight. The mixture was filtered though a pad of Celite on an SCX-2 column and washed with ethanol. The product was then eluted with 2 M methanolic ammonia. The solvent was concentrated in vacuo affording the title compound (35 mg, 87%) as a pale brown solid. $^1$H NMR (600 MHz, CDCl$_3$) δ 7.02 (br s, 1H), 5.83 (s, 1H), 4.18 (d, J=12.4 Hz, 2H), 3.95 (d, J=12.4 Hz, 2H), 3.44-3.39 (m, 2H), 2.37 (dd, J=15.2, 5.4 Hz, 2H), 2.00 (d, J=15.2 Hz, 2H), 1.33 (s, 3H).

Intermediate P2: rac-methyl-3,8-diazabicyclo[3.2.1]octan-2-one

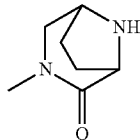

A mixture of sodium hydride (60% dispersion in mineral oil; 33 mg, 0.82 mmol) and rac-tert-butyl 2-oxo-3,8-diazabicyclo[3.2.1]octane-8-carboxylate (124 mg, 0.55 mmol) was stirred at 25° C. in DMF (6 mL) for 15 min. Iodomethane (0.20 mL, 3.29 mmol) was then added. The resulting solution was stirred at this temp for 16 h. Brine was added and the solution was extracted with EtOAc. The combined organic layers were washed with brine and water, dried (Na$_2$SO$_4$) and concentrated in vacuo affording the Boc-protected intermediate (78 mg) as a deep yellow solid. The solid was dissolved in CH$_2$Cl$_2$ (8 mL) and TFA (0.60 mL, 0.55 mmol) was added. The resulting solution was stirred at rt for 16 h. The reaction mixture was concentrated in vacuo and the residue was purified by SCX-2 (2 g) column affording the title compound (40 mg, 52%) as a colourless oil that was used without further purification. $^1$H NMR (500 MHz, methanol-d$_4$) δ 3.74 (ddt, J=6.3, 3.3, 1.0 Hz, 1H), 3.69-3.64 (m, 1H), 3.52 (ddd, J=11.6, 4.3, 1.1 Hz, 1H), 3.04 (dd, J=11.6, 1.0 Hz, 1H), 2.85 (s, 3H), 2.13-1.95 (m, 3H), 1.86-1.72 (m, 1H).

Intermediate P3: (1R,5S)—N,N-dimethyl-3-oxa-9-azabicyclo[3.3.1]nonane-7-carboxamide

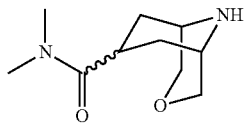

Dimethylamine (2 M in THF; 0.8 mL, 1.59 mmol) was added to a stirred solution of (1R,5S)-9-(tert-butoxycarbonyl)-3-oxa-9-azabicyclo[3.3.1]nonane-7-carboxylic acid (72 mg, 0.27 mmol) and HATU (121 mg, 0.32 mmol) in DMF (4 mL). The resulting solution was stirred at 25° C. for 16 h. Brine was added and the solution was extracted with EtOAc. The combined organic layers were washed with brine and water, dried (Na$_2$SO$_4$) and concentrated in vacuo affording the Boc-protected intermediate (67 mg) as a yellow wax. The crude product was then dissolved in CH$_2$Cl$_2$ (8 mL) and TFA (0.60 mL, 0.67 mmol) was added. The resulting solution was stirred at rt for 16 h. The reaction mixture was concentrated in vacuo, and the residue was purified by a SCX-2 (2 g) column affording the title compound (38 mg, 72% mmol) as a white solid which was used without further purification. $^1$H NMR (600 MHz, methanol-d$_4$) δ 4.16-4.08 (m, 1H), 3.98-3.86 (m, 4H), 3.16 (s, 3H), 3.00-2.96 (m, 2H), 2.95 (s, 3H), 2.10-2.02 (m, 2H), 1.93-1.85 (m, 2H).

Biological Assays
HTRF Assay

Each 15 μL HTRF reaction in a 384-well black Proxiplate (Perkin Elmer) contained 1 nM Trx-6×His-BCL6 (in house-produced, human BCL6 BTB domain covering amino-acid sequence 5-129), 300 nM BCOR-AF633 peptide (RSEII-STAPSSWWPGP-Cys-AlexaFluor 633-amide, Cambridge Research Biochemical) and 0.5 nM anti-6×His-Terbium cryptate (CisBio Bioassays, France), in assay buffer (25 mM Hepes pH8, 100 mM NaCl, 0.05% Tween20, 0.5 mM TCEP, 0.05% bovine serum albumin). Test compounds in DMSO or DMSO alone were added to the wells using an ECHO550 acoustic dispenser (Labcyte Inc) to give the appropriate test concentration in 0.7% v/v DMSO final. After 2 hours incubation at room temperature the plate was read on an Envision plate reader (Perkin Elmer) with 337 nm laser excitation, a first emission filter APC 665 nm and a second emission filter Europium 615 nm. The % inhibition at each concentration was calculated by normalising FRET ratio to the appropriate high (DMSO with all reagents) and low (DMSO without BCL6) controls. The compound IC$_{50}$s were determined using GraphPad Prism 6.0 or Dotmatics (Bishops Stortford, UK) software by fitting the normalised data to a sigmoidal four-parameter logistic fit equation.

The results of this assay are shown in Table 1 above.
NanoBRET Assay

A cellular nano-Bioluminescence Resonance Energy Transfer (nanoBRET) assay (Promega NanoBRET Nano-Glo Detection System, catalogue number N1662) was used to detect inhibition of the BCL6-NCOR2(SMRT) corepressor protein-protein interaction. DNA encoding full length BCL6 and NCOR2 were inserted into pFC32K.NanoLuc and pFC14K.HaloTag vectors (Promega) to produce C-terminal tagged fusion proteins BCL6-nanoLuc and NCOR2-HaloTag, respectively. HEK293T cells (8×10$^5$) were plated in each well of a 6-well plate and co-transfected 24 hours later with Fugene 6 (Promega cat. #E2691) reagent and 2.2 μg total DNA plasmids encoding BCL6-nanoLuc as donor and NCOR2-HaloTag as acceptor, at a donor:acceptor DNA ratio of 1:25. At 20 hr post-transfection, cells were collected, washed with PBS, and exchanged into media containing phenol red-free OptiMEM+4% FBS (Life Technology). The cell density was adjusted to 5×10$^5$ cells/ml and 20 μL plated in each well of the 384-well NUNC white assay plate (ThermoScientific NUNC cat. #10080681), containing test compounds in DMSO or DMSO alone to give 0-100 μM in 0.5% v/v DMSO final concentrations plus 0.5 μg/ml Nano-BRET 618 fluorescence ligand. Cells were incubated for 6 hr at 37° C./5% CO$_2$ then NanoBRET furimazine substrate (Promega) was added to give a final concentration of 10 μM. After a short centrifugation the plates were read on an Envision (Perkin Elmer) plate reader equipped with a LUM/D600 Dual mirror, Lum 450/40 nm bandpass and D605 nm longpass filters, with a 0.1 sec reading to determine the BRET ratio. The % inhibition at each test concentration was calculated by normalising the BRET ratio to the appropriate high and low controls. The compound IC$_{50}$s were determined using Graphpad Prism 6.0 or Dotmatics software by fitting the normalised data to a sigmoidal four-parameter logistic fit equation.

The results obtained using this assay are shown in Table 2 above.
Immunofluorescence-Based BCL6 Degradation Assay DC$_{50}$ values (compound concentration at which 50% of endogenous BCL6 protein is degraded) were determined in SUDHL-4 cells (American Type Culture Collection) in an immunofluorescence-based assay using an InCell2200 high content imaging system (GE Healthcare). Briefly, 40 μL of lymphoma suspension cells cultured in RPMI 1640-10% FBS (Sigma-Aldrich or PAN Biotech UK Ltd) were platted on fibronectin (Sigma catalogue F1141)-coated 384 well Cell Carrier Ultra plate (Perkin Elmer catalogue 6057300) at 1.2 104 cells/well. After 20 hours cell culture at 37° C./C02 incubator, compounds were dispensed in the cell culture plate using ECHO550 acoustic dispenser (Labcyte, Inc.), as 8 point-concentration response (ranging from 5 nM to 10 µM) in 0.67% final DMSO concentration. Cells were incubated with compound for 2 hours at 37° C./C02 incubator followed by fixation in 4.5% formaldehyde (37% formaldehyde solution, Sigma catalogue F8775) at room temperature for 15 min. After fixing, cells were washed in 1×TBS (Tris Buffer Saline) using a Power Washer 384 (Tecan Group Ltd). Blocking and cell permeabilisation were performed by incubating the fixed cells for 1 hour at room temperature in 1×TBS, 5% BSA, 1% Triton X100, followed by three washes on PW384 plate washer. Primary and secondary antibodies were prepared in 1×TBS, 1% BSA, 0.2% Triton X100. BCL6 expression was detected by incubating the cells for 1 h30 with BCL6 rabbit polyclonal antibody (Sigma Catalogue HPA004899) at 1:250, 0.8 µg/ml, followed by 1 hour in chicken anti-Rabbit Alexa 488 conjugated antibody (Life Technology) at 1:500. After incubation in each antibody, cells were washes four times in 1×TBS-0.05% tween on PW384 plate washer. Cells were finally incubated for 60 min with nuclear staining RedDot2 dye (Biotium) at 0.5× the stock concentration in 1×TBS. BCL6 expression in the absence or presence of compound was detected on InCell2200 with 20× objective and quantified on InCell Analyser 3.7.2 workstation (GE Healthcare). The % response at each concentration was calculated by normalising BCL6 expression in the presence of compound to the appropriate high (DMSO) and low (DMSO with 7 µM of a control compound (5-((5-chloro-2-((3R,5S)-4,4-difluoro-3,5-dimethylpiperidin-1-yl)pyrimidin-4-yl)amino)-3-(3-hydroxy-3-methylbutyl)-1-methyl-1,3-dihydro-2H-benzo[d]imidazol-2-one)) controls. The compound $DC_{50}$ values were determined using GraphPad Prism 6.0 or Dotmatics (Bishops Stortford, UK) software by fitting the normalised data to a sigmoidal four-parameter logistic fit equation.

The results obtained using this assay are shown in Table 3 above.

While specific embodiments of the invention have been described herein for the purpose of reference and illustration, various modifications will be apparent to a person skilled in the art without departing from the scope of the invention as defined by the appended claims.

The invention claimed is:

1. A compound of Formula (I), or a pharmaceutically acceptable salt or solvate thereof, as shown below:

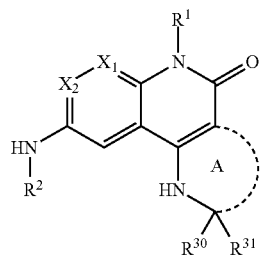

Formula (I)

wherein:
$X_1$ is selected from N or $CR^a$, wherein $R^a$ is selected from hydrogen, (1-2C)alkyl, halogen, (1-2C)alkoxy, (1-2C)haloalkyl, (1-2C)haloalkoxy, cyano or $NR^bR^c$, wherein $R^b$ and $R^c$ are each independently selected from hydrogen or (1-2C)alkyl;

$X_2$ is selected from N, CH, CF, CCl or C—CH$_3$;

$R^1$ is selected from hydrogen or a group of the formula:

-L-Y—Z wherein:
L is absent or (1-3C)alkylene;
Y is absent or O, C(O), C(O)O or C(O)N($R^e$), wherein $R^e$ is selected from hydrogen or (1-4C)alkyl; and
Z is hydrogen, (1-6C)alkyl, aryl, (3-6C)cycloalkyl, (3-6C)cycloalkenyl, 5 or 6 membered heteroaryl or 4 to 7 membered heterocyclyl; wherein Z is optionally further substituted by one or more substituent groups independently selected from oxo, (1-2C)alkyl, halo, (1-2C)haloalkyl, (1-2C)haloalkoxy, (1-2C)aminoalkyl, cyano, $NR^gR^h$ or $OR^g$; wherein $R^g$ and $R^h$ are each independently selected from hydrogen or (1-4C)alkyl;

$R^2$ is selected from a group of Formula A shown below:

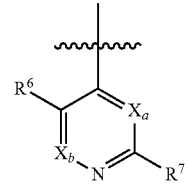

Formula A wherein:

denotes the point of attachment;
$X_a$ is selected from N, CH or CF;
$X_b$ is selected from N or $CR^{x1}$, wherein $R^{x1}$ is selected from hydrogen, fluoro, chloro, bromo, (1-2C)alkyl, (1-2C)alkoxy, cyano, acetylenyl, $CH_2F$, $CF_2H$ or $CF_3$;
$R^6$ is selected from hydrogen, fluoro, chloro, bromo, (1-2C)alkyl, (1-2C)alkoxy, cyano, acetylenyl, $CH_2F$, $CF_2H$ or $CF_3$;
$R^7$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—Y$_3$—Z$_3$ wherein:
$Y_3$ is absent or O, S, SO, SO$_2$, N($R^j$)($CR^jR^k$)$_{q1}$ (where $q_1$ is 0, 1 or 2), C(O), C(O)O, OC(O), C(O)N($R^j$), N($R^j$)C(O), N($R^j$)C(O)N($R^k$), N($R^j$)C(O)O, OC(O)N($R^j$), S(O)$_2$N($R^j$) or N($R^j$)SO$_2$, wherein $R^j$ and $R^k$ are each independently selected from hydrogen or (1-4C)alkyl; and
$Z_3$ is hydrogen, (1-6C)alkyl, aryl, (3-6C)cycloalkyl, (2-4C)alkenyl, (2-4C)alkynyl, (3-6C)cycloalkenyl, heteroaryl or 4 to 12-membered heterocyclyl; wherein $Z_3$ is optionally further substituted by one or more substituent groups independently selected from (1-4C)alkyl, (3-6C)cycloalkyl, halo, oxo, (1-4C)haloalkyl, (1-4C)haloalkoxy, (1-4C)alkoxyalkyl, cyano, $CO_2H$, $SO_2NH_2$, $C(O)NR^lR^m$, $NR^lR^m$, $OR^l$ or $SR^l$ wherein $R^l$ and $R^m$ are each independently selected from hydrogen, (1-4C)alkyl or (3-6C)cycloalkyl; or $Z^3$ is optionally further substituted by a group of the formula:

-$L_Z$-$W_Z$ wherein:

$L_Z$ is a (1-5C)alkylene optionally substituted by one or more substituents selected from (1-2C)alkyl or oxo; and $W_Z$ is halo, (1-4C)haloalkyl, (1-4C)haloalkoxy, cyano, hydroxy, (1-4C)alkoxy, $C(O)R^{xa}$, $COOR^{xa}$, $C(O)NR^{xa}R^{xb}$ or $NR^{xa}R^{xb}$, wherein $R^{xa}$ and $R^{xb}$ are each independently selected from hydrogen or (1-4C)alkyl;

$R^{30}$ is selected from (1-4C)alkyl, (3-6C)cycloalkyl, (1-4C)haloalkyl or cyano, wherein each (1-4C)alkyl and/or (3-6C)cycloalkyl substituent is optionally further substituted by one or more substituents selected from (1-4C)alkyl, (3-6C)cycloalkyl, hydroxy, (1-2C)alkoxy, $NR^uR^v$, (1-2C)aminoalkyl or halo, wherein $R^u$ and $R^v$ are independently selected from hydrogen or (1-2C)alkyl;

$R^{31}$ is selected from hydrogen, (1-4C)alkyl, cyano, (1-4C)haloalkyl or a group of the formula:

$Y_5$-$L_5$-$Z_5$ wherein:

$Y_5$ is absent or selected from $C(O)O$ or $C(O)N(R^w)$, wherein $R^w$ is selected from hydrogen or (1-2C)alkyl;

$L_5$ is absent or (1-2C)alkylene; and $Z_5$ is hydrogen, (1-6C)alkyl, aryl, (3-6C)cycloalkyl, 5 or 6 membered heteroaryl or 4 to 6-membered heterocyclyl; wherein $Z_5$ is optionally substituted by one or more substituents selected from (1-2C)alkyl, halo, (1-2C)haloalkyl, (1-2C)haloalkoxy, (1-2C)alkoxy, $NH_2$, cyano, nitro or hydroxy; or $R^{30}$ and $R^{31}$ are linked such that, together with the carbon atom to which they are attached, they form a 4-6 membered carbocyclic ring or a heterocyclic ring; and Ring A is a 6- or 7-membered heterocyclic ring, which, in addition to the substituent groups $R^{30}$ and $R^{31}$, is optionally further substituted by one or more substituent groups selected from oxo, (1-2C)alkyl, cyclopropyl, spiro-cyclopropyl, halo, (1-2C)haloalkyl, (1-2C)haloalkoxy, (1-2C)alkoxy, $NH_2$, cyano or hydroxy.

2. A compound, or a pharmaceutically acceptable salt or solvate thereof, according to claim 1, wherein $X_2$ is CH.

3. A compound, or a pharmaceutically acceptable salt or solvate thereof, according to claim 1, wherein $X_1$ is selected from N or CH.

4. A compound, or a pharmaceutically acceptable salt or solvate thereof, according to claim 1, wherein $R^2$ is a group of Formula A shown below:

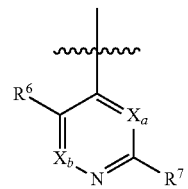

Formula A wherein:

denotes the point of attachment;

$X_a$ is selected from N, CH or CF;

$X_b$ is selected from N or $CR^{x1}$, wherein $R^{x1}$ is selected from hydrogen, fluoro, chloro, bromo, (1-2C)alkyl, (1-2C)alkoxy, cyano, acetylenyl, $CH_2F$, $CF_2H$ or $CF_3$;

$R^6$ is selected from hydrogen, fluoro, chloro, bromo, (1-2C)alkyl, cyano, acetylenyl, $CH_2F$, $CF_2H$ or $CF_3$;

$R^7$ is selected from hydrogen, halo, (1-2C)alkyl, (1-2C)alkoxy, (1-2C)haloalkyl, (1-2C)haloalkoxy, cyano or a group of the formula:

—$Y_3$—$Z_3$ wherein:

$Y_3$ is absent or O, C(O), C(O)O, OC(O), $C(O)N(R^j)$ or $N(R^j)C(O)$, wherein $R^j$ is selected from hydrogen or (1-4C)alkyl; and $Z_3$ is hydrogen, (1-6C)alkyl, (3-6C)cycloalkyl, 5- or 6-membered heteroaryl or 4 to 12-membered heterocyclyl; wherein $Z_3$ is optionally further substituted by one or more substituent groups independently selected from (1-4C)alkyl, halo, oxo, (1-4C)haloalkyl, (1-4C)haloalkoxy, (1-4C)alkoxyalkyl, cyano, $C(O)NR^lR^m$, $NR^lR^m$ or $OR^l$, wherein $R^l$ and $R^m$ are each independently selected from hydrogen, (1-4C)alkyl or (3-6C)cycloalkyl.

5. A compound, or a pharmaceutically acceptable salt or solvate thereof, according to claim 1, wherein the compound has the structural formula Ic shown below:

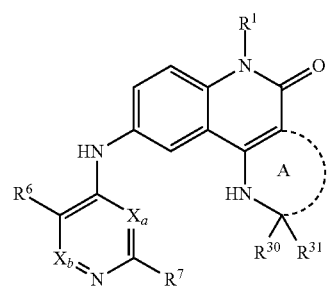

Formula Ic wherein each of $R^1$, $R^6$, $R^7$, $X_a$, $X_b$, $R^{30}$, $R^{31}$ and Ring A are as defined in claim 1.

6. A compound according to claim 5, wherein $X_b$ is selected from CH, CCl, CF, CBr or $CCH_3$.

7. A compound according to claim 5, wherein $R^6$ is selected from chloro, fluoro, bromo, methyl or cyano.

8. A compound according to claim 5, wherein $R^7$ is selected from hydrogen, halo, (1-2C)alkyl, (1-2C)alkoxy, (1-2C)haloalkyl, (1-2C)haloalkoxy, cyano or a group of the formula:

—$Y_3$—$Z_3$ wherein:
$Y_3$ is absent or O, C(O), C(O)O or C(O)N($R^j$), wherein $R^j$ is selected from hydrogen or (1-4C)alkyl; and
$Z_3$ is hydrogen, (1-6C)alkyl, (3-6C)cycloalkyl, 5- or 6-membered heteroaryl or 4 to 11-membered heterocyclyl; wherein $Z_3$ is optionally further substituted by one or more substituent groups independently selected from (1-4C)alkyl, halo, oxo, (1-4C)haloalkyl, (1-4C)haloalkoxy, (1-4C)alkoxyalkyl, cyano, C(O)N$R^l R^m$, N$R^l R^m$ or O$R^l$, wherein $R^l$ and $R^m$ are each independently selected from hydrogen, (1-4C)alkyl or (3-6C)cycloalkyl.

9. A compound, or a pharmaceutically acceptable salt or solvate thereof, according to claim 1, wherein $R^1$ is selected from hydrogen or a group of the formula:

-L-Z wherein:
L is absent or (1-3C)alkylene; and
Z is (1-6C)alkyl, aryl, (3-6C)cycloalkyl, (3-6C)cycloalkenyl, 5 or 6 membered heteroaryl or 5 or 6 membered heterocyclyl; wherein Z is optionally further substituted by one or more substituent groups independently selected from oxo, (1-2C)alkyl, halo, (1-2C)haloalkyl, (1-2C)haloalkoxy, (1-2C)aminoalkyl, cyano, N$R^g R^h$ or O$R^g$; wherein $R^g$ and $R^h$ are each independently selected from hydrogen or (1-2C)alkyl.

10. A compound, or a pharmaceutically acceptable salt or solvate thereof, according to claim 1, wherein $R^1$ is selected from hydrogen, (1-6C)alkyl or a group of the formula:

-L-Z wherein:
L is (1-2C)alkylene; and
Z is (3-6C)cycloalkyl or 4 to 7 membered heterocyclyl; wherein Z is optionally further substituted by one or more substituent groups independently selected from oxo, (1-2C)alkyl, halo, (1-2C)haloalkyl, (1-2C)haloalkoxy, (1-2C)aminoalkyl, cyano, N$R^g R^h$ or O$R^g$; wherein $R^g$ and $R^h$ are each independently selected from hydrogen or methyl.

11. A compound, or a pharmaceutically acceptable salt or solvate thereof, according to claim 1, wherein $R^{30}$ is selected from (1-4C)alkyl, (3-6C)cycloalkyl, (1-4C)haloalkyl, or cyano, wherein each (1-4C)alkyl and/or (3-6C)cycloalkyl substituent is optionally further substituted by one or more substituents selected from (1-4C)alkyl, cyclopropyl, hydroxy, (1-2C)alkoxy or halo.

12. A compound, or a pharmaceutically acceptable salt or solvate thereof, according to claim 1, wherein $R^{31}$ is selected from hydrogen, (1-4C)alkyl, cyano, (1-4C)haloalkyl or a group of the formula:

$Y_5$-$L_5$s-$Z_5$ wherein:
$Y_5$ is absent or C(O)N($R^w$), wherein $R^w$ is selected from hydrogen or methyl;
$L_5$ is absent or (1-2C)alkylene; and
$Z_5$ is hydrogen, (1-6C)alkyl, cyclopropyl or a 5 or 6 membered heteroaryl;

wherein is $Z_5$ optionally substituted by one or more substituents selected from (1-2C)alkyl, halo, (1-2C)haloalkyl, (1-2C)haloalkoxy, (1-2C)alkoxy, $NH_2$, cyano, nitro or hydroxy.

13. A compound, or a pharmaceutically acceptable salt or solvate thereof, according to claim 1, wherein Ring A is a 7-membered heterocyclic ring, which, in addition to the substituent groups $R^{30}$ and $R^{31}$, is optionally further substituted by one or more substituent groups selected from oxo, (1-2C)alkyl, cyclopropyl, spiro-cyclopropyl, halo, (1-2C)haloalkyl, (1-2C)haloalkoxy, (1-2C)alkoxy, $NH_2$, cyano or hydroxy.

14. A compound, or a pharmaceutically acceptable salt or solvate thereof, wherein the compound has the structural formula Id shown below:

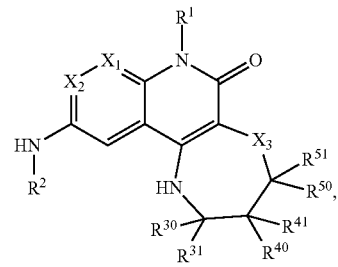

Formula Id wherein
$X_1$ is selected from N or C$R^a$, wherein $R^a$ is selected from hydrogen, (1-2C)alkyl, halogen, (1-2C)alkoxy, (1-2C)haloalkyl, (1-2C)haloalkoxy, cyano or N$R^b R^c$, wherein $R^b$ and $R^c$ are each independently selected from hydrogen or (1-2C)alkyl;
$X_2$ is selected from N, CH, CF, CCl or C—$CH_3$;
$R^1$ is selected from hydrogen or a group of the formula:

-L-Y—Z wherein:
L is absent or (1-3C)alkylene;
Y is absent or O, C(O), C(O)O or C(O)N($R^e$), wherein $R^e$ is selected from hydrogen or (1-4C)alkyl; and
Z is hydrogen, (1-6C)alkyl, aryl, (3-6C)cycloalkyl, (3-6C)cycloalkenyl, 5 or 6 membered heteroaryl or 4 to 7 membered heterocyclyl; wherein Z is optionally further substituted by one or more substituent groups independently selected from oxo, (1-2C)alkyl, halo, (1-2C)haloalkyl, (1-2C)haloalkoxy, (1-2C)aminoalkyl, cyano, N$R^g R^h$ or O$R^g$; wherein $R^g$ and $R^h$ are each independently selected from hydrogen or (1-4C)alkyl;
$R^2$ is selected from a group of Formula A shown below:

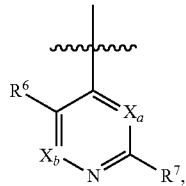

Formula A wherein:
⋰ denotes the point of attachment;
$X_a$ is selected from N, CH or CF;

$X_b$ is selected from N or $CR^{x1}$ wherein $R^{x1}$ is selected from hydrogen, fluoro, chloro, bromo, (1-2C)alkyl, (1-2C)alkoxy, cyano, acetylenyl, $CH_2F$, $CF_2H$ or $CF_3$;

$R^6$ is selected from hydrogen, fluoro, chloro, bromo, (1-2C)alkyl, (1-2C)alkoxy, cyano, acetylenyl, $CH_2F$, $CF_2H$ or $CF_3$;

$R^7$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—$Y_3$—$Z_3$ wherein:
$Y_3$ is absent or O, S, SO, $SO_2$, $N(R^j)(CR^jR^k)_{q1}$ (where $q_1$ is 0, 1 or 2), C(O), C(O)O, OC(O), $C(O)N(R^j)$, $N(R^j)C(O)$, $N(R^j)C(O)N(R^k)$, $N(R^j)C(O)O$, $OC(O)N(R^j)$, $S(O)_2N(R^j)$ or $N(R^j)SO_2$, wherein $R^j$ and $R^k$ are each independently selected from hydrogen or (1-4C)alkyl; and $Z_3$ is hydrogen, (1-6C)alkyl, aryl, (3-6C)cycloalkyl, (2-4C)alkenyl, (2-4C)alkynyl, (3-6C)cycloalkenyl, heteroaryl or 4 to 12-membered heterocyclyl; wherein $Z_3$ is optionally further substituted by one or more substituent groups independently selected from (1-4C)alkyl, (3-6C)cycloalkyl, halo, oxo, (1-4C)haloalkyl, (1-4C)haloalkoxy, (1-4C)alkoxyalkyl, cyano, $CO_2H$, $SO_2NH_2$, $C(O)NR^lR^m$, $NR^lR^m$, $OR^l$ or $SR^l$ wherein $R^l$ and $R^m$ are each independently selected from hydrogen, (1-4C)alkyl or (3-6C)cycloalkyl; or $Z^3$ is optionally further substituted by a group of the formula:

-$L_Z$-$W_Z$ wherein:
$L_Z$ is a (1-5C)alkylene optionally substituted by one or more substituents selected from (1-2C)alkyl or oxo; and $W_Z$ is halo, (1-4C)haloalkyl, (1-4C)haloalkoxy, cyano, hydroxy, (1-4C)alkoxy, $C(O)R^{xa}$, $COOR^{xa}$, $C(O)NR^{xa}R^{xb}$ or $NR^{xa}R^{xb}$, wherein $R^{xa}$ and $R^{xb}$ are each independently selected from hydrogen or (1-4C)alkyl;

$R^{30}$ is selected from (1-4C)alkyl, (3-6C)cycloalkyl, (1-4C)haloalkyl or cyano, wherein each (1-4C)alkyl and/or (3-6C)cycloalkyl substituent is optionally further substituted by one or more substituents selected from (1-4C)alkyl, (3-6C)cycloalkyl, hydroxy, (1-2C)alkoxy, $NR^uR^v$, (1-2C)aminoalkyl or halo, wherein $R^u$ and $R^v$ are independently selected from hydrogen or (1-2C)alkyl;

$R^{31}$ is selected from hydrogen, (1-4C)alkyl, cyano, (1-4C)haloalkyl or a group of the formula:

$Y_5$-$L_5$-$Z_5$ wherein:
$Y_5$ is absent or selected from C(O)O or $C(O)N(R^w)$, wherein $R^w$ is selected from hydrogen or (1-2C)alkyl;

$L_5$ is absent or (1-2C)alkylene; and $Z_5$ is hydrogen, (1-6C)alkyl, aryl, (3-6C)cycloalkyl, 5 or 6 membered heteroaryl or 4 to 6-membered heterocyclyl; wherein $Z_5$ is optionally substituted by one or more substituents selected from (1-2C)alkyl, halo, (1-2C)haloalkyl, (1-2C)haloalkoxy, (1-2C)alkoxy, $NH_2$, cyano, nitro or hydroxy; or $R^{30}$ and $R^{31}$ are linked such that, together with the carbon atom to which they are attached, they form a 4-6 membered carbocyclic ring or a heterocyclic ring; and Ring A is a 6- or 7-membered heterocyclic ring, which, in addition to the substituent groups $R^{30}$ and $R^{31}$, is optionally further substituted by one or more substituent groups selected from oxo, (1-2C)alkyl, cyclopropyl, spiro-cyclopropyl, halo, (1-2C)haloalkyl, (1-2C)haloalkoxy, (1-2C)alkoxy, $NH_2$, cyano or hydroxy;

$X_3$ is $CH_2$, O, S, $SO_2$ or NH; and $R^{40}$, $R^{41}$, $R^{50}$ and $R^{51}$ are independently selected from hydrogen, (1-2C)alkyl, (3-6C)cycloalkyl, halo, (1-2C)haloalkyl, (1-2C)haloalkoxy, (1-2C)alkoxy, (1-4C)alkoxyalkyl, (1-2C)aminoalkyl, $NH_2$, cyano, nitro, OH, $C(O)OR^{z1}$, $C(O)N(R^{z2})R^{z1}$ $NR^{z2}C(O)R^{z1}$, wherein $R^{z1}$ and $R^{z2}$ are each independently selected from hydrogen or (1-2C)alkyl; or $R^{40}$ and $R^{41}$, and/or $R^{50}$ and $R^{51}$, are linked such that, together with the carbon atom to which they are attached, they form a 3-6 membered carbocyclic ring or heterocyclic ring.

15. A compound, or a pharmaceutically acceptable salt or solvate thereof, according to claim 1, wherein $R^1$ is methyl.

16. A compound, or a pharmaceutically acceptable salt or solvate thereof, according to claim 1, wherein $R^{30}$ is cyclopropyl.

17. A compound, or a pharmaceutically acceptable salt or solvate thereof, according to claim 14, wherein one or more of the following statements apply:
(i) $X_3$ is O;
(ii) $R^{50}$ and $R^{51}$ are hydrogen; and/or
(iii) $R^{40}$ and $R^{41}$ are fluoro.

18. A compound, or a pharmaceutically acceptable salt or solvate thereof, selected from one of the following:
(S)-2-chloro-4-((2,7-dimethyl-6-oxo-1,2,3,4,6,7-hexahydro-[1,4]oxazepino[2,3-c]quinolin-10-yl)amino)nicotinonitrile;

(R)-2-chloro-4-((2,7-dimethyl-6-oxo-1,2,3,4,6,7-hexahydro-[1,4]oxazepino[2,3-c]quinolin-10-yl)amino)nicotinonitrile;

2-chloro-4-((2-ethyl-7-methyl-6-oxo-1,2,3,4,6,7-hexahydro-[1,4]oxazepino[2,3-c]quinolin-10-yl)amino)nicotinonitrile;

(R)-2-chloro-4-((2-cyclopropyl-7-methyl-6-oxo-1,2,3,4,6,7-hexahydro-[1,4]oxazepino[2,3-c]quinolin-10-yl)amino)nicotinonitrile;

(S)-2-chloro-4-((2-cyclopropyl-7-methyl-6-oxo-1,2,3,4,6,7-hexahydro-[1,4]oxazepino[2,3-c]quinolin-10-yl)amino)nicotinonitrile;

2-chloro-4-((2,2,7-trimethyl-6-oxo-1,2,3,4,6,7-hexahydro-[1,4]oxazepino[2,3-c]quinolin-10-yl)amino)nicotinonitrile;

2-chloro-4-((2-(methoxymethyl)-2,7-dimethyl-6-oxo-1,2,3,4,6,7-hexahydro-[1,4]oxazepino[2,3-c]quinolin-10-yl)amino)nicotinonitrile;

2-chloro-4-((2,3,3,7-tetramethyl-6-oxo-1,2,3,4,6,7-hexahydro-[1,4]oxazepino[2,3-c]quinolin-10-yl)amino)nicotinonitrile;

2-chloro-4-((2',7'-dimethyl-6'-oxo-1',2',6',7'-tetrahydro-4'H-spiro[cyclopropane-1,3'-[1,4]oxazepino[2,3-c]quinolin]-10'-yl)amino)nicotinonitrile;

2-chloro-4-(((2S,4S)-2,4,7-trimethyl-6-oxo-1,2,3,4,6,7-hexahydro-[1,4]oxazepino[2,3-c]quinolin-10-yl)amino)nicotinonitrile;

2-chloro-4-((2,6-dimethyl-5-oxo-2,3,5,6-tetrahydro-1H-[1,4]oxazino[2,3-c]quinolin-9-yl)amino)nicotinonitrile;
2-chloro-4-((2-ethyl-6-methyl-5-oxo-2,3,5,6-tetrahydro-1H-[1,4]oxazino[2,3-c]quinolin-9-yl)amino)nicotinonitrile;
2-chloro-4-((2-cyclopropyl-6-methyl-5-oxo-2,3,5,6-tetrahydro-1H-[1,4]oxazino[2,3-c]quinolin-9-yl)amino)nicotinonitrile;
2-chloro-4-((2-cyclobutyl-6-methyl-5-oxo-2,3,5,6-tetrahydro-1H-[1,4]oxazino[2,3-c]quinolin-9-yl)amino)nicotinonitrile;
2-chloro-4-((7'-methyl-6'-oxo-3',4,4',5,6',7'-hexahydro-1'H,2H-spiro[furan-3,2'-[1,4]oxazepino[2,3-c]quinolin]-10'-yl)amino)nicotinonitrile;
2-chloro-4-((2-(difluoromethyl)-7-methyl-6-oxo-1,2,3,4,6,7-hexahydro-[1,4]oxazepino[2,3-c]quinolin-10-yl)amino)nicotinonitrile;
2-chloro-4-((2-cyclopropyl-3,3-difluoro-7-methyl-6-oxo-1,2,3,4,6,7-hexahydro-[1,4]oxazepino[2,3-c]quinolin-10-yl)amino)nicotinonitrile;
(R)-2-cyclopropyl-10-((5,6-dichloro-2-((2S,6R)-2,6-dimethylmorpholino)pyrimidin-4-yl)amino)-7-methyl-1,2,3,4-tetrahydro-[1,4]oxazepino[2,3-c]quinolin-6(7H)-one;
(R)-2-chloro-4-((2-cyclopropyl-7-methyl-6-oxo-1,2,3,4,6,7-hexahydro-[1,4]thiazepino[2,3-c]quinolin-10-yl)amino)nicotinonitrile;
(S)-6-chloro-5-cyano-4-((2,7-dimethyl-6-oxo-1,2,3,4,6,7-hexahydro-[1,4]oxazepino[2,3-c]quinolin-10-yl)amino)picolinic acid;
(R)-6-chloro-5-cyano-4-((2-cyclopropyl-7-methyl-6-oxo-1,2,3,4,6,7-hexahydro-[1,4]oxazepino[2,3-c]quinolin-10-yl)amino)picolinic acid;
(S)-6-(azetidine-1-carbonyl)-2-chloro-4-((2,7-dimethyl-6-oxo-1,2,3,4,6,7-hexahydro-[1,4]oxazepino[2,3-c]quinolin-10-yl)amino)nicotinonitrile;
(R)-2-chloro-4-((2-cyclopropyl-7-methyl-6-oxo-1,2,3,4,6,7-hexahydro-[1,4]oxazepino[2,3-c]quinolin-10-yl)amino)-6-(3-(trifluoromethyl)azetidine-1-carbonyl)nicotinonitrile;
(S)-10-((2,3-dichloropyridin-4-yl)amino)-2,7-dimethyl-1,2,3,4-tetrahydro-[1,4]oxazepino[2,3-c]quinolin-6(7H)-one;
(S)-10-((5-chloro-2-((S)-2-(methoxymethyl)pyrrolidine-1-carbonyl)pyridin-4-yl)amino)-2,7-dimethyl-1,2,3,4-tetrahydro-[1,4]oxazepino[2,3-c]quinolin-6(7H)-one;
(R)-2-cyclopropyl-10-((2,3-dichloropyridin-4-yl)amino)-7-methyl-1,2,3,4-tetrahydro-[1,4]oxazepino[2,3-c]quinolin-6(7H)-one;
(R)-10-((5-chloro-2-(3-(trifluoromethyl)-1H-pyrazol-1-yl)pyrimidin-4-yl)amino)-2-cyclopropyl-7-methyl-1,2,3,4-tetrahydro-[1,4]oxazepino[2,3-c]quinolin-6(7H)-one;
10-((5-chloro-2-(3-(trifluoromethyl)-1H-pyrazol-1-yl)pyrimidin-4-yl)amino)-2-(methoxymethyl)-2,7-dimethyl-1,2,3,4-tetrahydro-[1,4]oxazepino[2,3-c]quinolin-6(7H)-one;
(S)-10-((5-chloro-2-(3-(trifluoromethyl)-1H-pyrazol-1-yl)pyrimidin-4-yl)amino)-2,7-dimethyl-1,2,3,4-tetrahydro-[1,4]oxazepino[2,3-c]quinolin-6(7H)-one;
(S)-1-(5-chloro-4-((2,7-dimethyl-6-oxo-1,2,3,4,6,7-hexahydro-[1,4]oxazepino[2,3-c]quinolin-10-yl)amino)pyrimidin-2-yl)-N,N-dimethylpiperidine-4-carboxamide;
(S)-10-((5-chloro-2-((3R,5S)-3,5-dimethylpiperidin-1-yl)pyrimidin-4-yl)amino)-2,7-dimethyl-1,2,3,4-tetrahydro-[1,4]oxazepino[2,3-c]quinolin-6(7H)-one;
(S)-10-((5-chloro-2-((3S,5R)-4,4-difluoro-3,5-dimethylpiperidin-1-yl)pyrimidin-4-yl)amino)-2,7-dimethyl-1,2,3,4-tetrahydro-[1,4]oxazepino[2,3-c]quinolin-6(7H)-one;
(S)-10-((5-chloro-2-((2S,6R)-2,6-dimethylmorpholino)pyrimidin-4-yl)amino)-2,7-dimethyl-1,2,3,4-tetrahydro-[1,4]oxazepino[2,3-c]quinolin-6(7H)-one;
(S)-10-((5-chloro-2-morpholinopyrimidin-4-yl)amino)-2,7-dimethyl-1,2,3,4-tetrahydro-[1,4]oxazepino[2,3-c]quinolin-6(7H)-one;
(R)-10-((5-chloro-2-((3S,5R)-4,4-difluoro-3,5-dimethylpiperidin-1-yl)pyrimidin-4-yl)amino)-2-cyclopropyl-7-methyl-1,2,3,4-tetrahydro-[1,4]oxazepino[2,3-c]quinolin-6(7H)-one;
10'-((5-chloro-2-(3-(trifluoromethyl)-1H-pyrazol-1-yl)pyrimidin-4-yl)amino)-7'-methyl-3',4,4',5-tetrahydro-1'H,2H-spiro[furan-3,2'-[1,4]oxazepino[2,3-c]quinolin]-6'(7'H)-one;
(R)-10-((5-chloro-2-(2,2,6,6-tetramethylmorpholino)pyrimidin-4-yl)amino)-2-cyclopropyl-7-methyl-1,2,3,4-tetrahydro-[1,4]oxazepino[2,3-c]quinolin-6(7H)-one;
(R)-10-((2-(3-oxa-8-azabicyclo[3.2.1]octan-8-yl)-5-chloropyrimidin-4-yl)amino)-2-cyclopropyl-7-methyl-1,2,3,4-tetrahydro-[1,4]oxazepino[2,3-c]quinolin-6(7H)-one;
(R)-10-((5-chloro-2-(4,4-difluoropiperidin-1-yl)pyrimidin-4-yl)amino)-2-cyclopropyl-7-methyl-1,2,3,4-tetrahydro-[1,4]oxazepino[2,3-c]quinolin-6(7H)-one;
(R)-10-((5-chloro-2-((1R,5S,7S)-7-hydroxy-3-oxa-9-azabicyclo[3.3.1]nonan-9-yl)pyrimidin-4-yl)amino)-2-cyclopropyl-7-methyl-1,2,3,4-tetrahydro-[1,4]oxazepino[2,3-c]quinolin-6(7H)-one;
(R)-10-((2-(2-oxa-6-azaadamantan-6-yl)-5-chloropyrimidin-4-yl)amino)-2-cyclopropyl-7-methyl-1,2,3,4-tetrahydro-[1,4]oxazepino[2,3-c]quinolin-6(7H)-one;
(R)-10-((5-chloro-2-((3S,5R)-4,4-difluoro-3,5-dimethylpiperidin-1-yl)pyrimidin-4-yl)amino)-2-cyclopropyl-1,2,3,4-tetrahydro-[1,4]oxazepino[2,3-c]quinolin-6(7H)-one;
(R)-10-((2-(3-oxa-8-azabicyclo[3.2.1]octan-8-yl)-5-chloropyrimidin-4-yl)amino)-2-cyclopropyl-7-((3,3-difluorocyclobutyl)methyl)-1,2,3,4-tetrahydro-[1,4]oxazepino[2,3-c]quinolin-6(7H)-one;
(R)-10-((2-(3-oxa-8-azabicyclo[3.2.1]octan-8-yl)-5-chloropyrimidin-4-yl)amino)-2-cyclopropyl-7-(cyclopropylmethyl)-1,2,3,4-tetrahydro-[1,4]oxazepino[2,3-c]quinolin-6(7H)-one;
(R)-10-((5-chloro-2-(4,4-difluoropiperidin-1-yl)pyrimidin-4-yl)amino)-2-cyclopropyl-7-methyl-1,2,3,4-tetrahydro-[1,4]oxazepino[2,3-c][1,8]naphthyridin-6(7H)-one;
(R)-10-((5-chloro-2-((3S,5R)-4,4-difluoro-3,5-dimethylpiperidin-1-yl)pyrimidin-4-yl)amino)-2-cyclopropyl-7-methyl-1,2,3,4-tetrahydro-[1,4]oxazepino[2,3-c][1,8]naphthyridin-6(7H)-one;
(R)-10-((5-chloro-2-((1R,5S,7S)-7-hydroxy-3-oxa-9-azabicyclo[3.3.1]nonan-9-yl)pyrimidin-4-yl)amino)-2-cyclopropyl-7-((3,3-difluorocyclobutyl)methyl)-1,2,3,4-tetrahydro-[1,4]oxazepino[2,3-c]quinolin-6(7H)-one;
(S)-2-chloro-4-((2,7-dimethyl-5,6-dioxo-1,2,3,5,6,7-hexahydro-[1,4]oxazepino[6,5-c]quinolin-10-yl)amino)nicotinonitrile;
(S)-2-chloro-4-((2-cyclopropyl-7-methyl-5,6-dioxo-1,2,3,5,6,7-hexahydro-[1,4]oxazepino[6,5-c]quinolin-10-yl)amino)nicotinonitrile;

2-chloro-4-((2-cyclopropyl-7-methyl-5,6-dioxo-1,2,3,5,6,7-hexahydro-[1,4]oxazepino[6,5-c]quinolin-10-yl)amino)nicotinonitrile;

2-chloro-4-((2,3,7-trimethyl-5,6-dioxo-1,2,3,5,6,7-hexahydro-[1,4]oxazepino[6,5-c]quinolin-10-yl)amino)nicotinonitrile;

(S)-10-((5-chloro-2-((tetrahydro-2H-pyran-4-yl)oxy)pyridin-4-yl)amino)-2,7-dimethyl-2,3-dihydro-[1,4]oxazepino[6,5-c]quinoline-5,6(1H,7H)-dione;

(S)-10-((5-chloro-2-((2S,6R)-2,6-dimethylmorpholino)pyrimidin-4-yl)amino)-2,7-dimethyl-2,3-dihydro-[1,4]oxazepino[6,5-c]quinoline-5,6(1H,7H)-dione;

(2S)-10-((2-(8-azabicyclo[3.2.1]octan-8-yl)-5-chloropyrimidin-4-yl)amino)-2,7-dimethyl-2,3-dihydro-[1,4]oxazepino[6,5-c]quinoline-5,6(1H,7H)-dione;

(S)-10-((5-chloro-2-((3S,5R)-4,4-difluoro-3,5-dimethylpiperidin-1-yl)pyrimidin-4-yl)amino)-2,7-dimethyl-2,3-dihydro-[1,4]oxazepino[6,5-c]quinoline-5,6(1H,7H)-dione;

(S)-1-(5-chloro-4-((2,7-dimethyl-5,6-dioxo-1,2,3,5,6,7-hexahydro-[1,4]oxazepino[6,5-c]quinolin-10-yl)amino)pyrimidin-2-yl)-N,N-dimethylpiperidine-4-carboxamide;

(S)-10-((5-chloro-2-(2-methyl-1-oxo-2,9-diazaspiro[5.5]undecan-9-yl)pyrimidin-4-yl)amino)-2,7-dimethyl-2,3-dihydro-[1,4]oxazepino[6,5-c]quinoline-5,6(1H,7H)-dione;

(2S)-10-((5-chloro-2-(3,3-difluoro-8-azabicyclo[3.2.1]octan-8-yl)pyrimidin-4-yl)amino)-2,7-dimethyl-2,3-dihydro-[1,4]oxazepino[6,5-c]quinoline-5,6(1H,7H)-dione;

(S)-10-((5-chloro-2-((3R,5S)-3,5-dimethylpiperidin-1-yl)pyrimidin-4-yl)amino)-2,7-dimethyl-2,3-dihydro-[1,4]oxazepino[6,5-c]quinoline-5,6(1H,7H)-dione;

(2S)-10-((2-(3-azabicyclo[3.2.1]octan-3-yl)-5-chloropyrimidin-4-yl)amino)-2,7-dimethyl-2,3-dihydro-[1,4]oxazepino[6,5-c]quinoline-5,6(1H,7H)-dione;

(S)-10-((5-chloro-2-(2-oxopyrrolidin-1-yl)pyrimidin-4-yl)amino)-2,7-dimethyl-2,3-dihydro-[1,4]oxazepino[6,5-c]quinoline-5,6(1H,7H)-dione;

(2S)-10-((2-(8-azabicyclo[3.2.1]octan-8-yl)-5-chloropyrimidin-4-yl)amino)-2-cyclopropyl-7-methyl-2,3-dihydro-[1,4]oxazepino[6,5-c]quinoline-5,6(1H,7H)-dione;

(S)-10-((5-chloro-2-((3S,5R)-4,4-difluoro-3,5-dimethylpiperidin-1-yl)pyrimidin-4-yl)amino)-2-cyclopropyl-7-methyl-2,3-dihydro-[1,4]oxazepino[6,5-c]quinoline-5,6(1H,7H)-dione;

(S)-10-((5-chloro-2-((3R,5S)-3,5-dimethylpiperidin-1-yl)pyrimidin-4-yl)amino)-2-cyclopropyl-7-methyl-2,3-dihydro-[1,4]oxazepino[6,5-c]quinoline-5,6(1H,7H)-dione;

(S)-1-(5-chloro-4-((2-cyclopropyl-7-methyl-5,6-dioxo-1,2,3,5,6,7-hexahydro-[1,4]oxazepino[6,5-c]quinolin-10-yl)amino)pyrimidin-2-yl)-N,N-dimethylpiperidine-4-carboxamide;

(S)-10-((5-chloro-2-((2S,6R)-2,6-dimethylmorpholino)pyrimidin-4-yl)amino)-2-cyclopropyl-7-methyl-2,3-dihydro-[1,4]oxazepino[6,5-c]quinoline-5,6(1H,7H)-dione;

10-((5-chloro-2-(4,4-difluoropiperidin-1-yl)pyrimidin-4-yl)amino)-2-cyclopropyl-7-methyl-2,3-dihydro-[1,4]oxazepino[6,5-c]quinoline-5,6(1H,7H)-dione;

rac-(2R,3S)-10-((5-chloro-2-((3S,5R)-3,5-dimethylpiperidin-1-yl)pyrimidin-4-yl)amino)-2,3,7-trimethyl-2,3-dihydro-[1,4]oxazepino[6,5-c]quinoline-5,6(1H,7H)-dione;

rac-(2R,3R)-10-((5-chloro-2-((3S,5R)-3,5-dimethylpiperidin-1-yl)pyrimidin-4-yl)amino)-2,3,7-trimethyl-2,3-dihydro-[1,4]oxazepino[6,5-c]quinoline-5,6(1H,7H)-dione;

(S)-2-chloro-4-((2,7-dimethyl-6-oxo-1,2,3,5,6,7-hexahydro-[1,4]oxazepino[6,5-c]quinolin-10-yl)amino)nicotinonitrile;

(S)-2-chloro-4-((2-cyclopropyl-7-methyl-6-oxo-1,2,3,5,6,7-hexahydro-[1,4]oxazepino[6,5-c]quinolin-10-yl)amino)nicotinonitrile;

2-chloro-4-((2,6-dimethyl-5-oxo-1,2,3,4,5,6-hexahydrobenzo[h][1,6]naphthyridin-9-yl)amino)nicotinonitrile;

2-chloro-4-((2,6-dimethyl-5-oxo-2,3,5,6-tetrahydro-1H-[1,4]thiazino[2,3-c]quinolin-9-yl)amino)nicotinonitrile;

(S)-2-chloro-4-((2-cyclopropyl-3,3-difluoro-7-methyl-6-oxo-1,2,3,4,6,7-hexahydro-[1,4]oxazepino[2,3-c]quinolin-10-yl)amino)nicotinonitrile;

10-((5-chloro-2-((1R,5S,7s)-7-hydroxy-3-oxa-9-azabicyclo[3.3.1]nonan-9-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-((1R,5S,7R)-7-hydroxy-3-oxa-9-azabicyclo[3.3.1]nonan-9-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(R)-10-((5-chloro-2-((1R,5S,7S)-7-hydroxy-3-oxa-9-azabicyclo[3.3.1]nonan-9-yl)pyrimidin-4-yl)amino)-2-cyclopropyl-7-methyl-1,2,3,4-tetrahydro-[1,4]oxazepino[2,3-c][1,8]naphthyridin-6(7H)-one;

(R)-10-((5-chloro-2-((1R,5S,7S)-7-hydroxy-3-oxa-9-azabicyclo[3.3.1]nonan-9-yl)pyrimidin-4-yl)amino)-2-cyclopropyl-7-methyl-1,2,3,4-tetrahydro-[1,4]thiazepino[2,3-c]quinolin-6(7H)-one;

(R)-10-((5-chloro-2-((3S,5R)-4,4-difluoro-3,5-dimethylpiperidin-1-yl)pyrimidin-4-yl)amino)-2-cyclopropyl-7-methyl-1,2,3,4-tetrahydro-[1,4]thiazepino[2,3-c]quinolin-6(7H)-one;

(R)-10-((5-chloro-2-((3S,5R)-4,4-difluoro-3,5-dimethylpiperidin-1-yl)pyrimidin-4-yl)amino)-2-cyclopropyl-7-(2-hydroxyethyl)-1,2,3,4-tetrahydro-[1,4]oxazepino[2,3-c]quinolin-6(7H)-one;

(R)-10-((5-chloro-2-((3S,5R)-4,4-difluoro-3,5-dimethylpiperidin-1-yl)pyrimidin-4-yl)amino)-2-cyclopropyl-7-(2-(methylamino)ethyl)-1,2,3,4-tetrahydro-[1,4]oxazepino[2,3-c]quinolin-6(7H)-one;

(R)-10-((5-chloro-2-((1R,3R,5S)-3-hydroxy-8-azabicyclo[3.2.1]octan-8-yl)pyrimidin-4-yl)amino)-2-cyclopropyl-7-methyl-1,2,3,4-tetrahydro-[1,4]oxazepino[2,3-c]quinolin-6(7H)-one;

(R)-10-((5-chloro-2-(3,3-dioxido-3-thia-8-azabicyclo[3.2.1]octan-8-yl)pyrimidin-4-yl)amino)-2-cyclopropyl-7-methyl-1,2,3,4-tetrahydro-[1,4]oxazepino[2,3-c]quinolin-6(7H)-one;

(R)-10-((5-chloro-2-(3-methyl-3,8-diazabicyclo[3.2.1]octan-8-yl)pyrimidin-4-yl)amino)-2-cyclopropyl-7-methyl-1,2,3,4-tetrahydro-[1,4]oxazepino[2,3-c]quinolin-6(7H)-one;

(R)-10-((2-(8-oxa-3-azabicyclo[3.2.1]octan-3-yl)-5-chloropyrimidin-4-yl)amino)-2-cyclopropyl-7-methyl-1,2,3,4-tetrahydro-[1,4]oxazepino[2,3-c]quinolin-6(7H)-one;

(R)-10-((5-chloro-2-(4-methyl-3-oxopiperazin-1-yl)pyrimidin-4-yl)amino)-2-cyclopropyl-7-methyl-1,2,3,4-tetrahydro-[1,4]oxazepino[2,3-c]quinolin-6(7H)-one;

(R)-10-((5-chloro-2-((3S,5R)-3-hydroxy-5-methylpiperidin-1-yl)pyrimidin-4-yl)amino)-2-cyclopropyl-7-methyl-1,2,3,4-tetrahydro-[1,4]oxazepino[2,3-c]quinolin-6(7H)-one;

(R)-10-((5-chloro-2-((3R,5S)-3-hydroxy-5-methylpiperidin-1-yl)pyrimidin-4-yl)amino)-2-cyclopropyl-7-methyl-1,2,3,4-tetrahydro-[1,4]oxazepino[2,3-c]quinolin-6(7H)-one;

(R)-10-((5-chloro-2-((3S,4R,5R)-4-fluoro-3,5-dimethylpiperidin-1-yl)pyrimidin-4-yl)amino)-2-cyclopropyl-7-methyl-1,2,3,4-tetrahydro-[1,4]oxazepino[2,3-c]quinolin-6(7H)-one;

(R)-10-((5-chloro-2-((R)-4,4-difluoro-3-methylpiperidin-1-yl)pyrimidin-4-yl)amino)-2-cyclopropyl-7-methyl-1,2,3,4-tetrahydro-[1,4]oxazepino[2,3-c]quinolin-6(7H)-one;

(R)-10-((5-chloro-2-((S)-4,4-difluoro-3-methylpiperidin-1-yl)pyrimidin-4-yl)amino)-2-cyclopropyl-7-methyl-1,2,3,4-tetrahydro-[1,4]oxazepino[2,3-c]quinolin-6(7H)-one;

(R)-10-((5-chloro-2-((R)-4,4-difluoro-3-hydroxypiperidin-1-yl)pyrimidin-4-yl)amino)-2-cyclopropyl-7-methyl-1,2,3,4-tetrahydro-[1,4]oxazepino[2,3-c]quinolin-6(7H)-one;

(R)-10-((5-chloro-2-((S)-4,4-difluoro-3-hydroxypiperidin-1-yl)pyrimidin-4-yl)amino)-2-cyclopropyl-7-methyl-1,2,3,4-tetrahydro-[1,4]oxazepino[2,3-c]quinolin-6(7H)-one;

(R)-10-((5-chloro-2-((S)-4,4-difluoro-3-(hydroxymethyl)piperidin-1-yl)pyrimidin-4-yl)amino)-2-cyclopropyl-7-methyl-1,2,3,4-tetrahydro-[1,4]oxazepino[2,3-c]quinolin-6(7H)-one;

(R)-10-((5-chloro-2-((R)-4,4-difluoro-3-(hydroxymethyl)piperidin-1-yl)pyrimidin-4-yl)amino)-2-cyclopropyl-7-methyl-1,2,3,4-tetrahydro-[1,4]oxazepino[2,3-c]quinolin-6(7H)-one;

(R)-2-chloro-4-((2-cyclopropyl-7-methyl-5,5-dioxido-6-oxo-1,2,3,4,6,7-hexahydro-[1,4]thiazepino[2,3-c]quinolin-10-yl)amino)nicotinonitrile;

(R)-10-((5-chloro-2-((1R,5S,7S)-7-hydroxy-7-methyl-3-oxa-9-azabicyclo[3.3.1]nonan-9-yl)pyrimidin-4-yl)amino)-2-cyclopropyl-7-methyl-1,2,3,4-tetrahydro-[1,4]oxazepino[2,3-c]quinolin-6(7H)-one;

(S)-10-((5-chloro-2-((3R,5S)-3-hydroxy-5-methylpiperidin-1-yl)pyrimidin-4-yl)amino)-2,7-dimethyl-1,2,3,4-tetrahydro-[1,4]oxazepino[2,3-c]quinolin-6(7H)-one;

(S)-10-((5-chloro-2-((3S,5R)-3-hydroxy-5-methylpiperidin-1-yl)pyrimidin-4-yl)amino)-2,7-dimethyl-1,2,3,4-tetrahydro-[1,4]oxazepino[2,3-c]quinolin-6(7H)-one;

(S)-10-((5-chloro-2-(4,4-difluoropiperidin-1-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-((3S,5R)-4,4-difluoro-3,5-dimethylpiperidin-1-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-(4-methyl-3-oxopiperazin-1-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-((R)-4,4-difluoro-3-(hydroxymethyl)piperidin-1-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-((S)-4,4-difluoro-3-(hydroxymethyl)piperidin-1-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-morpholinopyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-((R)-2-methylmorpholino)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-((S)-2-methylmorpholino)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((2-(8-oxa-3-azabicyclo[3.2.1]octan-3-yl)-5-chloropyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((2-(3-oxa-8-azabicyclo[3.2.1]octan-8-yl)-5-chloropyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-(3,3-dioxido-3-thia-8-azabicyclo[3.2.1]octan-8-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-((R)-4,4-difluoro-2-(hydroxymethyl)pyrrolidin-1-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

2-chloro-4-((2,7-dimethyl-5,6-dioxo-2,3,4,5,6,7-hexahydro-1H-[1,4]diazepino[6,5-c]quinolin-10-yl)amino)nicotinonitrile;

(S)-10-((5-chloro-2-(4-hydroxy-7,8-dihydropyrido[4,3-d]pyrimidin-6(5H)-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-((3R,5S)-3-hydroxy-5-methylpiperidin-1-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-((3S,5R)-3-hydroxy-5-methylpiperidin-1-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-((1S,5R)-3-methyl-2-oxo-3,8-diazabicyclo[3.2.1]octan-8-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(S)-10-((5-chloro-2-((1R,5S)-3-methyl-2-oxo-3,8-diazabicyclo[3.2.1]octan-8-yl)pyrimidin-4-yl)amino)-2-cyclopropyl-3,3-difluoro-7-methyl-1,2,3,4-tetrahydro-[1,4]oxazepino[2,3-c]quinolin-6(7H)-one;

(1R,5S,7S)-9-(5-chloro-4-(((S)-2-cyclopropyl-3,3-difluoro-7-methyl-6-oxo-1,2,3,4,6,7-hexahydro-[1,4]oxazepino[2,3-c]quinolin-10-yl)amino)pyrimidin-2-yl)-N,N-dimethyl-3-oxa-9-azabicyclo[3.3.1]nonane-7-carboxamide;

(1R,5S,7R)-9-(5-chloro-4-(((S)-2-cyclopropyl-3,3-difluoro-7-methyl-6-oxo-1,2,3,4,6,7-hexahydro-[1,4]oxazepino[2,3-c]quinolin-10-yl)amino)pyrimidin-2-yl)-N,N-dimethyl-3-oxa-9-azabicyclo[3.3.1]nonane-7-carboxamide;

(S)-10-((3-chloropyridin-4-yl)amino)-2-cyclopropyl-3,3-difluoro-7-methyl-1,2,3,4-tetrahydro-[1,4]oxazepino[2,3-c]quinolin-6(7H)-one;

(S)-3-(4-(5-chloro-4-((2-cyclopropyl-3,3-difluoro-7-methyl-6-oxo-1,2,3,4,6,7-hexahydro-[1,4]oxazepino[2,3-c]quinolin-10-yl)amino)pyrimidin-2-yl)piperazin-1-yl)propanenitrile;

(S)-2-cyclopropyl-3,3-difluoro-10-((5-fluoro-2-(4-methyl-3-oxopiperazin-1-yl)pyrimidin-4-yl)amino)-7-methyl-1,2,3,4-tetrahydro-[1,4]oxazepino[2,3-c]quinolin-6(7H)-one;

(S)-10-((2-(3-oxa-8-azabicyclo[3.2.1]octan-8-yl)-5-fluoropyrimidin-4-yl)amino)-2-cyclopropyl-3,3-difluoro-7-methyl-1,2,3,4-tetrahydro-[1,4]oxazepino[2,3-c]quinolin-6(7H)-one;

(2S)-10-((5-chloro-2-(3-methyl-3,6-diazabicyclo[3.1.1]heptan-6-yl)pyrimidin-4-yl)amino)-2-cyclopropyl-3,3-difluoro-7-methyl-1,2,3,4-tetrahydro-[1,4]oxazepino[2,3-c]quinolin-6(7H)-one; and (S)-10-((5-chloro-2-(6-methyl-2,6-diazaspiro[3.3]heptan-2-yl)pyrimidin-4-yl)amino)-2-cyclopropyl-3,3-difluoro-7-methyl-1,2,3,4-tetrahydro-[1,4]oxazepino[2,3-c]quinolin-6(7H)-one.

19. A pharmaceutical composition comprising a compound according to claim 1, or a pharmaceutically acceptable salt or hydrate thereof and a pharmaceutically acceptable carrier or excipient.

20. A method for the treatment of cancer in a subject in need of such treatment, said method comprising administering a therapeutically effective amount of i) a compound according to claim 1, or a pharmaceutically acceptable salt or hydrate thereof, or ii) a pharmaceutical composition comprising a compound to claim 1, or a pharmaceutically acceptable salt or hydrate thereof, and a pharmaceutical carrier or excipient, wherein said cancer is diffuse large B-cell lymphoma (DLBCL), follicular lymphoma (FL), Burkitt lymphoma (BL), angioimmunoblastic T-cell lymphoma (AITL), acute lymphoblastic leukaemia (ALL), chronic myeloid leukaemia (CML), multiple myeloma, breast cancer, non-small cell lung cancer (NSCLC) or squamous cell carcinomas (SCC) of the head and neck, oesophagus, lung or ovary.

* * * * *